(12) United States Patent
Venkateshappa et al.

(10) Patent No.: US 10,273,224 B2
(45) Date of Patent: Apr. 30, 2019

(54) SUBSTITUTED PYRIMIDINE COMPOUNDS, COMPOSITIONS AND MEDICINAL APPLICATIONS THEREOF

(71) Applicant: JUBILANT BIOSYS LIMITED, Bangalore (IN)

(72) Inventors: Chandregowda Venkateshappa, Bangalore (IN); Dhanalakshmi Sivanandhan, Bangalore (IN); Rajagopal Bakthavatchalam, Madison, CT (US); Raghava Reddy Kethiri, Bangalore (IN); Vellarkad Narayana Viswanadhan, Bangalore (IN); Sanjeev Giri, Allahabad (IN)

(73) Assignee: Jubilant Biosys Limited, Bangalore (IN)

( * ) Notice: Subject to any disclaimer, the term of this patent is extended or adjusted under 35 U.S.C. 154(b) by 0 days.

(21) Appl. No.: 14/913,508

(22) PCT Filed: Jul. 10, 2014

(86) PCT No.: PCT/IB2014/001304
§ 371 (c)(1),
(2) Date: Feb. 22, 2016

(87) PCT Pub. No.: WO2015/025197
PCT Pub. Date: Feb. 26, 2015

(65) Prior Publication Data
US 2016/0207905 A1    Jul. 21, 2016

(30) Foreign Application Priority Data
Aug. 22, 2013 (IN) .......................... 3726/CHE/2013

(51) Int. Cl.
| | | |
|---|---|---|
| *C07D 401/14* | (2006.01) | |
| *C07D 403/12* | (2006.01) | |
| *C07D 403/14* | (2006.01) | |
| *C07D 405/14* | (2006.01) | |
| *C07D 407/14* | (2006.01) | |
| *C07D 413/12* | (2006.01) | |
| *C07D 417/12* | (2006.01) | |
| *C07D 451/04* | (2006.01) | |
| *C07D 487/04* | (2006.01) | |

(52) U.S. Cl.
CPC ......... *C07D 401/14* (2013.01); *C07D 403/12* (2013.01); *C07D 403/14* (2013.01); *C07D 405/14* (2013.01); *C07D 407/14* (2013.01); *C07D 413/12* (2013.01); *C07D 417/12* (2013.01); *C07D 451/04* (2013.01); *C07D 487/04* (2013.01)

(58) Field of Classification Search
CPC .. C07D 401/14; C07D 403/12; C07D 403/14; C07D 405/14; C07D 407/14; C07D 413/12; C07D 417/12; C07D 451/04; C07D 487/04
See application file for complete search history.

(56) References Cited

U.S. PATENT DOCUMENTS

2010/0029610 A1   2/2010  Singh et al.
2010/0317680 A1  12/2010  Curtin et al.

FOREIGN PATENT DOCUMENTS

WO     WO 2014124230    *  8/2014

OTHER PUBLICATIONS

Morissette et al. (Advanced Drug Delivery Reviews, 56, 2004, 275-300).*
STN database search 2017.*
Byrn, Solid State Chemistry of Drugs, 1999 (Year: 1999).*

* cited by examiner

*Primary Examiner* — Umamaheswari Ramachandran
(74) *Attorney, Agent, or Firm* — Robert L. Stearns; Dickinson Wright PLLC

(57) ABSTRACT

The present disclosure relates to pyrimidine compounds of formula (I), their stereoisomers, tautomers, pharmaceutically acceptable salts, polymorphs, solvates, and hydrates thereof. The present disclosure also relates to process of preparation of these pyrimidine compounds, and to pharmaceutical compositions containing them. The compounds of the present disclosure are useful in the treatment, prevention or suppression of diseases and disorders mediated by epidermal growth factor receptor (EGFR) family kinases.

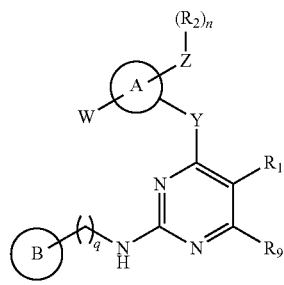

Formula I

7 Claims, No Drawings

SUBSTITUTED PYRIMIDINE COMPOUNDS, COMPOSITIONS AND MEDICINAL APPLICATIONS THEREOF

TECHNICAL FIELD

The present disclosure relates to a class of substituted pyrimidine compounds of formula (I), their stereoisomers, tautomers, pharmaceutically acceptable salts, polymorphs, solvates, and hydrates thereof. The present disclosure also relates to process of preparation of these pyrimidine compounds, and to pharmaceutical compositions containing them.

The present disclosure further relates to compounds useful in treating disease associated with epidermal growth factor receptor (EGFR) family kinases, and methods of using them. In particular, the present disclosure relates to compounds capable of inhibiting the function of the EGFR T790M enzyme by acting as covalent irreversible or reversible inhibitors. Such compounds may be useful to treat, prevent or modify a disease or condition associated with EGFR T790M activation, including non-small cell or small cell lung cancer or prostate cancer or head and neck cancer or breast cancer or conditions related to cancer.

BACKGROUND

Receptor tyrosine kinases (RTKs) are the main mediators of the signaling network that transmit extracellular signals into the cell, and control cellular differentiation and proliferation. Recent and rapid advances in our understanding of cellular signaling by RTKs, in normal and malignant cells, have brought to light the potential of RTKs as selective anti-cancer targets. Their activity is normally tightly controlled and regulated. Over expression of RTK proteins or functional alterations caused by mutations in the corresponding genes or abnormal stimulation by autocrine growth factor loops contribute to constitutive RTK signaling, resulting in dysregulated cell growth and cancer. The mechanisms of uncontrolled RTK signaling that lead to cancer have provided the rationale for anti-RTK drug development. Herceptin, Gleevec, and Iressa are the first examples of drugs which have successfully translated basic research on oncogenes into cancer therapeutics (Bennasroune et al., Crit Rev Oncol Hematol. 2004, 50, 23-38).

EGFR, a transmembrane glycoprotein, consisting of an extracellular ligand binding domain, a transmembrane domain and an intracellular tyrosine kinase domain, is a RTK whose activation initiates signal transduction through critical cellular pathways, such as those mediated by Akt (also known as Protein kinase B) and extracellular-signal-regulated kinases (ERK), and thus plays an important role in controlling cell homeostasis. Among the cognate ligands for EGFR, transforming growth factor- (TGF) and heparin-binding epidermal growth factor-like (HB-EGF) growth factor have been most strongly implicated in oncogenesis. Cell biological, in vitro and in vivo transgenic, clinical correlative, and therapeutic evidence point to a role for EGFR and its downstream cell signaling pathways, such as phosphoinositide 3-kinase (PI3K)/Akt and Ras/mitogen-activated protein kinase (MAPK) in the generation and malignant progression in various cancers. EGFR is mutated, over expressed, or aberrantly activated in different types of human tumors including head and neck, lung, and colorectal cancer, contributing to the malignant phenotype of cancer cells. Up-regulated EGFR is correlated with both poor prognosis and increased metastatic potential in numerous epithelial malignancies. Validation of EGFR as a target for therapeutic intervention in cancer has come from the clinical approval and use of various EGFR antagonists (including small molecule kinase inhibitors and monoclonal antibodies) in lung and colorectal cancer patients. Non-Small Cell Lung Cancer (NSCLC) patients with mutated EGFR show higher response rates and longer survival time when treated with EGFR kinase inhibitors such as Gefitinib and Erlotinib. EGFR inhibitors are being investigated as monotherapy and in combination with other targeted therapies in a wide range of tumor types (Nat. Rev. Cancer. 2010, 10, 760-74).

Although EGFR Tyrosine Kinase Inhibitors (TKIs) show a dramatic tumor response especially in NSCLC patients harboring EGFR mutations (such as L858R and Exon 19 deletion) and provide progression free survival and overall survival advantage, most patients relapse and develop resistance over time. Investigations of the reasons for resistance have revealed several mechanisms for resistance which include: i) secondary mutation in EGFR such as T790M; ii) amplification of c-Met, and iii) activation of TGFb-IL6-Jak/Stat axis.

Gefitinib, and Erlotinib, the two approved EGFR kinase inhibitors are highly effective against EGFR kinase domain mutants such as L858R, and delE746-A750. This is due to the increased affinity of the mutant proteins for Gefitinib, and Erlotinib as well as decreased affinity for ATP relative to WT protein. The clinical efficacy of these two drugs is ultimately limited by the appearance of acquired resistance as described above. The most common mechanism of resistance is the mutation of the gatekeeper residue Threonine 790 to Methionine (T790M). Interestingly, unlike the T315I mutation in ABL or the T670I in KIT (the targets of Imatinib in CML and GIST) both of which significantly alter drug binding to the target, T790M only modestly alters Gefitinib/Erlotinib binding to EGFR. In addition, T790M mutation restores the affinity of EGFR for ATP back to the WT level, thus contributing to the resistance of the mutation to Gefitinib/Erlotinib. This restored ATP affinity closes the therapeutic window provided by the diminished ATP affinity of the oncogenic mutants which are more easily inhibited by Gefitinib/Erlotinib relative to the WT EGFR.

There are number of second generation EGFR TKIs in clinical development (J. Clin. Oncol. 2010, 28, 3965-72; Mol. Cancer Ther. 2008, 7, 1880-89; J. Clin. Oncol. 2010, 28, 1301-07; Clin. Cancer Res. 2007, 13 (Suppl. 15), 4953s-4596s; J. Med. Chem. 2003, 46, 49-63; Chemistry & Biology 2013, 20, 146-149) Most of these inhibitors are irreversible inhibitors and have been touted to overcome T790M mediated resistance based on preclinical studies. These inhibitors are shown to be more potent against T790M mutation compared to Gefitinib or Erlotinib. The covalent binding nature of these inhibitors allows them to achieve greater potency (via greater occupancy of the ATP binding pocket) compared to reversible inhibitors. However, these inhibitors do not discriminate between WT EGFR and T790M mutation, thus limiting their clinical utility due to narrow therapeutic window.

All first and second generation reversible and irreversible EGFR, TKIs are based on quinazoline core. Recently there were few reports on selective EGFR T790M mutant inhibitors based on different cores (WO 2009/051822, WO 2012/167415, US 2012/0094999, WO 2010/129053 based on anilinopyrimidine core that fits the gatekeeper mutation while binding irreversibly to C797.

WZ4002 from Gatekeeper Pharmaceuticals is based on anilinopyrimidine core that fits the gatekeeper mutation while binding irreversibly to C797. In contrast to second generation irreversible TKIs, this inhibitor has greater potency towards double mutant EGFR (drug sensitizing L858R and drug resistant T790M) than either WT EGFR or drug sensitizing mutant EGFR both in vitro and in vivo. Hence, the expectation is that T790M mutant receptor will be effectively inhibited at drug concentration that will not affect WT EGFR, thus giving a bigger therapeutic window. Thus, a number of EGFR T790M inhibitors are known and some are being developed for medical uses (*J. Clin. Oncol.* 2010, 28, 3965-72; *Mol. Cancer Ther.* 2008, 7, 1880-89; *J. Clin. Oncol.* 2010, 28, 1301-07; *Clin. Cancer Res.* 2007, 13 (Suppl. 15), 4953-4596). Different classes of compounds may have different degrees of potency and selectivity for inhibiting EGFR T790M. There is a need to develop alternative EGFR T790M inhibitors with improved potency and/or beneficial activity profiles and/or beneficial selectivity profiles and/or increased efficacy and/or improved safety profiles (such as reduced side effects) and/or improved pharmacokinetic properties.

SUMMARY

The present disclosure provides compounds of general formula I

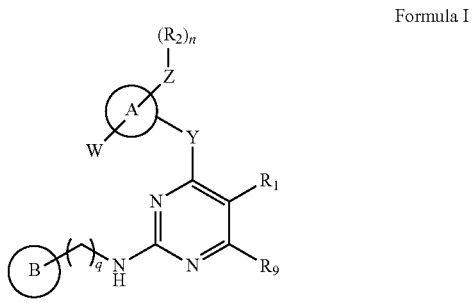

Formula I or its stereoisomers, tautomers, pharmaceutically acceptable salts, polymorphs, solvates and hydrates thereof wherein,
ring A is selected from the group consisting of aryl, heteroaryl, $C_{3-8}$ cycloalkyl, $C_{3-10}$ cycloaryl, $C_{4-6}$ heterocycloalkyl, and $C_{4-10}$ heterocycloaryl with heteroatoms selected from N, O, S;
ring-B is 5 membered mono or bicyclic ring containing 1-4 hetero atoms selected from N, O or S;
wherein ring B is optionally substituted with 1 to 4 substituents independently selected from the group consisting of hydrogen, halogen, cyano, $CF_3$, $C_{1-6}$ alkyl, $—C(R_aR_aR_a')$, $—C(R_aR_a)[C(R_aR_a)]_nOC(R_a')_p$, $—S(O)_pC(R_a')_p$, $—C(R_aR_a)C(R_aR_a)N(R_a')_p$, $—C(R_aR_a)C(R_aR_a)OR_a'$, $C_{3-6}$ cycloalkyl, $C_{5-6}$ aryl, $C_{5-6}$ heteroaryl, $C_{3-6}$ alkylcycloalkyl, alkyl $C_{3-6}$ heterocycloalkyl, monocyclic or bicyclic $C_{3-8}$ heterocycloalkyl with heteroatoms selected from N, O, S; wherein cycloalkyl, aryl, alkyl, heteroaryl, monocyclic or bicyclic heterocycloalkyl are further optionally substituted with one or more of the groups selected from hydrogen, $C_{1-6}$ alkyl, halogen, haloalkyl, OH, $—C(O)$;
W is selected from the group consisting of

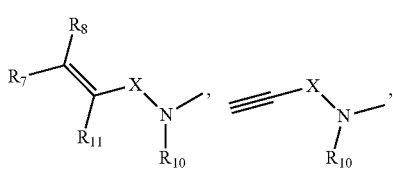

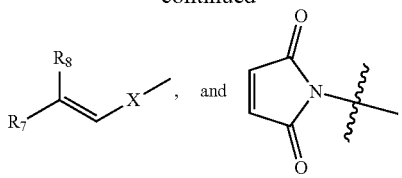

X is $—C(O)—$, $—S(O)_2—$ or $—S(O)—$;
$R_{11}$ is selected from the group consisting of hydrogen, alkyl, and halogen;
$R_{10}$ is H or alkyl;
Y is selected from the group of $—O—$, $—NR—$ and $—S—$;
where R is selected from H, alkyl;
Z is absent or $—O—$;
$R_2$ is selected from the group consisting of hydrogen, halogen, alkyl, $C_{3-6}$ cycloalkyl, and $C_{3-6}$ heterocycloalkyl;
$R_7$ is selected from the group consisting of hydrogen, halogen, methyl, and $—CH_2NR_aR_a$;
$R_8$ is selected from the group consisting of hydrogen, halogen, optionally substituted $C_{1-6}$ alkyl, $C_{4-6}$ cycloalkyl, and $C_{4-7}$ heterocycloalkyl; or
$R_7$ and $R_8$ taken together form a 4-7 membered cycloalkyl, 4-7 membered heterocycloalkyl, wherein said groups can be optionally substituted with 1 to 3 substituents independently selected from the group consisting of hydrogen, halogen, unsubstituted alkyl, haloalkyl;
$R_1$ is selected from the group consisting of hydrogen, halogen, $C_{1-6}$ alkyl, alkoxy, haloalkyl, $C_{3-6}$ cycloalkyl, $C_{5-6}$ aryl, $C_{5-6}$ heteroaryl, alkoxyalkyl, cyano, $—C(R_aR_aR_a')$, $—C(R_aR_a)[C(R_aR_a)]_nOC(R_a')_p$, $—S(O)_pC(R_a')_p$, $—C(R_aR_a)C(R_aR_a)N(R_a')_p$, $—C(R_aR_a)C(R_aR_a)OR_a'$, and monocyclic or bicyclic $C_{4-8}$ heterocycloalkyl with heteroatoms selected from N, O, S;
wherein $C_{1-6}$ alkyl, $C_{3-6}$ cycloalkyl, $C_{5-6}$ aryl, $C_{5-6}$ heteroaryl, monocyclic or bicyclic $C_{4-8}$ heterocycloalkyl with heteroatoms selected from N, O, S is optionally substituted with one or more of the groups selected from hydrogen, $C_{1-6}$ alkyl, halogen, OH, $—C(O)$;
$R_9$ is selected from the group consisting of hydrogen, halogen, alkyl, haloalkyl, alkoxy, alkoxyalkyl, and cyano;
$R_a$ is selected from the group consisting of hydrogen, $—CH_3$, $—CH_2—$, halogen, and OH;
$R_{a'}$ is selected from the group consisting of hydrogen, $—CH_3$, $—CH_2—$, and $C_{3-6}$ cycloalkyl;
or $R_a$ $R_{a'}$ taken together form a $C_{3-6}$ cycloalkyl ring, $C_{4-6}$ heterocycloalkyl ring;
q is 0 to 1;
n is 0, 1 and 2; and
p is 1, 2, 3 or 4;

The present disclosure discloses a process of preparation of compounds of formula (I), or its stereoisomers, tautomers, pharmaceutically acceptable salts, polymorphs, solvates and hydrates thereof, and to pharmaceutical compositions containing them.

The compounds of the present disclosure are useful in the treatment, prevention or suppression of diseases and disorders mediated by epidermal growth factor receptor (EGFR) family kinases.

These and other features, aspects, and advantages of the present disclosure will become better understood with reference to the following description. This statement is provided to introduce a selection of concepts in simplified form. This statement is not intended to identify key features or essential features of the subject matter, nor is it intended to be used to limit the scope of the subject matter.

DETAILED DESCRIPTION

In the structural formulae given herein and throughout the present disclosure, the following terms have the indicated meaning, unless specifically stated otherwise.

The term "optionally substituted" as used herein means that the group in question is either unsubstituted or substituted with one or more of the substituents specified. When the group in question is substituted with more than one substituent, the substituent may be same or different.

The term "alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "cycloalkyl" refers to unless otherwise mentioned, carbocyclic groups of from 3 to 8 carbon atoms having a single cyclic ring or multiple condensed rings or spirocyclic rings or bridged rings which may be saturated or partially unsaturated. Such cycloalkyl groups include, by way of example, single ring structures such as cyclopropyl, cyclobutyl, cyclopentyl, cyclopentenyl, cyclohexyl, cyclohexenyl, and the like.

"Halo" or "Halogen", alone or in combination with any other term means halogens such as chloro (Cl), fluoro (F), bromo (Br) and iodo (I).

The term "aryl" refers to an aromatic carbocyclic group of 5 to 20 carbon atoms having a single ring (e.g. phenyl) or multiple rings (e.g. biphenyl), or multiple condensed (fused) rings (e.g. naphthyl or anthranyl). Preferred aryls include phenyl, naphthyl and the like.

The term "heteroaryl" refers to an aromatic cyclic group having 1, 2, 3, 4, 5, 6, 7, 8, 9, 10, 11, 12, 13, 14, or 15 carbon atoms and 1, 2, 3 or 4 heteroatoms selected from oxygen, nitrogen and sulphur within at least one ring.

The term "heterocyclylalkyl" refers to a heterocyclyl group covalently linked to an alkylene group, where the term "heterocyclyl" refers to a saturated or partially unsaturated group having a single ring or multiple condensed rings or spirocyclic rings, or bridged rings unless otherwise mentioned, having from 1 to 40 carbon atoms and from 1 to 10 hetero atoms, preferably 1, 2, 3 or 4 heteroatoms, selected from nitrogen, sulphur, phosphorus, and/or oxygen within the ring, and the term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

The term "alkoxy" refers to the group R'"—O—, where R'" is optionally substituted alkyl or optionally substituted cycloalkyl, or optionally substituted alkenyl or optionally substituted alkynyl; or optionally substituted cycloalkenyl, where alkyl, alkenyl, alkynyl, cycloalkyl and cycloalkenyl are as defined herein. Representative examples of alkoxy groups include but are not limited to methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

"Haloalkyl" refers to a straight chain or branched chain haloalkyl group with 1 to 6 carbon atoms. The alkyl group may be partly or totally halogenated. Representative examples of haloalkyl groups include but are not limited to fluoromethyl, chloromethyl, bromomethyl, difluoromethyl, dichloromethyl, dibromomethyl, trifluoromethyl, trichloromethyl, 2-fluoroethyl, 2-chloroethyl, 2-bromoethyl, 2,2,2-trifluoroethyl, 3-fluoropropyl, 3-chloropropyl, 3-bromopropyl and the like.

"Alkoxyalkyl" refers to alkyl groups as defined above wherein at least one of the hydrogen atoms of the alkyl group is replaced by an alkoxy group as defined above. Representative examples of alkoxyalkyl groups include but are not limited to methoxymethyl, methoxyethyl, ethoxymethyl and the like.

The compounds of the present disclosure may have the ability to crystallize in more than one form, a characteristic known as polymorphism, and all such polymorphic forms ("polymorphs") are encompassed within the scope of the disclosure. Polymorphism generally can occur as a response to changes in temperature or pressure or both, and can also result from variations in the crystallization process. Polymorphs can be distinguished by various physical characteristics, and typically the X-ray diffraction patterns, solubility behaviour, and melting point of the compound are used to distinguish polymorphs.

The compounds described herein may contain one or more chiral centers and/or double bonds and therefore, may exist as stereoisomers, such as double-bond isomers (i.e., geometric isomers), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form and mixtures thereof. Accordingly, the chemical structures depicted herein encompass all possible tautomeric forms of the illustrated or identified compounds.

Compounds may exist in unsolvated forms as well as solvated forms, including hydrated forms and as N-oxides. In general, compounds may be hydrated, solvated or N-oxides. Certain compounds may exist in multiple crystalline or amorphous forms. Also contemplated within the scope of the disclosure are congeners, analogs, hydrolysis products, metabolites and precursor or prodrugs of the compound. In general, unless otherwise indicated, all physical forms are equivalent for the uses contemplated herein and are intended to be within the scope of the present disclosure.

"Pharmaceutically acceptable salt" embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

"Pharmaceutical composition" refers to one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition comprising a compound of the present disclosure and a pharmaceutically acceptable carrier.

"Carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

"Combined" or "in combination" or "combination" should be understood as a functional coadministration, wherein some or all compounds may be administered separately, in different formulations, different modes of administration (for example subcutaneous, intravenous or oral) and different times of administration. The individual compounds of such combinations may be administered either sequentially in separate pharmaceutical compositions as well as simultaneously in combined pharmaceutical compositions.

The present disclosure relates to a compound represented by Formula I

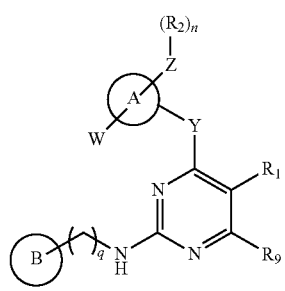

Formula I or its stereoisomers, tautomers, pharmaceutically acceptable salts, polymorphs, solvates and hydrates thereof wherein, ring A is selected from the group consisting of aryl, heteroaryl, $C_{3-8}$cycloalkyl, $C_{3-10}$ cycloaryl, $C_{4-6}$ heterocycloalkyl, and $C_{4-10}$ heterocycloaryl with heteroatoms selected from N, O, S;

ring-B is 5 membered mono or bicyclic ring containing 1-4 hetero atoms selected from N, O or S;

wherein ring B is optionally substituted with 1 to 4 substituents independently selected from the group consisting of hydrogen, halogen, cyano, $CF_3$, $C_{1-6}$ alkyl, —$C(R_aR_aR_a')$, —$C(R_aR_a)[C(R_aR_a)]_nOC(R_a')_p$, —$S(O)_pC(R_a')_p$, —$C(R_aR_a)C(R_aR_a)N(R_a')_p$, —$C(R_aR_a)C(R_aR_a)OR_a'$, $C_{3-6}$ cycloalkyl, $C_{5-6}$ aryl, $C_{5-6}$ heteroaryl, $C_{3-6}$ alkylcycloalkyl, alkyl $C_{3-6}$ heterocycloalkyl, monocyclic or bicyclic $C_{3-8}$ heterocycloalkyl with heteroatoms selected from N, O, S; wherein cycloalkyl, aryl, alkyl, heteroaryl, monocyclic or bicyclic heterocycloalkyl are further optionally substituted with one or more of the groups selected from hydrogen, $C_{1-6}$ alkyl, halogen, haloalkyl, OH, —C(O);

W is selected from the group consisting of

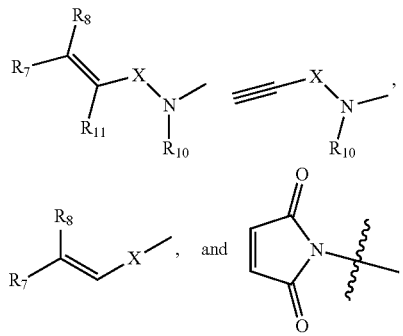

X is —C(O)—, —S(O)$_2$— or —S(O)—;

$R_{11}$ is selected from the group consisting of hydrogen, alkyl, and halogen;

$R_{10}$ is H or alkyl;

Y is selected from the group consisting of —O—, —NR— and —S—; where R is selected from H, alkyl;

Z is absent or —O—;

$R_2$ is selected from the group consisting of hydrogen, halogen, alkyl, $C_{3-6}$ cycloalkyl, and $C_{3-6}$ heterocycloalkyl.

$R_7$ is selected from the group consisting of hydrogen, halogen, methyl, and —$CH_2NR_aR_a$;

$R_8$ is selected from the group consisting of hydrogen, halogen, optionally substituted $C_{1-6}$ alkyl, $C_{4-6}$ cycloalkyl, and $C_{4-7}$ heterocycloalkyl; or $R_7$ and $R_8$ taken together form a 4-7 membered cycloalkyl, 4-7 membered heterocycloalkyl, wherein said groups can be optionally substituted with 1 to 3 substituents independently selected from the group consisting of hydrogen, halogen, unsubstituted alkyl, haloalkyl;

$R_1$ is selected from the group consisting of hydrogen, halogen, $C_{1-6}$ alkyl, alkoxy, haloalkyl, $C_{3-6}$ cycloalkyl, $C_{5-6}$ aryl, $C_{5-6}$ heteroaryl, alkoxyalkyl, cyano, —$C(R_aR_aR_a')$, —$C(R_aR_a)[C(R_aR_a)]_nOC(R_a')_p$, —$S(O)_pC(R_a')_p$, —$C(R_aR_a)C(R_aR_a)N(R_a')_p$, —$C(R_aR_a)C(R_aR_a)OR_a''$, and monocyclic or bicyclic $C_{4-8}$ heterocycloalkyl with heteroatoms selected from N, O, S;

wherein $C_{1-6}$ alkyl, $C_{3-6}$ cycloalkyl, $C_{5-6}$ aryl, $C_{5-6}$ heteroaryl, monocyclic or bicyclic $C_{4-8}$ heterocycloalkyl with heteroatoms selected from N, O, S is optionally substituted with one or more of the groups selected from hydrogen, $C_{1-6}$ alkyl, halogen, OH, —C(O);

$R_9$ is selected from the group consisting of hydrogen, halogen, alkyl, haloalkyl, alkoxy, alkoxyalkyl, and cyano;

$R_a$ is selected from the group consisting of hydrogen, —CH$_3$, —CH$_2$—, halogen, and OH;

$R_{a'}$ is selected from the group consisting of hydrogen, —CH$_3$, —CH$_2$—, and $C_{3-6}$ cycloalkyl;

or $R_a$ and $R_{a'}$ taken together form a $C_{3-6}$ cycloalkyl ring, $C_{4-6}$ heterocycloalkyl ring;

q is 0 to 1;
n is 0, 1 and 2;
p is 1, 2, 3 or 4.

According to an embodiment, the present disclosure relates to compounds of formula (I) or its stereoisomers, tautomers, pharmaceutically acceptable salts, polymorphs, solvates and hydrates thereof wherein ring-A is selected from the group consisting of According to another embodiment, the present disclosure relates to compounds of formula (I), or its stereoisomers, tautomers, pharmaceutically acceptable salts, polymorphs, solvates and hydrates thereof wherein ring-B is selected from the group consisting of

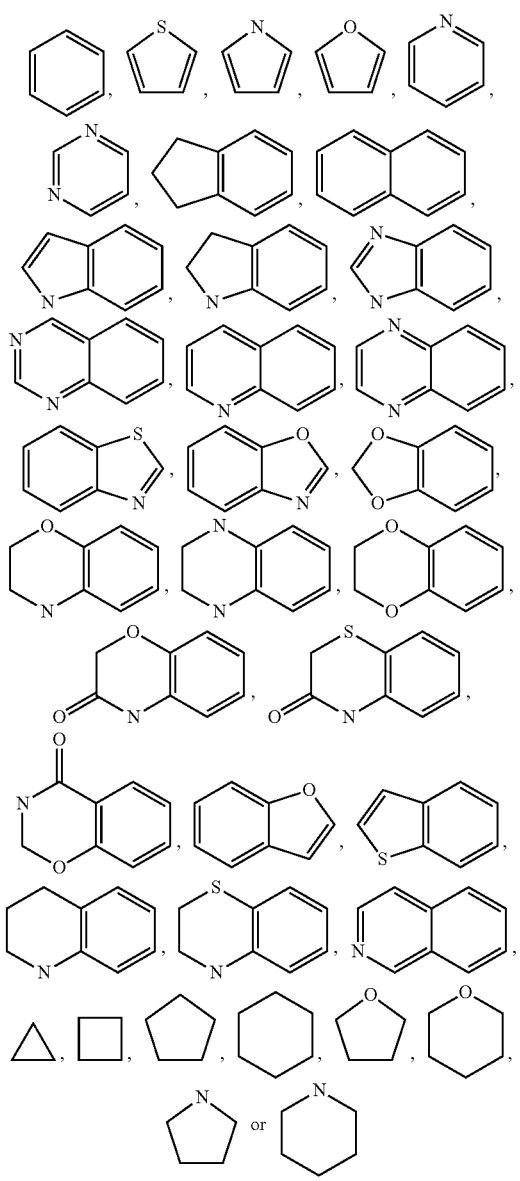

According to yet another embodiment, the present disclosure relates to compounds of formula (I), or its stereoisomers, tautomers, pharmaceutically acceptable salts, polymorphs, solvates and hydrates thereof wherein ring-A is selected from the group consisting of ring B is selected from the group consisting of

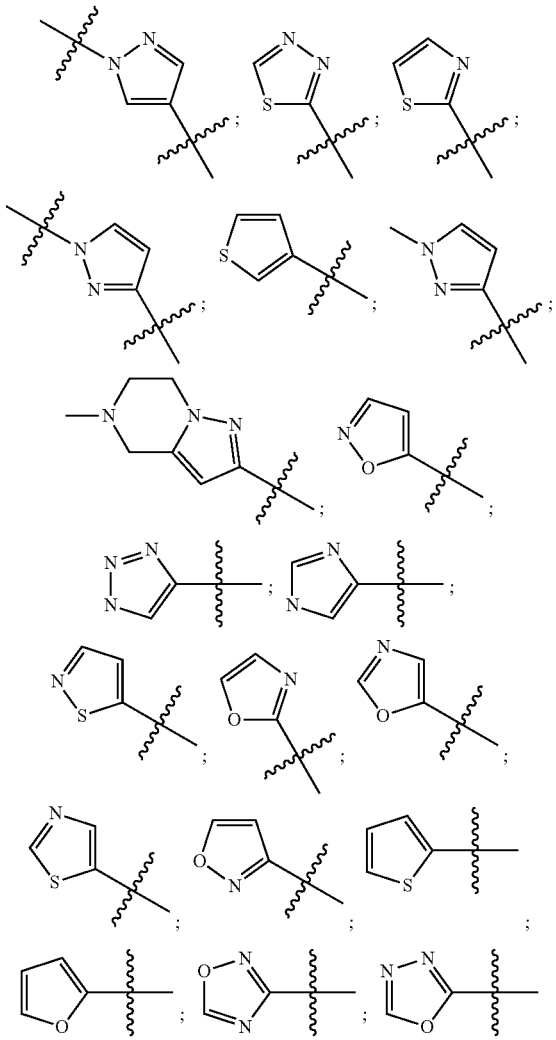

wherein ring B is optionally substituted with 1 to 4 substituents independently selected from the group consisting of hydrogen, halogen, cyano, $CF_3$, $C_{1-6}$ alkyl, —$C(R_aR_aR_a')$, —$C(R_aR_a)[C(R_aR_a)]_nOC(R_{a'})_p$, —$S(O)_pC(R_{a'})_p$, —$C(R_aR_a)C(R_aR_a)N(R_{a'})_p$, —$C(R_aR_a)C(R_aR_a)OR_{a'}$, $C_{3-6}$ cycloalkyl, $C_{5-6}$ aryl, $C_{5-6}$ heteroaryl, $C_{3-6}$ alkylcycloalkyl, alkyl $C_{3-6}$ heterocycloalkyl, monocyclic or bicyclic $C_{3-8}$ heterocycloalkyl with heteroatoms selected from N, O, S; wherein cycloalkyl, alkyl, aryl, heteroaryl, monocyclic or bicyclic heterocycloalkyl are further optionally substituted with one or more of the groups selected from hydrogen, $C_{1-6}$ alkyl, halogen, haloalkyl, OH, —C(O);

W is selected from the group consisting of

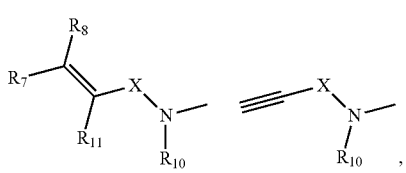

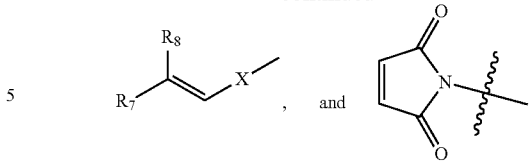

X is —C(O)—, —$S(O)_2$— or —S(O)—;
$R_{11}$ is selected from the group consisting of hydrogen, alkyl, and halogen;
$R_{10}$ is H or alkyl;
Y is selected from the group of —O—, —NR— and —S—; where R is selected from H, alkyl;
Z is absent or —O—;
$R_2$ is selected from the group consisting of hydrogen, halogen, alkyl, $C_{3-6}$ cycloalkyl, and $C_{3-6}$ heterocycloalkyl.
$R_7$ is selected from the group consisting of hydrogen, halogen, methyl, and —$CH_2NR_aR_a$;
$R_8$ is selected from the group consisting of hydrogen, halogen, optionally substituted $C_{1-6}$ alkyl, $C_{4-6}$ cycloalkyl, and $C_{4-7}$ heterocycloalkyl; or
$R_7$ and $R_8$ taken together form a 4-7 membered cycloalkyl, 4-7 membered heterocycloalkyl, wherein said groups can be optionally substituted with 1 to 3 substituents independently selected from the group consisting of hydrogen, halogen, unsubstituted alkyl, haloalkyl;
$R_1$ is selected from the group consisting of hydrogen, halogen, $C_{1-6}$ alkyl, alkoxy, haloalkyl, $C_{3-6}$ cycloalkyl, $C_{5-6}$ aryl, $C_{5-6}$ heteroaryl, alkoxyalkyl, cyano, —$C(R_aR_aR_a')$, —$C(R_aR_a)[C(R_aR_a)]_nOC(R_{a'})_p$, —$S(O)_pC(R_{a'})_p$, —$C(R_aR_a)C(R_aR_a)N(R_{a'})_p$, —$C(R_aR_a)C(R_aR_a)OR_{a'}$, and monocyclic or bicyclic $C_{4-8}$ heterocycloalkyl with heteroatoms selected from N, O, S;
wherein $C_{1-6}$ alkyl, $C_{3-6}$ cycloalkyl, $C_{5-6}$ aryl, $C_{5-6}$ heteroaryl, monocyclic or bicyclic $C_{4-8}$ heterocycloalkyl with heteroatoms selected from N, O, S is optionally substituted with one or more of the groups selected from hydrogen, $C_{1-6}$ alkyl, halogen, OH, —C(O).
$R_9$ is selected from the group consisting of hydrogen, halogen, alkyl, haloalkyl, alkoxy, alkoxyalkyl, and cyano;
$R_a$ is selected from the group consisting of hydrogen, —$CH_3$, —$CH_2$—, halogen, and OH;
$R_{a'}$ is selected from the group consisting of hydrogen, —$CH_3$, —$CH_2$—, and $C_{3-6}$ cycloalkyl;
or $R_a$ and $R_{a'}$ taken together form a $C_{3-6}$ cycloalkyl ring, $C_{4-6}$ heterocycloalkyl ring;
q is 0 to 1;
n is 0, 1 and 2;
p is 1, 2, 3 or 4.

According to yet another embodiment, the present disclosure relates to compounds of formula (I), or its stereoisomers, tautomers, pharmaceutically acceptable salts, polymorphs, solvates and hydrates thereof wherein ring-A is selected from the group consisting of

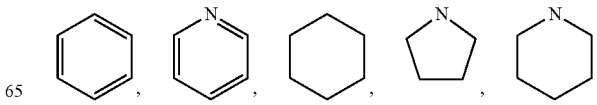

ring B is selected from the group consisting of

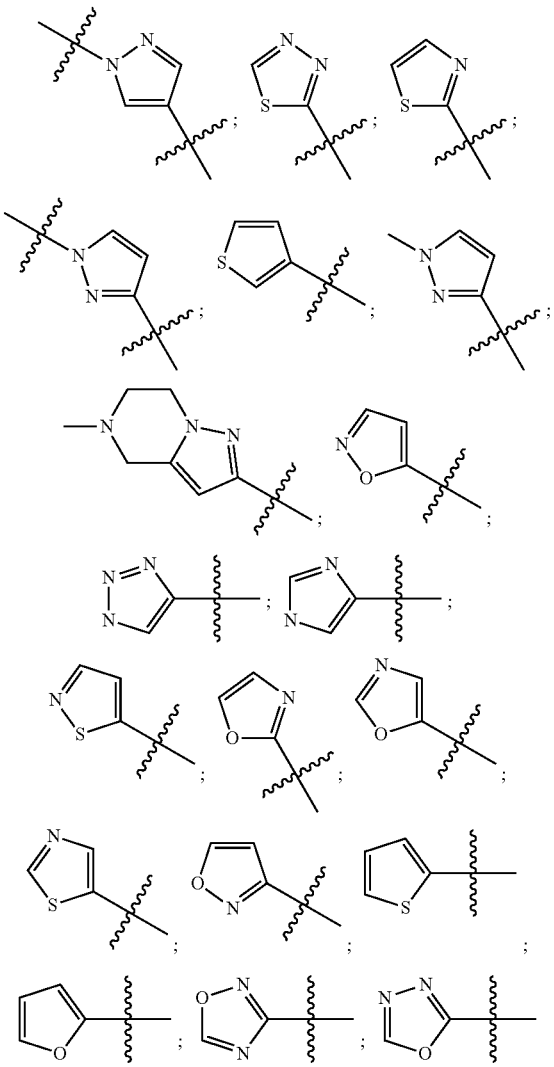

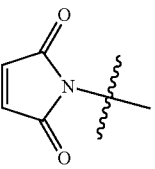

, and

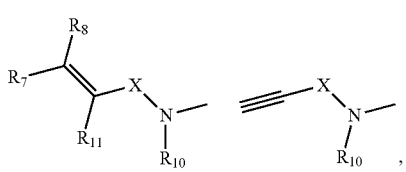

wherein ring B is optionally substituted with 1 to 4 substituents independently selected from the group consisting of hydrogen, CF$_3$, C$_{1-6}$ alkyl, —C(R$_a$R$_a$R$_{a'}$), —C(R$_a$R$_a$)[C(R$_a$R$_a$)]$_n$OC(R$_{a'}$)$_p$, —S(O)$_p$C(R$_{a'}$)$_p$, —C(R$_a$R$_a$)C(R$_a$R$_a$)N(R$_{a'}$)$_p$, —C(R$_a$R$_a$)C(R$_a$R$_a$)OR$_{a'}$, C$_{3-6}$ cycloalkyl, C$_{5-6}$ aryl, C$_{5-6}$ heteroaryl, C$_{3-6}$ alkylcycloalkyl, alkyl C$_{3-6}$ heterocycloalkyl, bicyclic C$_{4-8}$ heterocycloalkyl with heteroatoms selected from N, O; wherein cycloalkyl, alkyl, aryl, heteroaryl, bicyclic heterocycloalkyl are further optionally substituted with one or more of the groups selected from hydrogen, C$_{1-6}$ alkyl, halogen, haloalkyl, OH, —C(O);

W is selected from the group consisting of

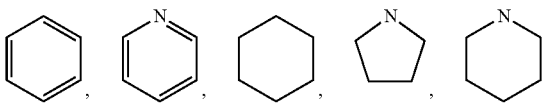

Z is absent;
R$_{11}$ is hydrogen;
R$_{10}$ is H or alkyl;
R$_2$ is selected from the group consisting of hydrogen, and halogen;
X is —C(O)— or —S(O)$_2$—;
Y is selected from the group the group consisting of —O—, and —NR—; wherein R is selected from hydrogen, alkyl;
R$_9$ is selected from the group consisting of hydrogen, halogen, alkyl, haloalkyl, alkoxy, alkoxyalkyl, and cyano;
R$_7$ is selected from the group consisting of hydrogen, methyl, and —CH$_2$NR$_a$R$_a$;
R$_8$ is selected from the group consisting of hydrogen, optionally substituted C$_{1-6}$ alkyl, C$_{4-6}$ cycloalkyl, and C$_{4-7}$ heterocycloalkyl; or
R$_7$ and R$_8$ taken together form a 4-7 membered cycloalkyl, 4-7 membered heterocycloalkyl, wherein said groups can be optionally substituted with 1 to 3 substituents independently selected from the group consisting of hydrogen, halogen;
R$_1$ is selected from the group consisting of hydrogen, halogen, C$_{1-6}$ alkyl, alkoxy, haloalkyl, and C$_{3-6}$ cycloalkyl;
R$_a$ is independently selected from the group consisting of hydrogen, —CH$_3$, —CH$_2$—, halogen, and OH;
R$_{a'}$ is selected from the group consisting of hydrogen, —CH$_3$, —CH$_2$—, and C$_{3-6}$ cycloalkyl;
q is 0;
n is 0, 1 and 2;
p is 1 to 4

According to an embodiment, the present disclosure relates to compounds of formula (I), or its stereoisomers, tautomers, pharmaceutically acceptable salts, polymorphs, solvates and hydrates thereof wherein ring-A is selected from the group consisting of

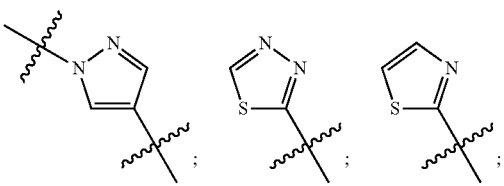

ring B is selected from the group consisting of

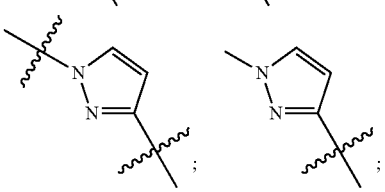

-continued

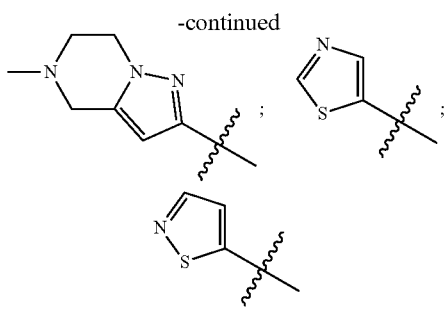

wherein ring B is optionally substituted with 1 to 4 substituents independently selected from the group consisting of hydrogen, halogen, cyano, $CF_3$, $C_{1-6}$ alkyl, —$C(R_aR_aR_{a'})$, —$C(R_aR_a)[C(R_aR_a)]_nOC(R_{a'})_p$, —$S(O)_pC(R_{a'})_p$, —$C(R_aR_a)C(R_aR_a)N(R_{a'})_p$, —$C(R_aR_a)C(R_aR_a)OR_{a''}$, $C_{3-6}$ cycloalkyl, $C_{5-6}$ aryl, $C_{5-6}$ heteroaryl, $C_{3-6}$ alkylcycloalkyl, alkyl $C_{3-6}$ heterocycloalkyl, monocyclic or bicyclic $C_{3-8}$ heterocycloalkyl with heteroatoms selected from N, O, S; wherein cycloalkyl, alkyl, aryl, heteroaryl, monocyclic or bicyclic heterocycloalkyl are further optionally substituted with one or more of the groups selected from hydrogen, $C_{1-6}$ alkyl, halogen, haloalkyl, OH, —C(O);

W is selected from the group consisting of

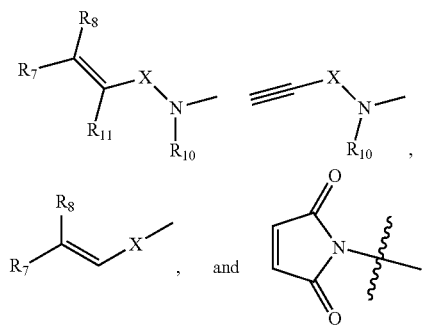

Z is absent or —O—;

$R_2$ is selected from the group consisting of hydrogen, halogen, alkyl, $C_{3-6}$ cycloalkyl, and $C_{3-6}$ heterocycloalkyl;

X is —C(O)— or —$S(O)_2$— or —S(O)—;

$R_7$ is selected from the group consisting of hydrogen, halogen, methyl, and —$CH_2NR_aR_a$;

$R_8$ is selected from the group consisting of hydrogen, halogen, optionally substituted $C_{1-6}$ alkyl, $C_{4-6}$ cycloalkyl, and $C_{4-7}$ heterocycloalkyl; or $R_7$ and $R_8$ taken together form a 4-7 membered cycloalkyl, 4-7 membered heterocycloalkyl, wherein said groups can be optionally substituted with 1 to 3 substituents independently selected from the group consisting of hydrogen, halogen, unsubstituted alkyl, haloalkyl;

$R_{11}$ is selected from the group consisting of hydrogen, alkyl, and halogen;

$R_{10}$ is H or alkyl;

Y is selected from the group the group consisting of —O—, —NR— and —S—; wherein R is selected from hydrogen, alkyl;

$R_1$ is selected from the group consisting of hydrogen, halogen, $C_{1-6}$ alkyl, alkoxy, haloalkyl, $C_{3-6}$ cycloalkyl, $C_{5-6}$ aryl, $C_{5-6}$ heteroaryl, alkoxyalkyl, cyano, —$C(R_aR_aR_{a'})$, —$C(R_aR_a)[C(R_aR_a)]_nOC(R_{a'})_p$, —$S(O)_pC(R_{a'})_p$, —$C(R_aR_a)C(R_aR_a)N(R_{a'})_p$, —$C(R_aR_a)C(R_aR_a)OR_{a''}$, and monocyclic or bicyclic $C_{4-8}$ heterocycloalkyl with heteroatoms selected from N, O, S;

wherein $C_{1-6}$ alkyl, $C_{3-6}$ cycloalkyl, $C_{5-6}$ aryl, $C_{5-6}$ heteroaryl, monocyclic or bicyclic $C_{4-8}$ heterocycloalkyl with heteroatoms selected from N, O, S is optionally substituted with one or more of the groups selected from hydrogen, $C_{1-6}$ alkyl, halogen, OH, —C(O).

$R_9$ is selected from the group consisting of hydrogen, halogen, alkyl, haloalkyl, alkoxy, alkoxyalkyl, and cyano;

$R_a$ is independently selected from the group consisting of hydrogen, —$CH_3$, —$CH_2$—, halogen, and OH;

$R_{a'}$ is selected from the group consisting of hydrogen, —$CH_3$, —$CH_2$—, and $C_{3-6}$ cycloalkyl;

or $R_a$ and $R_{a'}$ taken together form a $C_{3-6}$ cycloalkyl ring, $C_{4-6}$ heterocycloalkyl ring;

q is 0 to 1;

n is 0, 1 and 2;

p is 1 to 4.

According to an embodiment, the present disclosure relates to compounds of formula (I), or its stereoisomers, tautomers, pharmaceutically acceptable salts, polymorphs, solvates and hydrates thereof wherein ring-A is selected from the group consisting of

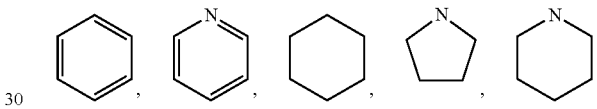

ring B is selected from the group consisting of

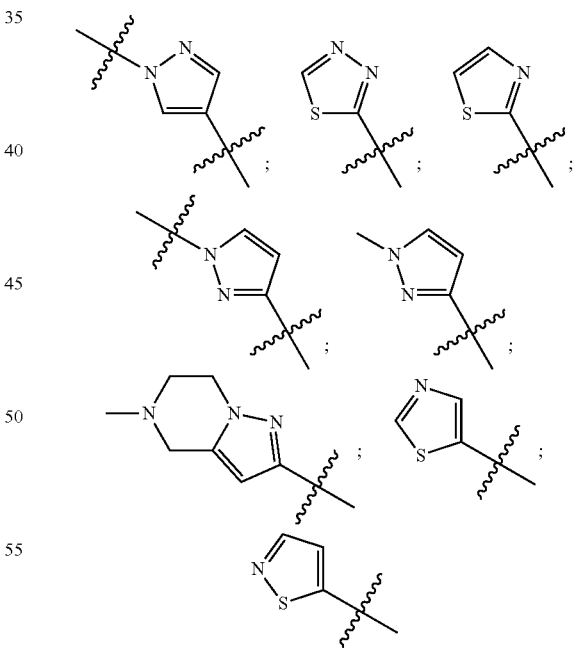

ring B is optionally substituted with 1 to 4 substituents independently selected from the group consisting of hydrogen, $CF_3$, $C_{1-6}$ alkyl, —$C(R_aR_aR_{a'})$, —$C(R_aR_a)[C(R_aR_a)]_nOC(R_{a'})_p$, —$S(O)_pC(R_{a'})_p$, —$C(R_aR_a)C(R_aR_a)N(R_{a'})_p$, —$C(R_aR_a)C(R_aR_a)OR_{a''}$, $C_{3-6}$ cycloalkyl, $C_{5-6}$ aryl, $C_{5-6}$ heteroaryl, $C_{3-6}$ alkylcycloalkyl, alkyl $C_{3-6}$ heterocycloalkyl, monocyclic or bicyclic $C_{3-8}$ heterocycloalkyl with heteroatoms selected from N, O; wherein cycloalkyl, alkyl, aryl, heteroaryl, monocyclic or bicyclic heterocycloalkyl are further optionally substituted with one or more of the groups selected from hydrogen, $C_{1-6}$ alkyl, halogen, haloalkyl, OH, —C(O);
W is selected from the group consisting of

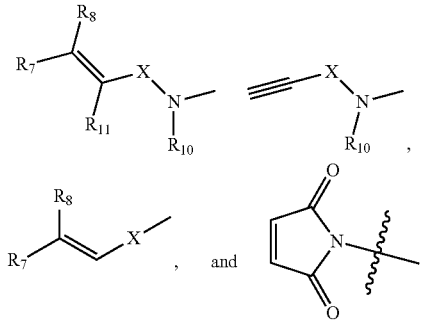

Z is absent;
$R_2$ is selected from the group consisting of hydrogen, and halogen;
X is —C(O)— or —S(O)$_2$—;
$R_7$ is selected from the group consisting of hydrogen, methyl, and —CH$_2$NR$_a$R$_a$;
$R_8$ is selected from the group consisting of hydrogen, optionally substituted $C_{1-6}$ alkyl, $C_{4-6}$ cycloalkyl, and $C_{4-7}$ heterocycloalkyl; or
$R_7$ and $R_8$ taken together form a 4-7 membered cycloalkyl, 4-7 membered heterocycloalkyl, wherein said groups can be optionally substituted with 1 to 3 substituents independently selected from the group consisting of hydrogen, halogen;
$R_1$ is selected from the group consisting of hydrogen, halogen, $C_{1-6}$ alkyl, alkoxy, haloalkyl, and $C_{3-6}$ cycloalkyl;
$R_9$ is selected from the group consisting of hydrogen, halogen, alkyl, haloalkyl, alkoxy, alkoxyalkyl, and cyano;
$R_{11}$ is hydrogen.
Y is selected from the group the group consisting of —O—, and —NR—; wherein R is selected from hydrogen, alkyl;
$R_{10}$ is H or alkyl;
$R_a$ is selected from the group consisting of hydrogen, —CH$_3$, —CH$_2$—, halogen, and OH;
$R_{a'}$ is selected from the group consisting of hydrogen, —CH$_3$, —CH$_2$—, and $C_{3-6}$ cycloalkyl;
q is 0;
n is 0, 1 and 2;
p is 1 to 4

According to another embodiment, the present disclosure relates to compounds of formula (I), or its stereoisomers, tautomers, pharmaceutically acceptable salts, polymorphs, solvates and hydrates thereof wherein, ring A is selected from the group consisting of aryl, heteroaryl, $C_{3-8}$ cycloalkyl, $C_{3-10}$ cycloaryl, $C_{4-6}$ heterocycloalkyl, $C_{4-10}$ heterocycloaryl with heteroatoms selected from N, O, S;
ring B is selected from the group consisting of

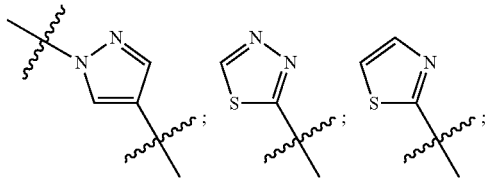

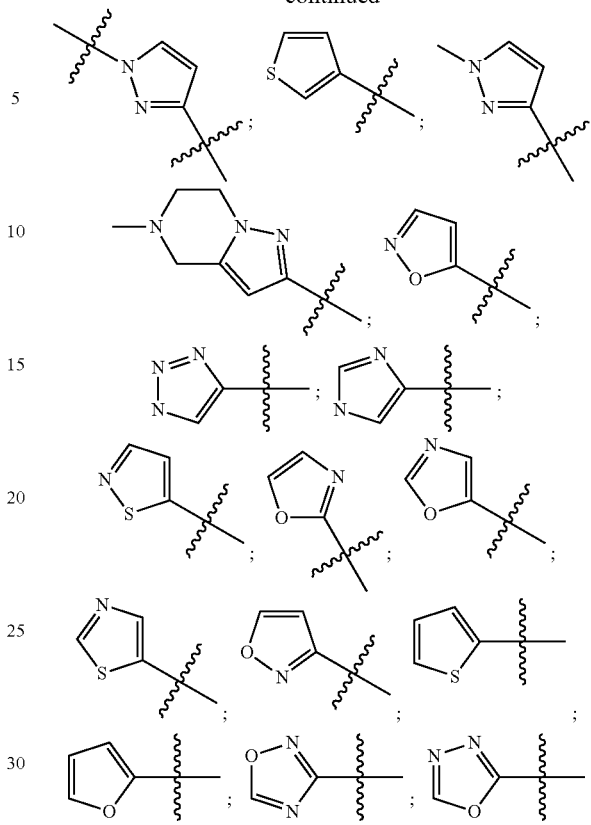

wherein ring B is optionally substituted with 1 to 4 substituents independently selected from the group consisting of hydrogen, halogen, cyano, CF$_3$, $C_{1-6}$ alkyl, —C(R$_a$R$_a$R$_a$'), —C(R$_a$R$_a$)[C(R$_a$R$_a$)]$_n$OC(R$_a$')$_p$, —S(O)$_p$C(R$_a$)$_p$, —C(R$_a$R$_a$)C(R$_a$R$_a$)N(R$_a$')$_p$, —C(R$_a$R$_a$)C(R$_a$R$_a$)OR$_a$', $C_{3-6}$ cycloalkyl, $C_{5-6}$ aryl, $C_{5-6}$ heteroaryl, $C_{3-6}$ alkylcycloalkyl, alkyl $C_{3-6}$ heterocycloalkyl, monocyclic or bicyclic $C_{3-8}$ heterocycloalkyl with heteroatoms selected from N, O, S; wherein cycloalkyl, aryl, alkyl, heteroaryl, monocyclic or bicyclic heterocycloalkyl are further optionally substituted with one or more of the groups selected from hydrogen, $C_{1-6}$ alkyl, halogen, haloalkyl, OH, —C(O);
W is

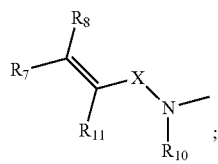

X is —C(O)—, —S(O)$_2$— or —S(O)—;
$R_{11}$ is selected from the group consisting of hydrogen, alkyl, and halogen;
$R_{10}$ is H or alkyl;
Y is selected from the group of —O—, —NR— and —S—; where R is selected from H, alkyl;
Z is absent or —O—;
$R_2$ is selected from the group consisting of hydrogen, halogen, alkyl, $C_{3-6}$ cycloalkyl, and $C_{3-6}$ heterocycloalkyl;
$R_7$ is selected from the group consisting of hydrogen, halogen, methyl, and —CH$_2$NR$_a$R$_a$;

R₈ is selected from the group consisting of hydrogen, halogen, optionally substituted $C_{1-6}$ alkyl, $C_{4-6}$ cycloalkyl, and $C_{4-7}$ heterocycloalkyl; or R₇ and R₈ taken together form a 4-7 membered cycloalkyl, 4-7 membered heterocycloalkyl, wherein said groups can be optionally substituted with 1 to 3 substituents independently selected from the group consisting of hydrogen, halogen, unsubstituted alkyl, haloalkyl;

R₁ is selected from the group consisting of hydrogen, halogen, $C_{1-6}$ alkyl, alkoxy, haloalkyl, $C_{3-6}$ cycloalkyl, $C_{5-6}$ aryl, $C_{5-6}$ heteroaryl, alkoxyalkyl, cyano, —C(R_aR_aR_a'), —C(R_aR_a)[C(R_aR_a)]_nOC(R_a')_p, —S(O)_pC(R_a')_p, —C(R_aR_a)C(R_aR_a)N(R_a')_p, —C(R_aR_a)C(R_aR_a)OR_a', and monocyclic or bicyclic $C_{4-8}$ heterocycloalkyl with heteroatoms selected from N, O, S;

wherein $C_{1-6}$ alkyl, $C_{3-6}$ cycloalkyl, $C_{5-6}$ aryl, $C_{5-6}$ heteroaryl, monocyclic or bicyclic $C_{4-8}$ heterocycloalkyl with heteroatoms selected from N, O, S is optionally substituted with one or more of the groups selected from hydrogen, $C_{1-6}$ alkyl, halogen, OH, —C(O);

R₉ is selected from the group consisting of hydrogen, halogen, alkyl, haloalkyl, alkoxy, alkoxyalkyl, and cyano;

R_a is selected from the group consisting of hydrogen, —CH₃, —CH₂—, halogen, and OH;

R_a' is selected from the group consisting of hydrogen, —CH₃, —CH₂—, and $C_{3-6}$ cycloalkyl;

or R_a R_a' taken together form a $C_{3-6}$ cycloalkyl ring, $C_{4-6}$ heterocycloalkyl ring;

q is 0 to 1;
n is 0, 1 and 2; and
p is 1, 2, 3 or 4;

According to yet another embodiment, the present disclosure relates to compounds of formula (I), or its stereoisomers, tautomers, pharmaceutically acceptable salts, polymorphs, solvates and hydrates thereof wherein, ring A is selected from the group consisting of aryl, heteroaryl, $C_{3-8}$ cycloalkyl, $C_{3-10}$ cycloaryl, $C_{4-6}$ heterocycloalkyl, and $C_{4-10}$ heterocycloaryl with heteroatoms selected from N, O, S;

ring B is selected from the group consisting of

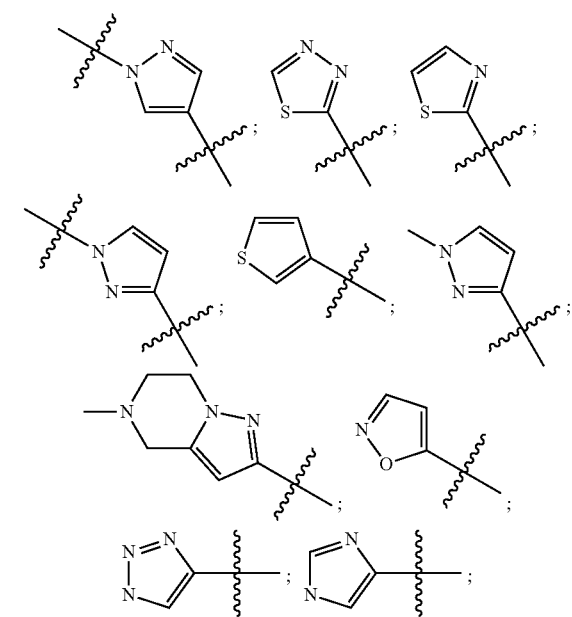

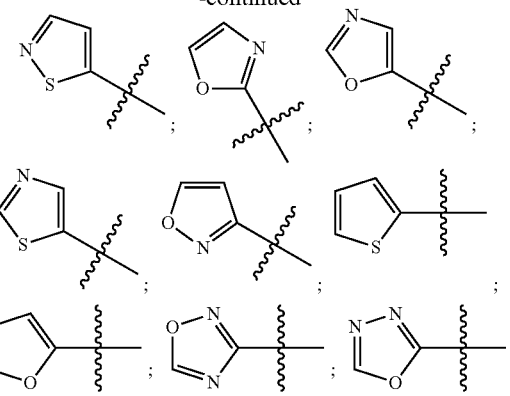

wherein ring B is optionally substituted with 1 to 4 substituents independently selected from the group consisting of hydrogen, halogen, cyano, CF₃, $C_{1-6}$ alkyl, —C(R_aR_aR_a'), —C(R_aR_a)[C(R_aR_a)]_nOC(R_a')_p, —S(O)_pC(R_a')_p, —C(R_aR_a)C(R_aR_a)N(R_a')_p, —C(R_aR_a)C(R_aR_a)OR_a', $C_{3-6}$ cycloalkyl, $C_{5-6}$ aryl, $C_{5-6}$ heteroaryl, $C_{3-6}$ alkylcycloalkyl, alkyl $C_{3-6}$ heterocycloalkyl, monocyclic or bicyclic $C_{3-8}$ heterocycloalkyl with heteroatoms selected from N, O, S;

wherein cycloalkyl, aryl, alkyl, heteroaryl, monocyclic or bicyclic heterocycloalkyl are further optionally substituted with one or more of the groups selected from hydrogen, $C_{1-6}$ alkyl, halogen, haloalkyl, OH, —C(O);

W is

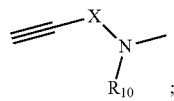

X is —C(O)—, —S(O)₂— or —S(O)—;
R₁₀ is H or alkyl;
Y is selected from the group of —O—, —NR— and —S—;
where R is selected from H, alkyl;
Z is absent or —O—;

R₂ is selected from the group consisting of hydrogen, halogen, alkyl, $C_{3-6}$ cycloalkyl, and $C_{3-6}$ heterocycloalkyl;

R₁ is selected from the group consisting of hydrogen, halogen, $C_{1-6}$ alkyl, alkoxy, haloalkyl, $C_{3-6}$ cycloalkyl, $C_{5-6}$ aryl, $C_{5-6}$ heteroaryl, alkoxyalkyl, cyano, —C(R_aR_aR_a'), —C(R_aR_a)[C(R_aR_a)]_nOC(R_a')_p, —S(O)_pC(R_a')_p, —C(R_aR_a)C(R_aR_a)N(R_a')_p, —C(R_aR_a)C(R_aR_a)OR_a', and monocyclic or bicyclic $C_{4-8}$ heterocycloalkyl with heteroatoms selected from N, O, S;

wherein $C_{1-6}$ alkyl, $C_{3-6}$ cycloalkyl, $C_{5-6}$ aryl, $C_{5-6}$ heteroaryl, monocyclic or bicyclic $C_{4-8}$ heterocycloalkyl with heteroatoms selected from N, O, S is optionally substituted with one or more of the groups selected from hydrogen, $C_{1-6}$ alkyl, halogen, OH, —C(O).

R₉ is selected from the group consisting of hydrogen, halogen, alkyl, haloalkyl, alkoxy, alkoxyalkyl, and cyano;

R_a is selected from the group consisting of hydrogen, —CH₃, —CH₂—, halogen, and OH;

R_a' is selected from the group consisting of hydrogen, —CH₃, —CH₂—, and $C_{3-6}$ cycloalkyl;

or R_a R_a' taken together form a $C_{3-6}$ cycloalkyl ring, $C_{4-6}$ heterocycloalkyl ring;

q is 0 to 1;

n is 0, 1 and 2; and p is 1, 2, 3 or 4;

According to an embodiment, the present disclosure relates to compounds of formula (I), or its stereoisomers, tautomers, pharmaceutically acceptable salts, polymorphs, solvates and hydrates thereof wherein, ring A is selected from the group consisting of aryl, heteroaryl, $C_{3-8}$ cycloalkyl, $C_{3-10}$ cycloaryl, $C_{4-6}$ heterocycloalkyl, and $C_{4-10}$ heterocycloaryl with heteroatoms selected from N, O, S;

ring B is selected from the group consisting of

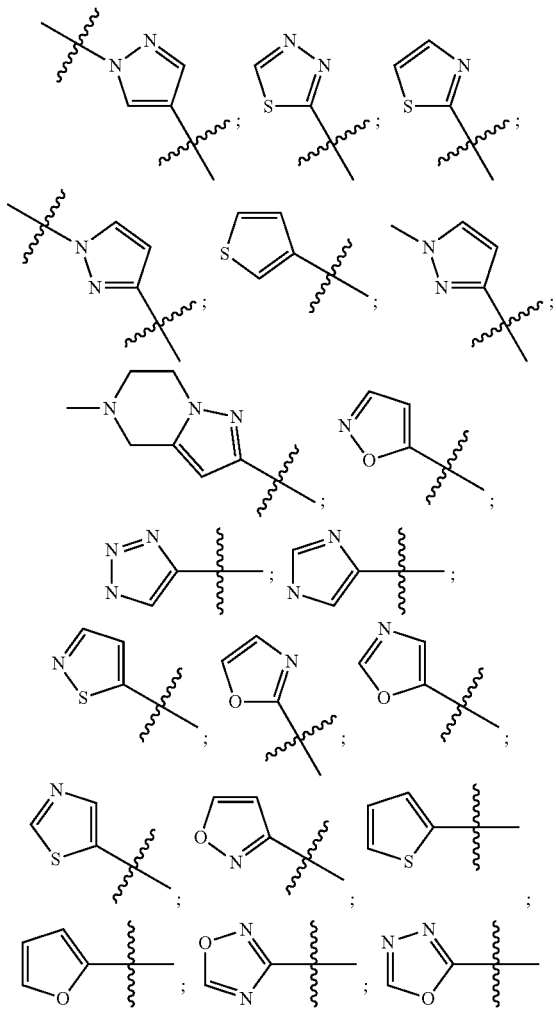

wherein ring B is optionally substituted with 1 to 4 substituents independently selected from the group consisting of hydrogen, halogen, cyano, $CF_3$, $C_{1-6}$ alkyl, $—C(R_aR_aR_a')$, $—C(R_aR_a)[C(R_aR_a)]_nOC(R_{a'})_p$, $—S(O)_pC(R_{a'})_p$, $—C(R_aR_a)C(R_aR_a)N(R_{a'})_p$, $—C(R_aR_a)C(R_aR_a)OR_{a'}$, $C_{3-6}$ cycloalkyl, $C_{5-6}$ aryl, $C_{5-6}$ heteroaryl, $C_{3-6}$ alkylcycloalkyl, alkyl $C_{3-6}$ heterocycloalkyl, monocyclic or bicyclic $C_{3-8}$ heterocycloalkyl with heteroatoms selected from N, O, S; wherein cycloalkyl, aryl, alkyl, heteroaryl, monocyclic or bicyclic heterocycloalkyl are further optionally substituted with one or more of the groups selected from hydrogen, $C_{1-6}$ alkyl, halogen, haloalkyl, OH, $—C(O)$;

W is

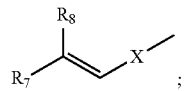

X is $—C(O)—$, $—S(O)_2—$ or $—S(O)—$;

Y is selected from the group of $—O—$, $—NR—$ and $—S—$; where R is selected from H, alkyl;

Z is absent or $—O—$;

$R_2$ is selected from the group consisting of hydrogen, halogen, alkyl, $C_{3-6}$ cycloalkyl, and $C_{3-6}$ heterocycloalkyl.

$R_1$ is selected from the group consisting of hydrogen, halogen, $C_{1-6}$ alkyl, alkoxy, haloalkyl, $C_{3-6}$ cycloalkyl, $C_{5-6}$ aryl, $C_{5-6}$ heteroaryl, alkoxyalkyl, cyano, $—C(R_aR_aR_a')$, $—C(R_aR_a)[C(R_aR_a)]_nOC(R_{a'})_p$, $—S(O)_pC(R_{a'})_p$, $—C(R_aR_a)C(R_aR_a)N(R_{a'})_p$, $—C(R_aR_a)C(R_aR_a)OR_{a'}$, and monocyclic or bicyclic $C_{4-8}$ heterocycloalkyl with heteroatoms selected from N, O, S;

wherein $C_{1-6}$ alkyl, $C_{3-6}$ cycloalkyl, $C_{5-6}$ aryl, $C_{5-6}$ heteroaryl, monocyclic or bicyclic $C_{4-8}$ heterocycloalkyl with heteroatoms selected from N, O, S is optionally substituted with one or more of the groups selected from hydrogen, $C_{1-6}$ alkyl, halogen, OH, $—C(O)$.

$R_9$ is selected from the group consisting of hydrogen, halogen, alkyl, haloalkyl, alkoxy, alkoxyalkyl, and cyano;

$R_a$ is selected from the group consisting of hydrogen, $—CH_3$, $—CH_2—$, halogen, and OH;

$R_{a'}$ is selected from the group consisting of hydrogen, $—CH_3$, $—CH_2—$, and $C_{3-6}$ cycloalkyl;

or $R_a$ $R_{a'}$ taken together form a $C_{3-6}$ cycloalkyl ring, $C_{4-6}$ heterocycloalkyl ring;

q is 0 to 1;

n is 0, 1 and 2; and p is 1, 2, 3 or 4;

According to another embodiment, the present disclosure relates to compounds of formula (I), or its stereoisomers, tautomers, pharmaceutically acceptable salts, polymorphs, solvates and hydrates thereof wherein, ring A is selected from the group consisting of aryl, heteroaryl, $C_{3-8}$ cycloalkyl, $C_{3-10}$ cycloaryl, $C_{4-6}$ heterocycloalkyl, $C_{4-10}$ heterocycloaryl with heteroatoms selected from N, O, S;

ring B is selected from the group consisting of

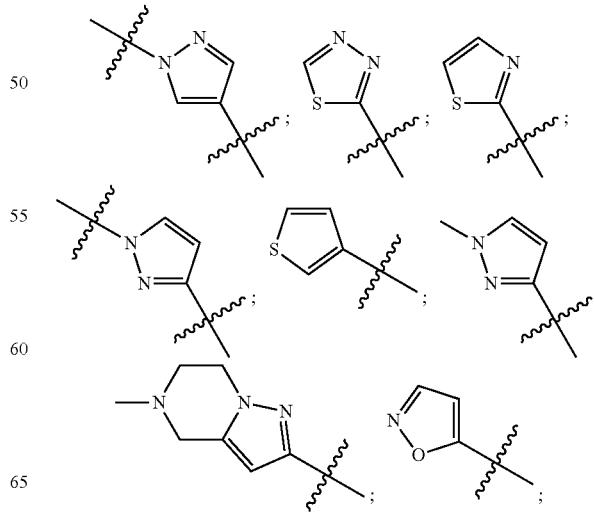

-continued

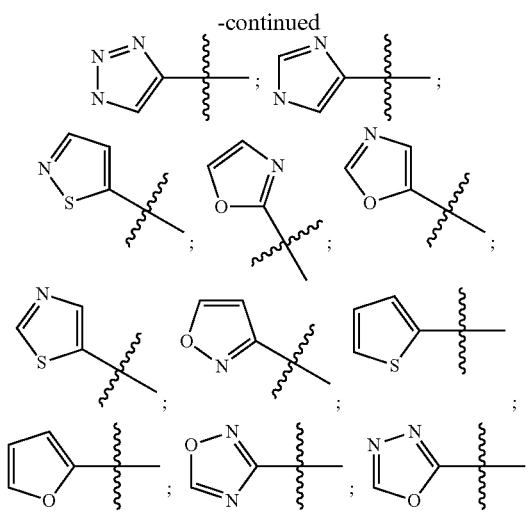

wherein ring B is optionally substituted with 1 to 4 substituents independently selected from the group consisting of hydrogen, halogen, cyano, $CF_3$, $C_{1-6}$ alkyl, —$C(R_aR_aR_a')$, —$C(R_aR_a)[C(R_aR_a)]_nOC(R_a)_p$, —$S(O)_pC(R_a)_p$, —$C(R_aR_a)C(R_aR_a)N(R_a)_p$, —$C(R_aR_a)C(R_aR_a)OR_a'$, $C_{3-6}$ cycloalkyl, $C_{5-6}$ aryl, $C_{5-6}$ heteroaryl, $C_{3-6}$ alkylcycloalkyl, alkyl $C_{3-6}$ heterocycloalkyl, monocyclic or bicyclic $C_{3-8}$ heterocycloalkyl with heteroatoms selected from N, O, S; wherein cycloalkyl, aryl, alkyl, heteroaryl, monocyclic or bicyclic heterocycloalkyl are further optionally substituted with one or more of the groups selected from hydrogen, $C_{1-6}$ alkyl, halogen, haloalkyl, OH, —C(O);

W is

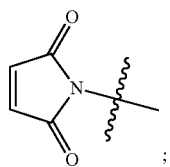 [SMILES: *N1C(=O)C=CC1=O]

Y is selected from the group of —O—, —NR— and —S—; where R is selected from H, alkyl;

Z is absent or —O—;

$R_2$ is selected from the group consisting of hydrogen, halogen, alkyl, $C_{3-6}$ cycloalkyl, and $C_{3-6}$ heterocycloalkyl.

$R_1$ is selected from the group consisting of hydrogen, halogen, $C_{1-6}$ alkyl, alkoxy, haloalkyl, $C_{3-6}$ cycloalkyl, $C_{5-6}$ aryl, $C_{5-6}$ heteroaryl, alkoxyalkyl, cyano, —$C(R_aR_aR_a')$, —$C(R_aR_a)[C(R_aR_a)]_nOC(R_a)_p$, —$S(O)_pC(R_a)_p$, —$C(R_aR_a)C(R_aR_a)N(R_a)_p$, —$C(R_aR_a)C(R_aR_a)OR_a"$, and monocyclic or bicyclic $C_{4-8}$ heterocycloalkyl with heteroatoms selected from N, O, S;

wherein $C_{1-6}$ alkyl, $C_{3-6}$ cycloalkyl, $C_{5-6}$ aryl, $C_{5-6}$ heteroaryl, monocyclic or bicyclic $C_{4-8}$ heterocycloalkyl with heteroatoms selected from N, O, S is optionally substituted with one or more of the groups selected from hydrogen, $C_{1-6}$ alkyl, halogen, OH, —C(O).

$R_9$ is selected from the group consisting of hydrogen, halogen, alkyl, haloalkyl, alkoxy, alkoxyalkyl, and cyano;

$R_a$ is selected from the group consisting of hydrogen, —$CH_3$, —$CH_2$—, halogen, and OH;

$R_{a'}$ is selected from the group consisting of hydrogen, —$CH_3$, —$CH_2$—, and $C_{3-6}$ cycloalkyl;

or $R_a$ $R_{a'}$ taken together form a $C_{3-6}$ cycloalkyl ring, $C_{4-6}$ heterocycloalkyl ring;

q is 0 to 1;

n is 0, 1 and 2; and p is 1, 2, 3 or 4;

According to an embodiment, the present disclosure relates to compounds of formula (I), or its stereoisomers, tautomers, pharmaceutically acceptable salts, polymorphs, solvates and hydrates thereof wherein ring A is selected from the group consisting of aryl, heteroaryl, $C_{3-8}$ cycloalkyl, $C_{3-10}$ cycloaryl, $C_{4-6}$ heterocycloalkyl, and $C_{4-10}$ heterocycloaryl with heteroatoms selected from N, O, S;

ring-B is 5 to 10 membered mono or bicyclic ring containing 1-4 hetero atoms selected from N, O or S; wherein ring B is optionally substituted with 1 to 4 substituents independently selected from the group consisting of hydrogen, halogen, cyano, $CF_3$, $C_{1-6}$ alkyl, —$C(R_aR_aR_a')$, —$C(R_aR_a)[C(R_aR_a)]_nOC(R_a)_p$, —$S(O)_pC(R_a)_p$, —$C(R_aR_a)C(R_aR_a)N(R_a)_p$, —$C(R_aR_a)C(R_aR_a)OR_a'$, $C_{3-6}$ cycloalkyl, $C_{5-6}$ aryl, $C_{5-6}$ heteroaryl, $C_{3-6}$ alkylcycloalkyl, alkyl $C_{3-6}$ heterocycloalkyl, monocyclic or bicyclic $C_{3-8}$ heterocycloalkyl with heteroatoms selected from N, O, S; wherein cycloalkyl, aryl, alkyl, heteroaryl, monocyclic or bicyclic heterocycloalkyl are further optionally substituted with one or more of the groups selected from hydrogen, $C_{1-6}$ alkyl, halogen, haloalkyl, OH, —C(O);

W is

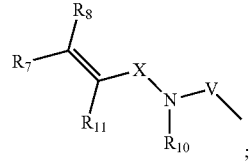

Z is absent;

$R_2$ is selected from the group consisting of hydrogen, and halogen;

X is —C(O)— or —$S(O)_2$—;

$R_7$ is selected from the group consisting of hydrogen, methyl, and —$CH_2NR_aR_a$;

$R_8$ is selected from the group consisting of hydrogen, optionally substituted $C_{1-6}$ alkyl, $C_{4-6}$ cycloalkyl, and $C_{4-7}$ heterocycloalkyl; or $R_7$ and $R_8$ taken together form a 4-7 membered cycloalkyl, 4-7 membered heterocycloalkyl, wherein said groups can be optionally substituted with 1 to 3 substituents independently selected from the group consisting of hydrogen, halogen;

$R_1$ is selected from the group consisting of hydrogen, halogen, $C_{1-6}$ alkyl, alkoxy, haloalkyl, and $C_{3-6}$ cycloalkyl;

$R_9$ is selected from the group consisting of hydrogen, halogen, alkyl, haloalkyl, alkoxy, alkoxyalkyl, and cyano;

$R_{11}$ is hydrogen.

Y is selected from the group the group consisting of —O—, and —NRV—; wherein R is selected from hydrogen, alkyl;

V is absent or substituted or unsubstituted $C_1$-$C_4$ alkyl;

$R_{10}$ is H or alkyl;

$R_a$ is selected from the group consisting of hydrogen, —$CH_3$, —$CH_2$—, halogen, and OH;

$R_{a'}$ is selected from the group consisting of hydrogen, —$CH_3$, —$CH_2$—, and $C_{3-6}$ cycloalkyl;

q is 0;

n is 0, 1 and 2;

p is 1 to 4

Particular embodiments of the present disclosure are compounds of formula I or its stereoisomers, tautomers, pharmaceutically acceptable salts, polymorphs, solvates and hydrates thereof, selected from the group consisting of, N-(3-((5-chloro-2-((1-(1-methylpiperidin-4-yl)-1H-pyrazol-4-yl)amino)pyrimidin-4-yl)amino)phenyl)acrylamide;

N-(3-((5-chloro-2-((1-(2-methoxyethyl)-3-methyl-1H-pyrazol-4-yl)amino)pyrimidin-4-yl)amino)phenyl)acrylamide;

N-(3-((5-chloro-2-((1-(2-methoxyethyl)-5-methyl-1H-pyrazol-4-yl)amino)pyrimidin-4-yl)amino)phenyl)acrylamide;

N-(3-((5-chloro-2-((1-isopropyl-1H-pyrazol-4-yl)amino)pyrimidin-4-yl)amino)phenyl)acrylamide;

N-(3-((5-chloro-2-((1-(2-(dimethylamino)ethyl)-1H-pyrazol-4-yl)amino)pyrimidin-4-yl)amino)phenyl)acrylamide;

N-(3-((5-chloro-2-((1-(2-methoxyethyl)-1H-pyrazol-4-yl)amino)pyrimidin-4-yl)amino)phenyl)-2-cyclohexylideneacetamide;

N-(3-((5-chloro-2-((1-(cyclopropylmethyl)-1H-pyrazol-4-yl)amino)pyrimidin-4-yl)amino)phenyl)acrylamide;

N-(3-((5-chloro-2-((3,5-dimethyl-1-(1-methylpiperidin-4-yl)-1H-pyrazol-4-yl)amino)pyrimidin-4-yl)amino)phenyl)acrylamide;

N-(3-((5-chloro-2-((1-(1-methylpiperidin-4-yl)-1H-pyrazol-4-yl)amino)pyrimidin-4-yl)amino)phenyl)methacrylamide;

N-(3-((5-chloro-2-((1-(methylsulfonyl)-1H-pyrazol-4-yl)amino)pyrimidin-4-yl)amino)phenyl)acrylamide;

N-(3-((5-chloro-2-((1,3,5-trimethyl-1H-pyrazol-4-yl)amino)pyrimidin-4-yl)amino)phenyl)acrylamide;

N-(3-((5-methoxy-2-((1-(1-methylpiperidin-4-yl)-1H-pyrazol-4-yl)amino)pyrimidin-4-yl)amino)phenyl)acrylamide;

N-(3-((5-methyl-2-((1-(1-methylpiperidin-4-yl)-1H-pyrazol-4-yl)amino)pyrimidin-4-yl)amino)phenyl)acrylamide;

N-(3-((2-((1-(1-methylpiperidin-4-yl)-1H-pyrazol-4-yl)amino)-5-(trifluoromethyl)pyrimidin-4-yl)amino)phenyl)acrylamide;

N-(3-((5-methyl-2-((1-methyl-1H-pyrazol-4-yl)amino)pyrimidin-4-yl)amino)phenyl)acrylamide;

N-(3-((5-chloro-2-((1-(1-(2-fluoroethyl)piperidin-4-yl)-1H-pyrazol-4-yl)amino)pyrimidin-4-yl)amino)phenyl)acrylamide;

N-(3-((5-chloro-2-((1-(2-hydroxy-2-methylpropyl)-1H-pyrazol-4-yl)amino)pyrimidin-4-yl)amino)phenyl)acrylamide;

N-(3-((5-fluoro-2-((1-(1-methylpiperidin-4-yl)-1H-pyrazol-4-yl)amino)pyrimidin-4-yl)amino)phenyl)acrylamide;

N-(3-((5-chloro-2-((1-methyl-1H-pyrazol-4-yl)amino)pyrimidin-4-yl)amino)phenyl)acrylamide;

N-(3-((5-chloro-2-((1-(2-methoxyethyl)-1H-pyrazol-4-yl)amino)pyrimidin-4-yl)amino)phenyl)acrylamide;

N-(3-((5-chloro-2-((1-(2-hydroxyethyl)-1H-pyrazol-4-yl)amino)pyrimidin-4-yl)amino)phenyl)acrylamide;

N-(3-((5-chloro-2-((1-(cyclopropylsulfonyl)-1H-pyrazol-4-yl)amino)pyrimidin-4-yl)amino)phenyl)acrylamide;

N-(3-((5-chloro-2-((1,5-dimethyl-1H-pyrazol-4-yl)amino)pyrimidin-4-yl)amino)phenyl)acrylamide;

N-(3-((5-chloro-2-((5-(methoxymethyl)-1-methyl-1H-pyrazol-3-yl)amino)pyrimidin-4-yl)amino)phenyl)acrylamide;

N-(3-((5-chloro-2-((1-(1-methylpiperidin-4-yl)-1H-pyrazol-4-yl)amino)pyrimidin-4-yl)amino)phenyl)-2-(4,4-difluorocyclohexylidene)acetamide;

N-(3-((5-chloro-2-((1-(1-methylpiperidin-4-yl)-1H-pyrazol-4-yl)amino)pyrimidin-4-yl)amino)phenyl)-2-(dihydro-2H-pyran-4(3H)-ylidene)acetamide;

N-(5-((5-chloro-2-((1-(1-methylpiperidin-4-yl)-1H-pyrazol-4-yl)amino)pyrimidin-4-yl)amino)-2-fluorophenyl)-2-cyclohexylideneacetamide;

N-(3-((5-chloro-2-((1-(1-methylpiperidin-4-yl)-1H-pyrazol-4-yl)amino)pyrimidin-4-yl)amino)phenyl)-2-cyclohexylideneacetamide;

N-(3-((5-chloro-2-((1-(1-methylpiperidin-4-yl)-1H-pyrazol-4-yl)amino)pyrimidin-4-yl)amino)phenyl)-2-cyclobutylideneacetamide;

N-(3-((5-chloro-2-((1-(1-methylpiperidin-4-yl)-1H-pyrazol-4-yl)amino)pyrimidin-4-yl)amino)phenyl)-2-cyclopentylideneacetamide;

N-(3-((5-chloro-2-((1-(oxetan-3-yl)-1H-pyrazol-4-yl)amino)pyrimidin-4-yl)amino)phenyl)acrylamide;

N-(3-((5-chloro-2-((1-methyl-1H-pyrazol-4-yl)amino)pyrimidin-4-yl)amino)phenyl)propiolamide;

N-(3-((5-chloro-2-((1-methyl-1H-pyrazol-4-yl)amino)pyrimidin-4-yl)amino)phenyl)-2-fluoroacrylamide;

N-(3-((5-chloro-2-((1,3-dimethyl-1H-pyrazol-4-yl)amino)pyrimidin-4-yl)amino)phenyl)acrylamide;

N-(3-chloro-5-((5-chloro-2-((1-methyl-1H-pyrazol-4-yl)amino)pyrimidin-4-yl)amino)phenyl)acrylamide;

N-(3-((5-chloro-2-((1-(3-hydroxycyclopentyl)-1H-pyrazol-4-yl)amino)pyrimidin-4-yl)amino)phenyl)acrylamide;

N-(3-((5-fluoro-2-((1-(3-hydroxycyclopentyl)-1H-pyrazol-4-yl)amino)pyrimidin-4-yl)amino)phenyl)acrylamide;

N-(3-((5-chloro-2-((1-(3-hydroxycyclohexyl)-1H-pyrazol-4-yl)amino)pyrimidin-4-yl)amino)phenyl)acrylamide;

N-(3-((5-chloro-2-((1-methyl-1H-pyrazol-4-yl)amino)pyrimidin-4-yl)amino)-4-fluorophenyl)acrylamide;

N-(3-((5-chloro-2-((5-(4-methylpiperazin-1-yl)thiazol-2-yl)amino)pyrimidin-4-yl)amino)phenyl)acrylamide;

N-(3-((5-chloro-2-((5-(4-methylpiperazin-1-yl)-1,3,4-thiadiazol-2-yl)amino)pyrimidin-4-yl)amino)phenyl)acrylamide;

N-(3-((2-((5-(azetidin-1-ylmethyl)-1-methyl-1H-pyrazol-3-yl)amino)-5-chloropyrimidin-4-yl)amino)phenyl)acrylamide, acetate salt;

N-(3-((5-chloro-2-((1-(2-oxopiperidin-4-yl)-1H-pyrazol-4-yl)amino)pyrimidin-4-yl)amino)phenyl)acrylamide;

N-(3-((5-chloro-2-((5-(trifluoromethyl)-1,3,4-thiadiazol-2-yl)amino)pyrimidin-4-yl)amino)phenyl)acrylamide;

N-(3-((5-chloro-2-((1-(tetrahydro-2H-pyran-4-yl)-1H-pyrazol-4-yl)amino)pyrimidin-4-yl)amino)phenyl)acrylamide;

N-(3-((5-chloro-2-((1-methyl-5-(morpholinomethyl)-1H-pyrazol-3-yl)amino)pyrimidin-4-yl)amino)phenyl)acrylamide;

N-(3-((5-chloro-2-((1-(2-hydroxyethyl)-1H-pyrazol-4-yl)amino)pyrimidin-4-yl)oxy)phenyl)acrylamide;

N-(3-((5-chloro-2-((1-(8-methyl-8-azabicyclo[3.2.1]octan-3-yl)-1H-pyrazol-4-yl)amino)pyrimidin-4-yl)amino)phenyl)acrylamide;

N-(3-((5-chloro-2-((1-(tetrahydrofuran-3-yl)-1H-pyrazol-4-yl)amino)pyrimidin-4-yl)amino)phenyl)acrylamide;

2-cyclohexylidene-N-(3-((5-fluoro-2-((1-(1-methylpiperidin-4-yl)-1H-pyrazol-4-yl)amino)pyrimidin-4-yl)amino)phenyl)acetamide;

(E)-N-(3-((5-chloro-2-((1-(1-methylpiperidin-4-yl)-1H-pyrazol-4-yl)amino)pyrimidin-4-yl)amino)phenyl)but-2-enamide;

N-(3-((5-chloro-2-((1-((6-methylpyridin-2-yl)methyl)-1H-pyrazol-4-yl)amino)pyrimidin-4-yl)amino)phenyl)acrylamide;

(E)-N-(3-((5-chloro-2-((1-(1-methylpiperidin-4-yl)-1H-pyrazol-4-yl)amino)pyrimidin-4-yl)amino)phenyl)-4-(dimethylamino)but-2-enamide;
N-(3-((5-chloro-2-((1-(piperidin-4-yl)-1H-pyrazol-4-yl)amino)pyrimidin-4-yl)amino)phenyl)acrylamide, 2,2,2-trifluoroacetate salt;
1-(3-((5-chloro-2-((1-methyl-1H-pyrazol-4-yl)amino)pyrimidin-4-yl)amino)phenyl)-1H-pyrrole-2,5-dione;
N-(5-((5-chloro-2-((1-(1-methylpiperidin-4-yl)-1H-pyrazol-4-yl)amino)pyrimidin-4-yl)amino)-2-fluorophenyl)ethenesulfonamide;
N-(3-((5-chloro-2-((1-methyl-1H-pyrazol-4-yl)amino)pyrimidin-4-yl)amino)phenyl)ethenesulfonamide;
N-(5-((5-chloro-2-((1-methyl-1H-pyrazol-4-yl)amino)pyrimidin-4-yl)amino)-2-fluorophenyl)acrylamide;
N-(5-((5-chloro-2-((1-(1-methylpiperidin-4-yl)-1H-pyrazol-4-yl)amino)pyrimidin-4-yl)amino)-2-fluorophenyl)acrylamide;
N-(5-((5-chloro-2-((1-methyl-1H-pyrazol-4-yl)amino)pyrimidin-4-yl)amino)-2,4-difluorophenyl)acrylamide;
N-(5-((5-chloro-2-((1-(1-methylpiperidin-4-yl)-1H-pyrazol-4-yl)amino)pyrimidin-4-yl)amino)-2,4-difluorophenyl)acrylamide;
N-(3-((5-chloro-2-((1,3-dimethyl-1H-pyrazol-4-yl)amino)pyrimidin-4-yl)amino)-4-fluorophenyl)acrylamide;
N-(3-((5-chloro-2-((1,5-dimethyl-1H-pyrazol-4-yl)amino)pyrimidin-4-yl)amino)-4-fluorophenyl)acrylamide;
N-(3-((5-chloro-2-((1-(1-methylpiperidin-4-yl)-1H-pyrazol-4-yl)amino)pyrimidin-4-yl)(methyl)amino)phenyl)acrylamide;
N-(6-((5-chloro-2-((1,3-dimethyl-1H-pyrazol-4-yl)amino)pyrimidin-4-yl)amino)pyridin-2-yl)acrylamide;
N-(6-((5-chloro-2-((1,5-dimethyl-1H-pyrazol-4-yl)amino)pyrimidin-4-yl)amino)pyridin-2-yl)acrylamide;
N-(6-((5-chloro-2-((1-methyl-1H-pyrazol-4-yl)amino)pyrimidin-4-yl)amino)pyridin-2-yl)acrylamide;
N-(3-((5-cyclopropyl-2-((1-methyl-1H-pyrazol-4-yl)amino)pyrimidin-4-yl)amino)phenyl)acrylamide;
N-(3-((5-chloro-2-((1-(1-methylpiperidin-4-yl)-1H-pyrazol-4-yl)amino)pyrimidin-4-yl)oxy)phenyl)acrylamide;
N-(3-((5-chloro-2-((5-methyl-4,5,6,7-tetrahydropyrazolo[1,5-a]pyrazin-2-yl)amino)pyrimidin-4-yl)oxy)phenyl)acrylamide;
N-(3-((5-chloro-2-((1-isopropyl-1H-pyrazol-4-yl)amino)pyrimidin-4-yl)oxy)phenyl)acrylamide;
N-(3-((5-chloro-2-((1-(2-(dimethylamino)ethyl)-1H-pyrazol-4-yl)amino)pyrimidin-4-yl)oxy)phenyl)acrylamide;
N-(3-((5-chloro-2-((1-(2-hydroxy-2-methylpropyl)-1H-pyrazol-4-yl)amino)pyrimidin-4-yl)oxy)phenyl)acrylamide;
N-(3-((5-chloro-2-((1-(cyclopropylmethyl)-1H-pyrazol-4-yl)amino)pyrimidin-4-yl)oxy)phenyl)acrylamide;
N-(3-((5-chloro-2-((3,5-dimethyl-1-(1-methylpiperidin-4-yl)-1H-pyrazol-4-yl)amino)pyrimidin-4-yl)oxy)phenyl)acrylamide;
N-(3-((5-chloro-2-((1,3,5-trimethyl-1H-pyrazol-4-yl)amino)pyrimidin-4-yl)oxy)phenyl)acrylamide;
N-(3-((5-chloro-2-((1-methyl-1H-pyrazol-4-yl)amino)pyrimidin-4-yl)oxy)phenyl)acrylamide;
N-(3-((5-chloro-2-((1-(2-hydroxyethyl)-1H-pyrazol-4-yl)amino)pyrimidin-4-yl)oxy)phenyl)acrylamide;
N-(3-((5-chloro-2-((1-(2-methoxyethyl)-1H-pyrazol-4-yl)amino)pyrimidin-4-yl)oxy)phenyl)acrylamide;
N-(3-((5-chloro-2-((2-methylpyrazolo[1,5-a]pyrimidin-7-yl)amino)pyrimidin-4-yl)oxy)phenyl)acrylamide;
N-(3-((5-chloro-2-((1-methyl-1H-pyrazol-4-yl)amino)pyrimidin-4-yl)amino)cyclohexyl)acrylamide;
1-(3-((5-chloro-2-((1-methyl-1H-pyrazol-4-yl)amino)pyrimidin-4-yl)amino)piperidin-1-yl)prop-2-en-1-one;
1-(3-((5-chloro-2-((1-methyl-1H-pyrazol-4-yl)amino)pyrimidin-4-yl)amino)piperidin-1-yl)prop-2-en-1-one;
(E)-1-(3-((5-chloro-2-((1-methyl-1H-pyrazol-4-yl)amino)pyrimidin-4-yl)amino)piperidin-1-yl)-4-(dimethylamino)but-2-en-1-one;
(E)-1-(3-((5-chloro-2-((1-methyl-1H-pyrazol-4-yl)amino)pyrimidin-4-yl)amino)piperidin-1-yl)-4-(dimethylamino)but-2-en-1-one;
1-(3-((5-chloro-2-((1-cyclobutyl-1H-pyrazol-4-yl)amino)pyrimidin-4-yl)amino)piperidin-1-yl)prop-2-en-1-one (Enantiomer 1);
1-(3-((5-chloro-2-((1-cyclobutyl-1H-pyrazol-4-yl)amino)pyrimidin-4-yl)amino)piperidin-1-yl)prop-2-en-1-one (Enantiomer 2);
1-(3-((5-chloro-2-((1-methyl-1H-pyrazol-4-yl)amino)pyrimidin-4-yl)amino)pyrrolidin-1-yl)prop-2-en-1-one;
1-(3-((5-chloro-2-((1-methyl-1H-pyrazol-4-yl)amino)pyrimidin-4-yl)oxy)pyrrolidin-1-yl)prop-2-en-1-one (Enantiomer 1);
1-(3-((5-chloro-2-((1-methyl-1H-pyrazol-4-yl)amino)pyrimidin-4-yl)oxy)pyrrolidin-1-yl)prop-2-en-1-one (Enantiomer 2);
1-(3-((5-chloro-2-((1-methyl-1H-pyrazol-4-yl)amino)pyrimidin-4-yl)oxy)piperidin-1-yl)prop-2-en-1-one (Enantiomer 1);
1-(3-((5-chloro-2-((1-methyl-1H-pyrazol-4-yl)amino)pyrimidin-4-yl)oxy)piperidin-1-yl)prop-2-en-1-one (Enantiomer 2).
N-(3-((5-chloro-2-((1-methyl-1H-pyrazol-4-yl)amino)pyrimidin-4-yl)amino)-4-((tetrahydrofuran-3-yl)oxy)phenyl)acrylamide;
N-(5-((5-chloro-2-((1-methyl-1H-pyrazol-4-yl)amino)pyrimidin-4-yl)amino)-2-((tetrahydrofuran-3-yl)oxy)phenyl)acrylamide;
N-(3-(1-((5-chloro-2-((1-methyl-1H-pyrazol-4-yl)amino)pyrimidin-4-yl)amino)ethyl)phenyl)acrylamide;
(E)-N-(3-(1-((5-chloro-2-((1-methyl-1H-pyrazol-4-yl)amino)pyrimidin-4-yl)amino)ethyl)phenyl)-4-(dimethylamino)but-2-enamide;
N-(3-((5-chloro-2-((3-chloro-1-methyl-1H-pyrazol-4-yl)amino)pyrimidin-4-yl)amino)-4-fluorophenyl)acrylamide;
N-(3-((5-chloro-6-methyl-2-((1-methyl-1H-pyrazol-4-yl)amino)pyrimidin-4-yl)amino)phenyl)acrylamide;
N-(3-((5-chloro-2-((1-methyl-1H-imidazol-4-yl)amino)pyrimidin-4-yl)amino)phenyl)acrylamide;
N-(3-((5-chloro-2-(((1-methyl-1H-pyrazol-4-yl)methyl)amino)pyrimidin-4-yl)amino)phenyl)acrylamide;
N-(3-((5-chloro-2-((1-methyl-1H-pyrazol-4-yl)amino)pyrimidin-4-yl)oxy)cyclohexyl)acrylamide (Isomer 1);
N-(3-((5-chloro-2-((1-methyl-1H-pyrazol-4-yl)amino)pyrimidin-4-yl)oxy)cyclohexyl)acrylamide (Isomer 2);
(E)-N-(3-((5-chloro-2-((1-methyl-1H-pyrazol-4-yl)amino)pyrimidin-4-yl)oxy)cyclohexyl)-4-(dimethylamino)but-2-enamide (Isomer 1);
(E)-N-(3-((5-chloro-2-((1-methyl-1H-pyrazol-4-yl)amino)pyrimidin-4-yl)oxy)cyclohexyl)-4-(dimethylamino)but-2-enamide (Isomer 2);
N-(3-((5-chloro-2-((1-methyl-1H-pyrazol-4-yl)amino)pyrimidin-4-yl)amino)cyclopentyl)acrylamide;
N-(4-((5-chloro-2-((1-methyl-1H-pyrazol-4-yl)amino)pyrimidin-4-yl)amino)cyclohexyl)acrylamide;
N-(3-((5-chloro-2-((3-chloro-1-methyl-1H-pyrazol-4-yl)amino)pyrimidin-4-yl)amino)cyclohexyl)acrylamide;

N-(3-((5-chloro-2-((1-methyl-1H-pyrazol-3-yl)amino)pyrimidin-4-yl)amino)cyclohexyl)acrylamide;

N-(3-((5-chloro-2-((5-chloro-1-methyl-1H-pyrazol-3-yl)amino)pyrimidin-4-yl)amino)cyclohexyl)acrylamide;

N-(3-((5-chloro-2-((5-(methoxymethyl)-1-methyl-1H-pyrazol-3-yl)amino)pyrimidin-4-yl)amino)cyclohexyl)acrylamide;

N-(3-((5-chloro-2-((1-(2-(dimethylamino)ethyl)-1H-pyrazol-4-yl)amino)pyrimidin-4-yl)amino)cyclohexyl)acrylamide;

N-(3-((5-methyl-2-((1-methyl-1H-pyrazol-4-yl)amino)pyrimidin-4-yl)amino)cyclohexyl)acrylamide;

(E)-N-(3-((5-chloro-2-((1-methyl-1H-pyrazol-4-yl)amino)pyrimidin-4-yl)amino)cyclohexyl)-4-(dimethylamino)but-2-enamide;

(E)-N-((1R,3R)-3-(((5-chloro-2-((1-methyl-1H-pyrazol-4-yl)amino)pyrimidin-4-yl)amino)methyl)cyclohexyl)-4-(dimethylamino)but-2-enamide (dieastereomer 1);

(E)-N-((1R,3R)-3-(((5-chloro-2-((1-methyl-1H-pyrazol-4-yl)amino)pyrimidin-4-yl)amino)methyl)cyclohexyl)-4-(dimethylamino)but-2-enamide (dieastereomer 2);

N-((1S,3R)-3-((5-chloro-2-((1-methyl-1H-pyrazol-4-yl)amino)pyrimidin-4-yl)amino)cyclohexyl)acrylamide (Enantiomer 3);

N-((1R,3S)-3-((5-chloro-2-((1-methyl-1H-pyrazol-4-yl)amino)pyrimidin-4-yl)amino)cyclohexyl)acrylamide (Enantiomer 4);

N-((1R,3R)-3-((5-chloro-2-((1-methyl-1H-pyrazol-4-yl)amino)pyrimidin-4-yl)amino)cyclohexyl)acrylamide (Enantiomer 1);

N-((1S,3S)-3-((5-chloro-2-((1-methyl-1H-pyrazol-4-yl)amino)pyrimidin-4-yl)amino)cyclohexyl)acrylamide (Enantiomer 2);

N-((3-((5-chloro-2-((1-methyl-1H-pyrazol-4-yl)amino)pyrimidin-4-yl)amino)cyclohexyl)methyl)acrylamide;

(E)-N-((3-((5-chloro-2-((1-methyl-1H-pyrazol-4-yl)amino)pyrimidin-4-yl)amino)cyclohexyl)methyl)-4-(dimethylamino)but-2-enamide;

N-(3-((5-chloro-2-((1-methyl-1H-pyrazol-4-yl)amino)pyrimidin-4-yl)amino)-4-fluorophenyl)-N-methylacrylamide;

N-(3-((5-chloro-2-((1-methyl-1H-pyrazol-4-yl)amino)pyrimidin-4-yl)(methyl)amino)-4-fluorophenyl)acrylamide;

N-((1S,3R)-3-((5-chloro-2-((1-methyl-1H-pyrazol-4-yl)amino)pyrimidin-4-yl)amino)cycloheptyl)acrylamide (Isomer 1);

N-((1R,3S)-3-((5-chloro-2-((1-methyl-1H-pyrazol-4-yl)amino)pyrimidin-4-yl)amino)cycloheptyl)acrylamide (Isomer 2);

N-(3-((5-chloro-2-((3-methylisothiazol-5-yl)amino)pyrimidin-4-yl)amino)cyclohexyl)acrylamide;

(E)-N-(3-((5-chloro-2-((3-methylisothiazol-5-yl)amino)pyrimidin-4-yl)amino)cyclohexyl)-4-(dimethylamino)but-2-enamide;

N-(2-((5-chloro-2-((1-methyl-1H-pyrazol-4-yl)amino)pyrimidin-4-yl)amino)pyridin-4-yl)acrylamide;

N-(3-((5-chloro-2-((3-methylisothiazol-5-yl)amino)pyrimidin-4-yl)amino)-4-fluorophenyl)acrylamide;

N-(3-((5-chloro-2-((3-methylisoxazol-5-yl)amino)pyrimidin-4-yl)amino)-4-fluorophenyl)acrylamide;

N-(3-((5-chloro-2-((3,4-dimethylisoxazol-5-yl)amino)pyrimidin-4-yl)amino)-4-fluorophenyl)acrylamide;

N-(3-((5-chloro-2-((5-chlorothiazol-2-yl)amino)pyrimidin-4-yl)amino)-4-fluorophenyl)acrylamide;

N-(3-((5-chloro-2-((5-cyanothiazol-2-yl)amino)pyrimidin-4-yl)amino)-4-fluorophenyl)acrylamide;

N-(3-((5-chloro-2-((3-methylisothiazol-5-yl)amino)pyrimidin-4-yl)amino)phenyl)acrylamide;

N-(3-((5-chloro-2-((5-methylthiazol-2-yl)amino)pyrimidin-4-yl)amino)phenyl)acrylamide;

N-(3-((5-chloro-2-((4-methylthiazol-2-yl)amino)pyrimidin-4-yl)amino)phenyl)acrylamide;

N-(3-((5-chloro-2-((3-methylisoxazol-5-yl)amino)pyrimidin-4-yl)amino)phenyl)acrylamide;

1-(4-((5-chloro-2-((1-methyl-1H-pyrazol-4-yl)amino)pyrimidin-4-yl)amino)piperidin-1-yl)prop-2-en-1-one;

1-(3-(((5-chloro-2-((1-methyl-1H-pyrazol-4-yl)amino)pyrimidin-4-yl)amino)methyl)piperidin-1-yl)prop-2-en-1-one and N-(3-((5-chloro-2-((1-methyl-1H-pyrazol-4-yl)amino)pyrimidin-4-yl)amino)cyclohexyl)acrylamide 4-methylbenzenesulfonate An embodiment of the present disclosure relates to a compound of formula (I) or its stereoisomers, tautomers, pharmaceutically acceptable salts, polymorphs, solvates and hydrates thereof, for treating disease associated with epidermal growth factor receptor (EGFR) family kinases.

Another embodiment of the present disclosure relates to a compound of formula (I) or its stereoisomers, tautomers, pharmaceutically acceptable salts, polymorphs, solvates and hydrates thereof, for treating cancer.

Another embodiment of the present disclosure relates to a compound formula (I), or its stereoisomers, tautomers, pharmaceutically acceptable salts, polymorphs, solvates and hydrates thereof, for treating disease or condition associated with non-small cell or small cell lung cancer or prostate cancer or head and neck cancer or breast cancer or conditions related to cancer.

The present disclosure relates to a pharmaceutical composition comprising a compound of formula (I) or a pharmaceutically acceptable salt thereof together with a pharmaceutically acceptable carrier, optionally in combination with one or more other pharmaceutical compositions.

The present disclosure further relates to the process of preparation of compounds of formula I or its stereoisomers, tautomers, pharmaceutically acceptable salts, polymorphs, solvates and hydrates thereof.

The present disclosure relates to a class of compounds that are useful as EGFR T790M inhibitors. The compounds of the present disclosure may have improved potency and/or beneficial activity profiles and/or beneficial selectivity profiles and/or increased efficacy and/or improved safety profiles (such as reduced side effects) and/or improved pharmacokinetic properties. Some of the preferred compounds may show selectivity for WT EGFR or over other receptors. Such compounds may be useful to treat, prevent or ameliorate a disease or condition associated with EGFR T790M activation, including non-small cell or small cell lung cancer or prostate cancer or head and neck cancer or breast cancer or colorectal cancer or conditions related to cancer.

EXPERIMENTAL

Yields reported herein refer to purified products (unless specified) and are not optimised. Analytical TLC was performed on Merck silica gel 60 $F_{254}$ aluminium-backed plates. Compounds were visualised by UV light and/or stained either with iodine, potassium permanganate or ninhydrin solution. Flash column chromatography was performed on silica gel (100-200 M) or flash chromatography. $^1$H-NMR spectra were recorded on a Bruker Avance-400 MHz spectrometer with a BBO (Broad Band Observe) and BBFO (Broad Band Fluorine Observe) probe. Chemical shifts (δ) are expressed in parts per million (ppm) downfield by reference to tetramethylsilane (TMS) as the internal standard. Splitting patterns are designated as s (singlet), d (doublet), t (triplet), q (quartet), m (multiplet) and br s (broad singlet). Coupling constants (J) are given in hertz (Hz). LC-MS analyses were performed on either an Acquity BEH C-18 column (2.10×100 mm, 1.70 μm) or on a Acquity HSS-T3 column (2.10×100 mm, 1.80 μm) using the Electrospray Ionisation (ESI) technique.

The following solvents, reagents or scientific terminology may be referred to by their abbreviations:
TLC Thin Layer Chromatography
DCM Dichloromethane
DCE 1,2-Dichloroethane
THF Tetrahydrofuran
MeOH Methanol
EtOH Ethanol
IPA Isopropyl alcohol
n-BuOH n-Butanol
EtOAc Ethyl acetate
Et$_2$O Diethyl ether
DMA N,N-Dimethylacetamide
DMF N,N-Dimethylformamide
TEA/Et$_3$N Triethylamine
DMSO Dimethylsulfoxide
DIPEA Diisopropylethylamine (Hunig's base)
MeI Methyliodide
NBS N-Bromosuccinimide
TBAB Tetrabutylammonium bromide
TBAI Tetrabutylammonium iodide
DIBAL-H Diisobutylaluminium hydride
DIAD Diisopropyl azodicarboxylate
TFA Trifluoroacetic acid
PTSA p-Toluenesulfonic acid
AcOH Acetic acid
T$_3$P 1-Propanephosphonic anhydride solution
Boc tert-butoxycarbonyl
Cat Catalytic
mL milliliters
mmol millimoles
h hour or hours
min minute or minutes
g grams
mg milligrams
μl Microliters
eq Equivalents
rt or RT Room temperature, ambient, about 27° C.
MS Mass spectrometry General synthetic scheme-1

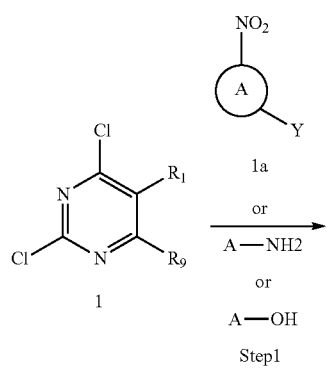

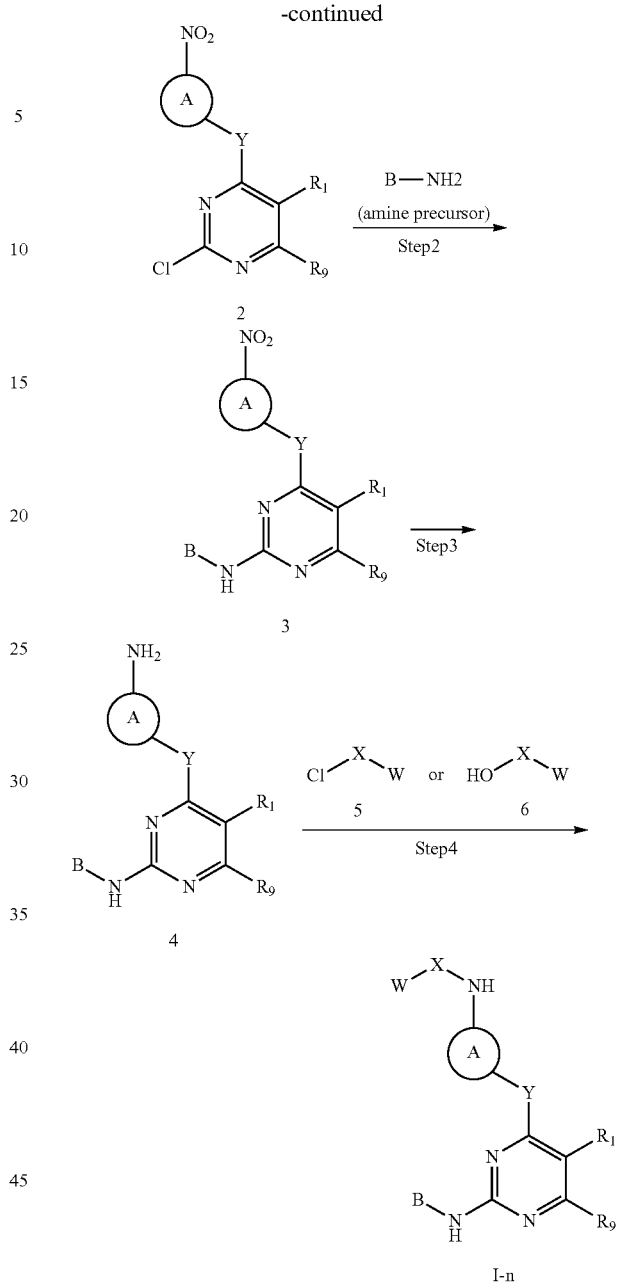

2,4-Dichloropyrimidine derivative 1 was reacted with variety of amines and alcohols in presence of base such as DIPEA or K$_2$CO$_3$ and organic solvent such as DMF, DMA, IPA, n-BuOH, MeOH, EtOH at –50° C. to 140° C., to obtain compound 2. Compound 2 was then reacted with variety of amines (B—NH$_2$) using acid catalyst such as TFA or PTSA or base such as DIPEA, K$_2$CO$_3$, or Buchwald condition or without catalyst in presence of organic solvent such as IPA, DMF, 2-butanol or 1,4-dioxane at rt to reflux temperature to produce compound-3. The nitro group of compound 3 was reduced using variety of reducing agents such as Zn/NH$_4$Cl, Fe/NH$_4$Cl, Fe/AcOH, SnCl$_2$, sodium dithionite, Pd/C/H$_2$, raney-Ni, hydrogen (atmospheric) in organic solvent such as MeOH or EtOH or IPA to get compound-4. Compound 4 was then reacted with different acid chlorides 5 such as acryloyl chloride in presence of base such as DIPEA, TEA, DMAP and using solvents such as DCM, THF, DMF preferably TEA and THF or DCM to obtain I-n, In some examples compound 4 was reacted with acid chloride 5 without base in presence of organic solvent such as DCM to obtain I-n. In another method of obtaining I-n, compound 4 was treated with different acids 6 in presence of different coupling reagents such as T3P or HOBt, and base such as TEA and organic solvent such as DCM or THF to obtain I-n.

General synthetic scheme-1A

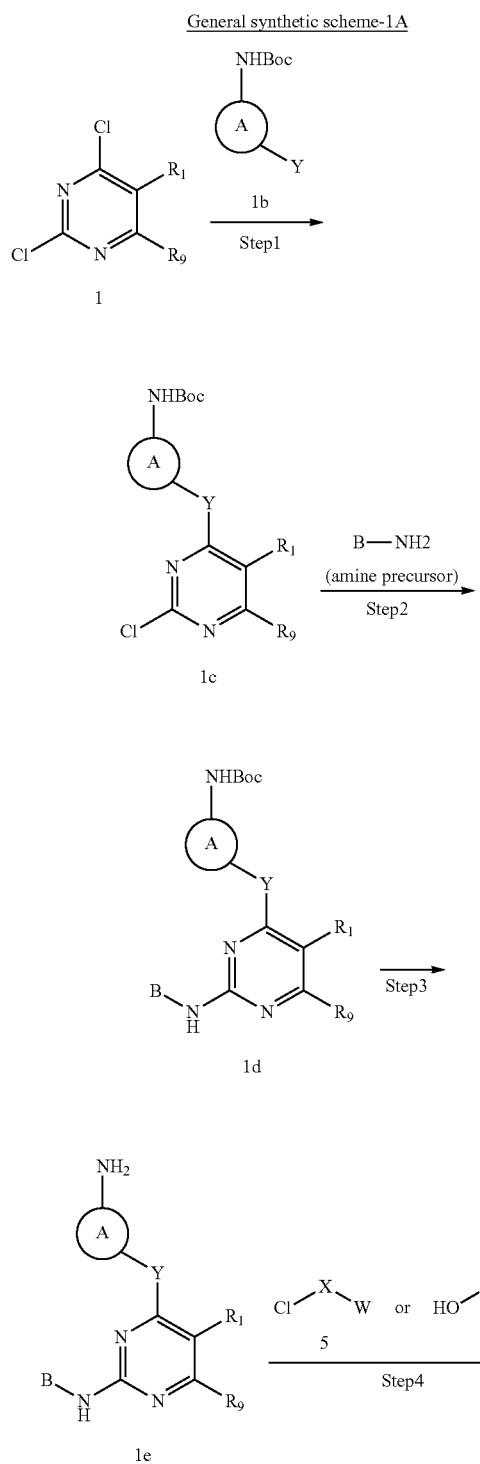

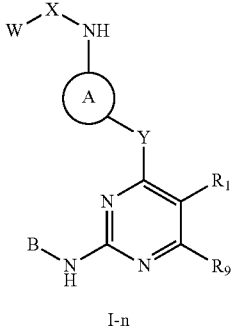

I-n 2,4-Dichloropyrimidine derivative 1 was reacted with variety of amines and alcohols (1b) in presence of base such as DIPEA or $K_2CO_3$ and organic solvent such as DMF, DMA, IPA, n-BuOH, MeOH, EtOH at −50° C. to 140° C., to obtain compound 1c. Compound 1c was then reacted with variety of amines (B—$NH_2$) using acid catalyst such as TFA or PTSA or base such as DIPEA, $K_2CO_3$, or Buchwald condition or without catalyst in presence of organic solvent such as IPA, DMF, 2-butanol or 1,4-dioxane at rt to reflux temperature to produce compound 1d. The Boc deprotection of 1d was performed using variety of acids such as HCl, TFA, $PCl_5$, $POCl_3$ preferably HCl or TFA in presence of organic solvent preferably MeOH, EtOH, IPA or DCM, EDC at 0° C. to rt to obtain compound 1e. In some examples of the disclosure, step 2 and step 3 reactions were concerted to obtain 1e. Intermediate 1e was then reacted with different acid chlorides such as acryloyl chloride in presence of base such as DIPEA, TEA, DMAP and using solvents such as DCM, THF, DMF preferably TEA and THF or DCM to obtain I-n, In some examples compound 1e was reacted with acid chloride 5 without base in presence of organic solvent such as DCM to obtain I-n. In another method of obtaining I-n, compound 1e was treated with different acids 6 in presence of different coupling reagents such as T3P or HOBt, and base such as TEA and organic solvent such as DCM or THF to obtain I-n.

In few examples of I-n the stereoisomers of I-n were separated by chiral column chromatography to get pure isomers.

General synthetic scheme-1B

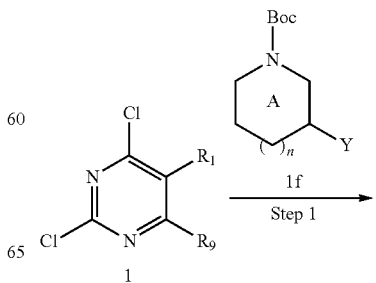

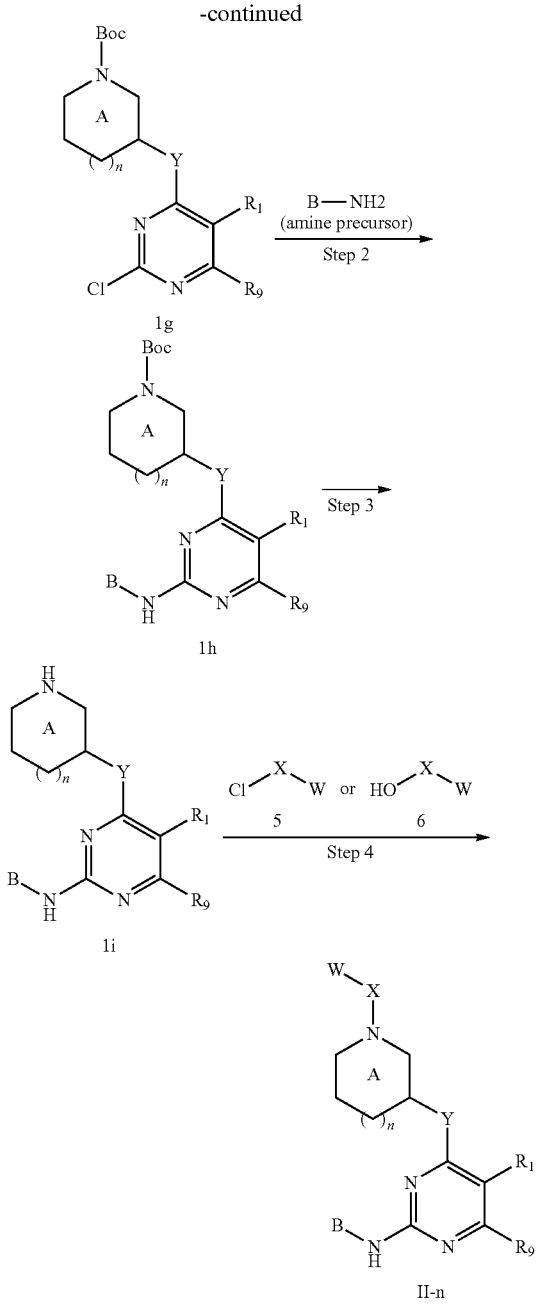

2,4-Dichloropyrimidine derivative 1 was reacted with variety of amines and alcohols (1f) in presence of base such as DIPEA or $K_2CO_3$ and organic solvent such as DMF, DMA, IPA, n-BuOH, MeOH, EtOH at −50° C. to 140° C., to obtain compound 1g. Compound 1g was then reacted with variety of amines (B—$NH_2$) using acid catalyst such as TFA or PTSA or base such as DIPEA, $K_2CO_3$, or Buchwald condition or without catalyst in presence of organic solvent such as IPA, DMF, 2-butanol or 1,4-dioxane at rt to reflux temperature to produce compound 1h. The Boc deprotection of 1h was performed using variety of acids such as HCl, TFA, $PCl_5$, $POCl_3$ preferably HCl or TFA in presence of organic solvent preferably MeOH, EtOH, IPA or DCM, EDC at 0° C. to rt to obtain compound 1i. In some examples of the disclosure, step 2 and step 3 reactions were concerted to obtain 1i. Intermediate 1i was then reacted with different acid chlorides such as acryloyl chloride in presence of base such as DIPEA, TEA, DMAP and using solvents such as DCM, THF, DMF preferably TEA and THF or DCM to obtain II-n, In some examples compound 1i was reacted with acid chloride 5 without base in presence of organic solvent such as DCM to obtain II-n. In another method of obtaining II-n, compound 1i was treated with different acids 6 in presence of different coupling reagents such as T3P or HOBt, and base such as TEA and organic solvent such as DCM or THF to obtain II-n. In few examples of II-n the stereoisomers of II-n were separated by chiral column chromatography to get pure isomers.

A resulting compound of the invention may be converted into any other compound of the invention by methods analogous to known methods. For example: a resulting compound of Formula I-n and II-n as described in general synthetic scheme 1, 1A and 1B may be converted into a salt or solvate thereof; the oxidation state of an atom in a heterocyclic ring may be increased or decreased by oxidation or reduction using known methods.

While most of the amine (B—$NH_2$) and acid precursors (5/6) were synthesized via procedures mentioned below, some of them, for which the synthesis procedure is not mentioned, were commercially procured.

General Method-A

To a stirred solution of chloropyrimidine derivative (1.0 eq), in DMF (~0.5 mL/mmol), corresponding amine (1.0 eq) and DIPEA (2-3 eq) were charged. The reaction mixture was heated at 70° C. to 140° C. for 1-16 h. The reaction mixture was diluted with EtOAc and washed with water (3 times). The combined organic layer was dried ($Na_2SO_4$) and evaporated to obtain the desired product 2 in moderate to excellent yields.

General Method-B

To a stirred solution of chloropyrimidine derivative (1.0 eq), in n-BuOH (~5 mL/mmol), corresponding amine (1.0 eq) and DIPEA (2-3 eq) were charged. The reaction mixture was heated at 100° C. for 2-16 h. Solvent was then evaporated and the crude thus obtained was purified by flash chromatography using 0-50% EtOAc-hexane as eluent to obtain the desired product 2 in moderate to excellent yields.

General Method-C

To a stirred solution of chloropyrimidine derivative (1.0 eq), in IPA (~5 mL/mmol), corresponding amine (1.0 eq) and DIPEA (2-3 eq) were charged. The reaction mixture was heated at 80-110° C. for 4-16 h. Solvent was then evaporated and the crude thus obtained was purified by flash chromatography using 0-50% EtOAc-hexane as eluent to obtain the desired product 2 in moderate to excellent yields.

General Method-D

To a solution of the intermediate prepared via general method-A to general method-C (1.0 eq) in IPA (~4 mL/mmol) were added the corresponding amine precursors (1.0 eq) followed by addition of TFA (few drops, catalytic). The resulting reaction mixture was stirred at 80-100° C. for 2-16 h. The solid thus precipitated in most cases was filtered and further purified via flash chromatography (0-10% MeOH-DCM) or reversed phase HPLC to get the desired product 3 in moderate to good yields.

General Method-E

To a solution of the intermediate prepared via general method-A to general method-C (1.0 eq) in n-butanol or 2-butanol (~4 mL/mmol) were added the corresponding amine precursors (1.0 eq) followed by addition of TFA (few drops, catalytic). The resulting reaction mixture was stirred at 80-120° C. for 2-16 h. The solid thus precipitated in most cases was filtered and further purified via flash chromatography (0-10% MeOH-DCM) or reversed phase HPLC to get the desired product 3 in moderate to good yields.

General Method-F

To a solution of the intermediate prepared via general method-A to general method-C (1.0 eq), corresponding amine precursors (1.0 eq) and p-toluenesulfonic acid (10 mol %, catalytic) were heated in 1,4-dioxane (~4 mL/mmol) at 100° C. for 14 h. Solvent was evaporated under reduced pressure and the crude thus obtained was purified by flash chromatography using 70% acetone in DCM as eluent) to obtain the desired product 3 in good yields.

General Method-G

To a solution of the intermediate prepared via general method-A to general method-C (1.0 eq), corresponding amine precursor (1.10 eq), and potassium phosphate (2.0 eq) were suspended in toluene (10 ml/mmol) in a sealed tube and the mixture was purged with argon for 5 min. $Pd_2(dba)_3$ (10 mol %) and XanthPhos (30 mol %) were added and purged with argon for further 5 min. The vial was closed and the mixture was heated at 80-120° C. for 1-16 h. The mixture as then cooled to rt, added water and extracted with EtOAc. The combined organics was washed with brine, dried ($Na_2SO_4$), filtered and concentrated under reduced pressure. The residue thus obtained was purified either by triturating with $Et_2O$-MeOH mixture or purified via flash chromatography. In some examples different catalyst was used and reaction was performed similarly to obtain product 3.

General Method-H

Raney nickel (0.10 g) was charged to a stirred solution of the nitro intermediate 3 (0.26 mmol) in MeOH (10 mL) and hydrogenated under atmospheric pressure for 2 h-12 h. The catalyst was filtered off by passing the mixture through a celite bed and the filtrate was concentrated to obtain the desired product 4 in good to excellent yields.

General Method-I

To a solution of the nitro intermediate 3 (1.0 eq) in acetic acid (10-20 mL/mmol), iron powder (10 eq) was added and the mixture was heated at 80° C. for 1 h. The mixture was then cooled to rt and filtered through a celite bed. The celite bed was washed with ethyl acetate. Saturated sodium bicarbonate solution was added to the combined filtrate till pH of the system raised to 8. The organic layer was separated and dried over anhydrous sodium sulfate. Solvents evaporated under reduced pressure to get the desired product 4 in good yields.

General Method-J

A solution of amine 4 (1.0 eq) in DCM (~15 mL/0.5 mmol for 4) (some cases THF or mixture of DCM and THF or DMA was used for better solubility of the starting materials) was cooled to 0 to −60° C., triethylamine (1.0 to 2.0 eq) was added and stirred for 10 min followed by addition of corresponding acid chloride or sulfonyl chloride (1.0 to 2.0 eq). The resulting reaction mixture was stirred for 0.5-6 h at 0° C. to −60° C. The reaction was monitored by TLC. After the completion of reaction, the reaction mixture was quenched with ice water at ~0-50° C. followed by sodium bicarbonate solution, extracted with DCM (100 mL), organic layer was washed with brine solution), dried over sodium sulfate and evaporated under reduced pressure to obtain crude product. The crude product was purified to get pure product. In some examples reaction was performed without base, Reacting 4 and acid chloride in DCM or DMA or THF at 0° C. to −20° C. obtained desired product I-n.

General Method-K

Amine 4, (1.0 eq) and the corresponding carboxylic acid (or its salt in few cases) (1.0 to 2.0 eq) were suspended in dichloromethane (~15 mL/mmol) (some cases mixture of DCM and THF or THF was used), triethylamine (2.0 to 3.0 eq) was added and cooled to 0° C. $T_3P$ (1.0 to 2.0 eq) was added drop-wise at 0° C. and the mixture was stirred at RT for 3-16 h. Completion of reaction was monitored by TLC. The reaction was partioned between 5% methanol in dichloromethane and saturated bicarbonate solution, the organic phase was dried over anhydrous sodium sulfate, filtered and concentrated and the crude obtained was purified by silica gel chromatography to obtain pure product I-n.

General Method-L

To a stirred solution of chloropyrimidine derivative (1.0 eq), in DMF (~5 mL/mmol), corresponding nitro phenol (1.0 eq) and $K_2CO_3$ (2-3 eq) were charged. The reaction mixture was heated to 80° C. to 100° C. for 2-16 h. The reaction mixture was then cooled to rt and poured onto chilled water. The precipitated solid was filtered and washed with water to obtain desired product in moderate to excellent yields. In some cases crude product was extracted with organic solvent and purified by silica gel chromatography to obtain pure product 2.

Synthesis of Intermediate Amines [A-$NH_2$ and B—$NH_2$) and Acid Precursors Used in Making Examples I-n and II-2

Scheme-2: Synthesis of 3-chloro-5-nitroaniline (Precursor-01)

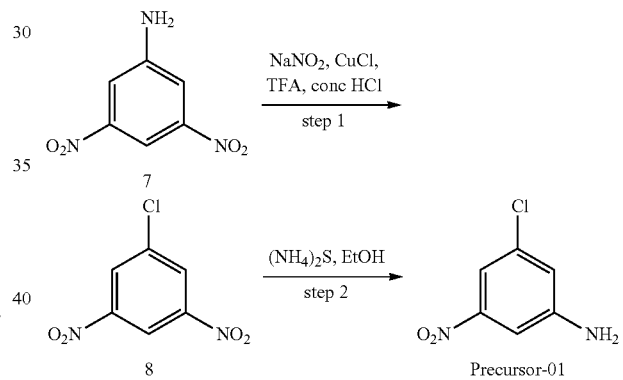

Synthesis of 1-chloro-3,5-dinitrobenzene (8)

To a stirred solution of 3,5-dinitroaniline 7 (5.00 g, 27 mmol) in trifluoroacetic acid (10 mL), sodium nitrite (3.80 g, 55 mmol) was added and the mixture was cooled to 0° C. Copper (I) chloride was dissolved in concentrated hydrochloric acid (10 mL) and added to the above mixture drop-wise. The reaction was stirred at 0° C. for 1 h. The mixture was then poured into chilled water and extracted with ethyl acetate. The organic layer was washed with saturated sodium bicarbonate solution, dried over anhydrous sodium sulfate, filtered and solvents evaporated to obtain a crude product. Purification of the crude product by flash chromatography on silica gel (using 80 g SNAP column and 12% ethyl acetate in hexane as eluent) gave 1-chloro-3,5-dinitrobenzene 8 in 69% yield as a light yellow solid. $^1$HNMR (400 MHz, $CDCl_3$): δ 8.97 (s, 1H), 8.56 (s, 2H).

Synthesis of 3-chloro-5-nitroaniline (Precursor-01)

To a stirred solution of 1-chloro-3,5-dinitrobenzene 8 (3.80 g, 19 mmol) in ethanol (60 mL) was added ammonium sulfide (20% aqueous solution, 20 mL) and the mixture was heated at 80° C. for 1 h. The mixture was then partitioned between water and ethyl acetate, the ethyl acetate layer was dried over anhydrous sodium sulfate, filtered and solvents evaporated to obtain a crude material, purification of which by flash chromatography on silica gel (using 40 g SNAP column and 30% ethyl acetate in hexane as eluent) afforded 3-chloro-5-nitroaniline precursor-01 in 28% yield as orange colored solid. MS: 171.02 (M+H)$^+$.

Scheme-3: Synthesis of N-methyl-3-nitroaniline (Precursor-02)

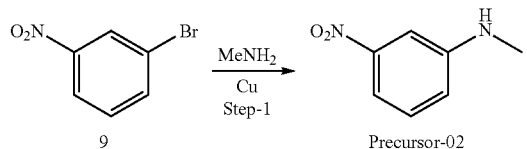

Synthesis of N-methyl-3-nitroaniline (Precursor-02)

To a stirred suspension of 1-bromo-3-nitrobenzene 9 (5.0 g, 24.75 mmol) and methyl amine (3.8 g, 3123.7 mmol) in water (7.0 mL), copper powder (0.079 g, 1.23 mmol) was charged and put on reflux for 4 hour. The crude reaction mixture was diluted with ethyl acetate (30 mL) and water (20 mL). The organic layer was dried (Na$_2$SO$_4$), filtered and evaporated to afford N-methyl-3-nitroaniline precursor-02: (3.1 g, 84% yield) as yellow solid. $^1$HNMR (400 MHz, DMSO-d$_6$): δ 7.32-7.34 (m, 2H), 7.27 (s, 1H), 7.27 (s, 1H), 6.41 (d, 1H), 2.73 (d, 3H). MS: 153.10 (M+H)$^+$.

Synthesis of tert-butyl 4-((methylsulfonyl)oxy)piperidine-1-carboxylate (11)

tert-Butyl 4-hydroxypiperidine-1-carboxylate 10 (39.0 g, 193 mmol) was taken in DCM (400 mL) in a 1L round bottom flask under N$_2$ and cooled it to 0° C. To it were sequentially added methanesulfonyl chloride (28.7 g, 250.0 mmol) and Et$_3$N (81 mL, 581.0 mmol). The reaction mixture was stirred at rt for 4 h. The reaction mixture was then poured into ice water and extracted with DCM (3×100 mL). The combined organic layer was washed with saturated NaHCO$_3$ solution (3×100 mL), dried over anhydrous Na$_2$SO$_4$ and concentrated under reduced pressure. The crude was further washed with n-pentane to afford 11 as an off-white solid (54.0 g, 99% yield). $^1$H NMR (400 MHz, CDCl$_3$): δ 4.85-4.88 (m, 1H), 3.67-3.70 (m, 2H), 3.25-3.32 (m, 2H), 3.02 (s, 3H), 1.93-1.94 (m, 2H), 1.76-1.84 (m, 2H), 1.44 (s, 9H).

Synthesis of tert-butyl 4-(4-nitro-1H-pyrazol-1-yl) piperidine-1-carboxylate (13)

tert-Butyl 4-((methylsulfonyl)oxy)piperidine-1-carboxylate 11 (54.0 g, 193.0 mmol) was taken in CH$_3$CN (400 mL) in a 1 L round bottom flask under N$_2$. To it were sequentially added 4-nitro-1H-pyrazole 12 (21.8 g, 193.0 mmol) and K$_2$CO$_3$ (86.7 g, 579.0 mmol). The reaction mixture was heated at 80° C. for 12 h. The reaction mixture was then poured into ice water and extracted with EtOAc (3×200 mL). The combined organic layer was dried over anhydrous Na$_2$SO$_4$ and concentrated under reduced pressure. The crude Scheme-4: Synthesis of 1-(1-methylpiperidin-4-yl)-1H-pyrazol-4-amine (Precursor-03) and tert-butyl 4-(4-amino-1H-pyrazol-1-yl)piperidine-1-carboxylate (Precursor-04)

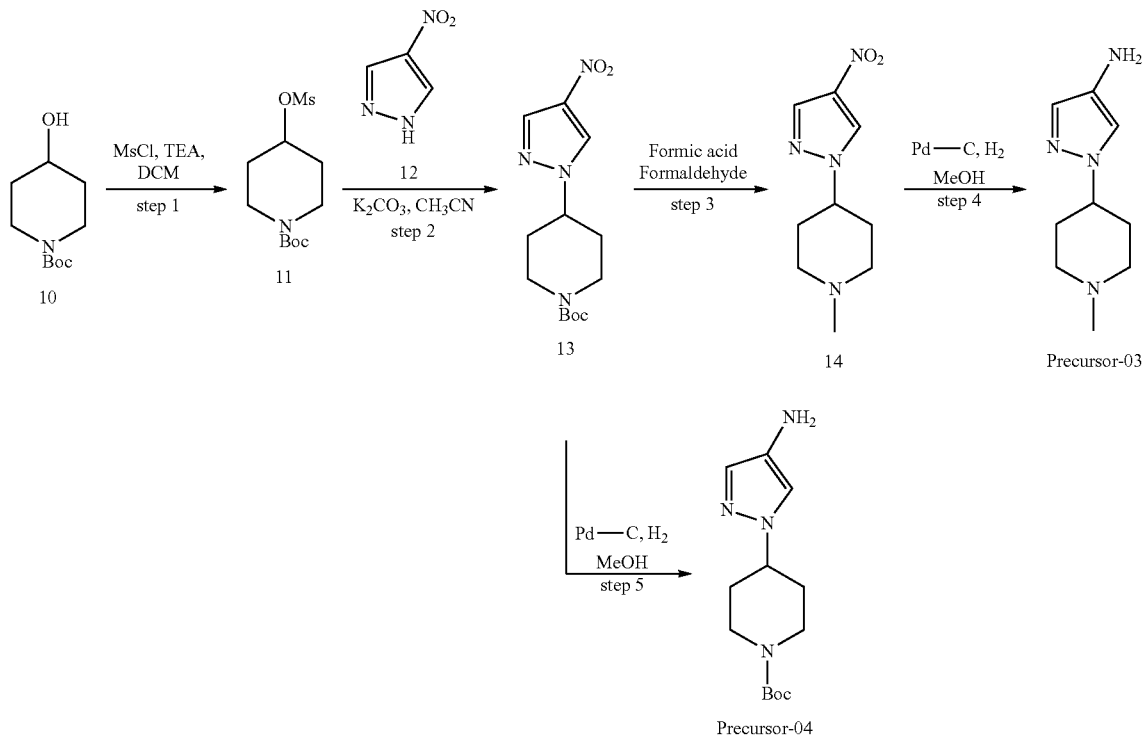

was purified by column chromatography on silica gel (100-200 mesh) using 25% EtOAc-hexane as eluent to afford 13 as a white solid (27.0 g, 47% yield). LC-MS: 355.15 $(M+H)^+$; 92% (purity).

Synthesis of 1-methyl-4-(4-nitro-1H-pyrazol-1-yl)piperidine (14)

tert-Butyl 4-(4-nitro-1H-pyrazol-1-yl)piperidine-1-carboxylate 13 (27.0 g, 91.1 mmol) was taken in $H_2O$ (250 mL) in a 500 mL round bottom flask followed by sequential addition of formic acid (41.9 g, 911.0 mmol) and formaldehyde (13.7 g, 455.0 mmol). The reaction mixture was heated at 100° C. for 16 h. After completion the reaction (monitored by TLC), the reaction mixture was quenched with aqueous $NaHCO_3$ solution till the pH of the solution became ~9 and extracted with EtOAc (3×200 mL). The combined organic layer was dried over anhydrous $Na_2SO_4$ and concentrated under reduced pressure. The crude was further washed was n-pentane to afford 14 as an off-white solid (16.0 g, 83% yield). $^1H$ NMR (400 MHz, $CDCl_3$): δ 8.15 (s, 1H), 8.06 (s, 1H), 4.09-4.15 (m, 1H), 2.96-3.01 (m, 3H), 2.32 (s, 3H), 1.95-2.14 (m, 5H).

Synthesis of 1-(1-methylpiperidin-4-yl)-1H-pyrazol-4-amine (Precursor-03)

A par flask was charged with 1-methyl-4-(4-nitro-1H-pyrazol-1-yl)piperidine 14 (16.0 g, 41.0 mmol) and ethanol (400 mL) followed by addition of Pd—C (40% w/w, 6.40 g). The flask was evacuated under vacuum and then purged with hydrogen. The reaction was stirred under hydrogen atmosphere (30 psi). The reaction was monitored by TLC. It was then filtered through sintered funnel with a pad of celite, washed with methanol and concentrated under reduced pressure to afford precursor-03 as a pink solid (11.0 g, 80% yield) that was taken as such for the next step without any further purification. $^1H$ NMR (400 MHz, DMSO-$d_6$): δ 7.04 (s, 1H), 6.89 (s, 1H), 3.83-3.89 (m, 3H), 2.79-2.82 (m, 2H), 2.01 (s, 3H), 1.90-2.01 (m, 2H), 1.75-1.86 (m, 4H). Similarly, tert-butyl 4-(4-amino-1H-pyrazol-1-yl)piperidine-1-carboxylate (Precursor-04) was prepared from 13 using the nitro group reduction condition described above. MS: 167.10 $(M+H)^+$.

Scheme 5: Synthesis of 1-methyl-1H-pyrazol-4-amine (Precursor-05)

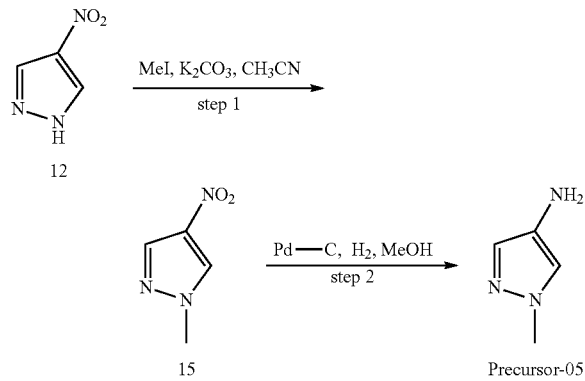

Synthesis of 1-methyl-4-nitro-1H-pyrazole (15)

4-Nitro-1H-pyrazole 12 (10.0 g, 88.4 mmol) was taken in $CH_3CN$ (100 mL) in a 250 mL round bottom flask under $N_2$. To it were sequentially added iodomethane (18.8 g, 132.0 mmol) and $K_2CO_3$ (30.5 g, 221.0 mmol). The reaction mixture was heated at 100° C. for 16 h. The reaction mixture was then poured into ice water (100 g) and extracted with EtOAc (3×100 mL). The combined organic layer was dried over anhydrous $Na_2SO_4$ and concentrated under reduced pressure. The crude was further washed with n-pentane to afford 15 as a light yellow solid (10.8 g, 96% yield). $^1H$ NMR (400 MHz, $CDCl_3$): δ 8.11 (s, 1H), 8.05 (s, 1H), 3.96 (s, 3H).

Synthesis of 1-methyl-1H-pyrazol-4-amine (Precursor-05)

A par flask was charged with 1-methyl-4-nitro-1H-pyrazole 15 (5.3 g, 41.0 mmol) and methanol (70 mL) followed by addition of Pd—C (50% w/w, 2.70 g). The flask was evacuated under vacuum and then purged with hydrogen. The reaction was stirred under hydrogen atmosphere (30 psi). The reaction was monitored by TLC. It was then filtered through sintered funnel with a pad of celite, washed with methanol and concentrated under reduced pressure to afford precursor-05 as a brown colored gummy solid (4.0 g, 99% yield) that was used as such for the next step without any further purification. $^1H$ NMR (400 MHz, $CDCl_3$): δ 7.12 (s, 1H), 6.97 (s, 1H), 3.78 (s, 3H), 2.87 (br s, 2H).

Scheme-6: Synthesis of 1-(2-methoxyethyl)-1H-pyrazol-4-amine (Precursor-06)

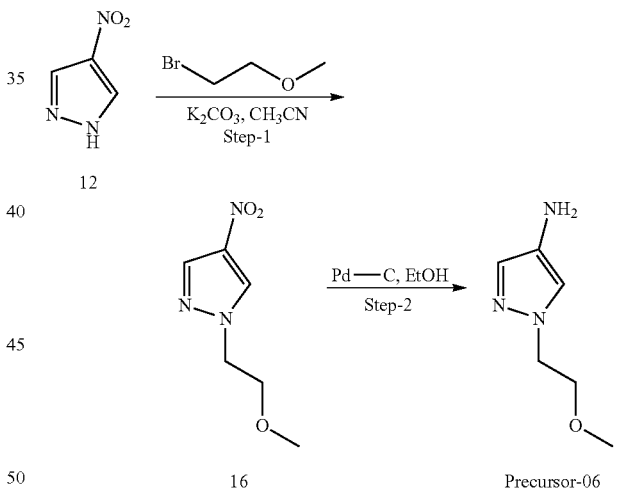

Synthesis of 1-(2-methoxyethyl)-4-nitro-1H-pyrazole (16)

To a solution of 4-nitro-1H-pyrazole 12 (1.70 g, 15.03 mmol) in $CH_3CN$ (50 mL) was added $K_2CO_3$ (3.11 g, 22.53 mmol) followed by addition of 1-bromo-2-methoxy-ethane (2.5 g, 18.0 mmol) at room temperature. The reaction mixture was heated to 90° C. for 5 h. After completion of reaction (monitored by TLC), the solvent was evaporated, added water and extracted with EtOAc (3×200 mL). The combined organics was washed with water, brine, dried over anhydrous sodium sulfate, filtered and concentrated under reduced pressure to afford 2.50 g (97% yield) of the title compound 16 as colorless liquid. $^1H$ NMR (400 MHz, DMDO-d$_6$): δ 8.85 (s, 1H), 8.27 (s, 1H), 4.36-4.33 (t, 2H), 3.77-3.72 (t, 2H), 3.23 (s, 3H). MS: 172.11 (M+H)$^+$.

Synthesis of 1-(2-methoxyethyl)-1H-pyrazol-4-amine (Precursor-06)

A par flask was charged with 1-(2-Methoxy-ethyl)-4-nitro-1H-pyrazole 16 (2.5 g, 14.60 mmol) in EtOH (250 mL) followed by addition of Pd—C (20% w/w, 0.50 g). The flask was evacuated under vacuum and then purged with hydrogen. The reaction was stirred under hydrogen atmosphere (1 atm) for 16 h. After the completion of reaction, the solution was filtered through sintered funnel with a pad of celite, washed with methanol and concentrated under reduced pressure to afford precursor-06 (2.0 g, 97% yield) that was taken as such for the next step without any further purification. $^1$H NMR (400 MHz, CDCl$_3$): δ 7.03 (s, 1H), 6.89 (s, 1H), 4.19-4.17 (t, 2H), 3.78 (br s, 2H), 3.67-3.64 (t, 2H), 3.21 (s, 3H). MS: 142.11 (M+H)$^+$.

Scheme-7: Synthesis of 2-(4-amino-1H-pyrazol-1-yl)ethanol (Precursor-07)

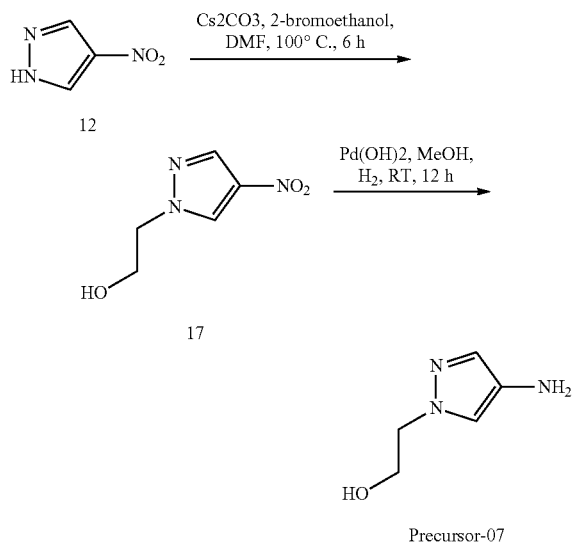

Synthesis of 2-(4-nitro-1H-pyrazol-1-yl)ethanol (17)

A stirred solution of 4-nitro-1H-pyrazole 12 (10.0 g, 88.4 mmol), 2-bromo ethanol (12.0 g, 97.3 mmol) and cesium carbonate (43.0 g, 132.6 mmol) in DMF (130 mL) was heated to 100° C. for 6 h. After the completion of reaction (TLC monitoring), the reaction mixture was cooled to RT, diluted with water (200 mL) and extracted with EtOAc (2×200 mL). The combined organic phase washed with water, dried over Na$_2$SO$_4$, concentrated to give 2-(4-nitro-1H-pyrazol-1-yl)ethanol 17 (6.0 g, 43% yield). $^1$HNMR (400 MHz, DMSO-d$_6$): δ 8.81 (s, 1H), 8.26 (s, 1H), 4.99 (t, 1H), 4.22 (t, 2H) 3.76-3.78 (m, 2H).

Synthesis of 2-(4-amino-1H-pyrazol-1-yl)ethanol (Precursor-07)

To a stirred solution of 2-(4-nitro-1H-pyrazol-1-yl)ethanol 17 (2.0 g, 1.23 mmol) in EtOH (25 mL), 0.40 g of Pd(OH)$_2$ added and then stirred reaction under H$_2$ gas atm for 14 h. After the completion of reaction (TLC monitoring) the reaction mixture was filtered through celite bed, washed with MeOH, concentrated the solvent and the crude compound was purified by triturating with ether and pentane to give 2-(4-amino-1H-pyrazol-1-yl)ethanol precursor-07 as brown solid (1.30 g, 81% yield). MS: 128.07 (M+H)$^+$.

Scheme 8: Synthesis of (Precursor-08)

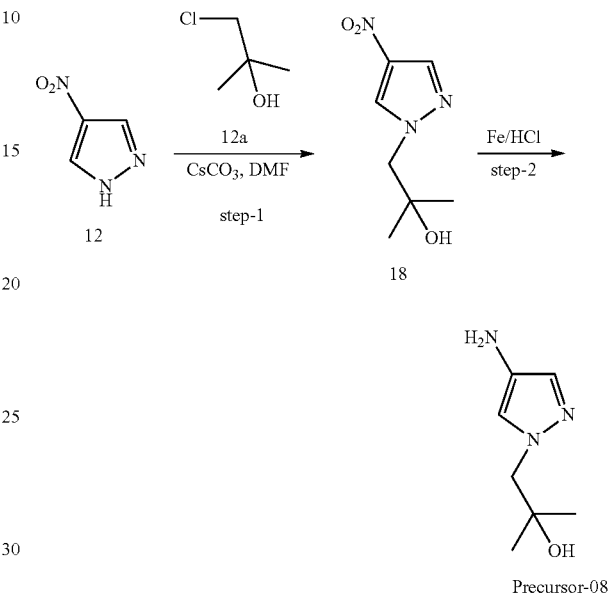

Synthesis of 2-methyl-1-(4-nitro-1H-pyrazol-1-yl)propan-2-ol (18)

To a stirred solution of 4-nitro-1H-pyrazole 12 (5.0 g, 44.0 mmol) and 1-chloro-2-methylpropan-2-ol 12a (9.5 g, 88.0 mmol) in DMF (60 mL), cesium carbonate (26 g, 88.0 mmol) was charged at room temperature. The reaction contents were heated at 100° C. for 14 h. The reaction mixture was cooled to room temperature, diluted with ethyl acetate (120 mL) and washed with water (2×100 mL). The organic layer was dried (Na$_2$SO$_4$), filtered and concentrated to give 2-methyl-1-(4-nitro-1H-pyrazol-1-yl)propan-2-ol 18 (5.2 g, 64% yield). $^1$HNMR (400 MHz, DMSO-d$_6$): δ 8.6 (s, 1H), 8.25 (s, 1H), 4.83 (s, 1H), 4.09 (s, 2H), 1.08 (s, 6H).

Synthesis of 1-(4-amino-1H-pyrazol-1-yl)-2-methyl-propan-2-ol (Precursor-08)

Iron (29.0 g, 54.0 mmol) was activated with catalytic HCl solution in 1,4-dioxane (4M, 0.7 mL, 2.7 mmol) and diluted with ethanol-dichloromethane mixture (1:1, 50 mL). The reaction mixture was charged with 2-methyl-1-(4-nitro-1H-pyrazol-1-yl)propan-2-ol 18 (5.0 g, 27.0 mmol) and put on stirring at reflux temperature for 16 h. The reaction mixture was concentrated and then diluted with sodium carbonate solution and dichloromethane (1:1, 50 mL). The reaction mixture was filtered on celite bed. The filtrate was partitioned. The organic layer was dried (Na$_2$SO$_4$), filtered and concentrated to obtain precursor-08 (2.7 g, 65% yield) as black solid. MS: 156.11 (M+H)$^+$.

Scheme 9: Synthesis of 5-methyl-4,5,6,7-tetrahydropyrazolo[1,5-a]pyrazin-2-amine (Precursor-09)

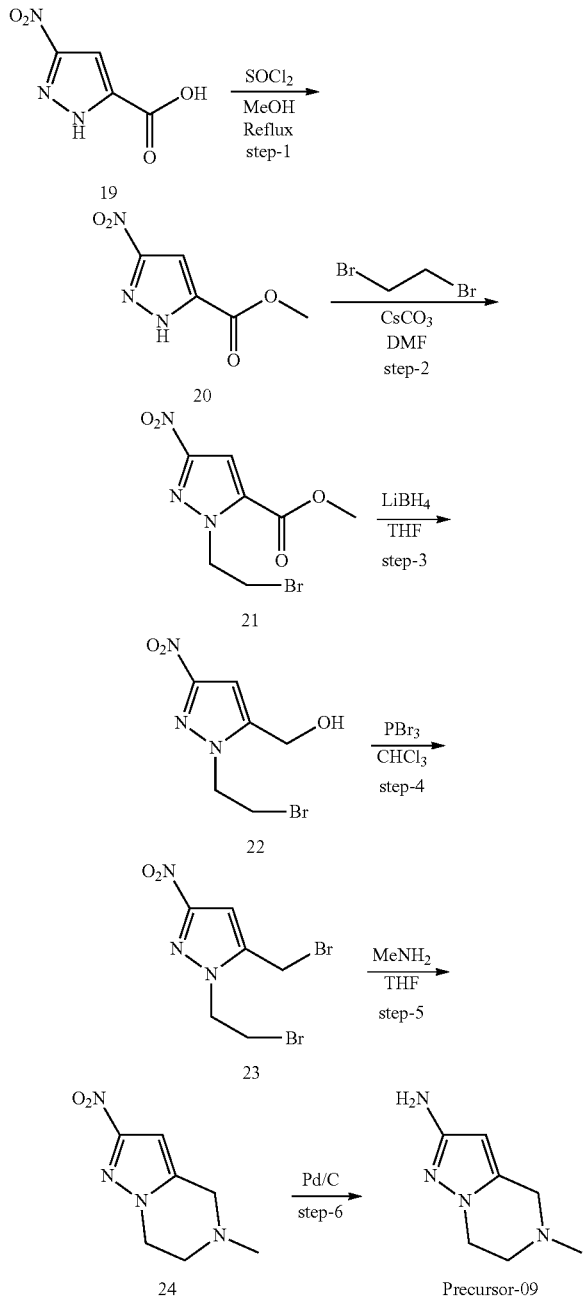

Synthesis of methyl 3-nitro-1H-pyrazole-5-carboxylate (20)

To a stirred solution of 3-nitro-1H-pyrazole-5-carboxylic acid 19 (2.0 g, 11.69 mmol)) in methanol (50 mL), thionyl chloride (2.07 g, 17.54 mmol) was charged at 0° C., in portions. The reaction mixture was heated at 70° C. for 4 hour. The reaction mixture was evaporated and basified with saturated sodium bicarbonate solution to pH 9. The aqueous layer was extracted with dichloromethane (2×100 mL). The combined organic extract was washed with water (3×30 mL). The organic layer was dried ($Na_2SO_4$), filtered and evaporated to obtain methyl 3-nitro-1H-pyrazole-5-carboxylate 20 (1.5 g, 74% yield) as brown sticky solid. MS: 171.03 $(M+H)^+$.

Synthesis of methyl 1-(2-bromoethyl)-3-nitro-1H-pyrazole-5-carboxylate (21)

To a stirred solution of 3-nitro-1H-pyrazole-5-carboxylate 20 (1.5 g, 0.87 mmol) in DMF (50 mL), cesium carbonate (5.7 g, 1.75 mmol) and then 1,2-dibromoethane (2.4 mL, 1.31 mmol) was charged portion wise at 0° C. The reaction mixture was heated at 100° C. for 4 hour. The reaction mixture was diluted with dichloromethane and water (2×100 mL). The combined organic extract was washed with water (3×30 mL). The organic layer was dried ($Na_2SO_4$), filtered and evaporated to obtain methyl 1-(2-bromoethyl)-3-nitro-1H-pyrazole-5-carboxylate 21 (2.0 g, quantitative yield) as brown sticky solid. MS: 276.97 $(M+H)^+$.

Synthesis of (1-(2-bromoethyl)-3-nitro-1H-pyrazol-5-yl)methanol (22)

To a stirred solution of methyl 1-(2-bromoethyl)-3-nitro-1H-pyrazole-5-carboxylate 21 (1.5 g, 0.54 mmol), in dry THF (60 mL), lithium borohydride (0.12 g, 0.54 mmol) was charged portion wise at 0° C. The reaction mixture was maintained under same condition for 4 hour. The reaction mixture was quenched with ammonium chloride solution (30 mL) and extracted with ethyl acetate (3×50 mL). The combined organic extract was dried ($Na_2SO_4$), filtered and evaporated to obtain (1-(2-bromoethyl)-3-nitro-1H-pyrazol-5-yl) methanol 22 (1.30 g, 97% yield) as brown solid. MS: 248.97 $(M+H)^+$.

Synthesis of 1-(2-bromoethyl)-5-(bromomethyl)-3-nitro-1H-pyrazole (23)

To a stirred suspension of (1-(2-bromoethyl)-3-nitro-1H-pyrazol-5-yl)methanol 22 (1.30 g, 0.52 mmol) in chloroform (50 mL), phosphorus tribromide (2.1 g, 0.78 mmol) was charged and refluxed for 2 hour. The reaction mixture was cooled to room temperature and basified with saturated sodium bicarbonate solution to pH 9. The aqueous layer was extracted with chloroform (2×100 mL). The combined organic extract was washed with water (3×30 mL). The organic layer was dried ($Na_2SO_4$), filtered and evaporated to obtain 1-(2-bromoethyl)-5-(bromomethyl)-3-nitro-1H-pyrazole 23 (1.30 g, 81% yield) as yellow solid. $^1$HNMR (400 MHz, DMSO-$d_6$): δ 7.20 (s, 1H), 4.86 (s, 2H), 4.71 (t, 2H), 3.93 (t, 2H).

Synthesis of 5-methyl-2-nitro-4,5,6,7-tetrahydropyrazolo[1,5-a]pyrazine (24)

To a stirred suspension of 1-(2-bromoethyl)-5-(bromomethyl)-3-nitro-1H-pyrazole 23 (1.30 g, 0.42 mmol)) in dry THF, methyl amine in THF (2M, 14.5 ml, 2.93 mmol) was charged at 0° C. The reaction was maintained at room temperature for 72 h. The reaction mixture was evaporated and basified with saturated sodium bicarbonate solution to pH 9. The aqueous layer was extracted with dichloromethane (2×100 mL). The combined organic extract was washed with water (3×30 mL). The organic layer was dried ($Na_2SO_4$), filtered and evaporated to obtain 5-methyl-2-nitro-4,5,6,7-tetrahydropyrazolo[1,5-a]pyrazine 24 (0.70 g, 92% yield) as white solid. ¹HNMR (400 MHz, DMSO-d₆): δ 6.84 (s, 1H), 4.20 (t, 2H), 3.62 (s, 2H), 2.90 (t, 2H), 2.39 (s, 3H).

Synthesis of 5-methyl-4,5,6,7-tetrahydropyrazolo[1,5-a]pyrazin-2-amine (Precursor-09)

To a stirred solution of 5-methyl-2-nitro-4,5,6,7-tetrahydropyrazolo[1,5-a]pyrazine 24 (0.50 g, 0.27 mmol) in ethanol (50 mL), palladium-carbon (0.15 g) was charged and stirred under hydrogen pressure (1 atm) for 12 hour. The reaction mixture was filtered through celite bed. The filtrate was evaporated to obtain 5-methyl-2-amino-4,5,6,7-tetrahydropyrazolo[1,5-a]pyrazine precursor-09 (0.45 g, quantitative yield) as brown sticky solid. ¹HNMR (400 MHz, DMSO-d₆): δ 5.15 (s, 1H), 4.47 (s, 2H), 3.80 (t, 2H), 3.32 (s, 2H), 2.70 (t, 2H), 2.31 (s, 3H). MS: 153.11 (M+H)⁺.

Scheme-10: Synthesis of 5-(methoxymethyl)-1-methyl-1H-pyrazol-3-amine (Precursor-10)

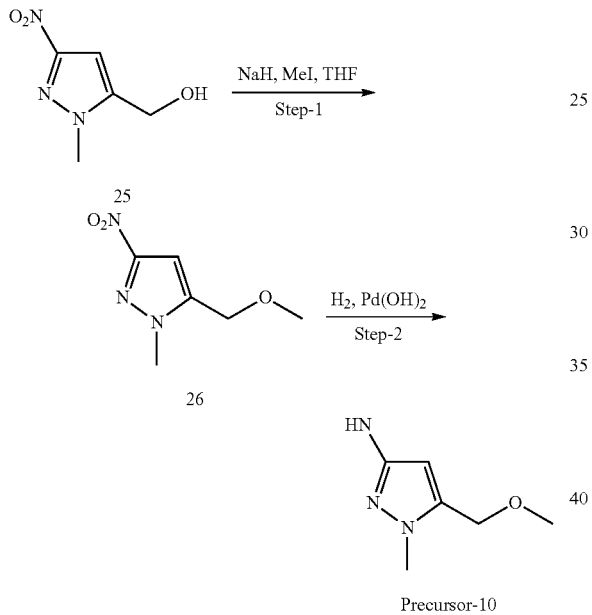

Synthesis of 5-(methoxymethyl)-1-methyl-3-nitro-1H-pyrazole (26)

To a stirred solution of (1-methyl-3-nitro-1H-pyrazol-5-yl)methanol 25 (1.0 g, 6.36 mmol) in THF (10 mL), sodium hydride (60% in mineral oil, 0.38 g, 9.55 mmol) was charged at 0° C., in portions. After 10 minutes, methyl iodide (0.6 mL, 9.55 mmol) was charged and reaction mixture was stirred at room temperature for 1 h. The reaction mixture was diluted with dichloromethane (50 mL) and washed with water (3×30 mL). The organic layer was dried (Na₂SO₄) and evaporated to obtain 5-(methoxymethyl)-1-methyl-3-nitro-1H-pyrazole 26 (0.80 g, 72% yield) as white solid. ¹HNMR (400 MHz, DMSO-d₆): δ 7.07 (s, 1H), 4.52 (s, 2H), 3.96 (s, 3H), 3.32 (s, 3H).

Synthesis of 5-(methoxymethyl)-1-methyl-1H-pyrazol-3-amine (Precursor-10)

To a stirred solution of 5-(methoxymethyl)-1-methyl-3-nitro-1H-pyrazole 26 (0.70 g, 4.09 mmol) in methanol (50 mL), palladium hydroxide (0.04 g) was charged and stirred under hydrogen pressure (1 atm) for 12 hour. The reaction mixture was filtered through celite bed. The filtrate was evaporated to obtain precursor-10 (0.53 g, 92% yield) as brown sticky solid. MS: 142.09 (M+H)⁺.

Scheme-11: Synthesis of 3,5-dimethyl-1-(1-methylpiperidin-4-yl)-1H-pyrazol-4-amine (Precursor-11)

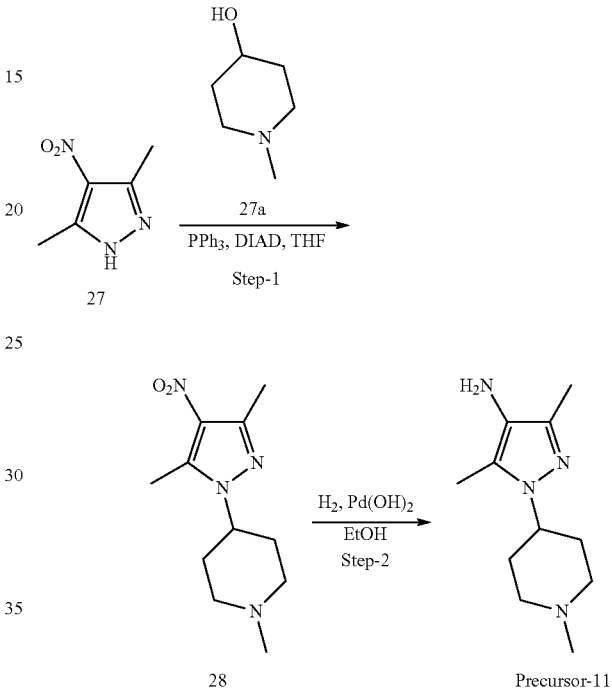

Synthesis of 4-(3,5-dimethyl-4-nitro-1H-pyrazol-1-yl)-1-methylpiperidine (28)

Diisopropyl azodicarboxylate (2.60 g, 12.75 mmol) was added dropwise to a cooled solution of 3,5-dimethyl-4-nitro-1H-pyrazole 27 (1.5 g, 10.63 mmol), triphenylphosphine (3.60 g, 13.82 mmol) and 1-methylpiperidin-4-ol 27a (1.2 g, 10.63 mmol) in THF (50 mL) at 0° C. The resulting solution was stirred for 30 minutes under same condition and for 24 h at room temperature. The mixture was partitioned between dichloromethane (200 mL) and aqueous HCl (1M, 50 mL). The organic phase was separated and then washed with aqueous HCl (1M, 2×25 mL). The combined aqueous phases were made basic by the addition of 40% NaOH solution and then extracted with dichloromethane (3×50 mL). The combined organic extracts were washed with brine, dried (Na₂SO₄), filtered and evaporated. The residue was purified by column chromatography (SiO₂, 10% MeOH-DCM) to afford 28 as brown sticky solid (2.0 g, 80% yield). MS: 239.14 (M+H)⁺.

Synthesis of 3,5-dimethyl-1-(1-methylpiperidin-4-yl)-1H-pyrazol-4-amine (Precursor-11)

To a solution of 4-(3,5-dimethyl-4-nitro-1H-pyrazol-1-yl)-1-methylpiperidine 28 (1.80 g, 18.06 mmol) in EtOH was added 10% palladium hydroxide (0.36 g) under nitrogen atmosphere. The resulting reaction mixture was stirred for 24 h at room temperature under hydrogen gas pressure (1 atm). The reaction mixture was filtered through celite bed. The filtrate was evaporated under reduced pressure to obtain precursor-11 as a dark brown solid (1.2 g, 80% yield). MS: 209.14 (M+H)$^+$.

Scheme-12: Synthesis of 1,3,5-trimethyl-1H-pyrazol-4-amine (Precursor-12)

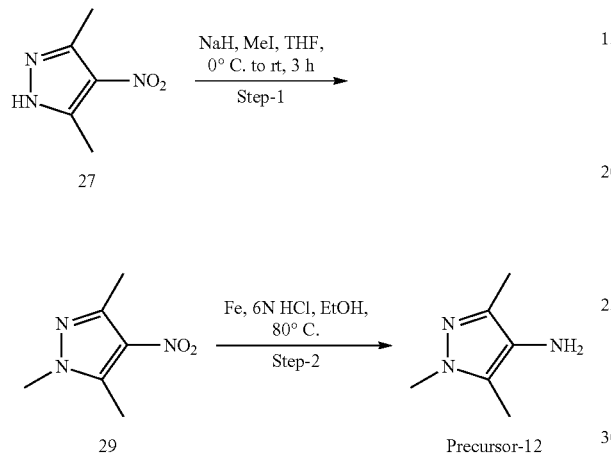

Scheme-13: Synthesis of 1-(1-(2-fluoroethyl)piperidin-4-yl)-1H-pyrazol-4-amine (Precursor-13)

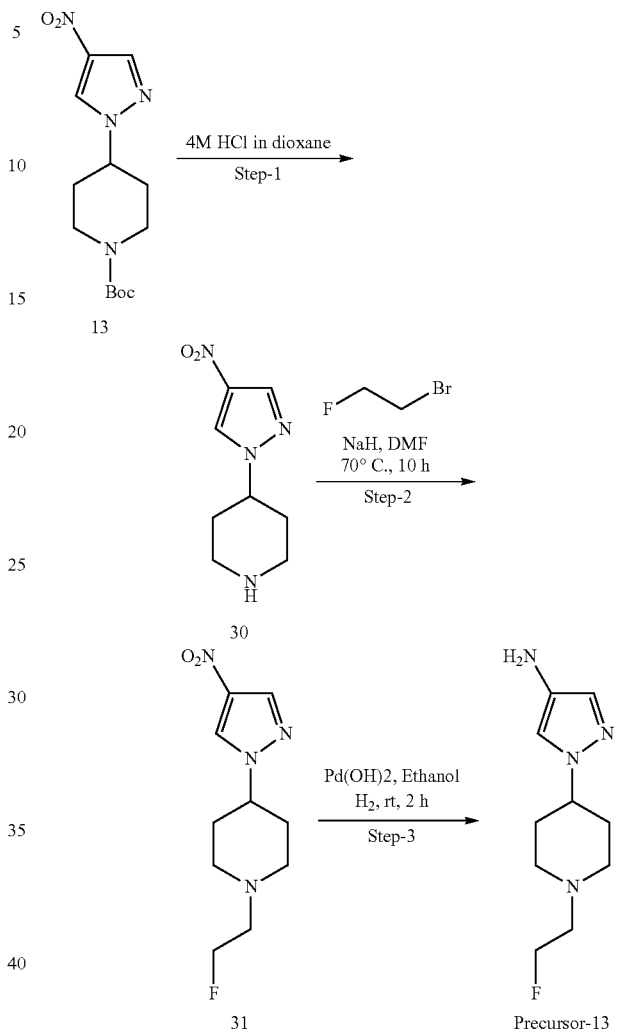

Synthesis of 1,3,5-trimethyl-4-nitro-1H-pyrazole (29)

To a stirred solution of 3,5-dimethyl-4-nitro-1H-pyrazole 27 (2.0 g, 1.41 mmol) in THF (20 mL), sodium hydride (0.4 g, 60% in mineral oil, 2.82 mmol) was charged at 0° C. After stirring for 10 minutes, iodomethane (0.87 mL, 1.41 mmol) was charged and stirred at room temperature for 2 h. The reaction mixture was diluted with water (50 mL) and ethyl acetate (50 mL). The organic layer was dried (Na$_2$SO$_4$), filtered and evaporated to obtain 1,3,5-trimethyl-4-nitro-1H-pyrazole 29 (2.1 g, 95% yield). $^1$HNMR (400 MHz, DMSO-d$_6$): δ 3.77 (s, 3H), 2.59 (s, 3H), 2.56 (s, 3H).

Synthesis of 1,3,5-trimethyl-1H-pyrazol-4-amine (Precursor-12)

To a solution of 1,3,5-trimethyl-4-nitro-1H-pyrazole 29 (2.1 g, 1.35 mmol) in EtOH (30 mL), iron powder (14.85 g, 27 mmol) and HCl in water (6N, 0.23 mL, 0.67 mmol) were charged and refluxed for 16 h. After the completion of reaction (TLC monitored), solvent was evaporated under reduced pressure. The crude mixture was basified with aqueous sodium hydroxide (0.5 N) solution and extracted with 10% MeOH-DCM (10%, 50 mL). The organic layer was dried (Na$_2$SO$_4$), filtered and evaporated to obtain precursor-12 as a beige solid (1.68 g, 99% yield). $^1$HNMR (400 MHz, DMSO-d$_6$): δ 3.50 (s, 3H), 3.27 (bs, 2H), 2.03 (s, 3H), 1.94 (s, 3H).

Synthesis of 4-(4-nitro-1H-pyrazol-1-yl)piperidine (30)

To a stirred suspension of tert-butyl 4-(4-nitro-1H-pyrazol-1-yl)piperidine-1-carboxylate 13 (0.8 g, 2.7 mmol) in dichloromethane (10.0 mL), 4M dioxane in HCl was charged and put on room temperature for 4 h. The reaction mixture was evaporated and basified with saturated sodium bicarbonate solution to pH 9. The aqueous layer was extracted with dichloromethane (2×50 mL). The combined organic extract was washed with water (3×10 mL). The organic layer was dried (Na$_2$SO$_4$), filtered and evaporated to obtain 4-(4-nitro-1H-pyrazol-1-yl)piperidine 30 (0.45 g, 85% yield). MS: 197.06 (M+H)$^+$.

Synthesis of 1-(2-fluoroethyl)-4-(4-nitro-1H-pyrazol-1-yl)piperidine (31)

To an ice-cold stirred solution of 4-(4-nitro-1H-pyrazol-1-yl) piperidine 30 (0.4 g, 2.04 mmol) in DMF (15 mL), sodium hydride (60% in mineral oil, 0.15 g, 3.06 mmol) was added to the reaction mixture followed by addition of 1-bromo-2-flouro ethane and then heated the reaction mixture to 70° C. for 10 h. After reaction was completed reaction mixture was quenched with water, compound was extracted with EtOAc (3×25 mL), dried over Na$_2$SO$_4$, concentrated, crude was purified by column chromatography (SiO$_2$ 100-200 mesh) by eluting 70% EtOAc-hexane, to get 1-(2-flouro Ethyl)-4-(4-nitro-1H-pyrazol-1-yl) piperidine 31 (0.280 g, 57% yield). $^1$HNMR (400 MHz, CDCl$_3$): δ 8.16 (s, 1H), 8.07 (s, 1H), 4.65 (t, 1H), 4.53 (t, 1H), 4.12-4.14 (m, 1H), 3.09-3.12 (m, 2H), 2.79 (t, 1H), 2.72 (t, 1H), 2.10-2.18 (m, 2H), 2.21-2.27 (m, 2H), 2.00-2.09 (m, 2H). MS: 243.12 (M+H)$^+$.

Synthesis of 1-(1-(2-fluoroethyl)piperidin-4-yl)-1H-pyrazol-4-amine (Precursor-13)

To a stirred solution of 1-(2-flouroethyl)-4-(4-nitro-1H-pyrazol-1-yl)piperidine 31 (0.25 g, 1 mmol) in Ethanol (10 mL) was added Pd(OH)$_2$ (0.025 g, 10% w/w) and the resulting reaction mixture was stirred under hydrogen atmosphere (1 atm) for 2 h. After reaction was completed, Pd(OH)$_2$ was filtered through celite bed, washed with ethyl acetate and the filtrate was distilled out. The crude was purified by 50% diethyl ether/pentane washing to get, 1-(1-(2-flouro Ethyl) piperidin-4-yl)-1H-pyrazol-4-amine precursor-13 as a brick red solid (0.17 g, 77% yield). $^1$HNMR (400 MHz, CDCl$_3$): δ 7.15 (s, 1H), 6.99 (s, 1H), 4.65 (t, 1H), 4.53 (t, 1H), 4.12-4.14 (m, 1H), 3.09-3.12 (m, 2H), 2.79 (t, 1H), 2.72 (t, 1H), 2.10-2.18 (m, 2H), 2.21-2.27 (m, 2H), 2.00-2.09 (m, 2H). MS: 213.12 (M+H)$^+$.

Scheme-14: Synthesis of 1-(cyclopropylsulfonyl)-1H-pyrazol-4-amine (Precursor-14)

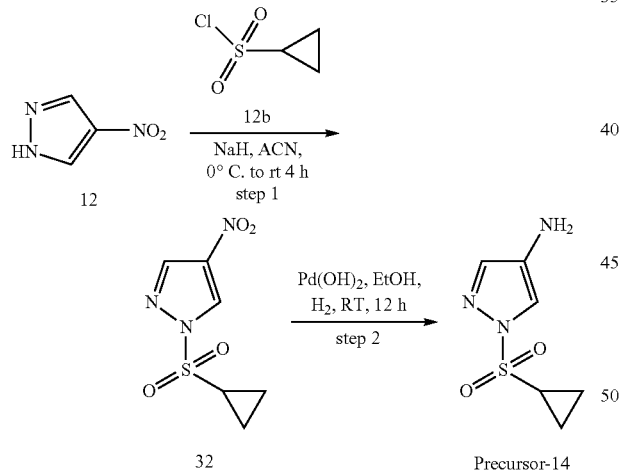

Synthesis of 1-(cyclopropylsulfonyl)-4-nitro-1H-pyrazole (32)

To a stirred suspension of sodium hydride (0.25 g, 60% in mineral oil, 10.5 mmol) in acetonitrile, a solution of 4-nitro-1H-pyrazole 12 (1.0 g, 7.0 mmol) and cyclopropyl sulfonyl chloride 12b (0.80 g, 7.0 mmol) in acetonitrile was charged and stirred for 16 h at room temperature. The reaction mixture was diluted with water (100 mL) and extracted with EtOAc (3×150 mL). The combined organic phase was separated, washed with water, dried over Na$_2$SO$_4$, concentrated in vacuo to give 1-(cyclopropylsulfonyl)-4-nitro-1H-pyrazole 32 (1.49 g, 82% yield). $^1$HNMR (400 MHz, DMSO-d$_6$): δ 9.42 (s, 1H), 8.20 (s, 1H), 1.41-1.24 (m, 5H).

Synthesis of 1-(cyclopropylsulfonyl)-1H-pyrazol-4-amine (Precursor-14)

To a stirred solution of 1-(cyclopropylsulfonyl)-4-nitro-1H-pyrazole 32 (1.0 g, 4.60 mmol) in EtOH (25 mL), 0.20 g of Pd(OH)$_2$ was added and stirred reaction under H$_2$ gas (1 atm) for 14 h. The reaction mixture was filtered through celite bed. The filtrate was evaporated to get crude product. The crude residue was triturated with ether to obtain 1-(cyclopropylsulfonyl)-1H-pyrazol-4-amine as off white solid precursor-14 (0.79 g, 81% yield). MS: 188.04 (M+H)$^+$.

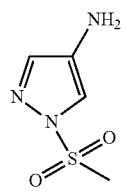

MS: 162.03 (M+H)$^+$.

Scheme-15: Synthesis of 2-methylpyrazolo[1,5-a]pyrimidin-7-amine (Precursor-16)

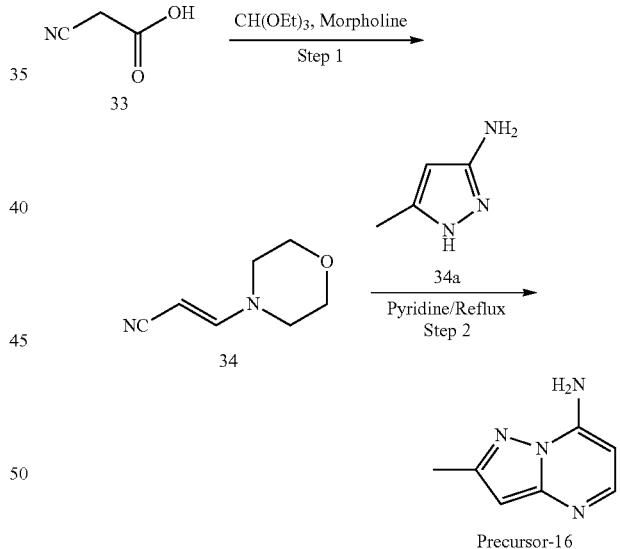

Synthesis of 3-morpholinoacrylonitrile (34)

The mixture of cyanoacetic acid 33 (10.0 g, 117.6 mmol), morpholine (12.30 g, 117.6 mmol) and triethylorthoformate (17.4 g, 117.6 mmol) was refluxed for 3 h. The reaction mixture was cooled to room temperature, basified with 1M NaOH solution to pH 10 and extracted with dichloromethane (3×100 mL). The organic layer was dried (Na$_2$SO$_4$) and evaporated to obtain 3-morpholinoacrylonitrile 34 (11.0 g, 75% yield) as brown oil. $^1$HNMR (400 MHz, CDCl$_3$): δ 7.16 (d, 1H), 4.16 (d, 1H), 3.57 (bs, 4H), 3.17 (bs, 4H). MS: 139 (M+H)$^+$.

Synthesis of 2-methylpyrazolo[1,5-a]pyrimidin-7-amine (Precursor-16)

To a stirred solution of 3-morpholinoacrylonitrile 34 (3.0 g, 21.7 mmol) in pyridine (15 mL), 5-methyl-1H-pyrazol-3-amine 34a (2.1 g, 21.7 mmol) was charged and refluxed for 48 h. The reaction mixture was evaporated to dryness. The crude mixture was purified by column chromatography (SiO$_2$, 230-400 mesh size, 5% MeOH/DCM) to obtain 2-methylpyrazolo[1,5-a]pyrimidin-7-amine precursor-16 (1.20 g, 37% yield). $^1$HNMR (400 MHz, CDCl$_3$): δ 7.96 (d, 1H), 7.58 (bs, 2H), 6.19 (s, 1H), 5.97 (d, 1H), 2.38 (s, 3H). MS: 149 (M+H)$^+$.

Scheme-16: Synthesis of 1-(oxetan-3-yl)-1H-pyrazol-4-amine (Precursor-17)

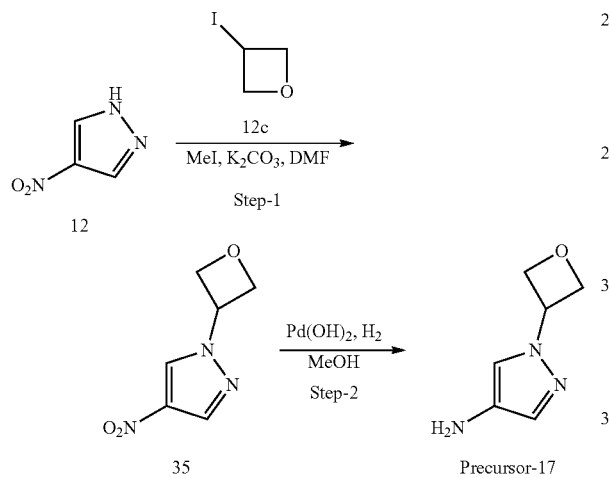

Synthesis of 4-nitro-1-(oxetan-3-yl)-1H-pyrazole (35)

To a stirred solution of 4-nitro-1H-pyrazole 12 (0.60 g, 5.3 mmol) and 3-iodooxitane 12c (1.10 g, 5.8 mmol) in DMF (20 mL), cesium carbonate (1.9 g, 5.8 mmol) was charged and the mixture was stirred at 100° C. for 24 h. Water was added and extracted with ethyl acetate. The organic layer was dried over anhydrous sodium sulfate, filtered and solvents removed under reduced pressure to obtain 4-nitro-1-(oxetan-3-yl)-1H-pyrazole 35 in 68% yield as a dark brown oil. $^1$HNMR (400 MHz, DMSO-d$_6$): δ 9.03 (s, 1H), 8.41 (s, 1H), 5.68-5.61 (m, 1H), 4.94-4.87 (m, 4H).

Synthesis of 1-(oxetan-3-yl)-1H-pyrazol-4-amine (Precursor-17)

To a stirred solution of 4-nitro-1-(oxetan-3-yl)-1H-pyrazole 2 (0.60 g, 3.6 mmol) in MeOH (50 mL), palladium hydroxide (0.60 g) was charged and stirred under hydrogen pressure (1 atm) for 8 h. The reaction mixture was filtered through celite bed. The filtrate was evaporated to obtain 1-(oxetan-3-yl)-1H-pyrazol-4-amine precursor-17 in 91% yield as brown solid. $^1$HNMR (400 MHz, DMSO-d$_6$): δ 7.16 (s, 1H), 7.03 (s, 1H), 5.39-5.32 (m, 1H), 4.98-4.79 (m, 4H), 3.90 (s, 2H).

Precursor-18 was prepared following procedure similar to scheme-16 using 12 and iodobutane

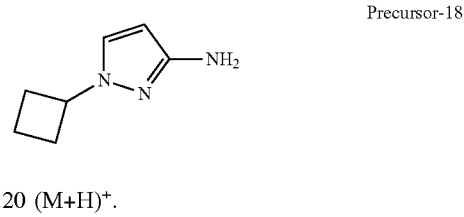

Precursor-18

MS: 138.20 (M+H)$^+$.

Scheme-17: Synthesis of 3-(4-amino-1H-pyrazol-1-yl)cyclopentanol (Precursor-19)

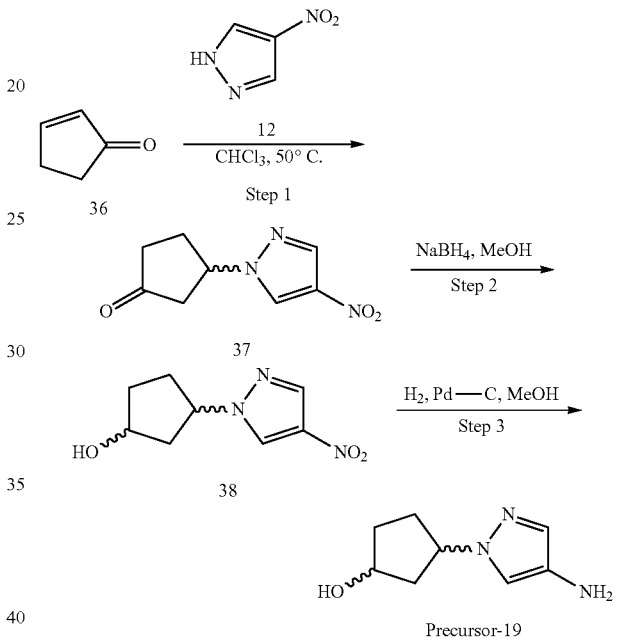

Synthesis of 3-(4-nitro-1H-pyrazol-1-yl)cyclopentanone (37)

Cyclopent-2-enone 36 (2.50 g, 30.40 mmol) and 4-nitro-1H-pyrazole (5.16 g, 45.7 mmol) were taken in chloroform (20 mL) and heated at 50° C. for 24 h. Water was added, the organic phase was separated, dried over anhydrous sodium sulfate, filtered and solvents evaporated to obtain a crude material, purification of which by flash chromatography on silica gel (100-200 mesh, 20% EtOAc-hexane) gave 3-(4-nitro-1H-pyrazol-1-yl)cyclopentanone 37 (7.0 g) as a off white solid. $^1$H NMR (400 MHz, DMSO-d$_6$): δ 9.02 (s, 1H), 8.30 (s, 1H), 5.19-5.13 (m, 1H), 2.85-2.80 (m, 1H), 2.67-2.61 (m, 1H), 2.44-2.22 (m, 4H).

Synthesis of 3-(4-nitro-1H-pyrazol-1-yl)cyclopentanol (38)

To a cooled (0° C.) solution of 3-(4-nitro-1H-pyrazol-1-yl)cyclopentanone 37 (6.00 g, 30.6 mmol) in MeOH (50 mL) under nitrogen atmosphere, sodium borohydride (2.30 g, 61.4 mmol) was added and the mixture was stirred at 0° C. for 10 min. The reaction was quenched by adding few drops of chilled water, solvents evaporated and the crude obtained was purified by flash chromatography on silica gel (100-200 mesh, 25% EtOAc-hexane as eluent) to obtain 3-(4-nitro-1H-pyrazol-1-yl)cyclopentanol 38 (4.0 g) as a yellow oil. $^1$H NMR (400 MHz, DMSO-$d_6$): δ 8.90 (s, 1H), 8.26 (s, 1H), 4.90-4.70 (m, 2H), 4.40-4.00 (m, 1H), 2.40-2.30 (m, 1H), 2.20-1.90 (m, 2H), 1.90-1.80 (m, 1H), 1.80-1.55 (m, 2H).

Synthesis of 3-(4-amino-1H-pyrazol-1-yl)cyclopentanol (Precursor-19)

To a stirred solution of 3-(4-nitro-1H-pyrazol-1-yl)cyclopentanol 38 (1.0 g, 5.07 mmol) in MeOH (20 mL), palladium hydroxide (0.10 g) was charged and stirred under hydrogen pressure (1 atm) for 8 h. The reaction mixture was filtered through celite bed. The filtrate was evaporated to get the desired product precursor-19 as dark brown sticky oil (0.75 g, 88% yield). MS: 168.09 (M+H)$^+$.

Precursor-20 was prepared following procedure similar to scheme-17 using cyclohex-2-enone and nitropyrazole

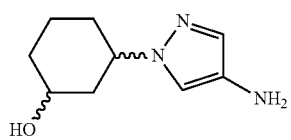

Precursor-20

MS: 182.04 (M+H)$^+$.

Scheme-18: Synthesis of 5-(4-methylpiperazin-1-yl)-1,3,4-thiadiazol-2-amine (Precursor-21)

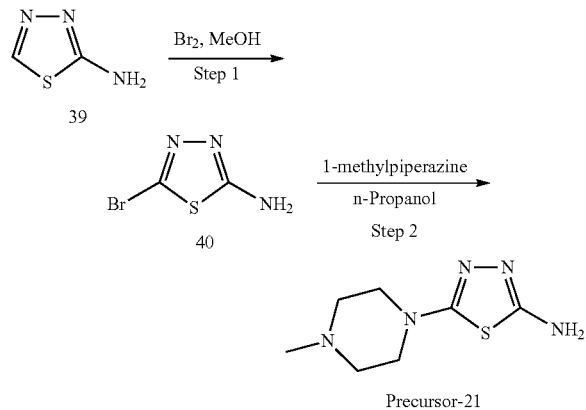

Synthesis of 5-bromo-1,3,4-thiadiazol-2-amine (40)

1,3,4-Thiadiazol-2-amine 39 (5.0 g, 49.5 mmol) was dissolved in MeOH (180 mL) under nitrogen atmosphere. Bromine (11.88 g, 74.25 mmol) was added and the mixture was stirred at rt for 6 h. On complete consumption of starting material, solvent was evaporated under reduced pressure added water and extracted with ethyl acetate. The organic extract was washed with brine, dried over anhydrous sodium sulfate, filtered and solvent evaporated to obtain 5-bromo-1,3,4-thiadiazol-2-amine 40 (2.30 g, 26% yield) as a brown solid. MS: 179.92 (M+H)$^+$.

Synthesis of 5-(4-methylpiperazin-1-yl)-1,3,4-thiadiazol-2-amine (Precursor-21)

5-Bromo-1,3,4-thiadiazol-2-amine 40 (2.20 g, 12.29 mmol) and 1-methylpiperazine (2.46 g, 24.6 mmol) were heated in n-propanol (30 mL) in a sealed tube at 100° C. for 8 h. The reaction was cooled to rt, solvents evaporated under reduced pressure and the crude obtained was triturated with MeOH to obtain 5-(4-methylpiperazin-1-yl)-1,3,4-thiadiazol-2-amine precursor-21 (1.3 g, 53% yield) as an off white solid. MS: 200.16 (M+H)$^+$.

Scheme-19: Synthesis of 4-(4-amino-1H-pyrazol-1-yl)piperidin-2-one (Precursor-22)

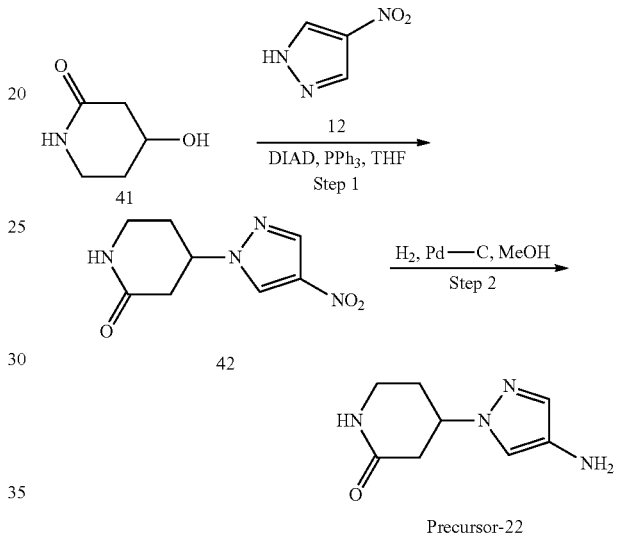

Synthesis of 4-(4-nitro-1H-pyrazol-1-yl)piperidin-2-one (42)

A solution of DIAD (5.3 g, 26.4 mmol) in dry THF (20 mL) was added to a solution of (4-hydroxypiperidin-2-one 41 (2.20 g, 19.4 mmol), 4-nitro-1H-pyrazole (2.0 g, 17.6 mmol) and triphenylphosphine (6.9 g, 26.4 mmol) in dry THF (80 mL) drop-wise at 0° C. over a period of 10 min. The mixture was then stirred at room temperature for 16 h. Solvents evaporated under reduced pressure to obtain a crude solid, which was purified by flash chromatography on silica gel using ethyl acetate as eluent to obtain 3 4-(4-nitro-1H-pyrazol-1-yl)piperidin-2-one 42 (1.8 g, 48% yield) as a white solid. $^1$H NMR (400 MHz, DMSO-$d_6$): δ 8.96 (s, 1H), 8.31 (s, 1H), 7.71 (s, 1H), 4.83-4.79 (m, 1H), 3.25-3.15 (m, 2H), 2.69-2.67 (m, 2H), 2.20-2.17 (m, 1H), 2.13-2.06 (m, 1H).

Synthesis of 4-(4-amino-1H-pyrazol-1-yl)piperidin-2-one (Precursor-22)

Title compound was prepared in a manner similar to procedure mentioned in step 3 of Scheme-17. MS: 181.02 (M+H)$^+$.

Scheme-20: Synthesis of 1-(8-methyl-8-azabicyclo[3.2.1]octan-3-yl)-1H-pyrazol-4-amine (Precursor-23)

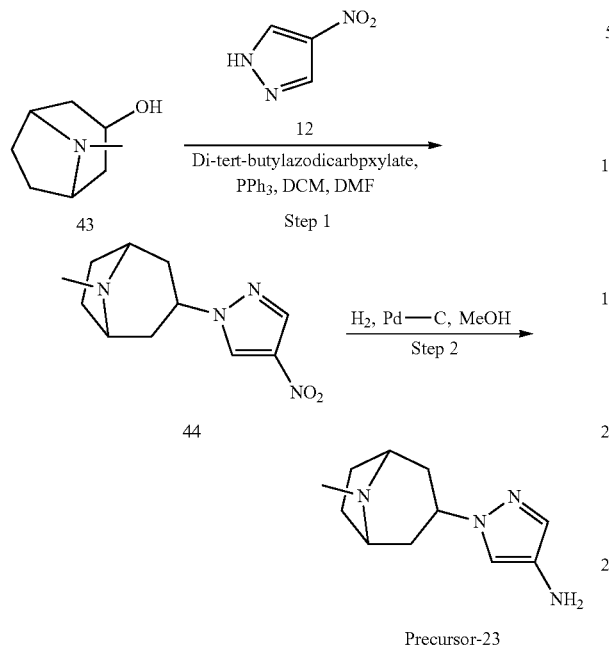

Precursor-23

Synthesis of 8-methyl-3-(4-nitro-1H-pyrazol-1-yl)-8-azabicyclo[3.2.1]octane (44)

A solution of 8-methyl-8-azabicyclo[3.2.1]octan-3-ol 43 (3.0 g, 29.2 mmol), 4-nitro-1H-pyrazole (3.0 g, 26.5 mmol) in a mixture of DMF (30 mL) and DCM (60 mL) was cooled to 0° C. and triphenylphosphine (20.0 g, 79.5 mmol) was added. The mixture was stirred for 10 min followed by addition of di-tert-butylazodicarboxylate (18.2 g, 79.5 mmol) and the mixture was stirred at rt for 4 days. Solvents evaporated under reduced pressure and the crude obtained was purified by flash chromatography on silica gel using 5% MeOH-DCM as eluent to obtain 8-methyl-3-(4-nitro-1H-pyrazol-1-yl)-8-azabicyclo[3.2.1]octane 44 (1.50 g, 36% yield) as an off white solid. $^1$H NMR (400 MHz, DMSO-d$_6$): δ 8.90 (s, 1H), 8.34 (s, 1H), 4.92-4.87 (m, 1H), 4.00 (s, 2H), 2.68 (s, 3H), 2.57-2.54 (m, 2H), 2.25-2.22 (m, 4H), 2.05-2.03 (m, 2H).

Synthesis of 1-(8-methyl-8-azabicyclo[3.2.1]octan-3-yl)-1H-pyrazol-4-amine (Precursor-23)

Title compound was prepared following procedure similar to mentioned in step 3 of Scheme-17 in 75% yield. MS: 207.20 (M+H)$^+$.

Scheme-21: Synthesis of 1-(tetrahydrofuran-3-yl)-1H-pyrazol-4-amine (Precursor-24)

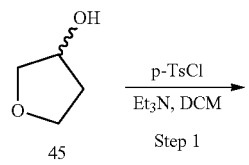

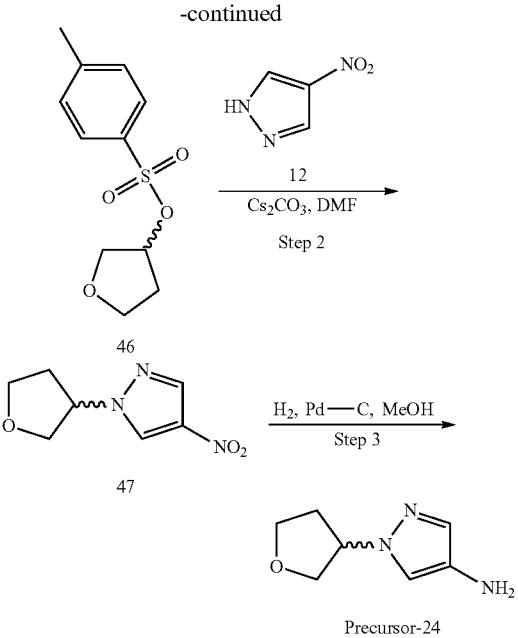

Precursor-24

Synthesis of tetrahydrofuran-3-yl 4-methylbenzenesulfonate (46)

To a cooled (0° C.) solution of DL-tetrahydrofuran-3-ol 45 (2.0 g, 22.7 mmol) in DCM (40 mL), triethylamine (9.0 mL, 68.1 mmol) was added followed by toluene-4-sulfonyl chloride (6.40 g, 34.0 mmol) and the mixture was stirred at rt for 30 min. Saturated sodium bicarbonate solution was added, the organic extract was separated, dried over anhydrous sodium sulfate and filtered. The filtrate was concentrated to dryness to obtain a white solid, which was purified by column chromatography on silica gel to obtain tetrahydrofuran-3-yl 4-methylbenzenesulfonate 46 (2.5 g, 45% yield) as an off white solid. $^1$H NMR (400 MHz, DMSO-d$_6$): δ 7.82-7.78 (d, 2H), 7.50-7.48 (d, 2H), 5.13-5.11 (m, 1H), 3.78-3.60 (m, 4H), 2.45 (s, 3H), 2.12-2.03 (m, 1H), 1.91-1.85 (m, 1H).

Synthesis of 4-nitro-1-(tetrahydrofuran-3-yl)-1H-pyrazole (47)

Tetrahydrofuran-3-yl 4-methylbenzenesulfonate 46 (2.5 g, 10.3 mmol), 4-nitro-1H-pyrazole (1.0 g, 9.2 mmol) and cesium carbonate (5.0 g, 15.4 mmol) were heated in dry DMF (15 mL) under nitrogen atmosphere at 80° C. for 16 h. The mixture was cooled to rt and partitioned between water and ethyl acetate, the organic extract was dried over anhydrous sodium sulfate, filtered and solvents evaporated under reduced pressure to obtain a solid, which was washed with n-pentane to obtain 4-nitro-1-(tetrahydrofuran-3-yl)-1H-pyrazole 47 (1.50 g, 79% yield) as an off white solid. $^1$H NMR (400 MHz, DMSO-d$_6$): δ 8.93 (s, 1H), 8.30 (s, 1H), 5.13-5.08 (m, 1H), 4.01-3.92 (m, 3H), 3.84-3.78 (m, 1H), 2.44-2.38 (m, 1H), 2.36-2.28 (m, 1H).

Synthesis of 1-(tetrahydrofuran-3-yl)-1H-pyrazol-4-amine (Precursor-24)

Title compound was prepared following procedure similar to mentioned in step 3 of Scheme-17 in 66% yield. MS: 154.0 (M+H)$^+$.

Scheme-22: Synthesis of a mixture of 1,3-dimethyl-1H-pyrazol-4-amine and 1,5-dimethyl-1H-pyrazol-4-amine (Precursor-25)

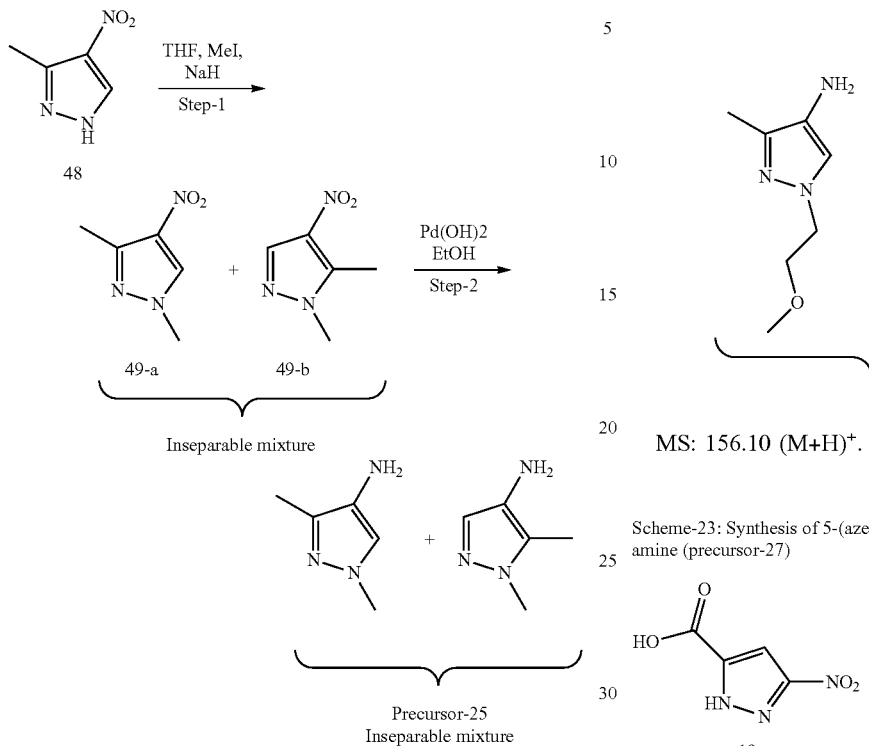

Precursor-26 was prepared following procedure similar to scheme-22 using corresponding alkyl halide and 3-methyl-4-nitro-1H-pyrazole

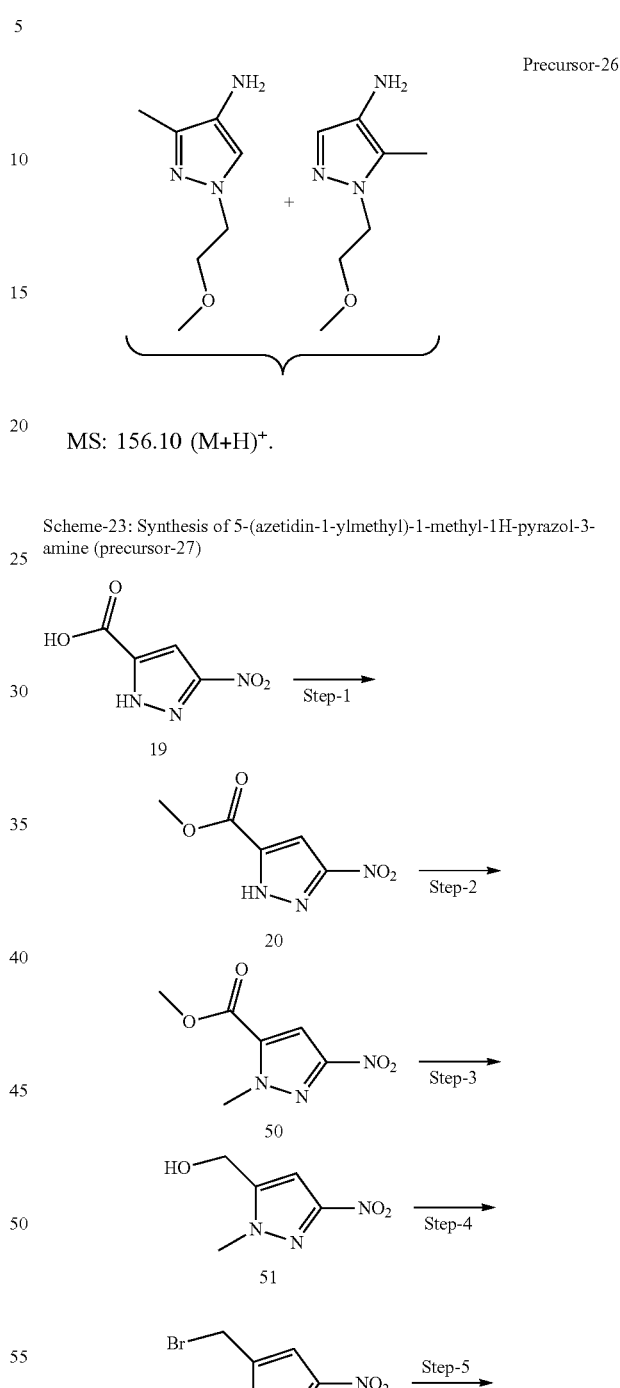

MS: 156.10 (M+H)⁺.

Scheme-23: Synthesis of 5-(azetidin-1-ylmethyl)-1-methyl-1H-pyrazol-3-amine (precursor-27)

Synthesis of a mixture of 1,3-dimethyl-4-nitro-1H-pyrazole and 1,5-dimethyl-4-nitro-1H-pyrazole (49-a and 49-b)

To a stirred suspension of sodium hydride (4.9 g, 60% in mineral oil, 20.74 mmol) in THF (100 mL), 3-methyl-4-nitro-1H-pyrazole 48 (10.0 g, 7.8 mmol) and iodomethane (21.0 g, 14.7 mmol) were charged at 0° C. Hydrogen gas evolved. The mixture was then stirred at room temperature for 4 h. The reaction mixture was diluted with water (100 mL) and extracted with EtOAc (3×150 mL). The combined organic phase was separated, washed with water, dried over $Na_2SO_4$, concentrated in vacuum to give an inseparable mixture of 1,3-dimethyl-4-nitro-1H-pyrazole 49-a and 1,5-dimethyl-4-nitro-1H-pyrazole 49-b (5.70 g, 78% yield) that was carried to the next step without further purification. ¹HNMR (400 MHz, CDCl₃): δ 8.04 (s, 1H), 3.84 (s, 3H), 2.52 (s, 3H).

Synthesis of a mixture of 1,3-dimethyl-1H-pyrazol-4-amine and 1,5-dimethyl-1H-pyrazol-4-amine (Precursor-25)

To a stirred solution 49-a and 49-b (5.7 g, 4.04 mmol) in ethanol (50 mL), 0.8 g of Pd(OH)₂ was added and then stirred reaction under H₂ gas atm for 14 h. After the completion of reaction (TLC monitoring), the solution was filtered through celite bed, washed with methanol and concentrated the solvent to get a crude mixture precursor-25 (3.0 g, 67% yield) that was carried as such for the next step without further purification. ¹HNMR (400 MHz, DMSO-d₆): δ 6.81 (s, 1H), 3.57 (s, 3H), 3.52 (s, 2H), 2.05 (s, 3H). MS: 112.08 (M+H)⁺.

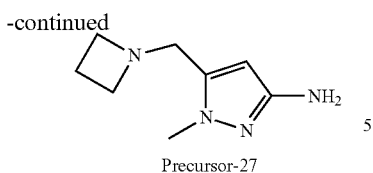

Precursor-27

Precursor-27 was synthesized starting from 3-nitro-1H-pyrazole-5-carboxylic acid as depicted in scheme 23 by the procedure described in PCT Int. Appl., 2012020008.

Similarly, precursor-28 was prepared.

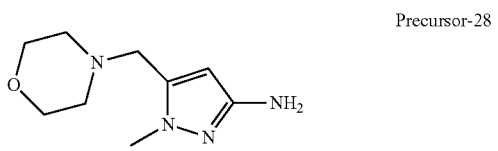

Precursor-28

MS: 197.20 (M+H)$^+$.

Scheme-24: Synthesis of 2-((3-aminocyclohexyl)methyl)isoindoline-1,3-dione (precursor-29) and tert-butyl (3-(aminomethyl)cyclohexyl)carbamate (precursor-30)

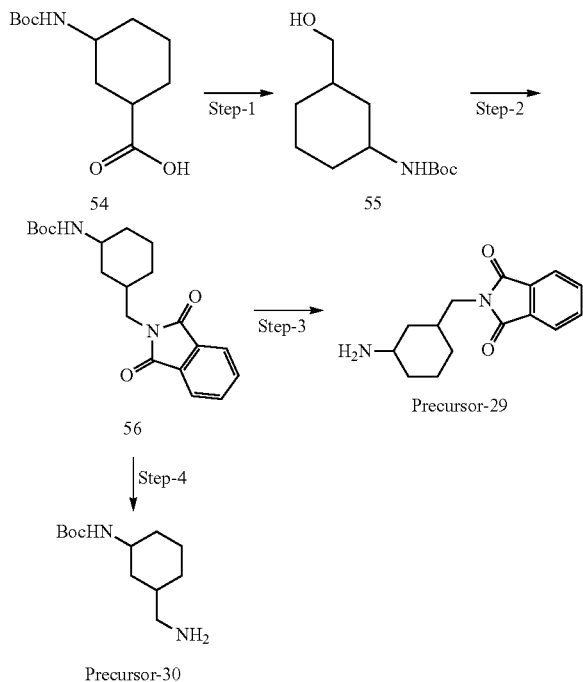

Synthesis of tert-butyl (3-(hydroxymethyl)cyclohexyl)carbamate (55)

To a stirred suspension of compound 54 (12.0 g, 49.00 mmol) in THF (60 mL), was drop wise added BH3.DMS (10.2 mL, 98.00 mmol) and stirred for 16 h at RT. Reaction was monitored by TLC, reaction mixture was quenched with saturated NaHCO$_3$ Solution at 0° C. & was extracted twice with ethyl acetate, organic layer was washed with water followed by brine solution, organic extracts were dried over Na$_2$SO$_4$ and concentrated to obtain transparent liquid compound as tert-butyl (3-(hydroxymethyl)cyclohexyl)carbamate, which was carried forward without any further purification (10.0 g, 89% yield). MS: 230.20 (M+H)$^+$.

Synthesis of tert-butyl (3-((1,3-dioxoisoindolin-2-yl)methyl)cyclohexyl)carbamate (56)

To a stirred suspension of compound 55 (6.0 g, 26.00 mmol), phthalimide (5.8 g, 31.3 mmol) & triphenyl phosphine (10.2 g, 39 mmol) in THF (200 mL), was drop wise added DIAD (7.9 g, 39.00 mmol) and stirred for 16 h at RT. Reaction was monitored by TLC, reaction mixture was quenched with saturated NaHCO$_3$ solution at 0° C. & was extracted twice with ethyl acetate, organic layer washed with water followed by brine solution, organic extracts were dried over Na$_2$SO$_4$ and concentrated to obtain crude. The crude was further purified by combiflash using 0-40% ethyl acetate in hexane to obtain tert-butyl (3-((1,3-dioxoisoindolin-2-yl)methyl)cyclohexyl)carbamate 56 as a white solid (7.0 g, 75.18% yield). MS: 359.20 (M+H)$^+$.

Synthesis of 2-((3-aminocyclohexyl)methyl) isoindoline-1,3-dione (Precursor-29)

To a stirred suspension of compound 56 (2.5 g, 6.9 mmol) in DCM was drop wise added TFA. Reaction mixture was stirred at RT for 16 h, Reaction was monitored by TLC. Reaction mixture was concentrated to obtain crude 2-((3-aminocyclohexyl)methyl)isoindoline-1,3-dione, which was proceeded as such for next step (1.40 g, quantitative yield). MS: 259.16 (M+H)$^+$.

Synthesis of tert-butyl (3-(aminomethyl)cyclohexyl)carbamate (Precursor-30)

To a solution of tert-butyl (3-((1,3-dioxoisoindolin-2-yl)methyl)cyclohexyl)carbamate 56 (2.0 g, 5.5 mmol) in ethanol (30 mL) was added hydrazine hydrate (0.31 ml, 11.1 mmol). The reaction mixture was stirred for 4 h at 80° C. The reaction was monitored by TLC, after the completion of reaction; the reaction mixture was concentrated fully, residue obtained was diluted with EtOAc and washed with 10% NaOH solution twice. The organic layer was washed with brine solution and dried over sodium sulphate and evaporated under reduced pressure to obtain crude product. The crude product was carried forward as such for next step (1.50 g, quantitative yield). MS: 229.18 (M+H)$^+$.

Scheme-25: Synthesis of tert-butyl 4-amino-1H-pyrazole-1-carboxylate (precursor-31)

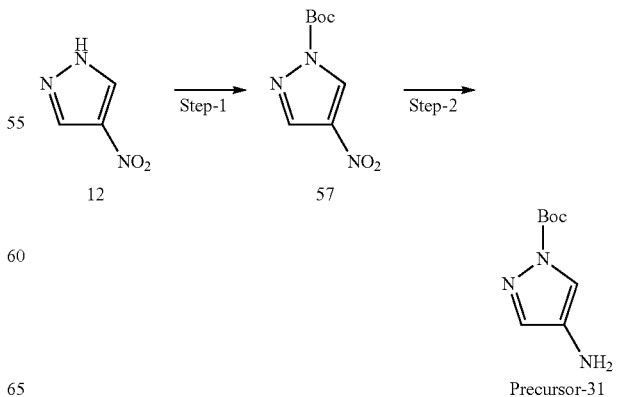

Precursor-31

Synthesis of tert-butyl 4-nitro-1H-pyrazole-1-carboxylate (57)

To a stirred suspension of 4-nitro-1H-pyrazole 12 (5.0 g, 44.22 mmol) & DMAP (0.54 g, 4.42 mmol) in DCM (500 mL), at 0° C. was drop wise added Boc anhydride (11.3 g, 53.06 mmol) and the reaction mixture was stirred at room temperature for about 4 h. Reaction mixture was quenched with 300 mL ice-water, DCM layer was separated & given brine wash & was dried over $Na_2SO_4$ and concentrated to obtain tert-butyl 4-nitro-1H-pyrazole-1-carboxylate (9.2 g, 97% Yield). $^1$HNMR (400 MHz, DMSO-d6): δ 9.30 (s, 1H), 8.53 (s, 1H), 1.60 (s, 9H).

Synthesis of tert-butyl 4-amino-1H-pyrazole-1-carboxylate (Precursor-31)

A round bottom flask was charged with tert-butyl 4-nitro-1H-pyrazole-1-carboxylate 57 (9.2 g, 43.17 mmol) and methanol (400 mL) followed by addition of Pd—C (10% w/w, 3.0 g). The flask was evacuated under vacuum and then purged with hydrogen. The reaction was stirred under hydrogen atmosphere (30 psi). The reaction was monitored by TLC. It was then filtered through sintered funnel with a pad of celite, washed with methanol and concentrated under reduced pressure to afford precursor-31 as a brown solid (5.7 g, 72% yield) that was taken as such for the next step without any further purification. $^1$H NMR (400 MHz, DMSO-$d_6$): δ 7.32-7.34 (m, 1H), 6.98 (s, 1H), 4.40 (s, 2H), 1.53 (s, 9H).

Scheme-26: Synthesis of 3-chloro-1-methyl-1H-pyrazol-4-amine

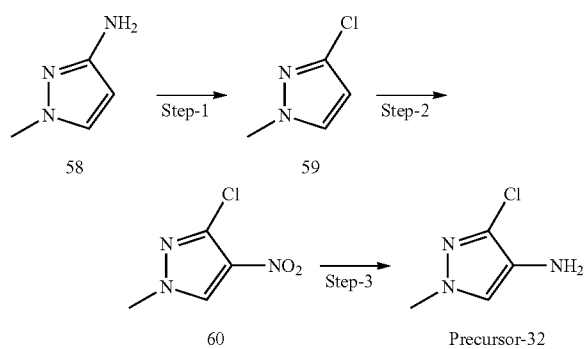

Synthesis of 3-chloro-1-methyl-1H-pyrazole (59)

To a stirred solution of 1-methyl-1H-pyrazol-3-amine 58 (5.0 g, 51.50 mmol) in Conc.HCl (40 mL) at 0° C., sodium nitrite (5.30 g, 77 mmol) in water was added at 0° C. and the mixture was stirred at RT for 30 min. Copper (I) chloride was dissolved in concentrated hydrochloric acid (10 mL) and added to the above mixture drop-wise. The reaction was heated at 60° C., catalytic amount of Cu(I)Cl was added at 60° C. (initiating the evolution of gas). Reaction mixture was stirred at 60° C. for 30 min. The mixture was then poured to chilled 50% NaOH solution & stirred properly; aqueous was extracted with DCM. The organic layer was washed with brine solution, dried over anhydrous sodium sulfate, filtered and solvents evaporated to obtain a crude product (5.50 g, quantitative yield). $^1$HNMR (400 MHz, $CDCl_3$): δ 7.27 (d, 1H), 6.15 (d, 1H), 3.85 (s, 3H).

Synthesis of 3-chloro-1-methyl-4-nitro-1H-pyrazole (60)

To a stirred solution of 3-chloro-1-methyl-1H-pyrazole 59 (4.0 g, 34 mmol) in Conc. H2SO4 (4.0 mL) was added Fuming HNO3 (3.6 g, 120.0 mmol) dropwise at 0° C. and the mixture was stirred at RT for 6 h. The mixture was then quenched slowly with ice, white solid precipitated out was filtered & dried over vacuum to obtain 3-chloro-1-methyl-4-nitro-1H-pyrazole (3.0 g, 54% yield) as white solid. $^1$HNMR (400 MHz, CDCl3): δ 8.16 (s, 1H), 3.94 (s, 3H).

Synthesis of 3-chloro-1-methyl-1H-pyrazol-4-amine (Precursor-32)

Raney nickel (0.5 g) was charged to a stirred solution of the 3-chloro-1-methyl-4-nitro-1H-pyrazole 60 (3.0 g, 18.6 mmol) in MeOH (30 mL) and hydrogenated under atmospheric pressure for 6 h. The catalyst was filtered off by passing the mixture through a celite bed and the filtrate was concentrated to obtain the desired product as crude. Crude was carried forward as such for next step. (1.90 g, 79% yield) $^1$HNMR (400 MHz, DMSO-d6): δ 7.09 (s, 1H), 3.88 (s, 2H), 3.64 (s, 3H).

Scheme-27: Synthesis of 5-nitro-2-((tetrahydrofuran-3-yl)oxy)aniline (Precursor-33)

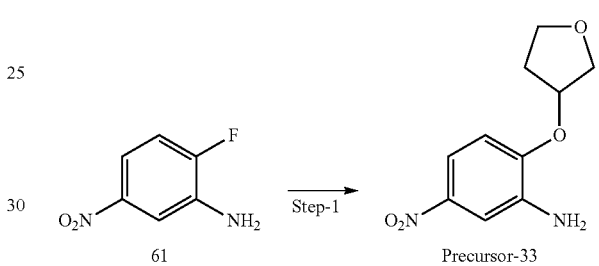

Synthesis of 5-nitro-2-((tetrahydrofuran-3-yl)oxy) aniline (Precursor-33)

To a stirred solution of 2-fluoro-5-nitroaniline 61 (2.0 g, 12.8 mmol) & tetrahydrofuran-3-ol (1.4 g, 16.65 mmol) in t-BuOH (20 ml) & DMF (4 ml) was dropwise added potassium tert Butoxide (1M in t-BuOH) (46 ml, 46.12 mmol) at RT was stirred at RT for 2 h, Reaction mixture was warmed to 40° C. for 4 h, reaction was monitored by TLC. After completion of reaction, reaction mixture was diluted with EtOAc and washed with brine solution. The organic phase was dried and concentrated to get crude material. The crude material was purified by flash column chromatography (SiO2), eluting with 40% EtOAc in hexane to get 5-nitro-2-((tetrahydrofuran-3-yl)oxy)aniline as brown liquid (1.0 g, 35% yield). $^1$HNMR (400 MHz, CDCl3): δ 7.66-7.63 (dd, 1H), 7.57-7.56 (m, 1H), 6.73 (d, 1H), 5.05-5.04 (m, 1H), 4.13-3.94 (m, 6H), 2.35-2.26 (m, 2H), MS: 225.03 (M+H)$^+$ Similarly prepared was the precursor-34 using 4-fluoro-3-nitroaniline.

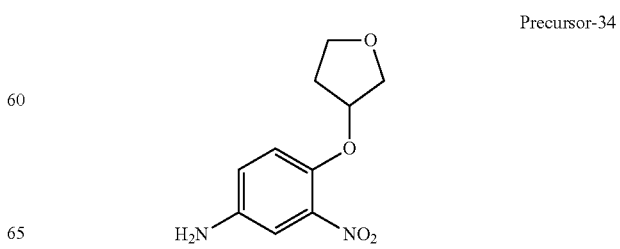

Precursor-34

Scheme-28: Synthesis of tert-butyl 3-(aminomethyl)piperidine-1-carboxylate (Precursor-35)

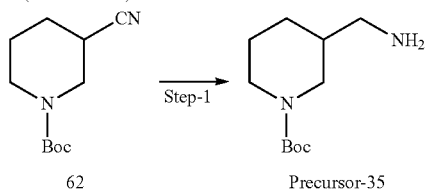

Synthesis of tert-butyl 3-(aminomethyl)piperidine-1-carboxylate (Precursor-35)

A solution of tert-butyl 3-cyanopiperidine-1-carboxylate 62 (5.0 g, 23.00 mmol) in Ether (40 mL) was cooled to −78° C. followed by drop wise addition of LAH (2.40 M solution in THF, 19.80 ml, 47.0 mmol). The resulting solution was then stirred for 30 min. at RT. Reaction was monitored by TLC, reaction mixture was quenched with saturated NaOH solution at 0° C. & reaction mixture was filtered through sodium sulfate, combined organic extracts were dried over $Na_2SO_4$ and concentrated to obtain crude compound (3.50 g, quantitative yield), which was carried forward as such for the next step. MS: 215.17 $(M+H)^+$.

Scheme-29: Synthesis of 1-(3-nitrophenyl)ethan-1-amine (Precursor-36)

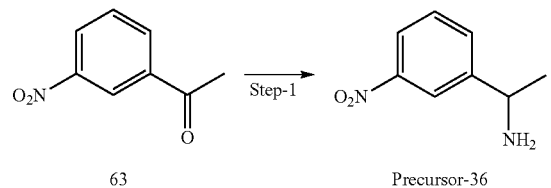

Synthesis of 2,5-dichloro-N-(2-fluoro-5-nitrophenyl)-N-methylpyrimidin-4-amine (Precursor-36)

To a stirred solution of compound 1-(3-nitrophenyl)ethan-1-one 63 (5.0 g, 30.27 mmol) in MeOH (100 mL) was added molecular sieves & ammonium acetate (23.33 g, 302.7 mmol), charged sodium cyano borohydride (1.38 g, 21.19 mmol) portion wise, reaction mixture was stirred at room temperature for 24 h, reaction was monitored by TLC. Solid obtained was filtered out & filtrate was concentrated to get crude. Crude was diluted with 10% IPA in DCM & organic layer was extracted at alkaline pH, organic layer was concentrated to obtain 1-(3-nitrophenyl) ethan-1-amine as colorless liquid (2.10 g, 42% yield). $^1$HNMR (400 MHz, DMSO-d6): δ 8.27 (s, 1H), 8.06 (d, 1H), 7.82 (d, 1H), 7.61-7.57 (m, 1H), 4.15-4.10 (m, 1H), 2.05 (br s, 1H), 1.27-1.26 (m, 3H) MS: 167.00 $(M+H)^+$.

Scheme-30: Synthesis of tert-butyl (3-aminocyclopentyl)carbamate (Precursor-37)

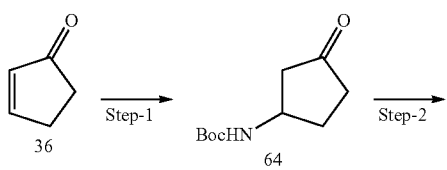

-continued

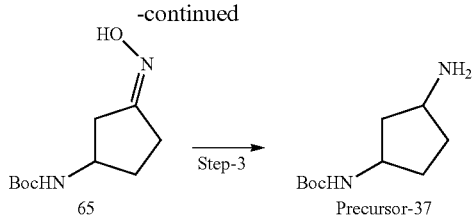

Synthesis of tert-butyl (3-oxocyclopentyl)carbamate (64)

To a stirred suspension of cyclopent-2-en-1-one 36 (2.50 g, 3.05 mmol) in DCM (60 mL), was added boc amine (3.60 g, 3.05 mmol) and stirred for 10-15 min. Bismuth nitrate (14.70 g, 3.05 mmol) was charged portion wise and allowed to stir at room temperature for about 5 h. After completion of reaction, the reaction mixture was diluted with DCM & was filtered through celite bed, filtrate obtained was quenched with saturated $NaHCO_3$ solution, DCM layer was separated, and aqueous layer was extracted with DCM, combined organic extracts were dried over $Na_2SO_4$ and concentrated to obtain crude compound. The crude was further purified by combiflash using 10-15% ethyl acetate in hexane to obtain tert-butyl (3-oxocyclopentyl)carbamate 64 as a white solid (6.50 g, 36% yield). MS: 200.20 $(M+H)^+$.

Synthesis of tert-butyl (E/Z)-(3-(hydroxyimino) cyclopentyl)carbamate (65)

To a stirred solution of tert-butyl (3-oxocyclopentyl) carbamate 64 (3.0 g, 1.5 mmol) in MeOH (150 mL) was added hydroxyl amine hydrochloride (1.0 g, 1.95 mmol) and stirred for 10 min. at room temperature. Charged sodium acetate portion wise, reaction mixture was stirred at room temperature for 30 min. Reaction mixture was concentrated fully to remove MeOH. The residue was distributed between a saturated $NaHCO_3$ solution & EtOAc. Organic layer was washed with water, dried over $Na_2SO_4$ and concentrated to get crude material. Crude was purified by column chromatography (Silica, 12 g Snap, 50% EtOAc in Hexane) to obtain 65 as white solid (2.60 g, quantitative yield). MS: 215.20 $(M+H)^+$.

Synthesis of tert-butyl (3-aminocyclopentyl)carbamate (Precursor-37)

To a stirred solution of compound 65 (2.60 g, 1.20 mmol) in MeOH (50 mL) was added aq. ammonia (2.6 ml), charged raney nickel (0.5 g) under $N_2$ atm. The resulting reaction mixture was stirred for 2 h at room temperature under hydrogen gas pressure (1 atm). The reaction was monitored by TLC. It was then filtered through sintered funnel with a pad of celite, washed with methanol and concentrated under reduced pressure to afford precursor-37 as a brown colored gummy liquid (2.4 g, quantitative yield) that was used as such for the next step without any further purification. MS: 201.18 $(M+H)^+$.

Similarly prepared was precursor-38 using cyclohept-2-enone as starting material.

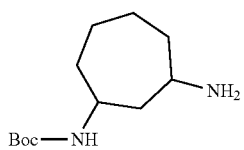

Precursor-38

MS: 229.20 (M+H)+

Scheme-31: Synthesis of tert-butyl (3-hydroxycyclohexyl)carbamate (Precursor-39)

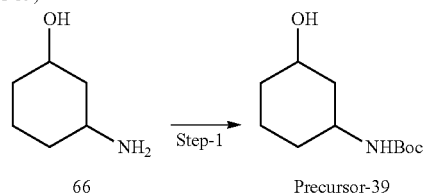

Synthesis of tert-butyl (3-hydroxycyclohexyl) carbamate (Precursor-39)

To a stirred suspension of compound 66 (5.0 g, 43.47 mmol) in 1,4-dioxane (40 mL), at RT was drop wise added Boc anhydride (11.0 g, 54.26 mmol) and reaction mixture was stirred at room temperature for about 16 h. The reaction mixture was quenched with 300 mL ice-water and aqueous layer was extracted thrice with EtOAc. The combined organic extracts were dried over $Na_2SO_4$ and concentrated to obtain crude compound as brownish liquid (9.0 g, quantitative yield). The crude was carried forward without further purification for the next step. MS: 216.20 $(M+H)^+$.

Scheme-32: Synthesis of 2-(4,4-difluorocyclohexylidene)acetic acid (Precursor-40)

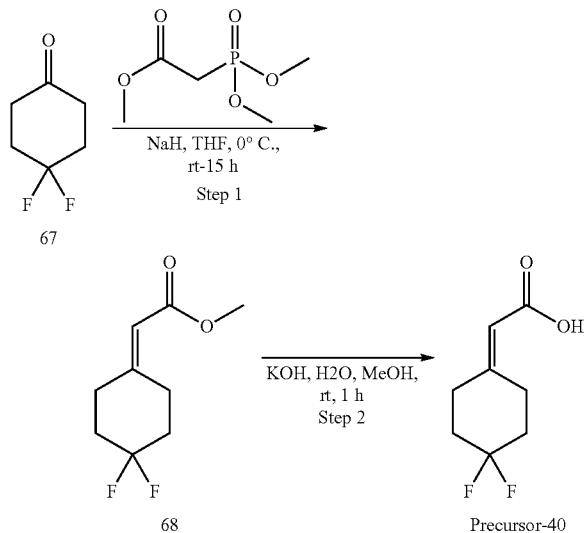

Synthesis of methyl 2-(4,4-difluorocyclohexylidene)acetate (68)

To a stirred suspension of 60% NaH (0.4 g, 10 mmol) in THF (10 mL), methyl 2-(dimethoxyphosphoryl)acetate (1.3 mL, 9 mmol) in 10 mL THF was added at 0° C. and stirred for 1 h at 0-50° C. 4,4-difluorocyclohexanone 67 (1 g, 7.5 mmol) in 10 mL THF was then added slowly at 0° C. and allowed to stir at room temperature for about 15 h. The reaction mixture was diluted with 20 mL THF and 50 mL ice-water, THF layer was separated and concentrated, residue was dissolved in ethyl acetate (50 mL), washed with water (20 mL), saturated $NaHCO_3$ solution (10 mL) and dried over $Na_2SO_4$ and concentrated under reduced pressure to obtain methyl 2-(4,4-difluorocyclohexylidene)acetate 68 as light brown liquid (0.8 g, 57% yield). $^1$HNMR (400 MHz, $CDCl_3$): δ 5.73 (s, 1H), 3.70 (s, 3H), 3.04 (t, 2H), 2.41 (t, 2H), 2.09-1.97 (m, 4H).

Synthesis of 2-(4,4-difluorocyclohexylidene)acetic acid (Precursor-40)

To a solution of KOH (0.2 g, 3.574 mmol) in $H_2O$ (2.4 mL) and MeOH (1.2 mL) was added methyl 2-(4,4-difluorocyclohexylidene)acetate 68 (0.4 g, 2.103 mmol) and stirred for 1 h at room temperature, reaction mixture was diluted with water (10 mL) and extracted with ethyl acetate (10 mL), aqueous layer was acidified with 1N HCl and extracted with ethyl acetate (2×20 mL), organic layer was washed with water, dried over $Na_2SO_4$ and concentrated to obtain pure compound 2-(4,4-difluorocyclohexylidene)acetic acid precursor-40 as off white solid (0.25 g, 68% yield). $^1$HNMR (400 MHz, $CDCl_3$): δ 10-11 (bs, 1H), 5.77 (s, 1H), 3.04 (t, 2H), 2.45 (t, 2H), 2.11-1.98 (m, 4H).

Scheme-33: Synthesis of 2-(dihydro-2H-pyran-4(3H)-ylidene)acetic acid (Precursor-41)

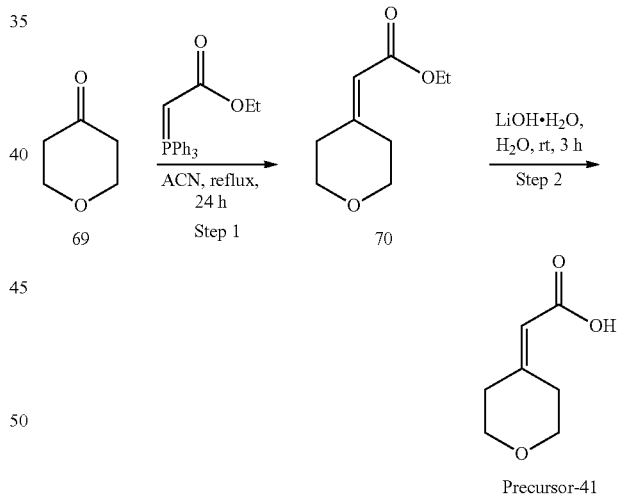

Synthesis of ethyl 2-(dihydro-2H-pyran-4(3H)-ylidene)acetate (70)

To a stirred solution of ethyl 2-(triphenylphosphoranylidene)acetate (1.09 g, 3.10 mmol) in acetonitrile (20 mL), dihydro-2H-pyran-4(3H)-one 69 (0.50 g, 5 mmol) was added and the reaction mixture was refluxed for about 24 h. Reaction mixture was cooled to room temperature and concentrated to get crude compound. The crude product was purified by combiflash using 0-25% ethyl acetate in hexane to obtain ethyl 2-(dihydro-2H-pyran-4(3H)-ylidene)acetate 70 as colorless oil (0.5 g, 58% yield). $^1$HNMR (400 MHz, CDCl$_3$): δ 5.68 (s, 1H), 4.15 (q, 2H), 3.78-3.72 (m, 4H), 3.0 (t, 2H), 2.32 (t, 2H), 1.28 (q, 3H).

Synthesis of 2-(dihydro-2H-pyran-4(3H)-ylidene) acetic acid (Precursor-41)

A solution of LiOH.H$_2$O (0.40 g, 2.3 mmol) in water (4 mL) was added to ethyl 2-(dihydro-2H-pyran-4(3H)-ylidene)acetate 70 and stirred for 3 h at room temperature, reaction mixture was acidified with dil HCl and extracted with ethyl acetate (2×10 mL), died over Na$_2$SO$_4$ and concentrated to obtain 2-(dihydro-2H-pyran-4(3H)-ylidene)acetic acid precursor-41 as off white solid (0.334 g, quantitative yield). $^1$HNMR (400 MHz, CDCl$_3$): δ 5.71 (s, 1H), 3.79 (t, 2H), 3.74 (t, 2H), 3.01 (t, 2H), 2.36 (t, 2H).

Scheme-34: Synthesis of 2-cyclohexylideneacetic acid (Precursor-42)

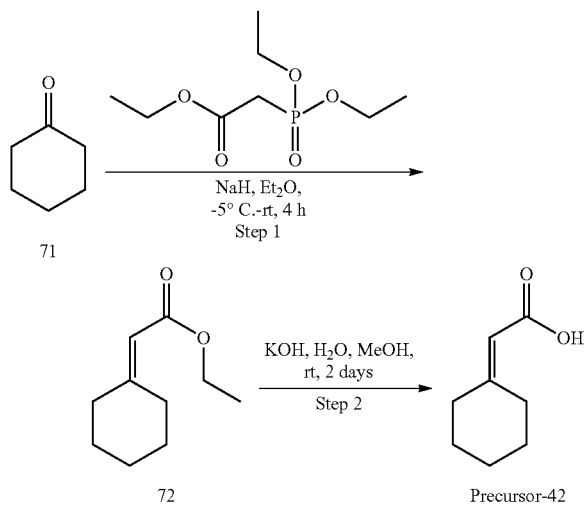

Synthesis of ethyl 2-cyclohexylideneacetate (72)

To a stirred suspension of 60% NaH (0.83 g, 20.75 mmol) in ether (60 mL), at −5° C. was drop wise added ethyl 2-(diethoxyphosphoryl)acetate (4.1 mL, 20.66 mmol) and stirred for 15 min (until H$_2$ evolution stopped). A solution of cyclohexanone 71 (2.09 mL, 20.2 mmol) in 10 mL diethylether was added slowly at −5° C., and allowed to stir at room temperature for about 5 h, reaction mixture was quenched with 50 mL ice-water, ether layer was separated, and aqueous layer was extracted with ethyl acetate, combined organic extracts were dried over Na$_2$SO$_4$ and concentrated to obtain crude compound. The crude was further purified by combiflash using 0-40% ethyl acetate in hexane to obtain ethyl 2-cyclohexylideneacetate 72 as a colorless liquid (2.6 g, 33% yield). $^1$HNMR (400 MHz, CDCl$_3$): δ 5.59 (s, 1H), 4.13 (q, 2H), 2.82 (t, 2H), 2.18 (t, 2H), 1.67-1.57 (m, 6H), 1.26 (t, 3H).

Synthesis of 2-cyclohexylideneacetic acid (Precursor-42)

To a solution of KOH (0.561 g, 10 mmol) in H$_2$O (7 mL) and MeOH (3 mL) was added ethyl 2-cyclohexylideneacetate 72 (1.0 g, 5.94 mmol) and stirred for two days at room temperature, reaction mixture was diluted with water (20 mL) and extracted with ethyl acetate (3×10 mL), aqueous layer was acidified with 1N HCl and extracted with ethyl acetate (2×20 mL), organic layer was washed with water, dried over Na$_2$SO$_4$ and concentrated to obtain pure compound 2-cyclohexylideneacetic acid precursor-42 as white solid (0.6 g, 72% yield). $^1$HNMR (400 MHz, CDCl$_3$): δ 11.84 (s, 1H), 5.52 (s, 1H), 2.74-2.72 (m, 2H), 2.14 (t, 2H), 1.53-1.52 (m, 6H). MS: 141.2 (M+H)$^+$.

Scheme-35: Synthesis of 2-cyclopentylideneacetic acid (Precursor-43)

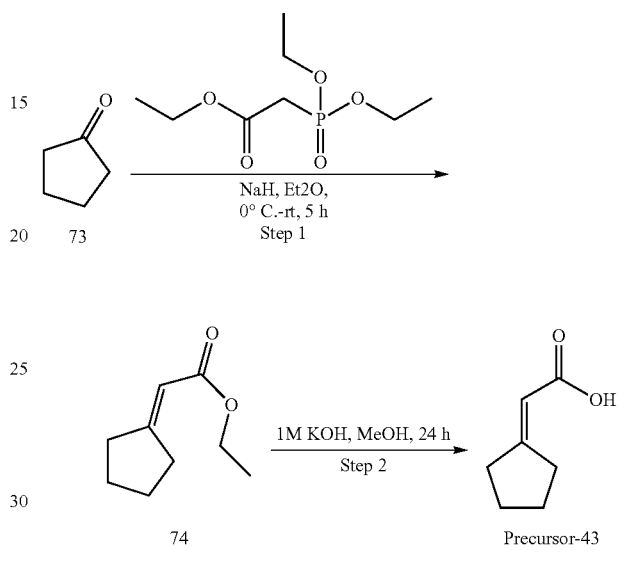

Synthesis of ethyl 2-cyclopentylideneacetate (74)

To a stirred suspension of 60% NaH (0.97 g, 40.40 mmol) in diethyl ether (50 mL), ethyl 2-(diethoxyphosphoryl)acetate (5.18 ml, 26.14 mmol) in 10 mL diethyl ether was added at 0° C. and stirred for 5 min until H$_2$ gas evolution stopped. Then cyclopentanone 73 (2 g, 23.77 mmol) in diethyl ether (10 mL) was added to it and allowed to stir at room temperature for 5 h. Then the reaction mixture was quenched with cold water and extracted with ethyl acetate. The combined organic layer was dried over Na$_2$SO$_4$ and concentrated under reduced pressure to obtain ethyl 2-cyclopentylideneacetate 74 as colorless liquid (2.10 g, 58% yield). $^1$HNMR (400 MHz, CDCl$_3$): δ 5.78 (s, 1H), 4.14 (q, 2H), 2.76 (t, 2H), 2.42 (t, 2H), 1.77-1.70 (m, 2H), 1.68-1.60 (m, 2H), 1.26 (t, 3H).

Synthesis of 2-cyclopentylideneacetic acid (Precursor-43)

To a solution of 1M KOH (3.5 mL) and 75% aqueous MeOH (5 mL) was added ethyl 2-cyclopentylideneacetate 74 (0.5 g, 3.24 mmol) and stirred for 24 h at room temperature, reaction mixture was acidified with 2M HCl to pH 2 and extracted with ethyl acetate (2×50 ml), organic layer was washed with water, dried over Na$_2$SO$_4$ and concentrated to obtain pure compound 2-cyclopentylideneacetic acid precursor-43 as off white solid (0.20 g, 50% yield). $^1$HNMR (400 MHz, CDCl$_3$): δ 5.82 (s, 1H), 2.78 (t, 2H), 2.47 (t, 2H), 1.79-1.63 (m, 4H).

Scheme-36: Synthesis of 2-cyclobutylideneacetic acid (Precursor-44)

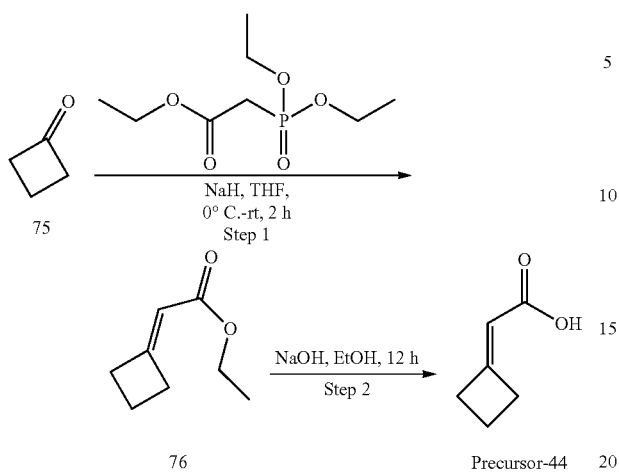

Synthesis of ethyl 2-cyclobutylideneacetate (76)

To a stirred suspension of 60% NaH (1.23 g, 51.35 mmol) in THF (50 mL), ethyl 2-(diethoxyphosphoryl)acetate (6.23 mL, 31.38 mmol) in 10 mL THF was added at 0° C. and stirred for 5 min at same temperature. Then cyclobutanone 75 (2 g, 28.53 mmol) in THF (10 mL) was added to it and allowed to stir at room temperature for 2 h. Then the reaction mixture was quenched with cold water and extracted with ethyl acetate. The combined organic layer was dried over $Na_2SO_4$ and concentrated under reduced pressure to obtain ethyl 2-cyclobutylideneacetate 76 as colorless liquid (0.65 g, 16% yield). $^1$HNMR (400 MHz, $CDCl_3$): δ 5.57 (s, 1H), 4.13 (q, 2H), 3.12 (t, 2H), 2.82 (t, 2H), 2.12-2.04 (m, 2H), 1.26 (t, 3H)

Synthesis of 2-cyclobutylideneacetic acid (Precursor-44)

To a solution of 25% NaOH in $H_2O$ (1.5 mL) and EtOH (1.5 mL) was added ethyl 2-cyclobutylideneacetate 76 (0.20 g, 1.42 mmol) and stirred for 12 h at room temperature, reaction mixture was concentrated to one third and acidified with 1N HCl to pH 2-3 and extracted with ethyl acetate (2×50 mL), organic layer was washed with water, dried over $Na_2SO_4$ and concentrated to obtain pure compound 2-cyclobutylideneacetic acid precursor-44 as off white solid (0.10 g, 62% Yield). $^1$HNMR (400 MHz, $CDCl_3$): δ 5.59 (t, 1H), 3.14 (t, 2H), 2.86 (t, 2H), 2.13-2.05 (m, 2H).

Scheme-36a: Synthesis of 5-chloro-1-methyl-1H-pyrazol-3-amine (Precursor-45)

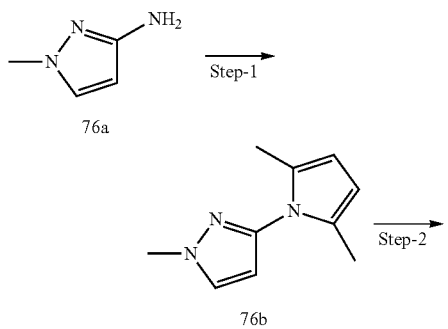

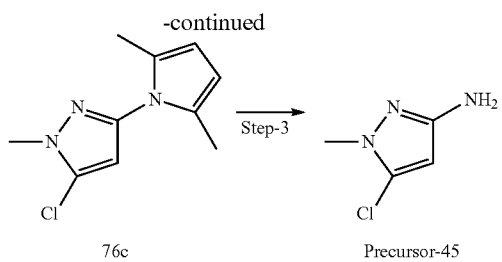

Synthesis of 3-(2,5-dimethyl-1H-pyrrol-1-yl)-1-methyl-1H-pyrazole (76b)

To a stirred suspension of 1-methyl-1H-pyrazol-3-amine 76a (0.5 g, 5.1 mmol) in toluene (20 mL) in an round bottom flask fitted with Dean-Stark apparatus was charged with hexane-2,5-dione (0.70 g, 6.1 mmol) followed by p-toluene sulfonic acid (0.097 g, 0.51 mmol) and the reaction mixture was heated at 115° C. for about 6 h. The reaction mixture was cooled to room temperature. Reaction mass was concentrated fully under reduced pressure, residue obtained was dissolved in DCM, given water wash followed by brine wash, dried over $Na_2SO_4$ and concentrated under reduced pressure to obtain 3-(2,5-dimethyl-1H-pyrrol-1-yl)-1-methyl-1H-pyrazole 76b (0.55 g, 55% yield) as green oil. $^1$HNMR (400 MHz, CDCl3): δ 7.39 (d, 1H), 6.15 (s, 1H), 5.85 (s, 2H), 3.92 (s, 3H), 2.10 (s, 6H), MS: 176.11 (M+H)$^+$.

Synthesis of 5-chloro-3-(2,5-dimethyl-1H-pyrrol-1-yl)-1-methyl-1H-pyrazole (76c)

A solution of 3-(2,5-dimethyl-1H-pyrrol-1-yl)-1-methyl-1H-pyrazole 76b (0.50 g, 2.85 mmol) in THF (25 mL) under nitrogen atmosphere was cooled to −78° C. followed by addition of n-BuLi (1.30 ml, 3.40 mmol) dropwise. The reaction mixture was stirred at −78° C. for 3 h followed by addition of hexachloroethane (0.74 g, 3.14 mmol) in THF (2.5 mL) drop wise & reaction mixture was again stirred at −78° C. for 30 min and then brought to RT & stirred for 2 h. Reaction was monitored by TLC. Reaction was quenched with saturated $NH_4Cl$ solution (10 mL) at 0° C. and extracted with diethyl ether (2×50 mL). The combined organics was washed with brine, dried and concentrated to get crude material. The crude material was purified by flash column chromatography (SiO2), eluting with 0-20% EtOAc-hexane to obtain 5-chloro-3-(2,5-dimethyl-1H-pyrrol-1-yl)-1-methyl-1H-pyrazole 76c (0.50 g, 84% yield) as greenish solid. $^1$H NMR (400 MHz, $CDCl_3$): δ 6.14 (s, 1H), 5.85 (s, 2H), 3.87 (s, 3H), 2.11 (s, 6H). MS: 210.06 (M+H)$^+$.

Synthesis of 5-chloro-1-methyl-1H-pyrazol-3-amine (Precursor-45)

A Seal Tube was charged with 5-chloro-3-(2,5-dimethyl-1H-pyrrol-1-yl)-1-methyl-1H-pyrazole 76c (0.50 g, 2.38 mmol) in EtOH (20 mL) and hydroxylamine hydrochloride (0.83 g, 12.0 mmol) in EtOH (5 mL) drop wise followed by drop wise addition of potassium hydroxide (0.30 g, 6.0 mmol) dissolved in water (10 mL). The reaction mixture was heated at 105° C. for 2 days. Reaction was monitored by TLC. Reaction mixture was concentrated fully to obtained crude, which was purified by column chromatography (SiO2), eluting with 0-30% EtOAc-hexane to obtain 5-chloro-1-methyl-1H-pyrazol-3-amine precursor-45 (0.29 g, 93% yield) as yellow liquid. $^1$H NMR (400 MHz, DMSO-$d_6$): δ 5.49 (s, 1H), 4.74 (s, 2H), 3.51 (s, 3H). MS: 131.94 (M+H)$^+$.

Example 1: Synthesis of N-(3-((5-chloro-2-((1-(1-methylpiperidin-4-yl)-1H-pyrazol-4-yl)amino)pyrimidin-4-yl)amino)phenyl)acrylamide (I-1)

Scheme 37:

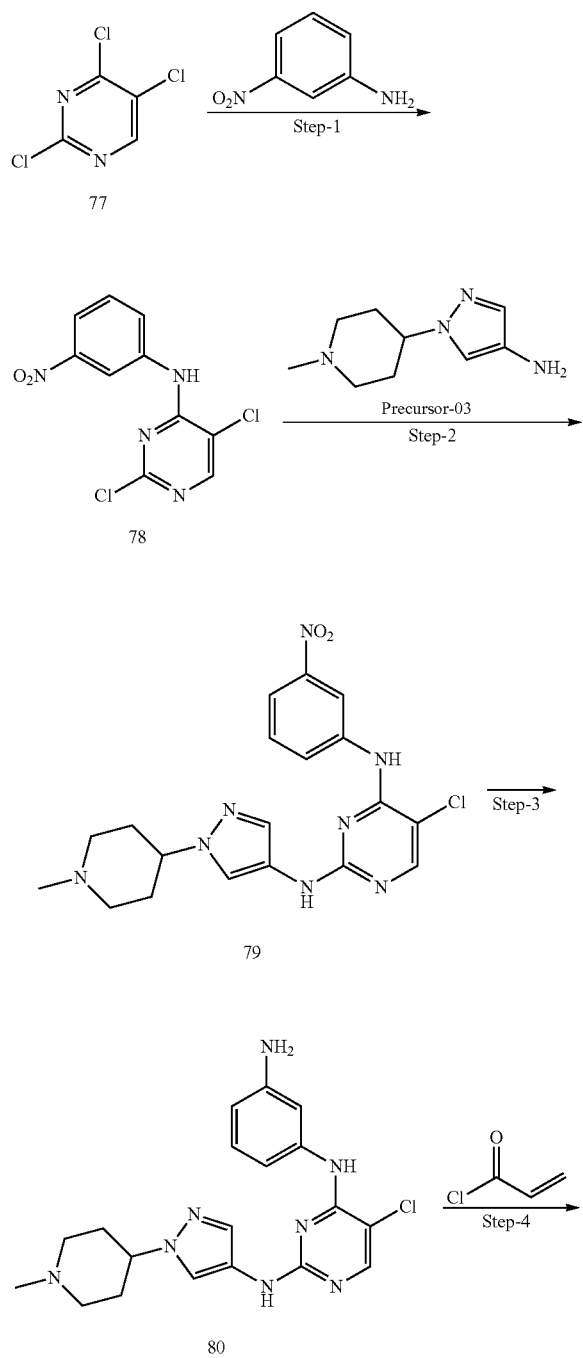

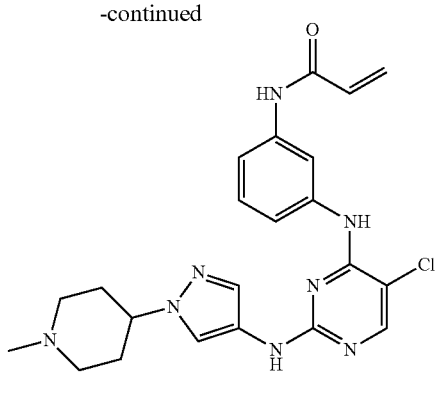

Synthesis of 2,5-dichloro-N-(3-nitrophenyl)pyrimidin-4-amine (78)

To a stirred solution of 2,4,5-trichloropyrimidine 77 (30.0 g, 160.0 mmol), in DMF (60 mL), 3-nitroaniline (22.0 g, 160.0 mmol) and DIPEA (41.3 g, 320 mmol) were charged. The reaction mixture was heated at 70° C. for 4 h. The reaction mixture was diluted with ethyl acetate (300 mL) and washed with water (3×100 mL). The organic layer was dried (Na$_2$SO$_4$) and evaporated to obtain 2,5-dichloro-N-(3-nitrophenyl)pyrimidin-4-amine 78 (30.0 g, 65% yield) as yellow solid. $^1$HNMR (400 MHz, DMSO-$d_6$): δ 9.89 (s, 1H), 8.62 (d, 1H), 8.47 (s, 1H), 8.12 (d, 1H), 8.00 (dd, 1H), 7.67 (t, 1H). MS: 284.8 (M+H)$^+$.

This step was performed via either general method A, B or C for all the targets.

Synthesis of 5-chloro-$N^2$-(1-(1-methylpiperidin-4-yl)-1H-pyrazol-4-yl)-$N^4$-(3-nitrophenyl)pyrimidine-2,4-diamine (79)

To a solution of 2,5-dichloro-N-(3-nitrophenyl)pyrimidin-4-amine 65 (5.0 g, 17.53 mmol) in 2-butanol (60 mL) and was added precursor-03 (3.80 g, 21.08 mmol) and TFA (1.5 g, catalytic) and the reaction mixture was heated at 100° C. for 16 h under N$_2$ atmosphere. After the completion of reaction (TLC monitored), reaction mixture was basified with saturated aqueous NaHCO$_3$ solution (50 mL) and extracted with ethyl acetate (3×50 mL). The combined organic layer was washed with brine (50 mL), dried over Na$_2$SO$_4$ and concentrated under reduced pressure. The residue obtained was purified through column chromatography (SiO$_2$, 60-120 mesh, 10% MeOH-DCM) to obtain 5-chloro-$N^2$-(1-(1-methylpiperidin-4-yl)-1H-pyrazol-4-yl)-$N^4$-(3-nitrophenyl)pyrimidine-2,4-diamine 79 (5.10 g, 66% yield) as a yellow solid. MS: 429.15 (M+H)$^+$.

This step was performed via either general method D, E, F or G for all the targets.

Synthesis of $N^4$-(3-aminophenyl)-5-chloro-$N^2$-(1-(1-methylpiperidin-4-yl)-1H-pyrazol-4-yl)pyrimidine-2,4-diamine (80)

To a solution of 5-chloro-$N^2$-(1-(1-methylpiperidin-4-yl)-1H-pyrazol-4-yl)-$N^4$-(3-nitrophenyl)pyrimidine-2,4-diamine 79 (10 g, 23.32 mmol) in MeOH, 1,4-dioxane (9:1, 105 mL) was added Pd—C (1.0 g) under nitrogen atmosphere. The resulting reaction mixture was stirred at rt under H$_2$ atmosphere for 16 h. After the completion of reaction (TLC monitored), diluted with methanol (25 mL) and filtered through celite. The residue obtained was purified through column chromatography (SiO$_2$, 60-120 mesh, 10% MeOH-DCM) to give N$^4$-(3-aminophenyl)-5-chloro-N$^2$-(1-(1-methylpiperidin-4-yl)-1H-pyrazol-4-yl)pyrimidine-2,4-diamine 80 (4.0 g, 47% yield) as white solid. $^1$HNMR (400 MHz, DMSO-d$_6$): δ 9.11 (s, 1H), 8.60 (s, 1H), 8.00 (s, 1H), 7.36-7.51 (m, 1H), 7.26 (s, 1H), 7.02-7.04 (m, 1H), 6.89-6.77 (m, 1H), 6.58-6.67 (m, 1H), 6.45-6.49 (bs, 1H), 5.12 (bs, 2H), 3.78-3.97 (m, 1H), 2.84-2.81 (m, 2H), 2.21 (s, 3H), 2.04-1.92 (m, 2H), 1.80-1.76 (m, 4H). MS: 399.20 (M+H)$^+$. Few of the compounds were also synthesized via either general method-H or general method-I.

Synthesis of N-(3-((5-chloro-2-((1-(1-methylpiperidin-4-yl)-1H-pyrazol-4-yl)amino)pyrimidin-4-yl)amino)phenyl)acrylamide (I-1)

To a solution of N$^4$-(3-aminophenyl)-5-chloro-N$^2$-(1-(1-methylpiperidin-4-yl)-1H-pyrazol-4-yl)pyrimidine-2,4-diamine 80 (0.120 g, 0.28 mmol) in DCM (10 mL), K$_2$CO$_3$ (0.038 g, 0.280 mmol) and acryloyl chloride (23 uL, 0.280 mmol) at −30° C. The reaction mixture was stirred for 30 min at same temperature. Solvent was evaporated under reduced pressure to get crude compound and purified by prep-HPLC to obtain N-(3-((5-chloro-2-((1-(1-methylpiperidin-4-yl)-1H-pyrazol-4-yl)amino)pyrimidin-4-yl)amino)phenyl)acrylamide I-1 (0.008 g, 6% yield) as white solid. The yields were better when followed general method-J. $^1$HNMR (400 MHz, DMSO): δ 10.22 (s, 1H), 9.24 (s, 1H), 8.88 (s, 1H), 8.06 (s, 1H), 7.75-7.71 (m, 2H), 7.36-7.10 (m, 4H), 6.47-6.40 (m, 1H), 6.27 (d, 1H), 5.76 (d, 1H), 3.81-3.61 (m, 1H), 2.89-2.78 (m, 2H), 2.28-2.21 (m, 3H), 2.16-1.90 (m, 2H), 1.84-1.68 (m, 4H) MS: 453.29 (M+H)$^+$.

The following compounds were prepared following similar to general method J or K

| Cmpd No. | Structure | Synthesis method | LCMS (M + 1) | $^1$H-NMR (400 MHz, DMSO-d$_6$) |
|---|---|---|---|---|
| I-2 (Regio-isomer 1) | 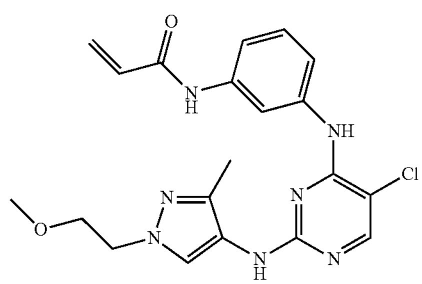 [SMILES: C=CC(=O)Nc1cccc(Nc2nc(Nc3cn(CCOC)nc3C)ncc2Cl)c1] | J | 428.36 | δ 10.13 (s, 1H), 8.83 (s, 1H), 8.61 (bs, 1H), (8.05 (s, 1H), 7.81-7.72 (s, 1H), 7.52-7.39 (m, 2H) 7.31-7.20 (m, 2H), 6.49-6.42 (m, 1H), 6.27 (dd, 1H), 5.77 (dd, 1H), 3.89-3.87 (m, 2H), 3.49-3.47 (m, 2H), 3.13 (s, 3H), 2.06(s, 3H) |
| I-3 (Regio-isomer 2) | 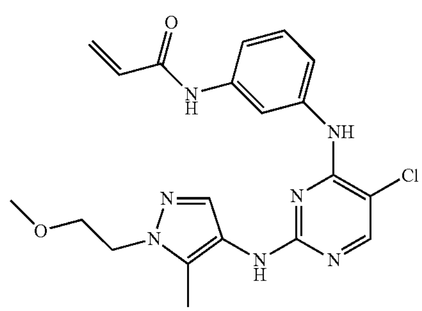 [SMILES: C=CC(=O)Nc1cccc(Nc2nc(Nc3cnn(CCOC)c3C)ncc2Cl)c1] | J | 428.36 | δ 10.08 (s, 1H), 8.70 (s, 1H), 8.49-8.30 (m, 1H), 8.01 (s, 1H), 7.85 (s, 1H), 7.41 (m, 3H) 7.29-7.19 (m, 1H), 6.50-6.43 (m, 1H), 6.27 (dd, 1H), 5.77 (dd, 1H), 4.09-4.07 (m, 2H), 3.59-3.57 (m, 2H), 3.18 (s, 3H) 2.08 (s, 3H) |
| I-4 | 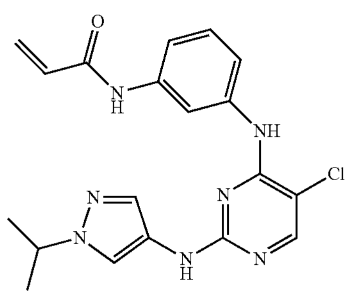 [SMILES: C=CC(=O)Nc1cccc(Nc2nc(Nc3cnn(C(C)C)c3)ncc2Cl)c1] | J | 398.45 | δ 10.20 (s, 1H), 9.23 (s, 1H), 8.90 (s, 1H), 8.06 (s, 1H), 7.79 (s, 1H), 7.65-7.60 (m, 1H), 7.5-7.15 (m, 4H), 6.47-6.40 (m, 1H), 6.26-6.22 (m, 1H), 5.76-5.73 (m, 1H), 4.11 (bs, 1H), 1.22 (d, 6H) |

-continued

| Cmpd No. | Structure | Synthesis method | LCMS (M + 1) | ¹H-NMR (400 MHz, DMSO-d$_6$) |
|---|---|---|---|---|
| I-5 | 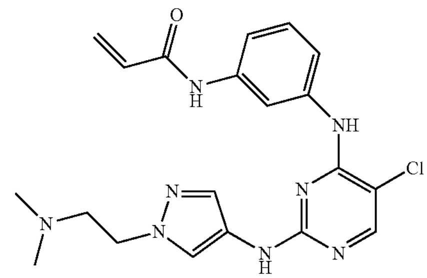 [SMILES: C=CC(=O)Nc1cccc(Nc2nc(Nc3cnn(CCN(C)C)c3)ncc2Cl)c1] | J | 427.25 | δ 10.21 (bs, 1H), 9.24 (bs, 1H), 8.93 (bs, 1H), 8.06 (s, 1H), 7.79 (s, 1H), 7.57 (bs, 1H), 7.46-7.17 (m, 4H), 6.47-6.41 (m, 1H), 6.27-6.22 (m, 1H), 5.76-5.73 (m, 1H), 3.84-3.92 (m, 2H), 2.96-3.04 (m, 2H), 2.05 (s, 6H) |
| I-6 | 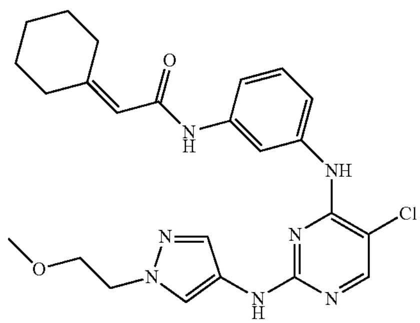 [SMILES: COCCn1cc(Nc2ncc(Cl)c(Nc3cccc(NC(=O)C=C4CCCCC4)c3)n2)cn1] | K | 482.2 | δ 9.99 (s, 1H), 9.28 (s, 1H), 8.89 (s, 1H), 8.05 (s, 1H), 7.83 (s, 1H), 7.12-7.59 (m, 5H), 4.19-4.09 (m, 2H), 3.56-3.50 (m, 2H), 3.13 (s, 3H), 2.84 (m, 2H), 2.17-2.15 (m, 2H), 1.60-1.05 (m, 6H). |
| I-7 | 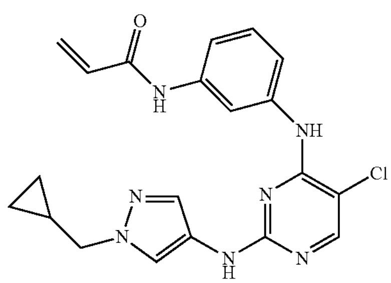 | J | 410.14 | δ 10.21 (s, 1H), 9.24 (s, 1H), 8.91 (s, 1H), 8.06 (s, 1H), 7.79 (s, 1H), 7.60 (s, 1H), 7.34-7.13 (m, 4H), 6.47-6.40 (m, 1H), 6.26 (dd, 1H), 5.76 (dd, 1H), 3.62-3.60 (m, 2H,) 0.95 (m, 1H), 0.38-0.12 (m, 4H). |
| I-8 | 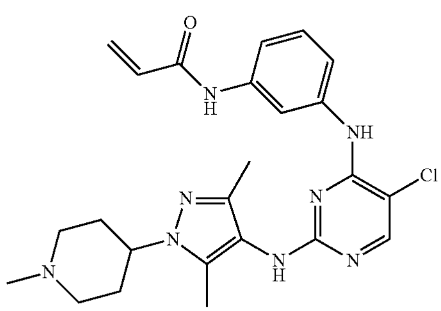 | J | 481.36 | δ 9.94 (s, 1H), 8.65 (s, 1H), 8.08-7.78 (m, 3H), 7.31-7.02 (m, 3H), 6.41 (dd, 1H), 6.28 (d, 1H), 5.75 (d, H), 3.91-3.87 (m, 1H), 2.86-2.84 (m, 2H), 2.19 (s, 3H), 2.03-1.96 (m, 7H), 1.93 (s, 3H), 1.71-1.68 (m, 2H). |
| I-9 | 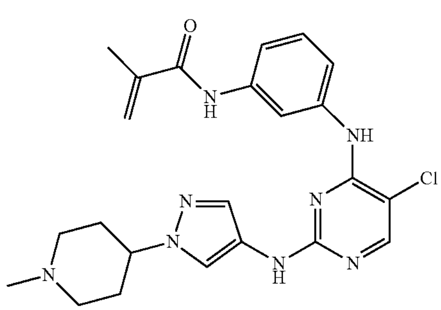 [SMILES: C=C(C)C(=O)Nc1cccc(Nc2nc(Nc3cnn(C4CCN(C)CC4)c3)ncc2Cl)c1] | J | 467.2 | δ 9.84 (s, 1H), 9.22 (s, 1H), 8.90 (s, 1H), 8.05 (s, 1H), 7.79-7.66 (m, 2H), 7.34-7.13 (m, 4H), 5.80 (s, 1H), 5.50 (s, 1H), 3.75-3.70 (m, 1H), 3.77-3.70 (m, 3H), 2.75-2.70 (m, 3H), 2.35-2.31 (m, 2H), 1.94 (s, 3H), 1.77-1.73 (m, 3H). |

| Cmpd No. | Structure | Synthesis method | LCMS (M + 1) | ¹H-NMR (400 MHz, DMSO-d₆) |
|---|---|---|---|---|
| I-10 | 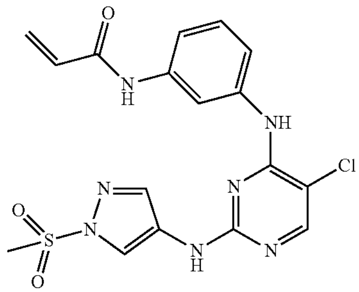 [SMILES: C=CC(=O)Nc1cccc(Nc2nc(Nc3cnn(S(C)(=O)=O)c3)ncc2Cl)c1] | J | 434.21 | δ 10.27 (s, 1H), 9.66 (s, 1H), 8.99-8.97 (m, 1H), 8.35 (s, 1H), 8.31 (s, 1H), 7.93-7.90 (m, 2H), 7.50 (s, 1H), 7.32-7.30 (m, 2H), 6.51-6.40 (m, 1H), 6.25 (d, 1H), 5.74 (d, 1H), 3.24 (s, 3H) |
| I-11 | 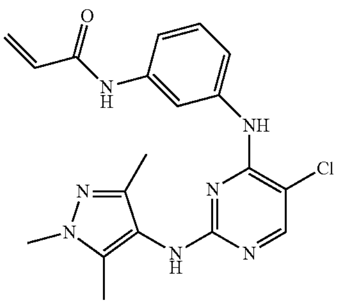 [SMILES: C=CC(=O)Nc1cccc(Nc2nc(Nc3c(C)nn(C)c3C)ncc2Cl)c1] | J | 398.13 | δ 7.87-7.93 (m, 2H), 7.40-7.29 (m, 2H), 7.21-7.17 (m, 1H), 6.49-6.40 (m, 1H), 6.36 (dd, 1H), 5.79 (dd, 1H), 3.69 (s, 3H), 2.06 (s, 6H) |
| I-12 | 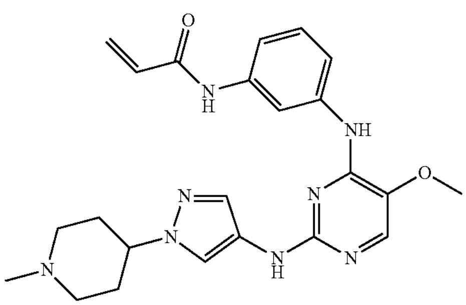 | J | 449.01 | δ 10.14 (s, 1H), 8.67 (d, 2H), 7.87-7.72 (m, 3H), 7.32-7.25 (m, 4H), 6.49-6.42 (m, 1H), 6.24 (d, 1H), 5.73 (d, 1H), 3.81-3.82 (m, 1H), 3.82 (s, 3H), 2.77-2.80 (m, 2H), 2.17 (s, 3H), 1.94-1.96 (m, 2H), 1.64-1.68 (m, 4H). |
| I-13 | 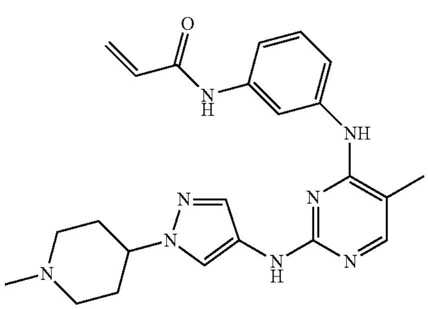 | J | 433.25 | δ 10.13 (s, 1H), 8.75 (s, 1H), 8.31 (s, 1H), 7.82-7.81 (m, 2H), 7.51-7.48 (m, 2H), 7.32-7.28 (m, 3H), 6.45-6.40 (m, 1H), 6.24 (dd, 1H), 5.74 (dd, 1H), 3.74-3.72 (m, 1H), 2.79-2.76 (m, 2H), 2.32 (s, 3H), 2.18 (s, 3H), 1.98-1.96 (m, 2H), 1.75-1.72 (m, 4H). |
| I-14 | 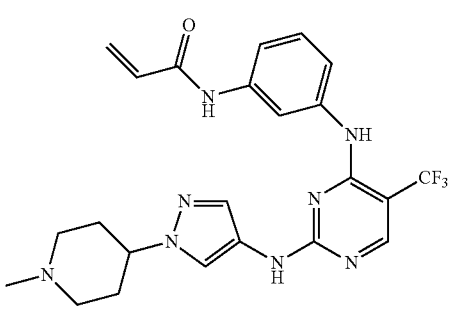 [SMILES: C=CC(=O)Nc1cccc(Nc2nc(Nc3cnn(C4CCN(C)CC4)c3)ncc2C(F)(F)F)c1] | J | 487.1 | δ 10.14 (s, 1H), 9.70-9.63 (m, 1H), 8.78 (bs, 1H), 8.29 (s, 1H), 8.15-8.07 (m, 1H), 7.91-7.73 (m, 2H), 7.39-7.32 (m, 2H), 7.25-7.21 (m, 1H), 6.49-6.42 (m, 1H), 6.24 (d, 1H), 5.75 (d, 1H), 3.94-3.92 (m, 1H), 2.84-2.81 (m, 2H), 2.19 (s, 3H), 2.02-1.97 (m, 2H), 1.87 (m, 4H) |

-continued

| Cmpd No. | Structure | Synthesis method | LCMS (M + 1) | ¹H-NMR (400 MHz, DMSO-d₆) |
|---|---|---|---|---|
| I-15 | 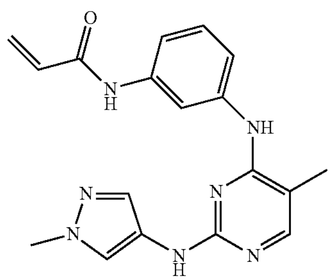 [SMILES: C=CC(=O)Nc1cccc(Nc2nc(Nc3cnn(C)c3)ncc2C)c1] | J | 350.2 | δ 10.14 (s, 1H), 8.76 (s, 1H), 8.33 (s, 1H), 7.85-7.82 (m, 2H), 7.59 (brs, 1H), 7.44 (brs, 2H), 7.30-7.26 (m, 3H), 6.46-6.40 (m, 1H), 6.25 (dd, 1H), 5.74 (dd, 1H), 3.61 (s, 3H), 2.07 (s, 3H) |
| I-16 | 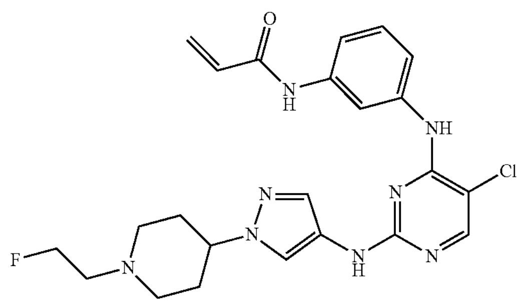 [SMILES: C=CC(=O)Nc1cccc(Nc2nc(Nc3cnn(C4CCN(CCF)CC4)c3)ncc2Cl)c1] | J | 485.39 | δ 10.18 (s, 1H), 9.31-9.13 (bs, 1H), 9.09-8.76 (bs, 1H), 8.05 (s, 1H), 7.90-7.64 (m, 2H), 7.43-7.13 (m, 4H), 6.46-6.40 (m, 1H), 6.24 (dd, 1H), 5.75 (dd, 1H), 4.61 (t, 1H), 4.50 (t, 1H), 3.69-3.67 (m, 1H), 2.91-2.89 (m, 2H), 2.67-2.60 (m, 2H), 2.11-2.07 (m, 2H), 1.85-1.68 (m, 4H) |
| I-17 | 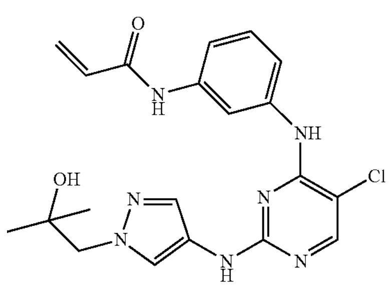 [SMILES: C=CC(=O)Nc1cccc(Nc2nc(Nc3cnn(CC(C)(C)O)c3)ncc2Cl)c1] | J | 428.08 | (CD3OD): δ 7.98 (s, 1H), 9.94-7.89 (m, 1H), 7.65-7.54 (m, 2H), 7.44 (s, 1H), 7.39-7.35 (m, 1H), 7.31 (m, 1H), 6.48-6.34 (m, 2H), 5.79-5.76 (m, 1H), 3.88 (s, 2H), 1.08 (s, 6H). |
| I-18 | 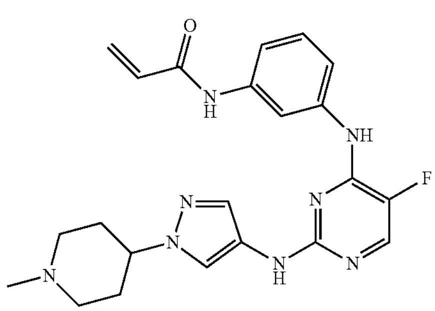 [SMILES: C=CC(=O)Nc1cccc(Nc2nc(Nc3cnn(C4CCN(C)CC4)c3)ncc2F)c1] | J | 437.29 | δ 10.15 (s, 1H), 9.32 (s, 1H), 9.00 (s, 1H), 8.04 (s, 1H), 7.84 (s, 1H), 7.69-7.62 (m, 1H), 7.58-7.45 (m, 2H), 7.32-7.27 (m, 2H), 6.48-6.42 (m, 1H), 6.27 (d, 1H), 5.76 (d, 1H), 3.81-3.61 (m, 1H), 2.89-2.78 (m, 2H), 2.28-2.21 (m, 5H), 1.84-1.68 (m, 4H) |
| I-19 | 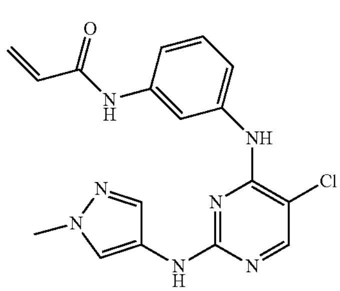 [SMILES: C=CC(=O)Nc1cccc(Nc2nc(Nc3cnn(C)c3)ncc2Cl)c1] | J | 370.2 | δ 10.15 (s, 1H), 9.14 (bs, 1H), 8.85 (bs, 1H), 8.04 (s, 1H), 7.80 (s, 1H), 7.53 (m, 1H), 7.34-7.23 (m, 4H), 6.46-6.40 (m, 1H), 6.21 (d, 1H), 5.73 (d, 1H), 3.57 (s, 3H). |

-continued

| Cmpd No. | Structure | Synthesis method | LCMS (M + 1) | ¹H-NMR (400 MHz, DMSO-d$_6$) |
|---|---|---|---|---|
| I-20 | 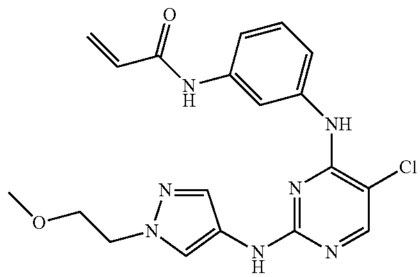 | J | 414.14 | δ 10.18 (s, 1H), 9.2 (bs, 1H), 8.92 (bs, 1H), 8.06 (s, 1H), 7.80 (s, 1H) 7.62-7.15 (m, 5H), 6.48-6.41 (m, 1H), 6.27 (d, 1H), 5.76 (d, 1H), 3.94-3.97 (m, 2H), 3.53-3.51 (m, 2H), 3.13 (s, 3H). |
| I-21 | 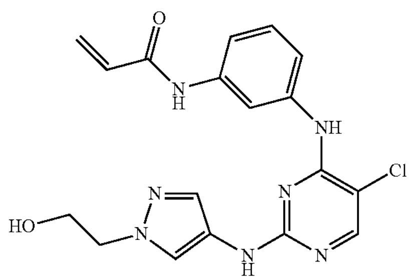 [SMILES: C=CC(=O)Nc1cccc(Nc2nc(Nc3cnn(CCO)c3)ncc2Cl)c1] | J | 400.02 | (CD3OD): δ 8.00 (s, 1H), 7.89 (bs,1H), 7.64 (bs, 1H), 7.54 (bs,1H), 7.42-7.27 (m, 3H), 6.48-6.34 (m, 2H), 5.76 (d, 1H), 4.01 (bs, 2H), 3.76 (bs, 2H) |
| I-22 | 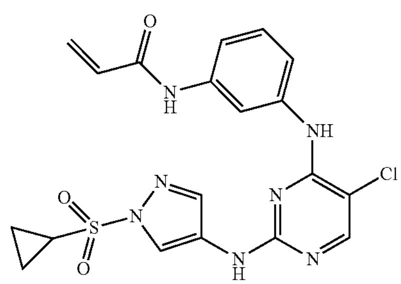 [SMILES: C=CC(=O)Nc1cccc(Nc2nc(Nc3cnn(S(=O)(=O)C4CC4)c3)ncc2Cl)c1] | J | 460.18 | δ 10.18 (s, 1H), 9.56 (s, 1H), 8.99 (s, 1H), 8.12 (s, 1H), 7.86 (m, 2H), 7.47-7.45 (m, 1H), 7.34-7.22 (m, 3H), 6.48-6.42 (m, 1H), 6.24 (d, 1H), 5.74 (d, 1H), 2.93-2.89 (m, 1H), 1.3-1.09 (m, 4H). |
| I-23 | 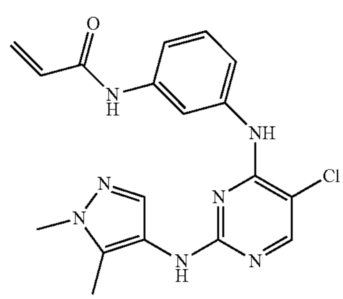 [SMILES: C=CC(=O)Nc1cccc(Nc2nc(Nc3cnn(C)c3C)ncc2Cl)c1] | J | 384.37 | δ 10.04 (s, 1H), 8.70 (s, 1H), 8.46-8.40 (m, 1H), 8.00 (s, 1H), 7.87 (s, 1H), 7.40-7.34 (m, 3H), 7.19 (s, 1H), 6.451-6.44 (m, 1H), 6.25 (d, 1H), 5.75 (d, 1H), 3.64 (s, 3H), 2.06 (s, 3H). |
| I-24 | 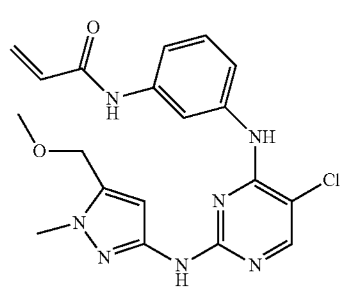 [SMILES: C=CC(=O)Nc1cccc(Nc2nc(Nc3cc(COC)n(C)n3)ncc2Cl)c1] | J | 414.21 | δ 10.11 (s, 1H), 9.35 (s, 1H), 8.84 (s, 1H), 8.07 (s, 1H), 7.87 (s, 1H), 7.57-7.55 (m, 1H), 7.35-7.27 (m, 2H), 6.48-6.41 (m, 1H), 6.27-6.23 (m, 2H), 5.75 (d, 1H), 4.22 (s, 2H), 3.61 (s, 3H), 3.15 (s, 3H). |

| Cmpd No. | Structure | Synthesis method | LCMS (M + 1) | ¹H-NMR (400 MHz, DMSO-d$_6$) |
|---|---|---|---|---|
| I-25 | 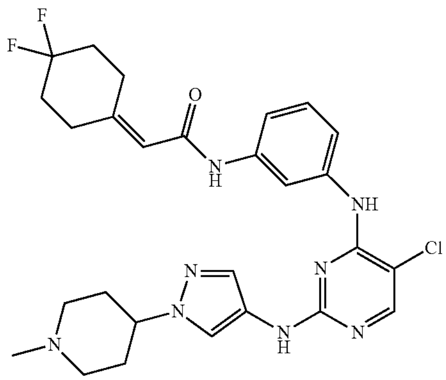 [SMILES: CN1CCC(n2cc(Nc3ncc(Cl)c(Nc4cccc(NC(=O)C=C5CCC(F)(F)CC5)c4)n3)cn2)CC1] | K | 558.4 | δ 10.02 (bs, 1H), 9.14 (brs, 1H), 8.82 (bs, 1H), 8.03 (s, 1H), 7.73 (s, 1H), 7.56 (bs, 1H), 7.41-7.3 (m, 3H), 7.11 (bs, 1H), 5.95 (s, 1H), 3.68 (bs, 1H), 3.02 (m, 2H), 2.78 (m, 2H), 2.35 (m, 2H), 2.20 (s, 3H), 2.0 (m, 6H), 1.72 (m, 4H) |
| I-26 | 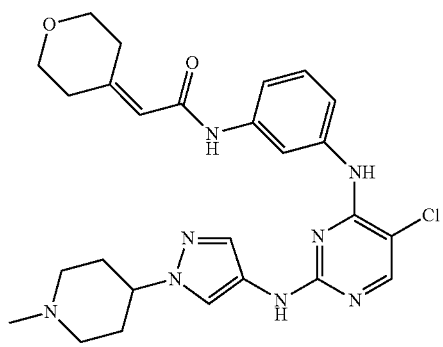 [SMILES: CN1CCC(n2cc(Nc3ncc(Cl)c(Nc4cccc(NC(=O)C=C5CCOCC5)c4)n3)cn2)CC1] | K | 558.4 | δ 9.95 (s, 1H), 9.15 (s, 1H), 8.81 (s, 1H), 8.02 (s, 1H), 7.72 (s, 1H), 7.62-7.54 (m, 2H), 7.29-7.23 (m, 2H), 7.07 (bs, 1H), 5.87 (s, 1H), 3.66-3.58 (m, 5H), 2.97 (m, 2H), 2.78-2.75 (m, 2H), 2.25 (m, 2H), 2.17 (s, 3H), 1.95 (m, 2H), 1.71 (m, 4H) |
| I-28 | 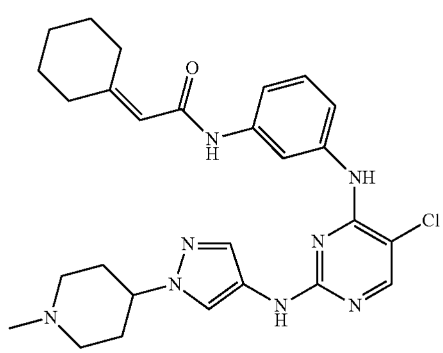 [SMILES: CN1CCC(n2cc(Nc3ncc(Cl)c(Nc4cccc(NC(=O)C=C5CCCCC5)c4)n3)cn2)CC1] | K | 523.3 (M + 2H)⁺ | δ 9.86 (s, 1H), 9.14 (bs, 1H), 8.79 (brs, 1H), 8.02 (s, 2H), 7.72 (s, 1H), 7.56-7.42 (m, 2H), 7.30-7.26 (m, 2H), 7.07 (m, 1H) 5.78 (s, 1H), 3.66 (bs, 1H), 2.83-2.76 (m, 4H), 2.18 (s, 3H), 2.15 (m, 2H), 1.97 (m, 2H), 1.71 (m, 4H), 1.53 (m, 6H) |
| I-29 | 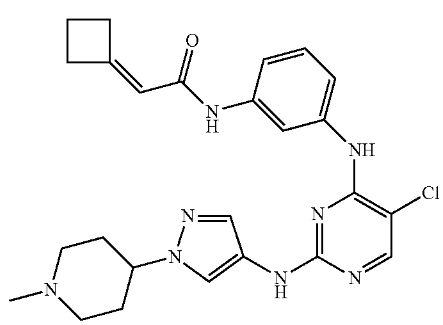 [SMILES: CN1CCC(n2cc(Nc3ncc(Cl)c(Nc4cccc(NC(=O)C=C5CCC5)c4)n3)cn2)CC1] | K | 493.3 [M +]⁺ | δ 9.80 (s, 1H), 9.15 (bs, 1H), 8.80 (bs, 1H), 8.02 (s, 1H), 7.72 (s, 1H), 7.54-7.47 (m, 2H), 7.28 (m, 2H), 7.07 (bs, 1H), 5.79 (s, 1H), 3.65 (bs, 1H), 3.07 (m, 2H), 2.80 (m, 4H), 2.19 (s, 3H), 2.04-2.00 (m, 4H), 1.72 (m, 4H) |

-continued

| Cmpd No. | Structure | Synthesis method | LCMS (M + 1) | $^1$H-NMR (400 MHz, DMSO-$d_6$) |
|---|---|---|---|---|
| I-30 | 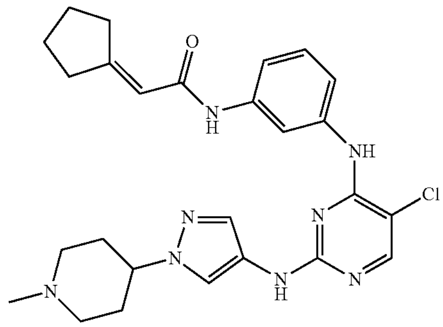 [SMILES: CN1CCC(n2cc(Nc3ncc(Cl)c(Nc4cccc(NC(=O)C=C5CCCC5)c4)n3)cn2)CC1] | K | 507.3 | δ 9.81(s, 1H), 9.13 (bs, 1H), 8.79 (bs, 1H), 8.02 (s, 1H), 7.74 (s,1H), 7.56 (bs, 1H), 7.43 (bs, 1H), 7.30-7.26 (m, 2H), 7.05 (bs, 1H), 6.00 (s, 1H), 4.04-4.00 (m, 1H), 3.66 (bs, 1H), 3.153 (s, 1H), 2.77-2.70 (m, 4H), 2.39 (t, 2H), 2.17 (s, 3H), 1.97-1.89 (m, 2H), 1.73-1.54 (m, 6H) |
| I-31 | 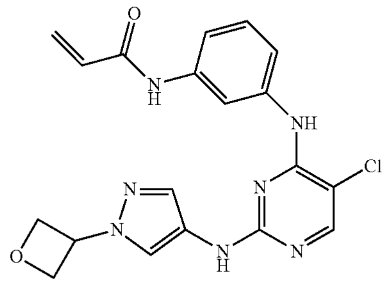 [SMILES: C=CC(=O)Nc1cccc(Nc2nc(Nc3cnn(C4COC4)c3)ncc2Cl)c1] | J | 412.4 | δ 10.22 (s, 1H), 9.30-9.25 (m, 1H), 8.94 (m, 1H), 8.08 (s, 1H), 7.87 (s, 1H), 7.56-7.19 (m, 5H), 6.48-6.41 (m, 1H), 6.25 (d, 1H), 5.74 (d, 1H), 5.16-5.08 (m, 1H), 4.79-4.64 (m, 4H). |
| I-32 | 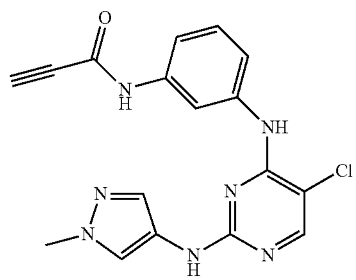 [SMILES: C#CC(=O)Nc1cccc(Nc2nc(Nc3cnn(C)c3)ncc2Cl)c1] | K | 368.35 | δ 10.89 (s, 1H), 9.23 (bs, 1H), 8.95 (bs, 1H), 8.07 (s, 1H), 7.78 (s, 1H), 7.46-7.24 (m, 5H), 4.43 (s, 1H), 3.60 (s, 3H). |
| I-33 | 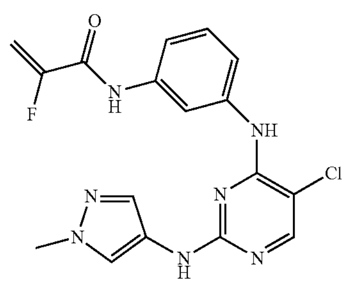 [SMILES: C=C(F)C(=O)Nc1cccc(Nc2nc(Nc3cnn(C)c3)ncc2Cl)c1] | K | 388.39 | δ 10.35 (s, 1H), 9.20 (bs, 1H), 8.93 (bs, 1H), 8.07 (s, 1H), 7.92 (s, 1H), 7.59-7.25 (m, 5H), 5.77-5.64 (m, 1H), 5.46-5.41 (m, 1H), 3.58 (bs, 3H) |
| I-34 | 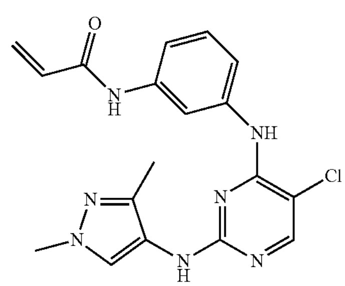 [SMILES: C=CC(=O)Nc1cccc(Nc2nc(Nc3cn(C)nc3C)ncc2Cl)c1] | J | 384.18 | δ 10.15 (s, 1H), 8.86 (bs, 1H), 8.71-8.57 (m, 1H), 8.05 (s, 1H), 7.83 (bs, 1H), 7.51-7.15 (m, 4H), 6.49-6.42 (m, 1H), 6.26 (d, 1H), 5.78 (d, 1H), 3.52 (bs, 3H), 2.06 (s, 3H); |

-continued
| Cmpd No. | Structure | Synthesis method | LCMS (M + 1) | ¹H-NMR (400 MHz, DMSO-d₆) |
|---|---|---|---|---|
| I-35 | 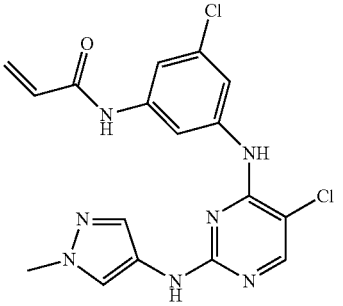 [SMILES: C=CC(=O)Nc1cc(Cl)cc(Nc2nc(Nc3cnn(C)c3)ncc2Cl)c1] | J | 404.34 | δ 10.36 (s, 1H), 9.32 (bs, 1H), 9.04 (bs, 1H), 8.12 (s, 1H), 7.72 (s, 2H), 7.45-7.28 (m, 3H), 6.46-6.391 (m, 1H), 6.28 (d, 1H), 5.80 (d, 1H), 3.61 (s, 3H). |
| I-36 | 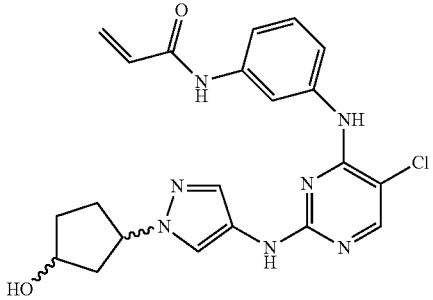 [SMILES: C=CC(=O)Nc1cccc(Nc2nc(Nc3cnn(C4CCC(O)C4)c3)ncc2Cl)c1] | J | 440.42 | δ 9.97 (s, 1H), 8.89 (s, 1H), 8.60 (s, 1H), 8.05 (s, 1H), 7.81 (s, 1H), 7.60-7.54 (m, 2H), 7.36 (s, 1H), 7.35-7.31 (m, 2H), 6.49-6.42 (m, 1H), 6.25 (d, 1H), 5.74 (d, 1H), 4.70-4.60 (m, 1H), 4.43-4.35 (m, 1H), 4.19-4.09 (m, 1H), 2.27-2.21 (m, 1H), 1.99-1.90 (m, 1H), 1.82-1.72 (m, 3H), 1.69-1.61 (m, 1H) |
| I-37 | 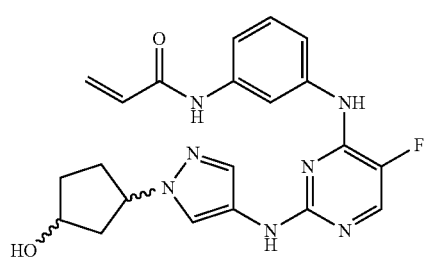 [SMILES: C=CC(=O)Nc1cccc(Nc2nc(Nc3cnn(C4CCC(O)C4)c3)ncc2F)c1] | J | 424.21 | δ 10.17 (s, 1H), 9.34 (s, 1H), 8.99 (s, 1H), 8.05 (s, 1H), 7.87 (s, 1H), 7.68 (bs, 1H), 7.54-7.30 (m, 4H), 6.49-6.43 (m, 1H), 6.25 (d, 1H), 5.75 (d, 1H), 4.86 (s, 1H), 4.43-4.38 (m, 1H), 4.11 (s, 1H), 1.92-1.89 (m, 2H), 1.81-1.64 (m, 4H) |
| I-38 | 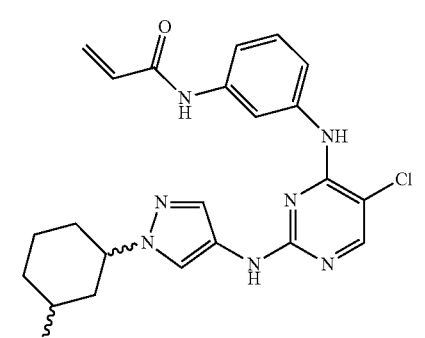 | J | 454.16 | δ 10.21 (s, 1H), 9.28 (s, 1H), 8.91 (s, 1H), 8.14 (s, 1H), 7.78 (s, 1H), 7.73-7.60 (m, 1H), 7.49-7.13 (m, 4H), 6.54-6.44 (m, 1H), 6.25 (d, 1H), 5.75 (d, 1H), 4.75-4.65 (m, 1H), 3.87-3.59 (m, 1H) 3.59-3.40 (m, 1H), 1.95-1.59 (m, 4H), 1.46-1.06 (m, 4H) |
| I-39 | 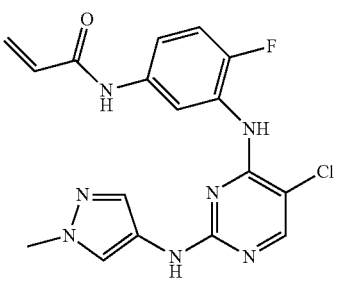 [SMILES: C=CC(=O)Nc1ccc(F)c(Nc2nc(Nc3cnn(C)c3)ncc2Cl)c1] | J | 388.2 | δ 10.24 (s, 1H), 9.10 (bs, 1H), 8.85 (bs, 1H), 8.03 (s, 1H), 7.75 (d, 1H), 7.64 (m, 1H), 7.33 (m, 1H), 6.98-7.20 (m, 2H) 6.40 (dd, 1H), 6.24 (dd, 1H), 5.74 (dd, 1H), 3.52 (s, 3H) |

| Cmpd No. | Structure | Synthesis method | LCMS (M + 1) | ¹H-NMR (400 MHz, DMSO-d$_6$) |
|---|---|---|---|---|
| I-40 | 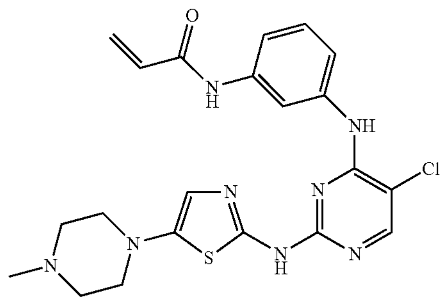 [SMILES: C=CC(=O)Nc1cccc(Nc2nc(Nc3ncc(N4CCN(C)CC4)s3)ncc2Cl)c1] | J | 471.18 | δ 10.83 (s, 1H), 10.14 (s, 1H), 9.15 (s, 1H), 8.20-8.17 (d, 1H), 7.76 (bs, 1H), 7.66 (bs, 1H), 7.34-7.30 (t, 1H), 7.21 (bs, 1H), 6.47-6.40 (m, 2H), 6.27-6.23 (d, 1H), 5.77-5.74 (d, 1H), 2.78 (s, 4H), 2.37 (s, 4H), 2.19 (s, 3H) |
| I-41 | 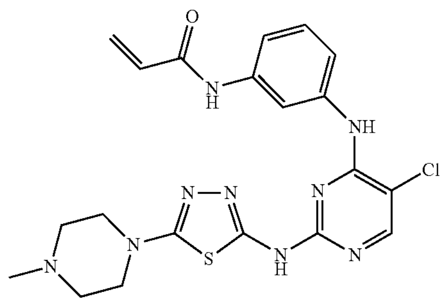 [SMILES: C=CC(=O)Nc1cccc(Nc2nc(Nc3nnc(N4CCN(C)CC4)s3)ncc2Cl)c1] | J | 472.14 | δ 11.05 (bs, 1H), 10.17 (s, 1H), 9.10 (bs, 1H), 8.14 (bs, 1H), 7.74-7.72 (m, 1H), 7.64-7.62 (m, 1H), 7.35-7.31 (t, 1H), 7.25 (bs, 1H), 6.48-6.41 (m, 1H), 6.28-6.23 (d, 1H), 5.77-5.74 (d, 1H), 3.12 (s, 4H), 2.34 (s, 4H), 2.19 (s, 3H) |
| I-42 | 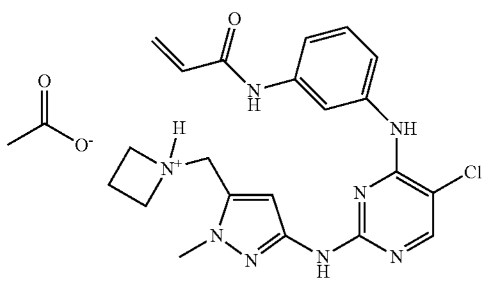 | J | 439.19 [M—CH3COOH + H ]⁺ | δ 10.18 (s, 1H), 9.33 (s, 1H), 8.85 (s, 1H), 8.07 (s, 1H), 7.85 (m, 1H), 7.64 (m, 1H), 7.35-7.30 (m, 2H), 6.50-6.43 (m, 1H), 6.29-6.15 (m, 2H), 5.76 (m, 1H), 3.60 (m, 5H), 3.02 (m, 6H), 1.91 (s, 3H) |
| I-43 | 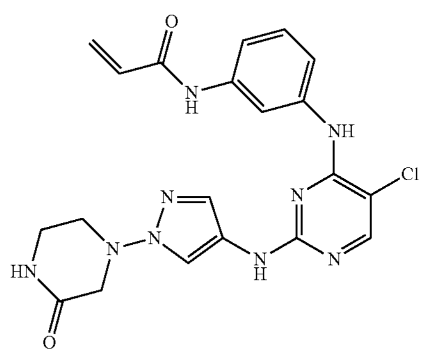 [SMILES: C=CC(=O)Nc1cccc(Nc2nc(Nc3cnn(N4CCNC(=O)C4)c3)ncc2Cl)c1] | J | 453.14 | δ 10.21 (s, 1H), 9.25 (bs, 1H), 8.95 (bs, 1H), 8.07 (s, 1H), 7.79 (s, 1H), 7.61-7.51 (m, 2H), 7.41-7.16 (m, 4H), 6.47-6.40 (m, 1H), 6.27-6.23 (d, 1H), 5.76-5.74 (d, 1H), 4.26-4.23 (m, 1H), 3.19-3.11 (m, 2H), 3.09-3.02 (m, 2H), 1.87-1.77 (m, 2H) |
| I-44 | 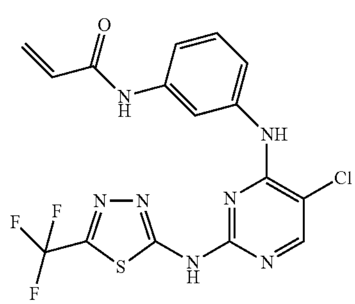 [SMILES: C=CC(=O)Nc1cccc(Nc2nc(Nc3nnc(C(F)(F)F)s3)ncc2Cl)c1] | J | 442.06 | δ 12.48 (s, 1H), 10.19 (s, 1H), 9.50 (s, 1H), 8.36 (s, 1H), 7.86 (s, 1H), 7.60-7.57 (m, 1H), 7.39-7.35 (m, 1H), 7.18 (bs, 1H), 6.45-6.38 (m, 1H), 6.24-6.20 (d, 1H), 5.75-5.72 (d, 1H) |

-continued

| Cmpd No. | Structure | Synthesis method | LCMS (M + 1) | ¹H-NMR (400 MHz, DMSO-d$_6$) |
|---|---|---|---|---|
| I-45 | 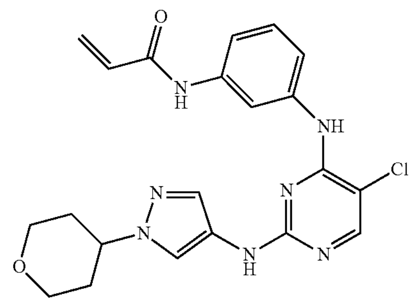 [SMILES: C=CC(=O)Nc1cccc(Nc2nc(Nc3cnn(C4CCOCC4)c3)ncc2Cl)c1] | J | 440.18 | δ 10.24 (s, 1H), 9.26 (s, 1H), 8.93 (s, 1H), 8.06 (s, 1H), 7.79 (s, 1H), 7.66 (bs, 1H), 7.42-7.11 (m, 4H), 6.47-6.41 (m, 1H), 6.27-6.23 (d, 1H), 5.77-5.74 (d, 1H), 3.90-3.87 (m, 3H), 3.45-3.32 (m, 2H), 1.79-1.65 (m, 4H) |
| I-46 | 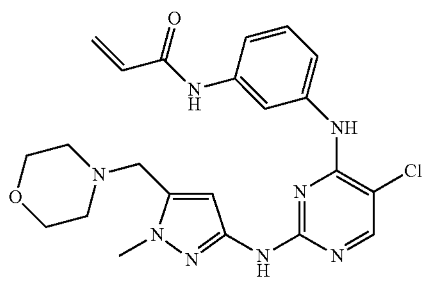 [SMILES: C=CC(=O)Nc1cccc(Nc2nc(Nc3cc(CN4CCOCC4)n(C)n3)ncc2Cl)c1] | J | 469.17 | δ 10.15 (s, 1H), 9.32 (s, 1H), 8.85 (s, 1H), 8.09 (s, 1H), 7.87 (s, 1H), 7.57-7.55 (d, 1H), 7.32-7.28 (m, 2H), 6.48-6.42 (m, 1H), 6.28-6.23 (d, 1H), 6.15 (bs, 1H), 5.77-5.75 (d, 1H), 3.64 (s, 3H), 3.50 (s, 4H), 3.28 (s, 2H), 2.25 (s, 4H) |
| I-47 | 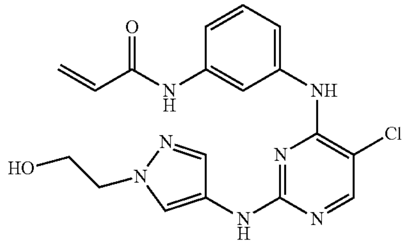 [SMILES: C=CC(=O)Nc1cccc(Nc2nc(Nc3cnn(CCO)c3)ncc2Cl)c1] | J | 401.14 | δ 10.39 (s, 1H), 9.79 (s, 1H), 8.40 (s, 1H), 7.86-7.50 (m, 4H), 7.08-7.84 (m, 2H), 6.46-6.39 (m, 1H), 6.28-6.24 (d, 1H), 5.79-5.76 (d, 1H), 4.79 (s, 1H), 3.78 (bs, 2H), 3.52 (bs, 2H) |
| I-48 | 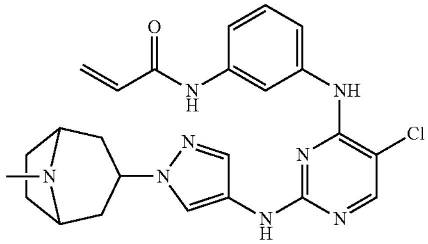 [SMILES: C=CC(=O)Nc1cccc(Nc2nc(Nc3cnn(C4CC5CCC(C4)N5C)c3)ncc2Cl)c1] | J | 479.24 | δ 10.28 (bs, 1H), 9.27 (bs, 1H), 8.92 (bs, 1H), 8.11 (s, 1H), 7.75-7.68 (m, 1H), 7.58-7.52 (m, 1H), 7.42-7.16 (m, 4H), 6.47-6.40 (m, 1H), 6.27-6.22 (m, 1H), 5.76 (d, 1H), 4.01-3.84 (m, 1H), 3.12 (m, 2H), 2.22 (s, 3H), 2.06-1.96-1.68 (m, 4H), 1.59-1.45 (m, 4H) |
| I-49 | 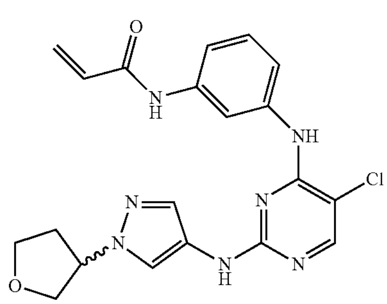 [SMILES: C=CC(=O)Nc1cccc(Nc2nc(Nc3cnn(C4CCOC4)c3)ncc2Cl)c1] | J | 426.43 | δ 10.22 (s, 1H), 9.25 (bs, 1H), 8.91 (bs, 1H), 8.07 (s, 1H), 7.82 (s, 1H), 7.56-7.17 (m, 5H), 6.49-6.42 (m, 1H), 6.27-6.23 (d, 1H), 5.77-5.74 (d, 1H), 4.93-4.59 (m, 1H), 3.86-3.64 (m, 4H), 2.32-2.14 (m, 1H), 2.12-2.05 (m, 1H) |

| Cmpd No. | Structure | Synthesis method | LCMS (M + 1) | ¹H-NMR (400 MHz, DMSO-d$_6$) |
|---|---|---|---|---|
| I-50 | 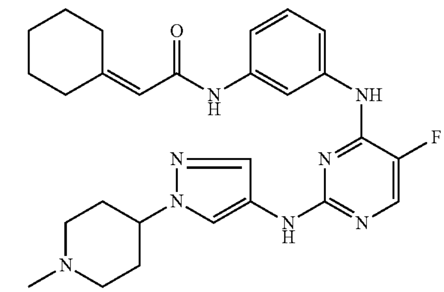 [SMILES: CN1CCC(n2cc(Nc3ncc(F)c(Nc4cccc(NC(=O)C=C5CCCCC5)c4)n3)cn2)CC1] | K | 505.7 | δ 9.84 (s, 1H), 9.35 (s, 1H), 9.03 (s, 1H), 8.02 (d, 1H), 7.76 (m, 2H), 7.40-7.24 (m, 4H), 5.80 (s, 1H), 3.66 (bs, 1H), 3.10-3.07 (m, 2H), 2.83-2.76 (m, 4H), 2.18 (s, 3H), 2.1-2.02 (m, 2H), 1.72-1.70 (m, 2H), 1.6-1.5 (m, 6H), 0.97-0.92 (m, 2H) |
| I-51 | 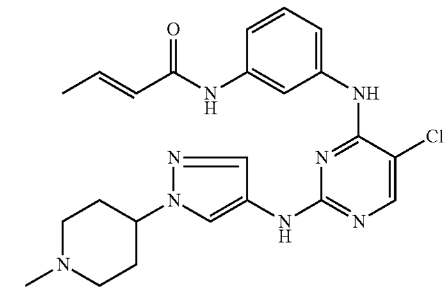 [SMILES: C/C=C/C(=O)Nc1cccc(Nc2nc(Nc3cnn(C4CCN(C)CC4)c3)ncc2Cl)c1] | J | 467.3 | δ 9.84 (s, 1H), 9.15 (bs, 1H), 8.82 (s, 1H), 8.03 (s, 1H), 7.75 (s, 1H), 7.57-7.41 (m, 2H), 7.35-7.2 (m, 2H), 7.09 (m, 1H), 6.81-6.72 (m, 1H), 6.11 (d, 1H), 3.65 (m, 1H), 2.77-2.75 (m, 2H), 2.17 (s, 3H), 1.95 (m, 2H), 1.85-1.83 (m, 3H), 1.69 (m, 2H) |
| I-52 | 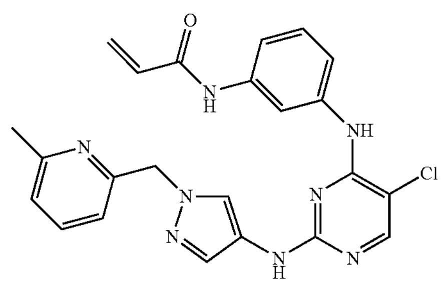 [SMILES: C=CC(=O)Nc1cccc(Nc2nc(Nc3cnn(Cc4cccc(C)n4)c3)ncc2Cl)c1] | J | 461.23 | δ 10.14 (s, 1H), 9.31 (bs, 1H), 9.23 (bs, 1H), 8.07 (s, 1H), 7.83 (d, 1H), 7.66-7.11 (m, 6H), 6.65-6.37 (m, 2H), 6.24-6.19 (m, 1H), 5.74-5.69 (m, 1H), 5.27-5.06 (m, 2H), 2.44 (s, 3H) |
| I-53 | 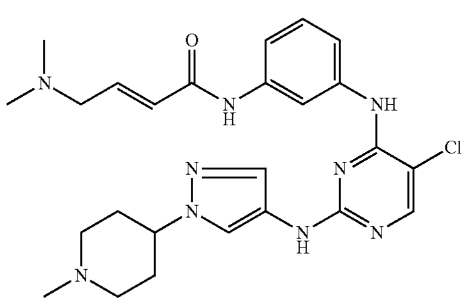 [SMILES: CN(C)C/C=C/C(=O)Nc1cccc(Nc2nc(Nc3cnn(C4CCN(C)CC4)c3)ncc2Cl)c1] | K | 510.3 | δ 10.10 (s, 1H), 9.15 (s, 1H), 8.83 (s, 1H), 8.03 (s, 1H), 7.75 (m, 1H), 7.59 (m, 1H), 7.50-7.11 (m, 4H), 6.75-6.67 (m, 1H), 6.27 (d, 1H), 3.70 (m, 1H), 3.07-3.05 (m, 2H), 2.82 (m, 2H), 2.23 (s, 3H), 2.17 (s, 6H), 2.1-2.02 (m, 2H), 1.78-1.62 (m, 4H) |
| I-54 | 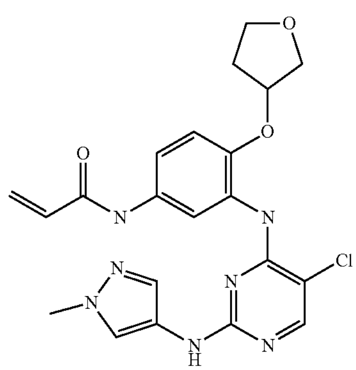 [SMILES: C=CC(=O)Nc1ccc(OC2CCOC2)c(Nc2nc(Nc3cnn(C)c3)ncc2Cl)c1] | J | 456.13 | δ 10.10 (br s, 1H), 9.19 (br s, 1H), 8.29 (br s, 1H), 8.05 (s, 1H), 7.82-7.83 (m, 1H), 7.64 (m, 1H), 7.10-7.12 (m, 3H), 6.39-6.46 (m, 1H), 6.23 (d, 1H), 5.74 (d, 1H), 4.95 (br s, 1H), 3.54-3.78 (m, 7H), 2.06-2.07 (m, 1H), 1.86 (m, 1H) |

-continued

| Cmpd No. | Structure | Synthesis method | LCMS (M + 1) | ¹H-NMR (400 MHz, DMSO-d$_6$) |
|---|---|---|---|---|
| I-55 | 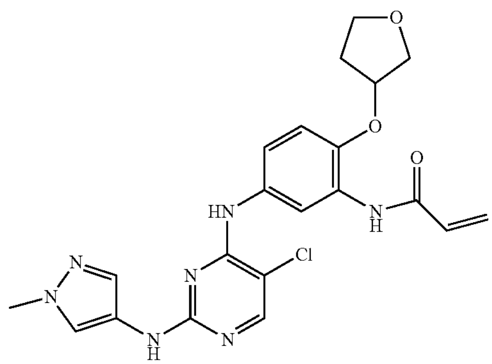 [SMILES: C=CC(=O)Nc1cc(Nc2nc(Nc3cnn(C)c3)ncc2Cl)ccc1OC1CCOC1] | J | 456.49 | δ 8.99- 9.19 (m, 2H), 8.78 (br s, 1H), 8.18 (s, 1H), 8.01 (s, 1H), 7.20-7.57 (m, 2H), 7.08 (m, 1H), 6.67-6.74 (m, 1H), 6.22 (d, 1H), 5.74 (d, 1H), 5.05 (br s, 1H), 3.89-3.93 (m, 3H), 3.74-3.79 (m, 1H), 3.59 (br s, 3H), 2.08-2.29 (m, 2H), 1.23 (m, 1H) |
| I-56 | 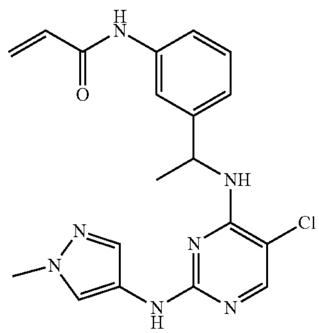 [SMILES: C=CC(=O)Nc1cccc(C(C)Nc2nc(Nc3cnn(C)c3)ncc2Cl)c1] | J | 398.13 | δ 10.23 (s, 1H), 9.10-9.00 (m, 1H), 7.90 (s, 1H), 7.65 (s, 1H), 7.57-7.55 (m, 1H), 7.45-7.37 (m, 1H), 7.31-7.21 (m, 3H), 7.15-7.13 (d, 1H), 6.46-6.39 (m, 1H), 6.31-6.22 (m, 1H), 5.72-5.32 (m, 1H), 5.31 (bs, 1H), 3.71 (s, 3H) and 1.55-1.53 (d, 3H) |
| I-57 | 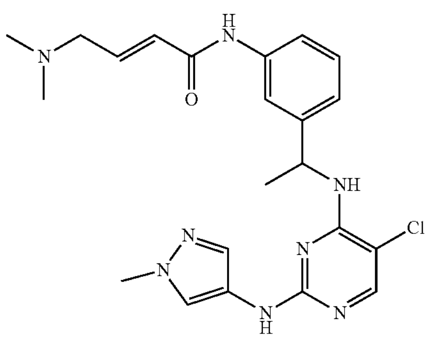 [SMILES: CC(Nc1nc(Nc2cnn(C)c2)ncc1Cl)c1cccc(NC(=O)/C=C/CN(C)C)c1] | K | 455.19 | δ 10.06 (s, 1H), 8.99-8.92 (bs, 1H), 7.89 (s, 1H), 7.65 (s, 1H), 7.59-7.52 (m, 1H), 7.49-7.39 (m, 2H), 7.35-7.20 (m, 2H), 7.13-7.11 (m, 1H), 6.74-6.67 (m, 1H), 6.28-6.24 (d, 1H), 5.37-5.30 (m, 1H), 3.71 (s, 3H), 3.09-3.08 (d, 2H), 2.19 (s, 6H), 1.55-1.53 (d, 3H) |
| I-58 | 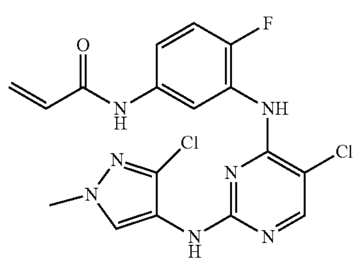 [SMILES: C=CC(=O)Nc1ccc(F)c(Nc2nc(Nc3cn(C)nc3Cl)ncc2Cl)c1] | J | 422.18 | δ 10.26 (br s, 1H), 8.92 (br s, 1H), 8.54 (br s, 1H), 8.07 (s, 1H), 7.77 (d, 1H), 7.62 (m, 1H), 7.30-7.34 (m, 2H), 6.39-6.45 (m, 1H), 6.26 (d, 1H), 5.77 (d, 1H), 3.56 (s, 3H) |
| I-59 | 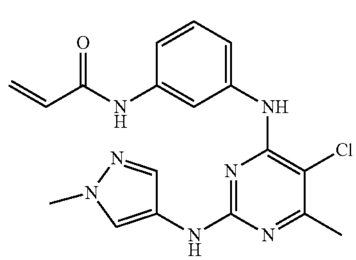 [SMILES: C=CC(=O)Nc1cccc(Nc2nc(Nc3cnn(C)c3)nc(C)c2Cl)c1] | J | 384.07 | δ 10.19 (br s, 1H), 9.18 (br s, 1H), 8.82 (br s, 1H), 7.79 (s, 1H), 7.56 (m, 1H), 7.43 (m, 2H), 7.18 (m, 2H), 6.41-6.48 (m, 1H), 6.25 (d, 1H), 5.75 (d, 1H), 3.53 (s, 3H), 2.33 (s, 3H) |

| Cmpd No. | Structure | Synthesis method | LCMS (M + 1) | $^1$H-NMR (400 MHz, DMSO-d$_6$) |
|---|---|---|---|---|
| I-60 | 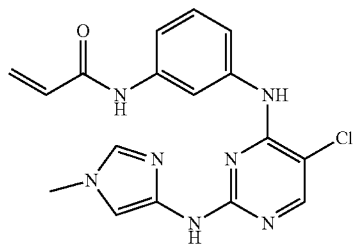 [SMILES: C=CC(=O)Nc1cccc(Nc2nc(Nc3cn(C)cn3)ncc2Cl)c1] | J | 370.4 | δ 10.13 (s, 1H), 9.13 (s, 1H), 8.83 (s, 1H), 8.05 (s, 1H), 7.87 (bs, 1H), 7.60-7.58 (m, 1H), 7.33 (bs, 1H), 7.24 (s, 2H), 6.56 (bs, 1H), 6.47-6.40 (m, 1H), 6.26-6.22 (d, 1H), 5.75-5.73 (d, 1H), 3.40 (s, 3H) |
| I-61 | 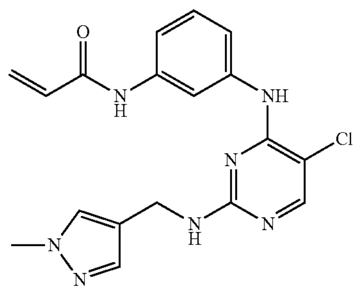 [SMILES: C=CC(=O)Nc1cccc(Nc2nc(NCc3cnn(C)c3)ncc2Cl)c1] | J | 384.84 | δ 10.04 (s, 1H), 8.56 (s, 1H), 8.04 (bs, 1H), 7.95 (s, 1H), 7.39-7.31 (m, 2H), 7.25-7.10 (m, 3H), 6.46-6.39 (m, 1H), 6.25-6.21 (d, 1H), 5.74-5.71 (d, 1H), 4.19 (s, 2H), 3.69 (s, 3H) |
Example 2: Synthesis of N-(3-((5-chloro-2-((1-(piperidin-4-yl)-1H-pyrazol-4-yl)amino)pyrimidin-4-yl)amino)phenyl)acrylamide trifluoroacetate (I-62)
Scheme-38:
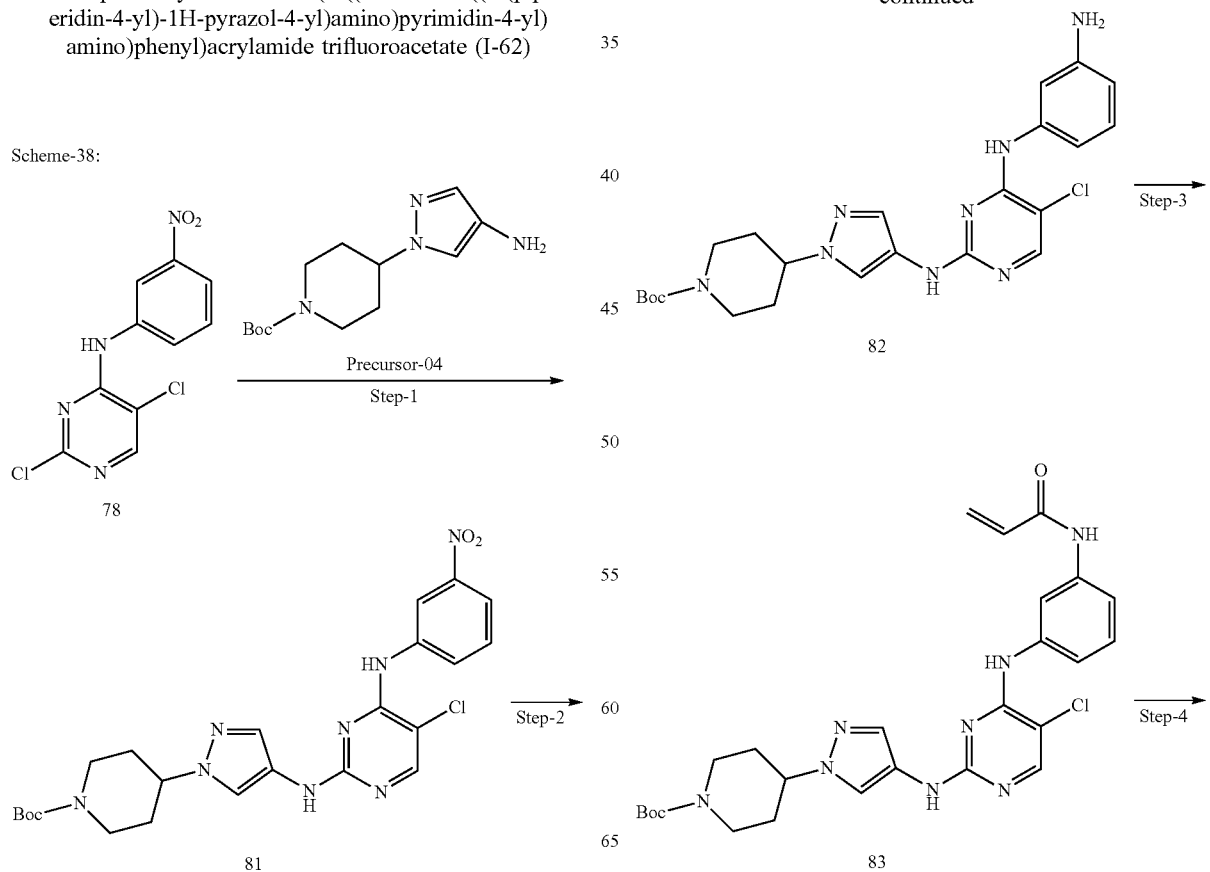

-continued

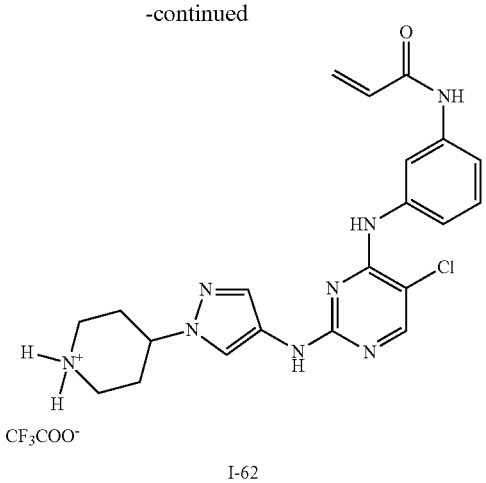

I-62

Synthesis of tert-butyl 4-(4-((5-chloro-4-((3-nitrophenyl)amino)pyrimidin-2-yl)amino)-1H-pyrazol-1-yl)piperidine-1-carboxylate (81)

To a solution of tert-butyl 4-(4-amino-1H-pyrazol-1-yl)piperidine-1-carboxylate precursor-04 (0.80 g, 3.0 mmol) and 2,5-dichloro-N-(3-nitrophenyl)pyrimidin-4-amine 78 (0.85 g, 3.0 mmol) in DMF (10 mL), $K_2CO_3$ (0.41 g, 3.0 mmol) was charged and heated at 85° C. for 4 h. The reaction mixture was cooled to room temperature and diluted with water (20 mL). The reaction mixture was extracted with ethyl acetate (2×50 mL). The combined organic extract was dried over $Na_2SO_4$ evaporated to obtain tert-butyl 4-(4-((5-chloro-4-((3-nitrophenyl)amino)pyrimidin-2-yl)amino)-1H-pyrazol-1-yl)piperidine-1-carboxylate 81 (0.50 g, 34% yield) as pale yellow solid. MS: 515.0 $(M+H)^+$.

Synthesis of tert-butyl 4-(4-((4-((3-aminophenyl)amino)-5-chloropyrimidin-2-yl)amino)-1H-pyrazol-1-yl)piperidine-1-carboxylate (82)

To a solution of tert-butyl 4-(4-((5-chloro-4-((3-nitrophenyl)amino)pyrimidin-2-yl)amino)-1H-pyrazol-1-yl)piperidine-1-carboxylate 81 (0.27 g, 0.5 mmol) in ethanol (10 mL) was added raney-Ni (0.05 g) under nitrogen atmosphere. The resulting reaction mixture was stirred at rt under $H_2$ atmosphere for 12 h. After the completion of reaction (TLC monitored), diluted with ethanol (10 mL) and filtered through celite. Filtrate was evaporated under reduced pressure to obtain tert-butyl 4-(4-((4-((3-aminophenyl)amino)-5-chloropyrimidin-2-yl)amino)-1H-pyrazol-1-yl)piperidine-1-carboxylate 82 (0.22 g, 86% yield) as a brown solid. MS: 485.2 $(M+H)^+$.

Synthesis of tert-butyl 4-(4-((4-((3-acrylamidophenyl)amino)-5-chloropyrimidin-2-yl)amino)-1H-pyrazol-1-yl)piperidine-1-carboxylate (83)

Title compound was prepared following method substantially similar to general method J and obtained title compound in 16% yield. $^1$HNMR (400 MHz, DMSO): δ 10.35 (s, 1H), 8.74 (s, 1H), 8.39 (s, 1H), 8.17 (s, 1H), 7.75 (m, 2H), 7.42-7.24 (m, 3H), 7.16 (s, 1H), 6.47 (dd, 1H), 6.27 (d, 1H), 5.76 (d, 1H), 3.91-3.98 (m, 1H), 3.02 (s, 2H), 2.01-2.07 (m, 2H), 1.68-1.84 (m, 4H), 1.49 (s, 9H). MS: 539.03 $(M+H)^+$.

Synthesis of N-(3-((5-chloro-2-((1-(piperidin-4-yl)-1H-pyrazol-4-yl)amino)pyrimidin-4-yl)amino)phenyl)acrylamide trifluoroacetate (I-62)

To a solution of tert-butyl 4-(4-((4-((3-acrylamidophenyl)amino)-5-chloropyrimidin-2-yl)amino)-1H-pyrazol-1-yl)piperidine-1-carboxylate 83 (0.4 g, 0.074 mmol) in dry DCM (3 mL) was added TFA (23 μL, 0.297 mmol) at 0° C. The reaction mixture was stirred for 8 h at room temperature. The reaction was monitored on TLC using methanol:dichloromethane (10:90) as mobile phase. Solvent was evaporated under reduced pressure to obtain N-(3-((5-chloro-2-((1-(piperidin-4-yl)-1H-pyrazol-4-yl)amino)pyrimidin-4-yl)amino)phenyl) acrylamide trifluoroacetate I-62 (0.03 g, 92% yield) as white solid. 1HNMR (400 MHz, DMSO-d6): δ 10.2 (bs, 1H), 9.26 (bs, 1H), 8.92 (bs, 1H), 8.61 (bs, 1H), 8.29 (bs, 1H), 8.06 (s, 1H), 7.66 (m, 2H), 7.35-7.07 (m, 4H), 6.46-6.42 (m, 1H), 6.27-6.22 (m, 1H), 5.76-5.74 (m, 1H), 3.49 (m, 1H), 3.37-3.33 (m, 2H), 3.00 (m, 2H), 1.94 (m, 4H). LCMS: 437.2 $(M-TFA-H)^+$; purity: 96%.

Example-3: Synthesis of 1-(3-((5-chloro-2-((1-methyl-1H-pyrazol-4-yl)amino)pyrimidin-4-yl)amino)phenyl)-1H-pyrrole-2,5-dione (I-63)

Scheme-39:

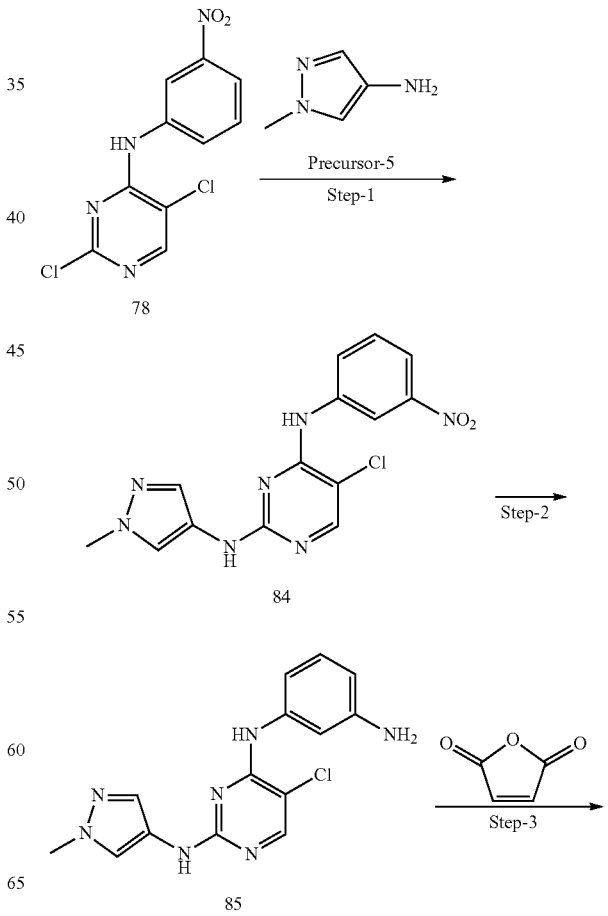

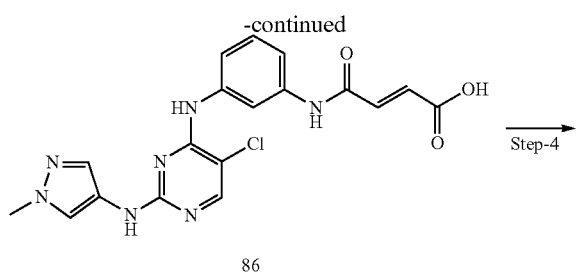

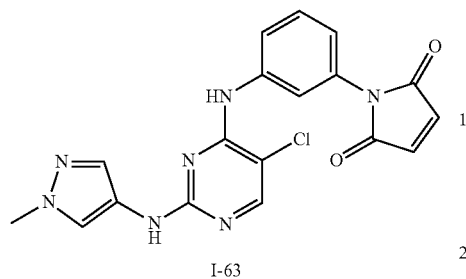

Synthesis of 5-chloro-$N^2$-(1-methyl-1H-pyrazol-4-yl)-$N^4$-(3-nitrophenyl)pyrimidine-2,4-diamine (84)

Title compound was prepared following procedure similar to general method F in 71% yield.
MS: 346.10 (M+H)+.

Synthesis of $N^4$-(3-aminophenyl)-5-chloro-$N^2$-(1-methyl-1H-pyrazol-4-yl)pyrimidine-2,4-diamine (85)

Title compound was prepared following method substantially similar to general method H in 95% yield.
MS: 316.10 (M+H)+.

Synthesis of (E)-4-((3-((5-chloro-2-((1-methyl-1H-pyrazol-4-yl)amino)pyrimidin-4-yl)amino)phenyl)amino)-4-oxobut-2-enoic acid (86)

To a solution of $N^4$-(3-aminophenyl)-5-chloro-$N^2$-(1-methyl-1H-pyrazol-4-yl)pyrimidine-2,4-diamine (1.50 g, 4.75 mmol) in DMF (20 ml) was added maleic anhydride (0.70 g, 7.12 mmol) and the reaction mixture was stirred at rt for 3 h. After the completion of reaction (TLC monitoring), ice-cold water was added to the mixture followed by extraction with 20% IPA-CHCl$_3$ (3×50 mL). The combined organics was dried over Na$_2$SO$_4$, filtered and concentrated under reduced pressure. The residue was triturated with Et$_2$O to get the desired product (1.30 g, 66% yield). MS: 414.10 (M+H)+.

Synthesis of 1-(3-((5-chloro-2-((1-methyl-1H-pyrazol-4-yl)amino)pyrimidin-4-yl)amino)phenyl)-1H-pyrrole-2,5-dione (I-63)

To a stirred solution of (E)-4-((3-((5-chloro-2-((1-methyl-1H-pyrazol-4-yl)amino)pyrimidin-4-yl)amino)phenyl)amino)-4-oxobut-2-enoic acid 86 (0.40 g, 0.96 mmol) in 1:1 mixture of water (8 mL) and 1,2-dichloroethane (8 mL), TBAB (0.090 g, 0.29 mmol) and sodium carbonate (0.120 g, 1.1 mmol) were added. dimethyl sulfate (0.180 g, 1.4 mmol) was added drop wise and the mixture was stirred at rt for 2 h. Solvent evaporated under nitrogen atmosphere, the precipitated solid was filtered and washed with dichloromethane and diethyl ether to obtain 1-(3-((5-chloro-2-((1-methyl-1H-pyrazol-4-yl)amino)pyrimidin-4-yl)amino)phenyl)-1H-pyrrole-2,5-dione I-63 in 13% yield as a yellow solid. $^1$HNMR (400 MHz, DMSO-d6): δ 9.30 (s, 1H), 9.17-9.10 (bs, 1H), 8.18 (s, 1H), 8.09-6.96 (m, 8H), 3.64 (s, 3H). LCMS: 396.36 (M+H)+, LCMS purity 96%.

Example 4: Synthesis of N-(5-((5-chloro-2-((1-(1-methylpiperidin-4-yl)-1H-pyrazol-4-yl)amino)pyrimidin-4-yl)amino)-2-fluorophenyl)ethenesulfonamide (I-64)

Scheme-40:

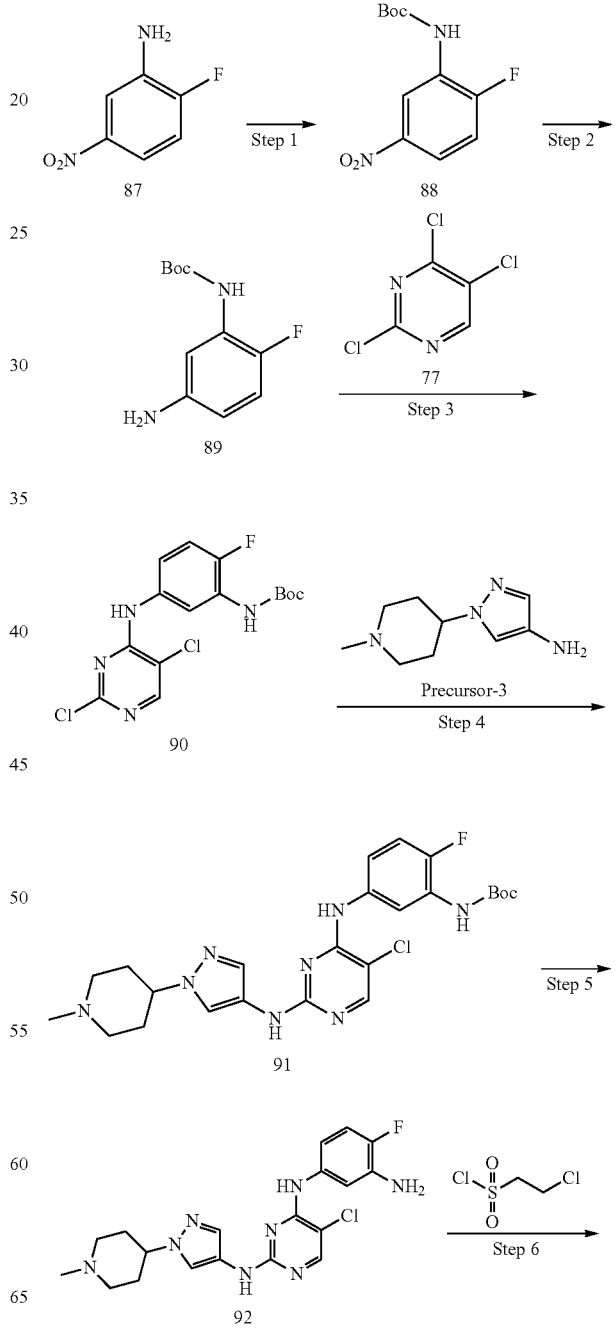

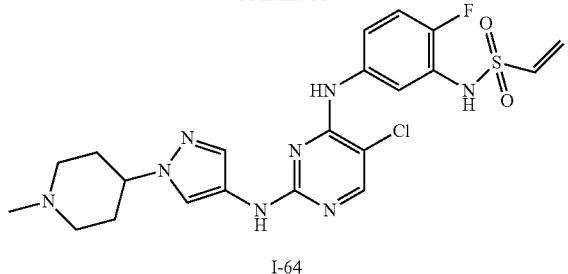

I-64

Synthesis of tert-butyl (2-fluoro-5-nitrophenyl)carbamate (88)

A suspension of 2-fluoro-5-nitroaniline 87 (10 g, 64 mmol) and bocanhydride (34.8 g, 159 mmol) was heated to 80° C., and stirred for 24 h. Reaction mixture was cooled to rt and diluted with DCM (20 mL) and absorbed onto silica gel and purified by silica gel chromatography to obtain pure product tert-butyl (2-fluoro-5-nitrophenyl)carbamate 88 as pale yellow liquid (6.3 g, 40% yield). MS: 255.0 (M+H)$^+$

Synthesis of tert-butyl (5-amino-2-fluorophenyl)carbamate (89)

To a solution of tert-butyl (2-fluoro-5-nitrophenyl)carbamate (88) (6.3 g, 24.58 mmol) in EtOH (60 ml) and THF (10 ml) (6:1) was added 10% Pd/C (1 g) under nitrogen atm. Then the reaction mixture was stirred for 16 h at RT under hydrogen atm. The reaction was monitored by TLC, after the completion of reaction; the reaction mixture was filtered through ceilite washed with MeOH. The filtrate was concentrated under vacuum to get crude product 89. The crude product was taken to next step without further purification. (4.92 g, 88% yield). MS: 227.2 (M+H)$^+$.

Synthesis of tert-butyl (5-((2,5-dichloropyrimidin-4-yl)amino)-2-fluorophenyl)carbamate (90)

To a solution of 2,4,5-trichloropyrimidine 77 (1 g, 5.45 mmol) in n-butanol (15 ml) were added tert-butyl (5-amino-2-fluorophenyl)carbamate 89 (1.4 g, 6.54 mmol) and DIPEA (1.05 g, 8.17 mmol). The reaction mixture was stirred for 16 h at 100° C. The reaction was monitored by TLC, after the completion of reaction, the reaction mixture was concentrated completely and diluted with water (100 ml) and extracted with DCM (2×100 ml). The organic layer was washed with brine (50 ml) and dried over sodium sulphate and evaporated under reduced pressure to obtain crude product. The crude product was purified using combiflash with 5-10% EtOAc in hexane as a solvent to get pure product as tert-butyl (5-((2,5-dichloropyrimidin-4-yl)amino)-2-fluorophenyl)carbamate 90 (1.1 g, 54% yield). MS: 375.0 (M+H)$^+$.

Synthesis of tert-butyl (5-((5-chloro-2-((1-(1-methylpiperidin-4-yl)-1H-pyrazol-4-yl)amino)pyrimidin-4-yl)amino)-2-fluorophenyl)carbamate (91)

To a solution of tert-butyl (5-((2,5-dichloropyrimidin-4-yl)amino)-2-fluorophenyl)carbamate 90 (0.5 g, 1.34 mmol) in n-butanol (10 ml) was added 1-(1-methylpiperidin-4-yl)-1H-pyrazol-4-amine precursor-3 (0.289 g, 1.6 mmol) and TFA (0.183 g, 1.6 mmol). The reaction mixture was heated for 16 h at 100° C. Reaction was monitored by TLC, after the completion of reaction, reaction mixture was concentrated, water (10 ml) and sat. sodium bicarbonate (20 mL) were added to the residue and extracted with DCM (3×100 ml), organic layer was washed with brine solution (10 ml), organic layer was dried over sodium sulphate and evaporated under reduced pressure to obtain crude product. The crude product was purified by using combiflash with 0-5% DCM in MeOH as a solvent to get pure product as tert-butyl (5-((5-chloro-2-((1-(1-methylpiperidin-4-yl)-1H-pyrazol-4-yl)amino)pyrimidin-4-yl)amino)-2-fluorophenyl)carbamate 91 as off white solid with 35% yield. MS: 519.3 (M+2H)$^+$.

Synthesis of N$^4$-(3-amino-4-fluorophenyl)-5-chloro-N$^2$-(1-(1-methylpiperidin-4-yl)-1H-pyrazol-4-yl)pyrimidine-2,4-diamine (92)

To a solution of tert-butyl (5-((5-chloro-2-((1-(1-methylpiperidin-4-yl)-1H-pyrazol-4-yl)amino)pyrimidin-4-yl)amino)-2-fluorophenyl)carbamate 91 (0.12 g, 0.232 mmol) in MeOH (3 mL) was cooled to 0° C., then dioxane in HCl (3 mL) was added. The reaction mixture was stirred for 16 h at RT. Reaction was monitored by TLC, after the completion of reaction, reaction mixture was concentrated, water (10 mL) and sat. sodium bicarbonate (10 mL) were added to the residue and extracted with DCM (3×50 mL), organic layer was washed with brine solution (10 ml), organic layer was dried over sodium sulphate and evaporated under reduced pressure to obtain crude product. The crude product was purified by using combiflash with 5-8% DCM in MeOH as a solvent to get pure product as N4-(3-amino-4-fluorophenyl)-5-chloro-N2-(1-(1-methylpiperidin-4-yl)-1H-pyrazol-4-yl)pyrimidine-2,4-diamine 92 (0.08 g, 88% yield). MS: 417.0 (M+H)$^+$.

Synthesis of N-(5-((5-chloro-2-((1-(1-methylpiperidin-4-yl)-1H-pyrazol-4-yl)amino)pyrimidin-4-yl)amino)-2-fluorophenyl)ethenesulfonamide (I-64)

Title compound was prepared following method substantially similar to general method J.

To a solution of as N$^4$-(3-amino-4-fluorophenyl)-5-chloro-N$^2$-(1-(1-methylpiperidin-4-yl)-1H-pyrazol-4-yl)pyrimidine-2,4-diamine 92 (0.09 g, 0.216 mmole) in THF (5 mL) was cooled to −50° C., triethyl amine (0.12 g, 1.18 mmol) was added and stirred for 10 min, then 2-chloroethanesulfonyl chloride (0.07 g, 0.432 mmol) was added and the reaction mixture was stirred for 3 h. The reaction was monitored by TLC. After the completion of reaction, reaction mixture was quenched with ice water at −50° C. and sodium bicarbonate solution, extracted with DCM (2×50 mL), organic layer was washed with brine solution (10 ml), organic layer was separated and dried over sodium sulphate and evaporated under reduced pressure to obtain crude product. The crude product was purified by using combiflash with 0-5% DCM in MeOH as a solvent to get pure product as N-(5-((5-chloro-2-((1-(1-methylpiperidin-4-yl)-1H-pyrazol-4-yl)amino)pyrimidin-4-yl)amino)-2-fluorophenyl)ethenesulfonamide I-64 (0.018 g, 17% yield). $^1$H-NMR (400 MHz, CD$_3$OD): δ 7.83 (s, 1H), 7.54 (s, 1H), 7.18 (s, 1H), 7.07 (t, 1H), 6.94 (bs, 1H), 6.59-6.52 (dd, 1H), 5.92 (d, 1H), 5.67 (d, 1H), 4.10 (m, 1H), 2.52 (m, 5H), 1.93 (m, 4H), 1.19 (m, 2H); MS: 507.2 (M+H)$^+$.

The following compound was prepared similarly:

| Compd ID | Structure | LCMS (M + H)+ | 1H-NMR (400 MHz, DMSO-d6) |
|---|---|---|---|
| I-65 | 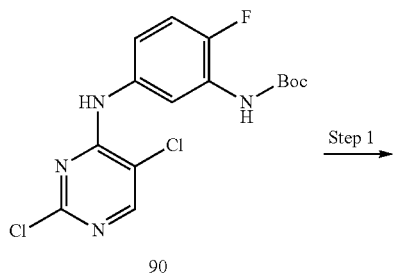 | 406.38 | δ 10.08 (s, 1H), 9.26 (bs, 1H), 8.93 (bs, 1H), 8.07 (s, 1H), 7.48-7.46 (m, 5 H), 7.00 (s, 1H), 6.82-6.76 (m, 1H), 6.16-6.12 (d, 1H), 6.02-6.00 (d, 1H), 3.66 (s, 3H) |

Example 5: Synthesis of N-(5-((5-chloro-2-((1-methyl-1H-pyrazol-4-yl)amino)pyrimidin-4-yl)amino)-2-fluorophenyl)acrylamide (I-66)

Scheme-33:

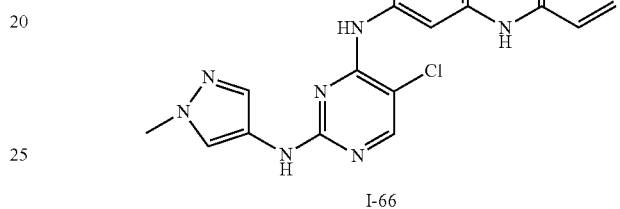

Synthesis of N4-(3-amino-4-fluorophenyl)-5-chloro-N2-(1-methyl-1H-pyrazol-4-yl)pyrimidine-2,4-diamine (93)

Title compound was prepared in a manner substantially similar to general method-E using n-BuOH as a solvent to obtain desired product as off white solid with 26% yield. MS: 334.1 (M+H)+.

Synthesis of N-(5-((5-chloro-2-((1-methyl-1H-pyrazol-4-yl)amino)pyrimidin-4-yl)amino)-2-fluorophenyl)acrylamide (I-66)

Title compound was prepared in a manner substantially similar to general method-J.

N4-(3-amino-4-fluorophenyl)-5-chloro-N2-(1-methyl-1H-pyrazol-4-yl)pyrimidine-2,4-diamine 93 and acryloyl chloride gave N-(5-((5-chloro-2-((1-methyl-1H-pyrazol-4-yl)amino)pyrimidin-4-yl)amino)-2-fluorophenyl)acrylamide I-66 as white solid with 15% yield. 1HNMR (400 MHz, DMSO-d6): δ 9.98 (s, 1H), 9.18 (bs, 1H), 8.95 (bs, 1H), 8.14-8.13 (m, 1H), 8.05 (s, 1H), 7.86 (bs, 1H), 7.29-7.05 (m, 3H), 6.65-6.58 (m, 1H), 6.25-6.21 (m, 1H), 5.76-5.74 (m, 1H), 3.61 (s, 3H). LCMS: 386.2 (M−H)+; HPLC purity: 99%.

The following compound was prepared similarly:

| Compd ID | Structure | Synthesis method | LCMS (M + H)+ | 1H-NMR (400 MHz, DMSO-d6) |
|---|---|---|---|---|
| I-67 | 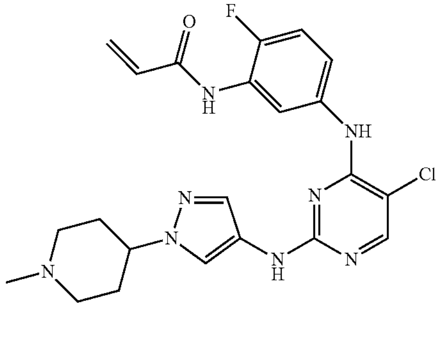 [SMILES: C=CC(=O)Nc1cc(Nc2nc(Nc3cnn(C4CCN(C)CC4)c3)ncc2Cl)ccc1F] | J | 471.2 | δ 10.09 (s, 1H), 9.14 (s, 1H), 8.85 (s, 1H), 8.10 (d, 1H), 8.03 (s, 1H), 7.37-7.16 (m, 4H), 6.65-6.58 (m, 1H), 6.26-6.22 (d, 16.8 Hz, 1H), 5.77-5.74 (d, 11.6 Hz, 1H), 3.9-3.63 (m, 1H), 2.96 (s, 2H), 2.4-2.2 (m, 5H), 1.9-1.7 (m, 4H) |

| Compd ID | Structure | Synthesis method | LCMS (M + H)+ | ¹H-NMR (400 MHz, DMSO-d₆) |
|---|---|---|---|---|
| I-27 | 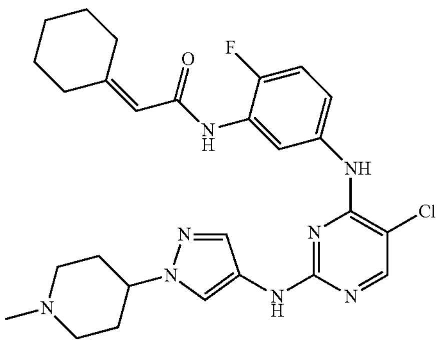 [SMILES: CN1CCC(n2cc(Nc3ncc(Cl)c(Nc4ccc(F)c(NC(=O)C=C5CCCCC5)c4)n3)cn2)CC1] | K | 541.3 (M + 2H)+ | δ 9.65 (bs, 1H), 9.15 (bs, 1H), 8.83 (bs, 1H), 8.03 (s, 2H), 7.25 (m, 4H), 5.96 (s, 1H), 3.53 (bs, 1H), 2.80 (m, 2H), 2.48 (m, 2H), 2.32 (m, 2H), 2.16 (s, 3H), 1.89-1.72 (m, 4H), 1.59-1.39 (m, 8H) |

Example-6: Synthesis of N-(5-(((5-chloro-2-((1-methyl-1H-pyrazol-4-yl)amino)pyrimidin-4-yl)amino)-2,4-difluorophenyl)acrylamide (I-68)

Scheme-42:

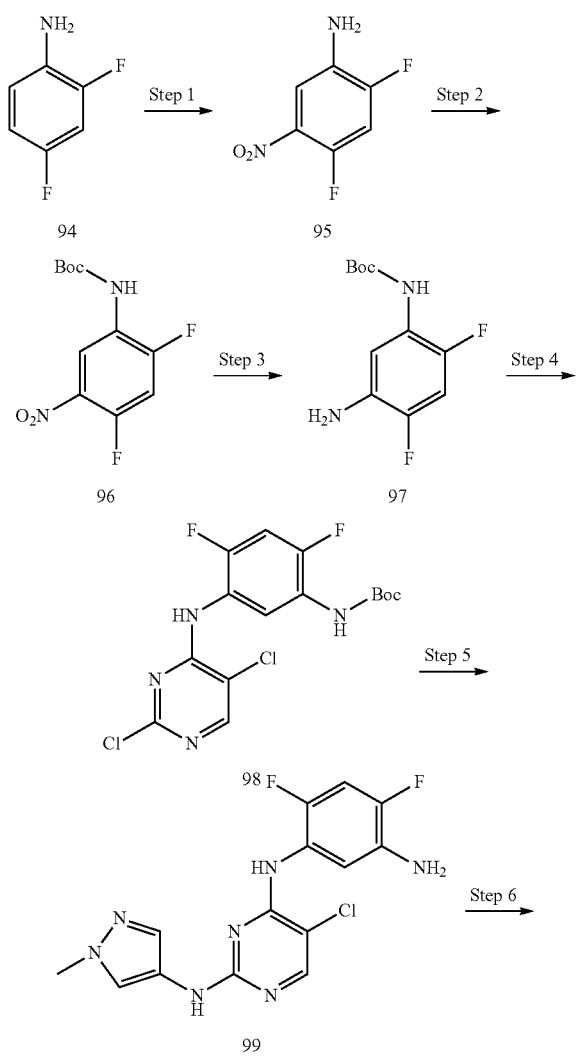

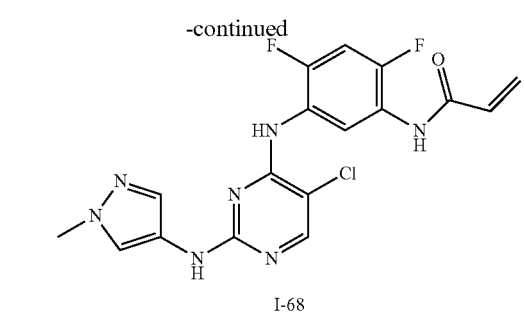

I-68

Synthesis of 2,4-difluoro-5-nitroaniline (95)

A solution 2,4-difluoroaniline 94 was cooled to −10° C., sulphuric acid (4 mL) was added slowly through addition funnel. Then the nitrating mixture prepared by mixing sulphuric acid (1 mL) and fuming nitric acid (0.161 mL) was added slowly over 15 min. Then the reaction mixture was stirred for 1 h at −10° C. to 0° C. The reaction was monitored by TLC, after the completion of reaction, the reaction mixture was poured into crushed ice and extracted with EtOAc (3×100 mL). The organic layer was washed with brine (50 mL) and dried over sodium sulphate and evaporated under reduced pressure to obtain crude product 95. The crude product was taken to next step without further purification (5.0 g, 75% yield). MS: 173.1 (M−H)+.

Synthesis of tert-butyl (2,4-difluoro-5-nitrophenyl)carbamate (96)

To a solution of 2,4-difluoro-5-nitroaniline 95 (3.70 g, 21.2 mmol) was added di-tert-butyl dicarbonate (11.59 g, 53.16 mmol). The reaction mixture was stirred for 2 h at 80° C. The reaction was monitored by TLC, after the completion of reaction; silica gel was added to the reaction mixture and loaded onto the column. The crude product was purified using combiflash with 0-5% EtOAc in hexane as a solvent to get pure product as tert-butyl (2,4-difluoro-5-nitrophenyl) carbamate 96 (2.0 g, 34% yield). MS: 273.1 (M−H)+.

Synthesis of tert-butyl (5-amino-2, 4-difluorophenyl)carbamate (97)

To a solution tert-butyl (2,4-difluoro-5-nitrophenyl) carbamate 96 (1.50 g, 5.47 mmol) in EtOH (20 mL) was added 10% Pd/C (0.3 g) under nitrogen atm. Then the reaction mixture was stirred for 16 h at rt under hydrogen atmosphere. The reaction was monitored by TLC, after the completion of reaction; the reaction mixture was filtered through celite and washed with MeOH. The filtrate was concentrated under vacuum to get crude product 97. The crude product was taken to next step without further purification (1.35 g, 59% yield). MS: 245.2 (M+H)$^+$.

Synthesis of tert-butyl (5-((2,5-dichloropyrimidin-4-yl)amino)-2,4-difluorophenyl)carbamate (98)

To a solution of 2,4,5-trichloropyrimidine 77 (1 g, 5.45 mmol) in n-butanol (15 mL) were added tert-butyl (5-amino-2, 4-difluorophenyl)carbamate 97 (1.59 g, 6.54 mmol) and DIPEA (1.05 g, 8.17 mmol). The reaction mixture was stirred for 16 h at 100° C. The reaction was monitored by TLC, after the completion of reaction, the reaction mixture was concentrated completely and diluted with water (100 mL) and extracted with DCM (2×100 mL). The organic layer was washed with brine (50 mL) and dried over sodium sulphate and evaporated under reduced pressure to obtain crude product. The crude product was purified using combiflash with 5-10% EtOAc in hexane as a solvent to get pure product as tert-butyl (5-((2,5-dichloropyrimidin-4-yl)amino)-2,4-difluorophenyl)carbamate 98 (1.40 g, 66% yield). MS: 391.1 (M+H)$^+$.

Synthesis of N$^4$-(5-amino-2, 4-difluorophenyl)-5-chloro-N$^2$-(1-methyl-1H-pyrazol-4-yl)pyrimidine-2, 4-diamine (99)

Title compound was prepared following a general method-E using n-BuOH as a solvent as off white solid with 17% yield. MS: 352.1 (M+H)$^+$.

Synthesis of N-(5-((5-chloro-2-((1-methyl-1H-pyrazol-4-yl)amino)pyrimidin-4-yl)amino)-2,4-difluorophenyl)acrylamide (I-68)

Title compound was prepared in a manner substantially similar to general method-J.
N$^4$-(5-amino-2,4-difluorophenyl)-5-chloro-N$^2$-(1-methyl-1H-pyrazol-4-yl)pyrimidine-2,4-diamine 99 and acryloyl chloride gave N-(5-((5-chloro-2-((1-methyl-1H-pyrazol-4-yl)amino)pyrimidin-4-yl)amino)-2,4-difluorophenyl)acrylamide I-68 as white solid with 16% yield.
$^1$HNMR (400 MHz, DMSO-d$_6$): δ 10.03 (s, 1H), 9.18 (bs, 1H), 8.86 (s, 1H), 8.03-7.98 (m, 2H), 7.54 (s, 1H), 7.12-7.00 (m, 2H), 6.60-6.53 (m, 1H), 6.26-6.22 (d, 17.2 Hz, 1H), 5.77-5.73 (m, 1H), 3.57 (s, 3H). LCMS: 406.1 (M+H)$^+$; HPLC purity: 99%.

The following compound was prepared similarly:

| Compd ID | Structure | LCMS (M + H)$^+$ | $^1$H-NMR (400 MHz, DMSO-d$_6$) |
|---|---|---|---|
| I-69 | (structure) | 489.3 | δ 10.05 (s, 1H), 9.21 (s, 1H), 8.83 (s, 1H), 8.03 (s, 2H), 7.52 (m, 1H), 7.14 (bs, 2H), 6.61-6.54 (m, 1H), 6.26-6.22 (d, 1H), 5.78-5.75 (d, 1H), 3.64 (m, 1H), 2.79-2.76 (m, 2H), 2.17 (s, 3H), 1.99-1.92 (m, 2H), 1.69 (bs, 4H) |

Example-7: Synthesis of N-(3-((5-chloro-2-((1,3-dimethyl-1H-pyrazol-4-yl)amino)pyrimidin-4-yl)amino)-4-fluorophenyl)acrylamide (I-70) and N-(3-((5-chloro-2-((1,5-dimethyl-1H-pyrazol-4-yl)amino)pyrimidin-4-yl)amino)-4-fluorophenyl)acrylamide (I-71)

Scheme-43:

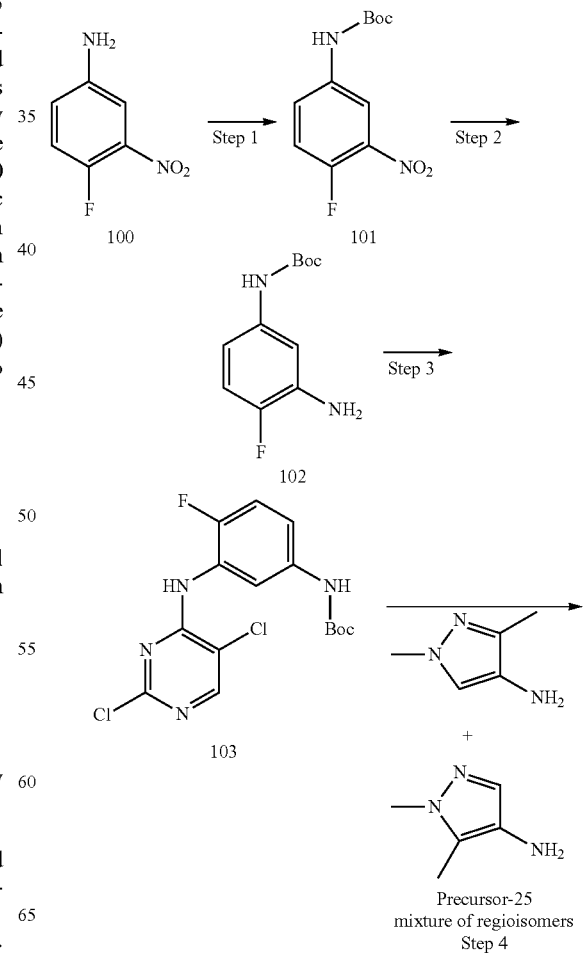

Precursor-25
mixture of regioisomers
Step 4

-continued

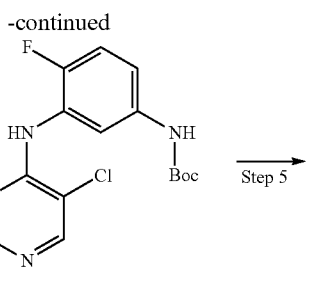

104
X1 = Me; X2 = H
X1 = H; X2 = Me
mixture of regioisomers

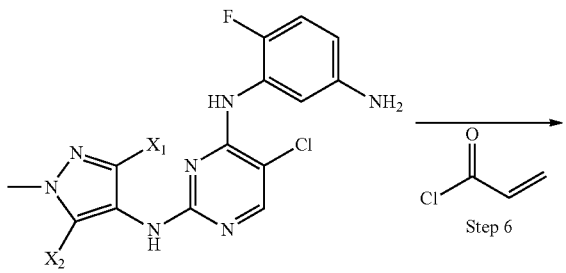

105
X1 = Me; X2 = H
X1 = H; X2 = Me
mixture of regioisomers

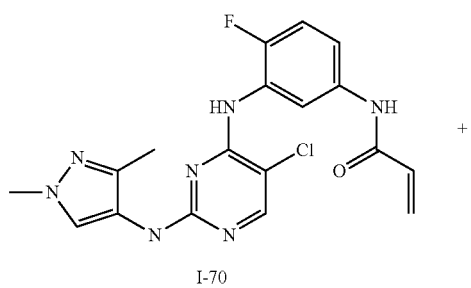

I-70

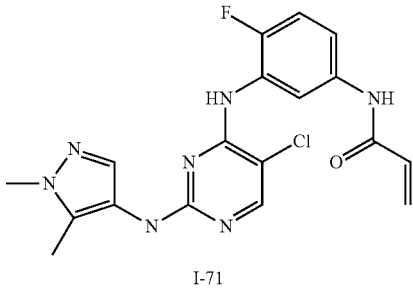

I-71

Synthesis of tert-butyl (4-fluoro-3-nitrophenyl)carbamate (101)

To a solution of 4-fluoro-3-nitroaniline 100 (5 g, 32.02 mmol) in THF (20 mL) was added di-tert-butyl dicarbonate (8.38 g, 38.43 mmol). The reaction mixture was stirred for 24 h at 78° C. The reaction was monitored by TLC, after the completion of reaction. The reaction mixture was concentrated completely. The crude product was purified using combiflash with 0-20% EtOAc in hexane as a solvent to get pure product tert-butyl (4-fluoro-3-nitrophenyl) carbamate 101 (5.8 g, 71% yield). MS: 255.2 (M–H)$^+$.

Synthesis of tert-butyl (4-fluoro-3-nitrophenyl) carbamate (102)

To a solution of tert-butyl (4-fluoro-3-nitrophenyl) carbamate 101 (5.8 g, 22.64 mmol) in MeOH (60 mL) was added 10% Pd/C (1 g) under nitrogen atmosphere. Then the reaction mixture was stirred for 16 h at RT under hydrogen atmosphere. The reaction was monitored by TLC, after the completion of reaction; the reaction mixture was filtered through celite and washed with MeOH. The filtrate was concentrated under vacuum to get crude product 102. The crude product was taken to next step without further purification (5.0 g, 98% yield). MS: 227.2 (M–H)$^+$.

Synthesis of tert-butyl (3-((2,5-dichloropyrimidin-4-yl)amino)-4-fluorophenyl)carbamate (103)

To a solution of 2,4,5-trichloropyrimidine (1 g, 5.45 mmol) in EtOH (15 mL) were added tert-butyl (3-amino-4-fluorophenyl)carbamate 102 (1.4 g, 6.54 mmol) and DIPEA (1.4 g, 10.9 mmol). The reaction mixture was stirred for 16 h at 75° C. The reaction was monitored by TLC, after the completion of reaction, the reaction mixture was concentrated completely and diluted with water (100 mL) and extracted with DCM (2×100 mL). The organic layer was washed with brine (50 mL) and dried over sodium sulphate and evaporated under reduced pressure to obtain crude product. The crude product was purified using combiflash with 10-30% EtOAc in hexane as a solvent to get pure product tert-butyl (3-((2,5-dichloropyrimidin-4-yl)amino)-4-fluorophenyl)carbamate 103 (1.10 g, 50% yield). MS: 373.1 (M+H)$^+$.

Synthesis of tert-butyl (3-((5-chloro-2-((1,3-dimethyl-1H-pyrazol-4-yl)amino)pyrimidin-4-yl) amino)-4-fluorophenyl)carbamate (104)

Title compound was prepared in a manner similar to general method-E using n-butanol as a solvent and obtained 104 as off white solid with 45% yield. MS: 448.2 (M+H)$^+$.

Synthesis of N$^4$-(5-amino-2-fluorophenyl)-5-chloro-N$^2$-(1,3-dimethyl-1H-pyrazol-4-yl)pyrimidine-2,4-diamine (105)

The title compound was synthesized by stirring tert-butyl (3-((5-chloro-2-((1,3-dimethyl-1H-pyrazol-4-yl)amino)pyrimidin-4-yl)amino)-4-fluorophenyl)carbamate 104 in a solution of TFA-DCM at 0° C. for 30 min and then stirring for 16 h at rt resulting in 77% yield. MS: 348.2 (M+H)$^+$.

Synthesis of N-(3-((5-chloro-2-((1,3-dimethyl-1H-pyrazol-4-yl)amino)pyrimidin-4-yl)amino)-4-fluorophenyl)acrylamide (I-70) and N-(3-((5-chloro-2-((1,5-dimethyl-1H-pyrazol-4-yl)amino)pyrimidin-4-yl) amino)-4-fluorophenyl)acrylamide (I-71)

Title compound was prepared in a manner similar to general method-J.
N$^4$-(5-amino-2-fluorophenyl)-5-chloro-N$^2$-(1,3-dimethyl-1H-pyrazol-4-yl)pyrimidine-2,4-diamine 105 and acryloyl chloride gave a mixture of isomers. It was separated by chiral HPLC to obtain isomer 1, N-(3-((5-chloro-2-((1,3-dimethyl-1H-pyrazol-4-yl)amino)pyrimidin-4-yl)amino)-4-fluorophenyl)acrylamide I-70 as white solid with 25% yield. $^1$HNMR (400 MHz, DMSO-d$_6$): δ 10.26 (s, 1H), 8.87 (s, 1H), 8.70 (bs, 1H), 8.05 (s, 1H), 7.75-7.76 (m, 1H), 7.64

(s, 1H), 7.33-7.31 (m, 1H), 7.04-6.98 (m, 1H), 6.45-6.38 (m, 1H), 6.28-6.24 (m, 1H), 5.78-5.75 (m, 1H), 3.44 (s, 3H), 2.04 (s, 3H). LCMS: 402.44 (M+H)$^+$; LC purity: 99.6% and N-(3-((5-chloro-2-((1,5-dimethyl-1H-pyrazol-4-yl)amino)pyrimidin-4-yl)amino)-4-fluorophenyl)acrylamide I-71 as white solid with 18% yield. $^1$HNMR (400 MHz, DMSO-d$_6$): δ 10.21 (s, 1H), 8.84 (s, 1H), 8.75-8.50 (m, 1H), 8.30 (s, 1H), 8.01-7.93 (m, 1H), 7.77-7.74 (m, 1H), 7.37-7.06 (m, 2H), 6.45-6.35 (m, 1H), 6.28-6.23 (m, 1H), 5.78-5.71 (m, 1H), 3.59 (s, 3H), 2.02 (s, 3H). LCMS: 402.2 (M+H)$^+$; HPLC purity: 97%.

Example-8: Synthesis of N-(3-((5-chloro-2-((1-(1-methylpiperidin-4-yl)-1H-pyrazol-4-yl)amino)pyrimidin-4-yl)(methyl)amino)phenyl)acrylamide (I-72)

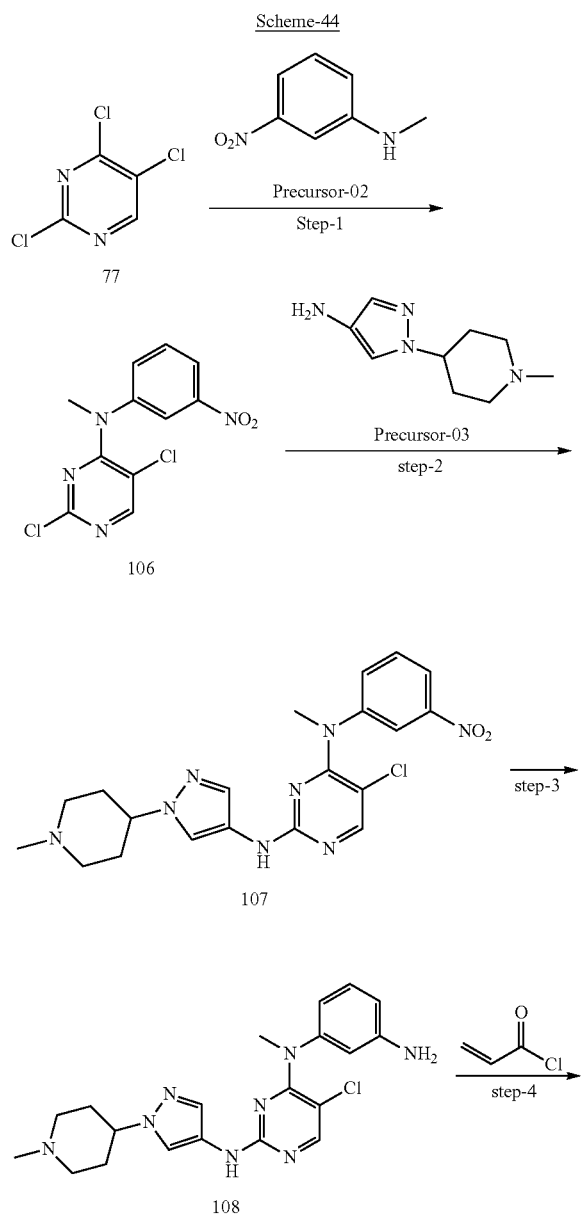

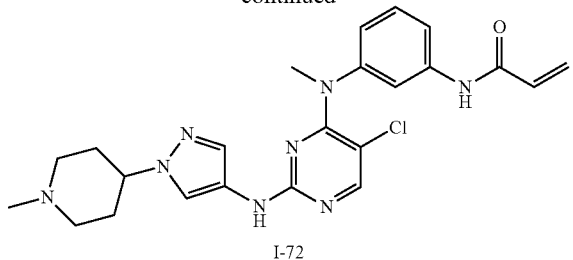

Synthesis of 2,5-dichloro-N-methyl-N-(3-nitrophenyl)pyrimidin-4-amine (106)

To a stirred suspension of N-methyl-3-nitroaniline precursor-02 (0.50 g, 3.28 mmol) and 2,4,5-trichloropyrimidine 77 (0.724 g, 3.94 mmol) in ethanol (7.0 mL), DIPEA (0.85 g, 6.57 mmol) was charged and refluxed for 4 hour. The reaction mixture was evaporated to dryness. The crude mixture was diluted with EtOAc (30 mL) and water (20 mL). The organic layer was dried (Na$_2$SO$_4$), filtered and evaporated to afford 2,5-dichloro-N-methyl-N-(3-nitrophenyl)pyrimidin-4-amine 106 (0.4 g, 41% yield) as yellow solid. MS: 299.10 (M+H)$^+$.

Synthesis of 5-chloro-N$^4$-methyl-N$^2$-(1-(1-methylpiperidin-4-yl)-1H-pyrazol-4-yl)-N$^4$-(3-nitrophenyl)pyrimidine-2,4-diamine (107)

To a stirred suspension of 2,5-dichloro-N-methyl-N-(3-nitrophenyl)pyrimidin-4-amine 106 (0.4 g, 1.34 mmol) and 1-(1-methylpiperidin-4-yl)-1H-pyrazol-4-amine precursor-03 (0.24 g, 1.34 mmol) in 2-butanol (15.0 mL), trifluoro acetic acid (0.15 g, 1.34 mmol) was charged and put on reflux for 4 hour. The reaction mixture was evaporated and basified with saturated sodium bicarbonate solution to pH 9. The aqueous layer was extracted with DCM (2×100 mL). The combined organic extracts were washed with water (3×60 mL). The organic layer was dried (Na$_2$SO$_4$), filtered and evaporated to obtain 5-chloro-N$^4$-methyl-N$^2$-(1-(1-methylpiperidin-4-yl)-1H-pyrazol-4-yl)-N$^4$-(3-nitrophenyl)pyrimidine-2,4-diamine 107 (0.5 g, 84%) as orange yellow solid. MS: 443.17 (M+H)$^+$.

Synthesis of N$^4$-(3-aminophenyl)-5-chloro-N$^4$-methyl-N2-(1-(1-methylpiperidin-4-yl)-1H-pyrazol-4-yl)pyrimidine-2,4-diamine (108)

To a stirred solution of 5-chloro-N$^4$-methyl-N$^2$-(1-(1-methylpiperidin-4-yl)-1H-pyrazol-4-yl)-N$^4$-(3-nitrophenyl)pyrimidine-2,4-diamine 107 (0.30 g, 0.68 mmol) in ethanol-dichloromethane mixture (1:1), Raney-Ni was charged and put on stirring under hydrogen pressure (1 atm) at room temperature for 16 hour. The reaction mixture was filtered on celite bed. The filtrate was evaporated to dryness to obtain N$^4$-(3-aminophenyl)-5-chloro-N$^4$-methyl-N$^2$-(1-(1-methylpiperidin-4-yl)-1H-pyrazol-4-yl)pyrimidine-2,4-diamine 108 (0.25 g, 89% yield) as pale brown solid. MS: 413.2 (M+H)$^+$.

Synthesis of N-(3-((5-chloro-2-((1-(1-methylpiperidin-4-yl)-1H-pyrazol-4-yl)amino)pyrimidin-4-yl)(methyl)amino)phenyl)acrylamide (I-72)

Title compound was prepared in a manner similar to general method-J using N$^4$-(3-aminophenyl)-5-chloro-N$^4$- methyl-N²-(1-(1-methylpiperidin-4-yl)-1H-pyrazol-4-yl)pyrimidine-2,4-diamine 108 and in acryloyl chloride and obtained N-(3-((5-chloro-2-((1-(1-methylpiperidin-4-yl)-1H-pyrazol-4-yl)amino)pyrimidin-4-yl)(methyl)amino)phenyl)acrylamide I-72 in 18% yield as a white solid. ¹HNMR (400 MHz, DMSO-d₆): δ 10.18 (s, 1H), 9.41 (s, 1H), 8.02 (s, 1H), 7.86 (s, 1H), 7.46-7.51 (m, 3H), 7.34 (t, 1H), 6.92 (d, 1H), 6.42 (dd, 1H), 6.25 (dd, 1H), 5.76 (dd, 1H), 4.01 (s, 1H) 3.44 (s, 3H), 2.80-2.83 (m, 2H), 2.18 (s, 3H), 1.99-2.01 (m, 2H), 1.82-1.91 (m, 4H). MS: 467.2 (M+H)⁺.

Example 9: Synthesis of N-(6-((5-chloro-2-((1,3-dimethyl-1H-pyrazol-4-yl)amino)pyrimidin-4-yl)amino)pyridin-2-yl)acrylamide (I-73) and N-(6-((5-chloro-2-((1,5-dimethyl-1H-pyrazol-4-yl)amino)pyrimidin-4-yl)amino)pyridin-2-yl)acrylamide (I-74)

Synthesis of N²-(2,5-dichloropyrimidin-4-yl)pyridine-2,6-diamine (109)

To a solution of 2,4,5-trichloropyrimidine 77 (2.0 g, 10.9 mmol) in IPA (20 mL) were added pyridine-2,6-diamine (1.40 g, 130.0 mmol) and DIPEA (2.80 g, 21.8 mmol). The reaction mixture was stirred for 16 h at 82° C. The reaction was monitored by TLC, after the completion of reaction, the reaction mixture was concentrated completely and diluted with water (100 mL) and extracted with DCM (2×100 mL). The organic layer was washed with brine (50 mL) and dried over sodium sulphate and evaporated under reduced pressure to obtain crude product. The crude product was purified using combiflash with 40-50% EtOAc in hexane as a solvent to get pure product N²-(2,5-dichloropyrimidin-4-yl)pyridine-2,6-diamine 109 (2.0 g, 72% yield). MS: 256.1 (M+H)⁺.

Scheme-45:

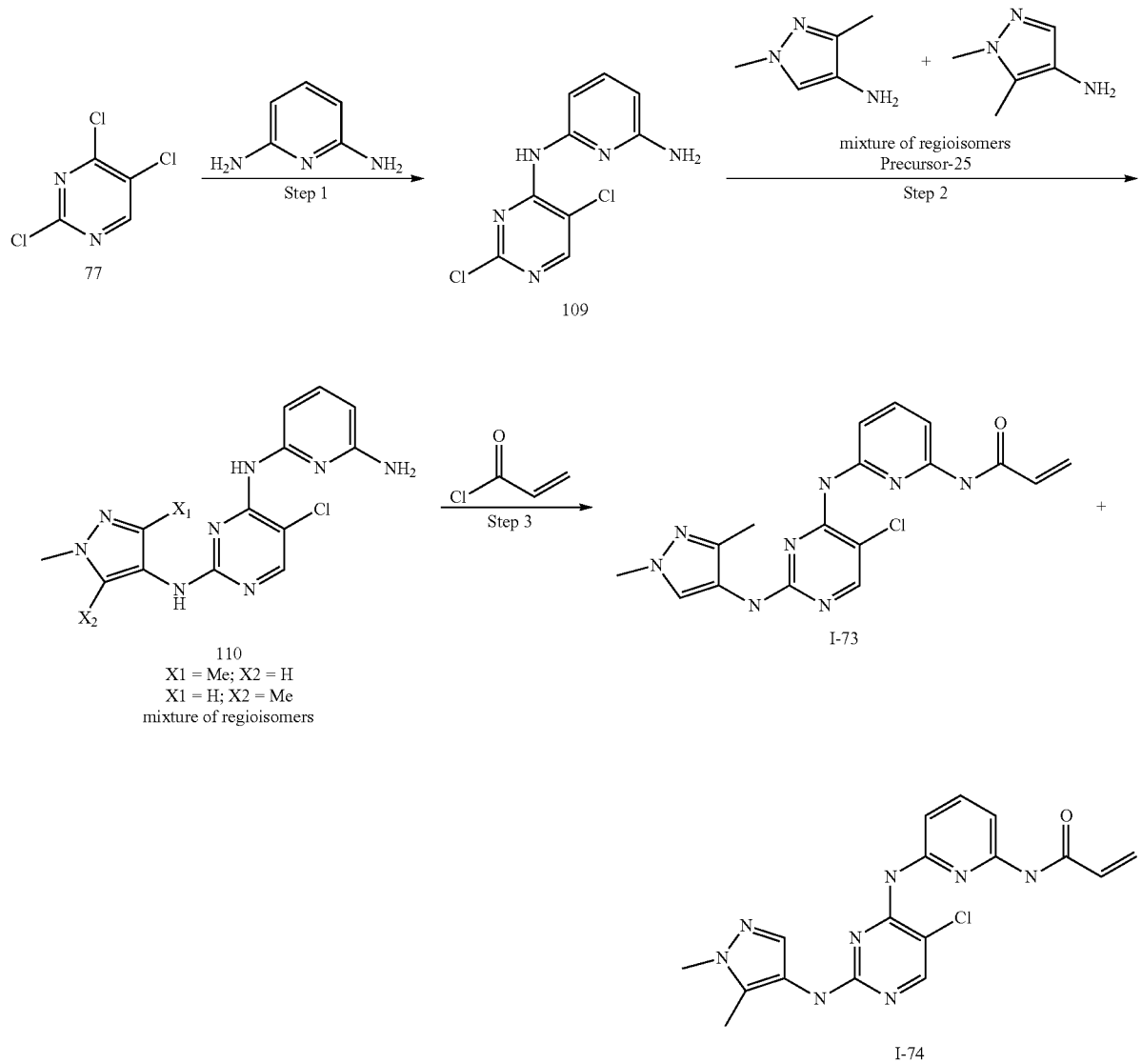

Synthesis of N⁴-(6-aminopyridin-2-yl)-5-chloro-N²-(1,3-dimethyl-1H-pyrazol-4-yl)pyrimidine-2,4-diamine (110)

Title compound was prepared in a manner similar to general method-E.
N²-(2,5-dichloropyrimidin-4-yl)pyridine-2,6-diamine 109 and 1,3-dimethyl-1H-pyrazol-4-amine gave N⁴-(6-aminopyridin-2-yl)-5-chloro-N²-(1,3-dimethyl-1H-pyrazol-4-yl)pyrimidine-2,4-diamine 110 as brownish solid with 35% yield. MS: 331.4 (M+H)⁺.

Synthesis of N-(6-((5-chloro-2-((1,3-dimethyl-1H-pyrazol-4-yl)amino)pyrimidin-4-yl)amino)pyridin-2-yl)acrylamide (I-73) and N-(6-((5-chloro-2-((1,5-dimethyl-1H-pyrazol-4-yl)amino)pyrimidin-4-yl)amino)pyridin-2-yl)acrylamide (I-74)

Title compound was prepared in a manner similar to general method-J.
N⁴-(6-aminopyridin-2-yl)-5-chloro-N²-(1,3-dimethyl-1H-pyrazol-4-yl)pyrimidine-2,4-diamine 110 and acryloyl chloride gave mixture of isomers. It was separated by chiral HPLC to obtain isomer 1, N-(6-((5-chloro-2-((1,3-dimethyl-1H-pyrazol-4-yl)amino)pyrimidin-4-yl)amino)pyridin-2-yl)acrylamide I-73 as white solid with 5% yield; ¹HNMR (400 MHz, DMSO-d₆): δ 10.62 (s, 1H), 8.68 (s, 1H), 8.13 (s, 1H), 8.01 (bs, 1H), 7.92-7.90 (d, 1H), 7.75-7.61 (m, 3H), 6.60-6.53 (m, 1H), 6.31-6.27 (d, 1H), 5.77-5.74 (d, 1H), 3.66 (s, 3H), 2.05 (s, 3H). LCMS: 385.1 (M+H)⁺, HPLC purity: 99% and isomer 2, N-(6-((5-chloro-2-((1,5-dimethyl-1H-pyrazol-4-yl)amino)pyrimidin-4-yl)amino)pyridin-2-yl)acrylamide I-74 as white solid with 6% yield; ¹HNMR (400 MHz, DMSO-d₆): δ 10.59 (s, 1H), 8.65 (s, 1H), 8.11 (s, 1H), 7.88-7.85 (m, 2H), 7.68 (bs, 2H), 7.36 (s, 1H), 6.59-6.52 (m, 1H), 6.30-6.26 (d, 17.2 Hz, 1H), 5.77-5.74 (d, 10.8 Hz, 1H), 3.70 (s, 3H), 2.09 (s, 3H). LCMS: 385.2 (M+H)⁺, HPLC purity: 98%.

The following compound was prepared similarly:

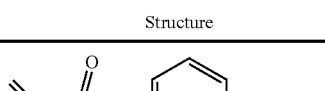

| Compd ID | Structure | LCMS (M + H)⁺ | ¹H-NMR (400 MHz, DMSO-d₆) |
|---|---|---|---|
| I-75 | 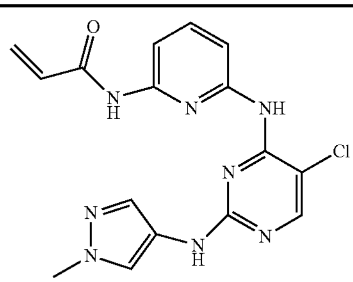 | 371.2 | δ 10.64 (s, 1H), 9.32 (s, 1H), 8.51 (bs, 1H), 8.17 (s, 1H), 7.95 (s, 2H), 7.85-7.81 (m, 1H), 7.74 (bs, 1H), 7.36 (s, 1H), 6.61-6.54 (m, 1H), 6.32-6.27 (m, 1H), 5.77-5.73 (m, 1H), 3.70 (s, 3H) |

Example 10: N-(3-((5-cyclopropyl-2-((1-methyl-1H-pyrazol-4-yl)amino)pyrimidin-4-yl)amino)phenyl)acrylamide (I-76)

Scheme-46:

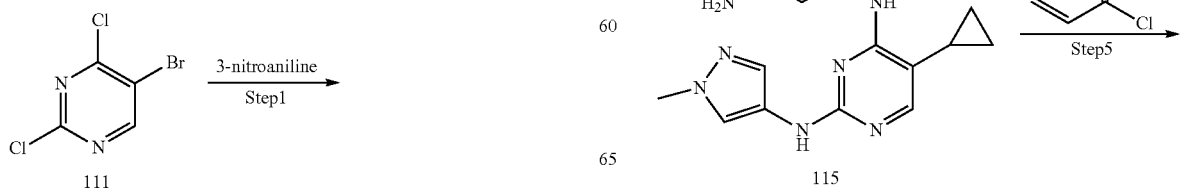

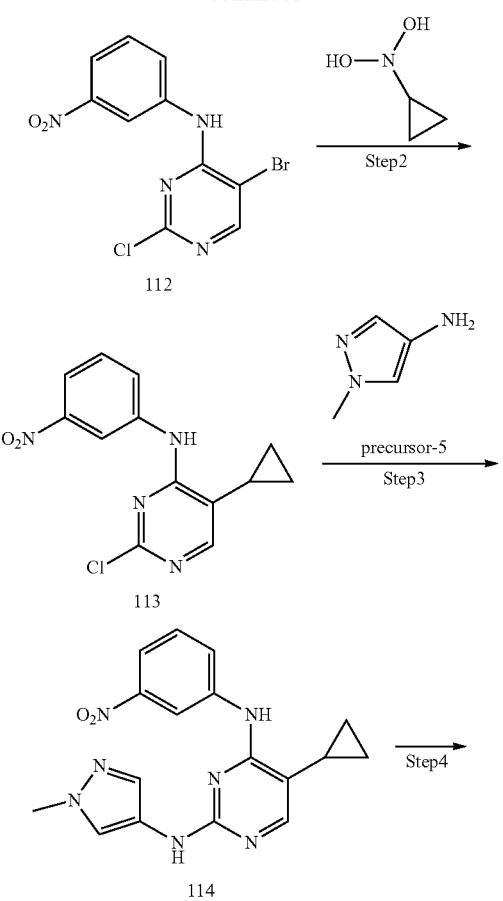

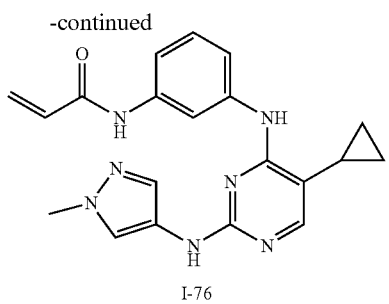

I-76

Synthesis of 5-Bromo-2-chloro-N-(3-nitrophenyl)pyrimidin-4-amine (12)

Title compound was prepared in a manner similar to procedure described in general method C.

3-Nitroaniline and 2,4-dichloro-5-bromo-pyrimidine 111 gave 5-bromo-2-chloro-N-(3-nitrophenyl)pyrimidin-4-amine 112 in 72% yield as a yellowish brown solid. MS: 328.75 (M–H)+

Synthesis of 2-Chloro-5-cyclopropyl-N-(3-nitrophenyl)pyrimidin-4-amine (113)

5-Bromo-2-chloro-N-(3-nitrophenyl)pyrimidin-4-amine 112 (3.00 g, 9.1 mmol), cyclopropylboronic acid (0.94 g, 10.9 mmol), tricyclohexyl phosphine (0.250 g, 0.91 mmol) and potassium phosphate (6.78 g, 32 mmol) were taken in a 10:1 mixture of toluene (40 ml) and water (4 ml) and the mixture was purged with argon for 10 min. Palladium (II) acetate (0.102 g, 0.45 mmol) was added and the mixture was heated at 100° C. for 6 h. Reaction was cooled to rt, the mixture was partitioned between ethyl acetate and water and the organic layer was separated. The organic layer was washed with water, dried over anhydrous sodium sulfate, filtered and solvents evaporated to obtain a crude material, which was triturated with methanol to obtain 2,5-dichloro-N-(1-(4-fluorophenyl)-1H-pyrazol-4-yl)pyrimidin-4-amine 113 (2.6 g, 98% yield) as a light yellowish brown solid. MS: 291.06 (M+H)+

Synthesis of 5-Cyclopropyl-N2-(1-methyl-1H-pyrazol-4-yl)-N4-(3-nitrophenyl)pyrimidine-2,4-diamine (114)

Title compound was prepared using similar to procedure described in general method F.

2-chloro-5-cyclopropyl-N-(3-nitrophenyl)pyrimidin-4-amine (113) and 1-methyl pyrazole 4-amine gave 5-cyclopropyl-N2-(1-methyl-1H-pyrazol-4-yl)-N4-(3-nitrophenyl)pyrimidine-2,4-diamine 114 in 70% yield as a light brown solid. MS: 351.98 (M+H)+

Synthesis of N4-(3-Aminophenyl)-5-cyclopropyl-N2-(1-methyl-1H-pyrazol-4-yl)pyrimidine-2,4-diamine (115)

Title compound was prepared using similar to procedure described in general method H.

5-cyclopropyl-N2-(1-methyl-1H-pyrazol-4-yl)-N4-(3-nitrophenyl)pyrimidine-2,4-diamine 114 gave N2-(3-aminophenyl)-5-chloro-N4-(1-(4-fluorophenyl)-1H-pyrazol-4-yl)pyrimidine-2,4-diamine 115 in 92% yield as a light brown solid. MS: 322.3 (M+H)+322.17

N-(3-((5-Cyclopropyl-2-((1-methyl-1H-pyrazol-4-yl)amino)pyrimidin-4-yl)amino)phenyl)acrylamide (I-76)

Title compound was prepared using similar to procedure described in general method J.

N4-(3-aminophenyl)-5-cyclopropyl-N2-(1-methyl-1H-pyrazol-4-yl)pyrimidine-2,4-diamine 115 and acryloyl chloride gave N-(3-((5-Cyclopropyl-2-((1-methyl-1H-pyrazol-4-yl)amino)pyrimidin-4-yl)amino)phenyl)acrylamide I-76 in 14% yield as a off white solid. 1HNMR (400 MHz, DMSO-d6): δ 10.1 (s, 1H), 8.76 (s, 1H), 8.36 (s, 1H), 7.84 (s, 1H), 7.75 (s, 1H), 7.59 (m, 1H), 7.46-7.44 (m, 1H), 7.32-7.26 (m, 3H), 6.47-6.39 (m, 1H), 6.26-6.21 (m, 1H), 5.73 (d, 1H), 3.61 (s, 3H), 1.71 (m, 1H), 0.87 (d, 2H), 0.52 (m, 2H). MS: 376.2 (M+H)+.

Example 11: Synthesis of N-(3-((5-chloro-2-((1-(1-methylpiperidin-4-yl)-1H-pyrazol-4-yl)amino)pyrimidin-4-yl)oxy)phenyl)acrylamide (I-77)

Scheme-47:

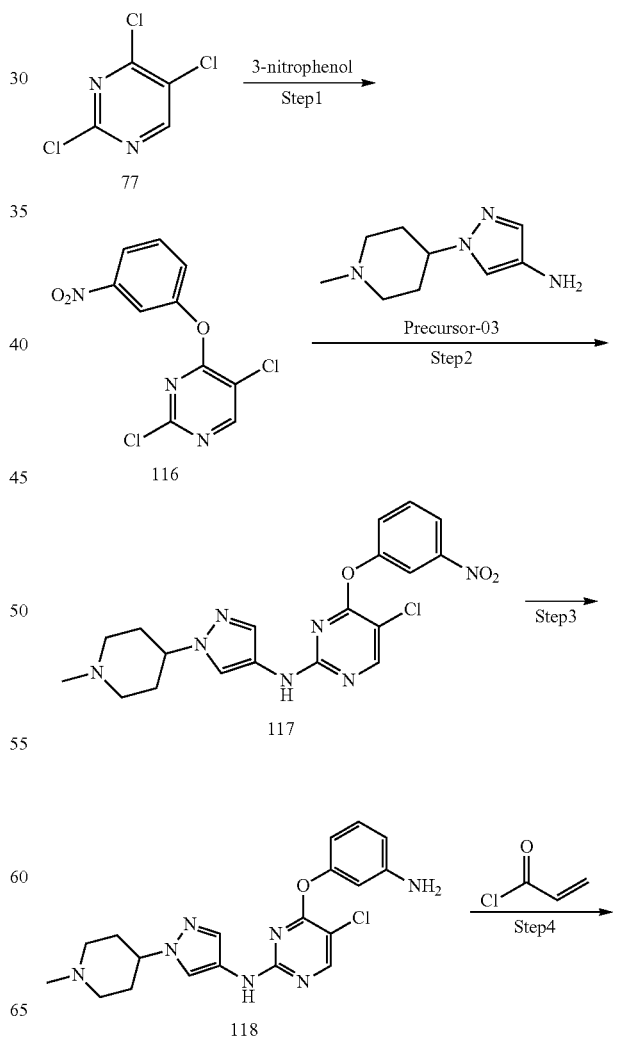

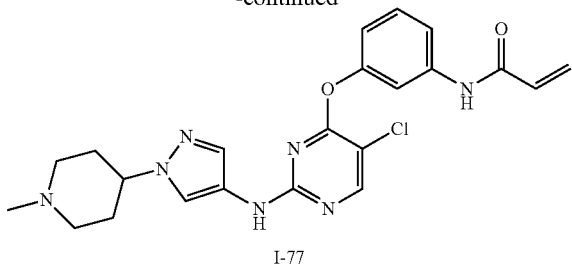

I-77

Synthesis of 2,5-dichloro-4-(3-nitrophenoxy)pyrimidine (116)

To a stirred solution of 77 (20.0 g, 109.0 mmol), in DMF (100.0 mL) was added 3-nitrophenol (15.10 g, 109.0 mmol) and $K_2CO_3$ (16.0 g, 116.0 mmol) and the reaction mixture was heated at 60° C. for 3 h. It was then cooled, ice cooled water (150 mL) was added, precipitation was observed that was filtered through sintered funnel. Filter cake was washed with ether (50 mL) and concentrated under reduced pressure. The residue obtained was further purified via column chromatography ($SiO_2$, 100-200 mesh, 10% EtOAc-hexane) to obtain 2,5-dichloro-4-(3-nitrophenoxy)pyrimidine 116 (27 g, 87% yield) as white solid. $^1$HNMR (400 MHz, DMSO): δ 9.88 (s, 1H), 8.29 (t, 1H), 8.23 (dd, 1H), 8.02 (dd, 1H), 7.68 (t, 1H). MS: 286.01 (M+H)$^+$.

Synthesis of 5-chloro-N-(1-(1-methylpiperidin-4-yl)-1H-pyrazol-4-yl)-4-(3-nitrophenoxy)pyrimidin-2-amine (117)

To a solution of 2,5-dichloro-4-(3-nitrophenoxy)pyrimidine 116 (0.50 g, 1.76 mmol) in 2-butanol (20 mL) and was added 1-(1-methylpiperidin-4-yl)-1H-pyrazol-4-amine precursor-03 (0.35 g, 1.93 mmol) and trifluoroacetic acid (0.22 g, 1.93 mmol) and the reaction mixture was heated at 100° C. for 16 h under $N_2$ atmosphere. After the completion of reaction (TLC monitored), reaction mixture was basified with saturated aqueous $NaHCO_3$ solution (50 mL) and extracted with ethyl acetate (3×50 mL). The combined organic layer was washed with brine (50 mL), dried over $Na_2SO_4$ and concentrated under reduced pressure. The residue obtained was purified through column chromatography ($SiO_2$, 60-120 mesh, 10% MeOH-DCM) to obtain 5-chloro-N-(1-(1-methylpiperidin-4-yl)-1H-pyrazol-4-yl)-4-(3-nitrophenoxy)pyrimidin-2-amine 117 (0.5 g, 66% yield) as yellow solid. MS: 430.03 (M+H)$^+$.

Synthesis of 4-(3-aminophenoxy)-5-chloro-N-(1-(1-methylpiperidin-4-yl)-1H-pyrazol-4-yl)pyrimidin-2-amine (118)

To a solution of 5-chloro-N-(1-(1-methylpiperidin-4-yl)-1H-pyrazol-4-yl)-4-(3-nitrophenoxy)pyrimidin-2-amine 117 (1.30 g, 3.03 mmol) in MeOH, 1,4-dioxane (9:1, 30 mL) was added Pd—C (0.130 g) under nitrogen atmosphere. The resulting reaction mixture was stirred at rt under $H_2$ atmosphere for 16 h. After the completion of reaction (TLC monitored), diluted with MeOH (15 mL) and filtered through celite. The residue obtained was purified through column chromatography ($SiO_2$, 60-120 mesh, 10% MeOH-DCM) to obtain 4-(3-aminophenoxy)-5-chloro-N-(1-(1-methylpiperidin-4-yl)-1H-pyrazol-4-yl)pyrimidin-2-amine 118 (0.90 g, 75%) as yellow solid. $^1$H-NMR (400 MHz, DMSO-$d_6$): δ 9.75 (s, 1H), 8.34 (s, 1H), 7.08-7.16 (m, 3H), 6.57 (bs, 1H), 6.40-6.34 (m, 2H), 3.74-3.71 (m, 1H), 2.89-2.87 (m, 1H), 2.33-2.19 (m, 5H), 2.09-2.00 (m, 2H), 1.10-1.74 (m, 4H). MS: 400.03 (M+H)$^+$.

Synthesis of N-(3-((5-chloro-2-((1-(1-methylpiperidin-4-yl)-1H-pyrazol-4-yl)amino)pyrimidin-4-yl)oxy)phenyl)acrylamide (I-77)

To a solution of 4-(3-aminophenoxy)-5-chloro-N-(1-(1-methylpiperidin-4-yl)-1H-pyrazol-4-yl)pyrimidin-2-amine 118 (0.25 g, 0.62 mmol) in N,N-dimethylacetamide (20 mL) and acryloyl chloride (50 uL, 0.62 mmol) at −20° C. The reaction mixture was stirred for 1 h at same temperature. The reaction was monitored on TLC using IPA:Dichloromethane (10:90) as mobile phase. Solvent was evaporated under reduced pressure to get crude compound and purified by prep-HPLC to obtain N-(3-((5-chloro-2-((1-(1-methylpiperidin-4-yl)-1H-pyrazol-4-yl)amino)pyrimidin-4-yl)oxy)phenyl)acrylamide I-77 (16 mg, 6% yield) as pale yellow solid. $^1$HNMR (400 MHz, DMSO-$d_6$): δ 10.17 (bs, 1H), 9.39 (s, 1H), 8.34 (s, 1H), 7.68-7.64 (m, 2H), 7.47-7.43 (m, 1H), 7.26 (m, 2H), 6.97 (d, 1H), 6.45 (dd, 1H), 6.29-6.24 (d, 1H), 5.75 (d, 1H), 3.83 (m, 3H), 2.94-2.89 (m, 2H), 2.35-2.33 (m, 5H), 1.83 (m, 4H). MS: 454.1 (M+H)$^+$.

The following compounds were prepared similarly:

| Compd ID | Structure | LCMS (M + H)$^+$ | $^1$H-NMR (400 MHz, DMSO-$d_6$) |
|---|---|---|---|
| I-78 | 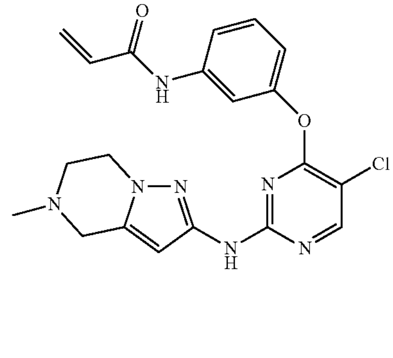 [SMILES: C=CC(=O)Nc1cccc(Oc2nc(Nc3cc4n(n3)CCN(C)C4)ncc2Cl)c1] | 426.25 | δ 10.37 (s, 1H), 10.02 (s, 1H), 8.40 (s, 1H), 7.65-7.63 (m, 2H), 7.44 (t, 1H), 6.97 (d, 1H), 6.47-6.40 (m, 1H), 6.28-6.24 (m, 1H), 5.80-5.77 (m, 1H), 5.49-5.40 (m, 1H), 3.85 (m, 2H), 3.33 (s, 2H), 2.73-2.70 (m, 2H), 2.30 (s, 3H) |

-continued
| Compd ID | Structure | LCMS (M + H)+ | 1H-NMR (400 MHz, DMSO-d6) |
|---|---|---|---|
| I-79 | 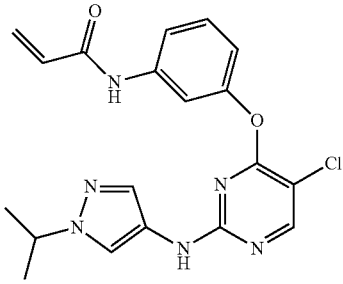 [SMILES: C=CC(=O)Nc1cccc(Oc2nc(Nc3cnn(C(C)C)c3)ncc2Cl)c1] | 399.35 | δ 10.41 (s, 1H), 9.81 (s, 1H), 8.40 (s, 1H), 7.70-7.65 (m, 2H), 7.56-7.34 (m, 1H), 7.11 (m, 1H), 7.06-7.00 (m, 1H), 6.92 (m, 1H), 6.45-6.38 (m, 1H), 6.27-6.23 (m, 1H), 5.81-5.76 (m, 1H), 4.18-4..05 (bm 1H), 1.16 (bs, 6H). |
| I-80 | 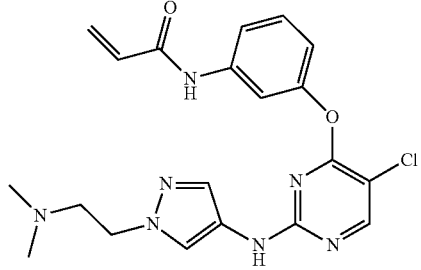 [SMILES: C=CC(=O)Nc1cccc(Oc2nc(Nc3cnn(CCN(C)C)c3)ncc2Cl)c1] | 428.35 | δ 10.46 (s, 1H), 9.77 (m, 1H), 8.55 (s, 1H), 7.74-7.51 (m, 3H), 7.16-7.01 (m, 2H), 6.86 (m, 1H), 6.47-6.39 (m, 1H), 6.28-6.23 (m, 1H), 5.79 (d, 1H), 3.84-3.79 (m, 2H), 2.39 (m, 2H), 2.06 (s, 6H). |
| I-81 | 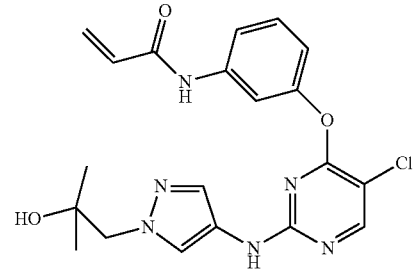 [SMILES: C=CC(=O)Nc1cccc(Oc2nc(Nc3cnn(CC(C)(C)O)c3)ncc2Cl)c1] | 429.23 | δ 10.37 (s, 1H), 9.79 (s, 1H), 8.40 (s, 1H), 7.88.7.49 (m, 4H), 7.11 (s, 1H), 7.01-6.99 (m, 1H), 6.42 (dd, 1H), 6.25 (d, 1H), 5.77 (d, 1H), 4.48 (s, 1H), 3.63 (m, 2H), 1.04-0.91 (m, 6H), |
| I-82 | 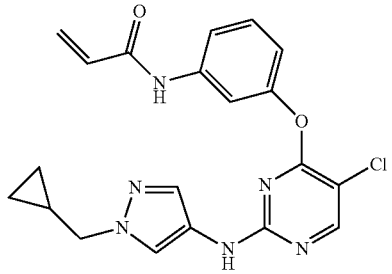 [SMILES: C=CC(=O)Nc1cccc(Oc2nc(Nc3cnn(CC4CC4)c3)ncc2Cl)c1] | 411.08 | δ 9.93 (s, 1H), 9.21 (s, 1H), 8.34 (s, 1H), 7.63-7.61 (m, 2H), 7.43 (t, 1H), 7.29-7.26 (m, 1H), 6.96 (d, 1H), 6.46-6.39 (m, 1H), 6.28-6.23 (m, 1H), 5.73 (d, 1H), 3.73 (d, 2H), 1.1-1.06 (m, 1H), 0.50-0.43 (m, 2H), 0.27-0.21 (m, 2H). |
| I-83 | 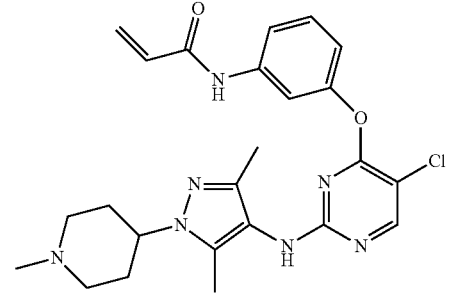 [SMILES: C=CC(=O)Nc1cccc(Oc2nc(Nc3c(C)nn(C4CCN(C)CC4)c3C)ncc2Cl)c1] | 482.13 | δ 10.29 (s, 1H), 8.65-8.27 (m, 2H), 7.57-7.24 (m, 3H), 6.97-6.68 (m, 1H), 6.41 (dd, 1H), 6.27 (dd, 1H), 5.79 (d, 1H), 3.91-3.87 (m, 1H), 2.83-2.81 (m, 2H), 2.18 (s, 3H), 1.96-1.86 (m, 10H), 1.58-1.55 (m, 2H). |

-continued
| Compd ID | Structure | LCMS (M + H)+ | 1H-NMR (400 MHz, DMSO-d6) |
|---|---|---|---|
| I-84 | 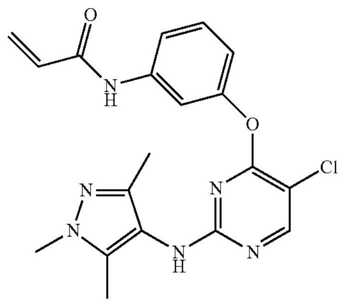 [SMILES: C=CC(=O)Nc1cccc(Oc2nc(Nc3c(C)nn(C)c3C)ncc2Cl)c1] | 399.1 | δ 10.31 (s, 1H), 8.55 (s, 1H), 8.25 (s, 1H), 7.59-7.38 (m, 3H), 6.96 (m, 1H), 6.46-6.39 (dd, 1H), 6.25 (d, 1H), 5.78 (dd, 1H), 3.56 (bs, 3H), 1.93 (bs, 3H), 1..84 (s, 3H). |
| I-85 | 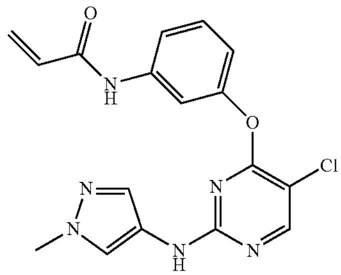 [SMILES: C=CC(=O)Nc1cccc(Oc2nc(Nc3cnn(C)c3)ncc2Cl)c1] | 371.03 | δ 10.41 (s, 1H), 9.83 (s, 1H), 8.39 (s, 1H), 7.78-7.47 (m, 3H), 7.08-6.96 (m, 2H), 6.82 (s, 1H), 6.46-6.39 (dd, 1H), 6.27 (dd, H), 5.78 (dd, 1H), 3.50 (s, 3H). |
| I-86 | 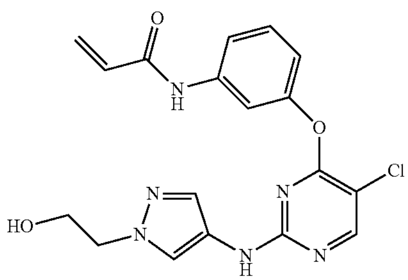 [SMILES: C=CC(=O)Nc1cccc(Oc2nc(Nc3cnn(CCO)c3)ncc2Cl)c1] | 401.02 | (CD3OD): δ 8.25 (s, 1H), 7.64 (m, 2H), 7.52 (bs, 1H), 7.22 (bs, 1H), 7.01-6.99 (m, 2H), 6.47-6.34 (m, 2H), 5.80-5.77 (m, 1H), 3.96 (bs, 2H), 3.69 (bs, 2H), |
| I-87 | 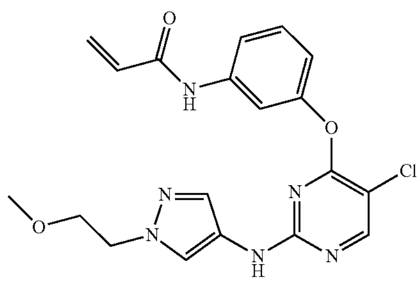 [SMILES: C=CC(=O)Nc1cccc(Oc2nc(Nc3cnn(CCOC)c3)ncc2Cl)c1] | 415.23 | δ 10.40 (s, 1H), 9.81 (s, 1H), 8.36 (s, 1H), 7.76-7.50 (m, 3H), 7.11 (s, 1H), 7.02 (m, 1H), 6.82 (m, 1H), 6.46-6.39 (dd, 1H), 6.28-6.24 (dd, 1H), 5.83-5.72 (dd, 1H), 3.87 (m, 2H), 3.42 (m, 2H), 3.12 (s, 3H). |
Example 12: Synthesis of 1-(3-((5-chloro-2-((1-methyl-1H-pyrazol-4-yl)amino)pyrimidin-4-yl)amino)piperidin-1-yl)prop-2-en-1-one (II-1 & II-2)
Scheme-48:
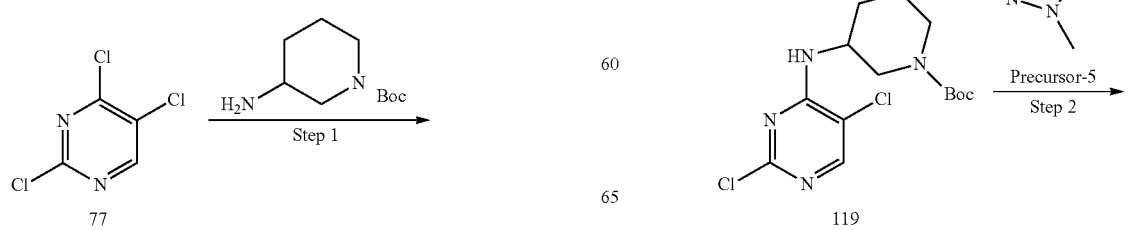

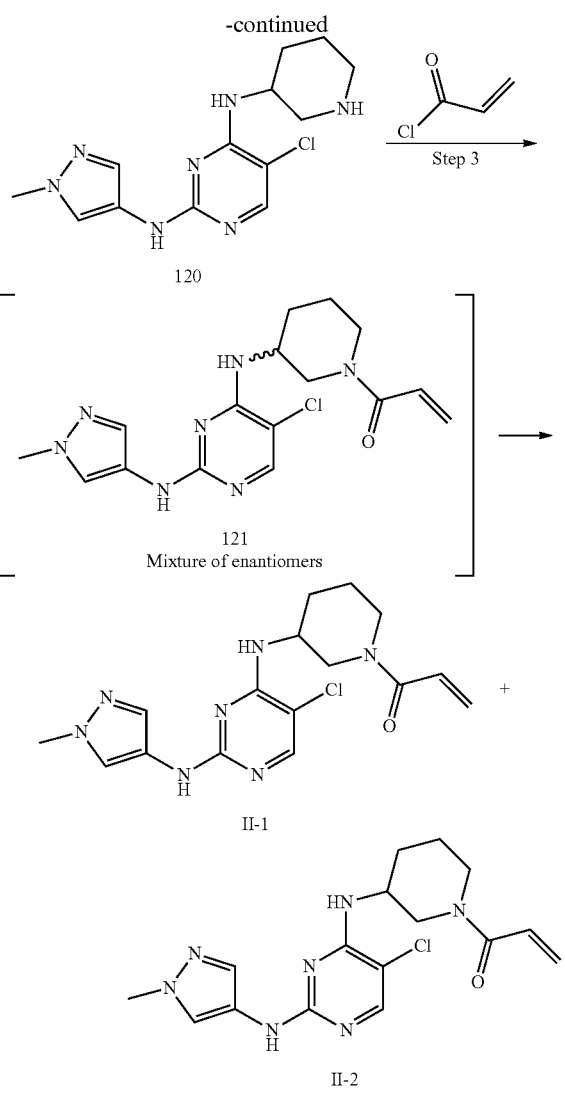

Synthesis of tert-butyl 3-((2,5-dichloropyrimidin-4-yl)amino)piperidine-1-carboxylate (119)

To a solution of 2,4,5-trichloropyrimidine 77 (5 g, 27.25 mmol) in IPA (50 mL) were added tert-butyl 3-aminopiperidine-1-carboxylate (5.34 g, 26.71 mmol) and DIPEA (4.57 g, 35.43 mmol). The reaction mixture was stirred for 3 h at 80° C. The reaction was monitored by TLC, after the completion of reaction, the reaction mixture was concentrated completely and diluted with water (300 mL) and extracted with EtOAc (3×200 mL). The organic layer was washed with brine (50 mL) and dried over sodium sulphate and evaporated under reduced pressure to obtain crude product 119. The crude product was taken to next step without further purification (9.2 g, 98% yield). MS: 349.1 (M+H)$^+$.

Synthesis of 5-chloro-N2-(1-methyl-1H-pyrazol-4-yl)-N4-(piperidin-3-yl)pyrimidine-2,4-diamine (120)

Title compound was prepared following similar to general procedure D.

tert-butyl 3-((2,5-dichloropyrimidin-4-yl)amino)piperidine-1-carboxylate 119 and 1-methyl-1H-pyrazol-4-amine precursor-5 gave 5-chloro-N2-(1-methyl-1H-pyrazol-4-yl)-N4-(piperidin-3-yl)pyrimidine-2,4-diamine 120 as off white solid with 57% yield. MS: 308.2 (M+H)$^+$.

Synthesis of 1-(3-((5-chloro-2-((1-methyl-1H-pyrazol-4-yl)amino)pyrimidin-4-yl)amino)piperidin-1-yl)prop-2-en-1-one (II-1 & II-2)

Title compound was prepared following similar to general procedure J 5-chloro-N2-(1-methyl-1H-pyrazol-4-yl)-N4-(piperidin-3-yl)pyrimidine-2,4-diamine 120 and acryloyl chloride gave 1-(3-((5-chloro-2-((1-methyl-1H-pyrazol-4-yl)amino)pyrimidin-4-yl)amino)piperidin-1-yl)prop-2-en-1-one 121 as mixture of enantiomers, it was further purified by chiral HPLC using CHIRALPAK IA column and Mobile phase: n-Hexane:EtOH (85:15) with 0.1% DEA to get pure enantiomers. Enantiomers 1 (II-1); $^1$HNMR (400 MHz, DMSO-d6): δ 9.01 (s, 1H), 7.87 (s, 1H), 7.76-7.67 (m, 1H), 7.36-7.30 (d, 1H), 6.86-6.60 (m, 2H), 6.13-6.00 (m, 1H), 5.69-5.50 (m, 1H), 4.48-4.18 (m, 1H), 4.00 (bs, 2H), 3.69 (s, 3H), 3.27-3.02 (m, 1H), 2.75-2.65 (m, 1H), 1.93 (bs, 1H), 1.75 (bs, 2H), 1.43 (bs, 1H); MS: 362.2 (M+H); Enantiomers 2 (II-2); δ 9.01 (s, 1H), 7.87 (s, 1H), 7.76-7.67 (m, 1H), 7.36-7.30 (d, 1H), 6.86-6.60 (m, 2H), 6.13-6.00 (m, 1H), 5.69-5.50 (m, 1H), 4.48-4.18 (m, 1H), 4.00 (bs, 2H), 3.69 (s, 3H), 3.27-3.02 (m, 1H), 2.75-2.65 (m, 1H), 1.93 (bs, 1H), 1.75 (bs, 2H), 1.43 (bs, 1H); MS: 362.2 (M+H).

The following compounds were prepared similarly using general method-J and K.

| Cmpd No. | Structure | Synthesis method | LCMS (M + 1) | $^1$H-NMR (400 MHz, DMSO-d$_6$) |
|---|---|---|---|---|
| II-3 (Enantiomer 1) | 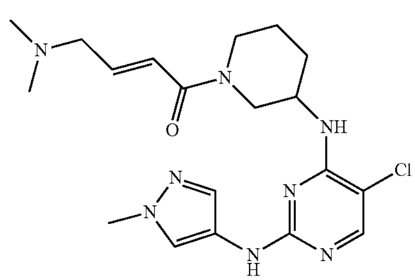 [SMILES: CN(C)C/C=C/C(=O)N1CCCC(Nc2nc(Nc3cnn(C)c3)ncc2Cl)C1] | K | 419.2 | δ 9.02 (s, 1H), 7.87 (s, 1H), 7.76-7.68 (m, 1H), 7.37-7.30 (d, 1H), 6.69-6.48 (m, 3H), 4.02-3.94 (m, 3H), 3.69 (s, 3H), 3.04 (s, 2H), 2.83-2.48 (m, 2H), 2.15 (s, 3H), 2.01 (s, 3H), 1.93-1.75 (m, 3H), 1.44 (bs, 1H) |

-continued

| Cmpd No. | Structure | Synthesis method | LCMS (M + 1) | ¹H-NMR (400 MHz, DMSO-d₆) |
|---|---|---|---|---|
| II-4 (Enantiomer 2) | | K | 419.2 | δ 9.02 (s, 1H), 7.87 (s, 1H), 7.76-7.68 (m, 1H), 7.37-7.30 (d, 1H), 6.69-6.48 (m, 3H), 4.02-3.94 (m, 3H), 3.69 (s, 3H), 3.04 (s, 2H), 2.83-2.48 (m, 2H), 2.15 (s, 3H), 2.01 (s, 3H), 1.93-1.75 (m, 3H), 1.44 (bs, 1H) |
| II-5 (Enantiomer 1) | | J | 402.2 | δ 8.71 (s, 1H), 7.87 (s, 1H), 7.78 (s, 1H), 7.42 (s, 1H), 6.67 (bs, 1H), 6.37-6.35 (m, 1H), 6.07-6.03 (d, 16.4 Hz, 1H), 5.60-5.57 (m, 1H), 4.71-4.63 (m, 1H), 4.09-3.82 (m, 3H), 3.01 (bs, 1H), 2.48-2.34 (m, 4H), 2.07-1.97 (m, 1H), 1.78-1.70 (m, 4H), 1.51-1.41 (m, 1H), 1.34-1.25 (m, 1H) |
| II-6 (Enantiomer 2) | | J | 402.2 | δ 8.71 (s, 1H), 7.87 (s, 1H), 7.78 (s, 1H), 7.42 (s, 1H), 6.67 (bs, 1H), 6.37-6.35 (m, 1H), 6.07-6.03 (d, 16.4 Hz, 1H), 5.60-5.57 (m, 1H), 4.71-4.63 (m, 1H), 4.09-3.82 (m, 3H), 3.01 (bs, 1H), 2.48-2.34 (m, 4H), 2.07-1.97 (m, 1H), 1.78-1.70 (m, 4H), 1.51-1.41 (m, 1H), 1.34-1.25 (m, 1H) |
| II-7 (Racemic) | | J | 348.2 | δ 9.04 (s, 1H), 7.89 (s, 1H), 7.72 (s, 1H), 7.41 (s, 1H), 7.07-7.00 (m, 1H), 6.62-6.48 (m, 1H), 6.15-6.05 (m, 1H), 5.67-5.61 (m, 1H), 4.65-4.54 (m, 1H), 3.96-3.53 (m, 7H), 2.24-2.02 (m, 4H) |
| II-8 | | J | 362.27 | δ 9.06 (br s, 1H), 7.88 (s, 1H), 7.76 (s, 1H), 7.41 (s, 1H), 6.82-6.89 (m, 1H), 6.76-6.78 (m, 1H), 6.11 (dd, 1H), 5.68 (dd, 1H), 4.48-4.51 (m, 1H), 4.13-4.22 (m, 2H), 3.78 (s, 3H), 3.16-3.17 (m, 1H), 2.67 (m, 1H), 1.93-2.02 (m, 2H), 1.49-1.55 (m, 2H) |

| Cmpd No. | Structure | Synthesis method | LCMS (M + 1) | ¹H-NMR (400 MHz, DMSO-d₆) |
|---|---|---|---|---|
| II-9 | 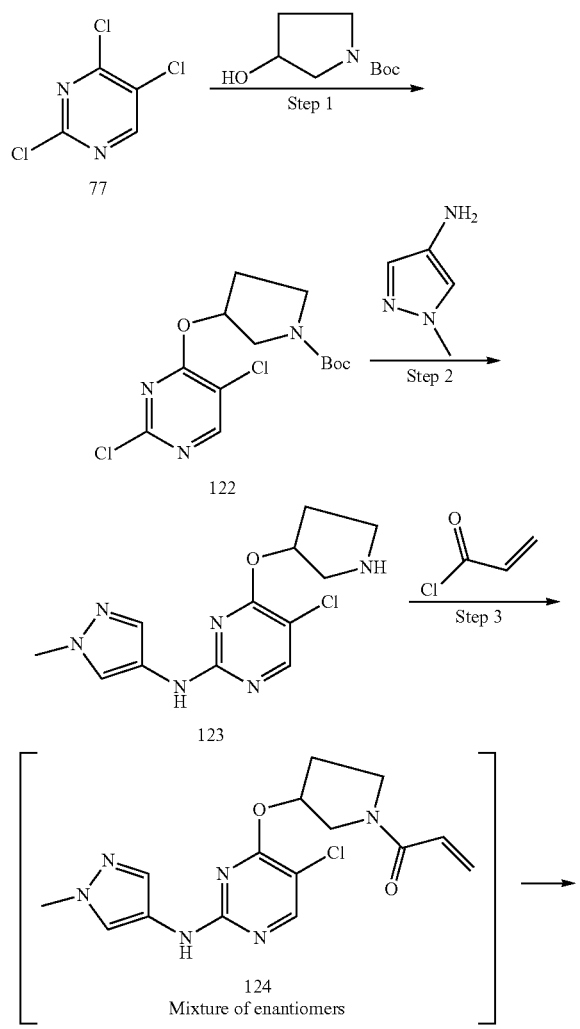 | J | 376.10 | δ 9.02 (br s, 1H), 7.86 (s, 1H), 7.73-7.76 (m, 1H), 7.39-7.43 (m, 1H), 7.18 (m, 1H), 6.61-6.81 (m, 1H), 5.99-6.06 (m, 1H), 5.63 (d, 1H), 4.27-4.30 (m, 1H), 4.05-4.08 (m, 1H), 3.78 (s, 3H), 3.32 (m, 1H), 3.18 (m, 1H), 2.94-2.97 (m, 1H), 2.57 (m, 1H), 1.82 (m, 2H), 1.69 (m, 1H), 1.19-1.33 (m, 2H) |

Example 13: Synthesis of 1-(3-((5-chloro-2-((1-methyl-1H-pyrazol-4-yl)amino)pyrimidin-4-yl)oxy)pyrrolidin-1-yl)prop-2-en-1-one (II-10 & II-11)

Scheme-49:

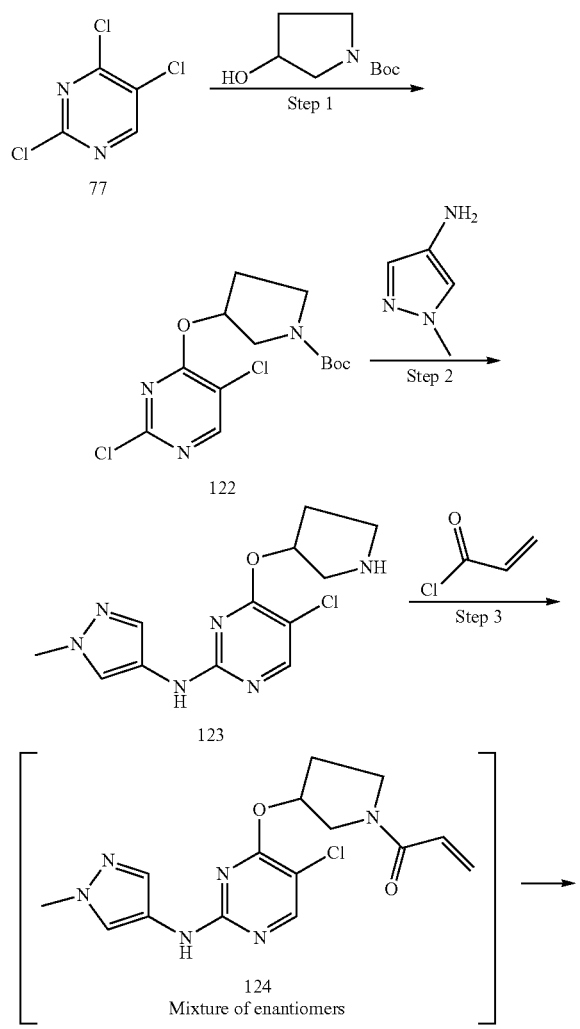

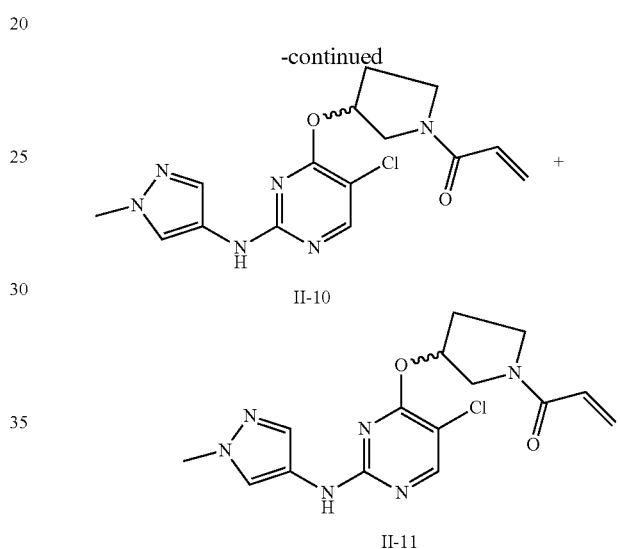

Synthesis of tert-butyl 3-((2,5-dichloropyrimidin-4-yl)oxy)pyrrolidine-1-carboxylate (122)

To a solution of 2,4,5-trichloropyrimidine 77 (5 g, 27.25 mmol) in DMF (50 mL) was added tert-butyl 3-hydroxy-pyrrolidine-1-carboxylate (5.1 g, 27.25 mmol) and potassium carbonate (11.3 g, 81.77 mmol). The reaction mixture was stirred for 16 h at 80° C. The reaction was monitored by TLC, after the completion of reaction; the reaction mixture was diluted with ice water (200 mL) and extracted with diethylether (3×200 mL). The organic layer was washed with brine (50 mL) and dried over sodium sulphate and evaporated under reduced pressure to obtain crude product. The crude product was purified using combiflash with 0-20% EtOAc in hexane as a solvent to get pure product as tert-butyl 3-((2,5-dichloropyrimidin-4-yl)oxy)pyrrolidine-1-carboxylate 122 (2.8 g, 31% yield). MS: 234.2 (M-Boc+H)⁺.

Synthesis of 5-chloro-N-(1-methyl-1H-pyrazol-4-yl)-4-(pyrrolidin-3-yloxy)pyrimidin-2-amine (123)

Title compound was prepared in a manner similar to general method-E.
tert-butyl 3-((2,5-dichloropyrimidin-4-yl)oxy)pyrrolidine-1-carboxylate 109 and 1-methyl-1H-pyrazol-4-amine gave 5-chloro-N-(1-methyl-1H-pyrazol-4-yl)-4-(pyrrolidin-3-yloxy)pyrimidin-2-amine 123 as white solid with 52% yield. MS: 295.3 (M+H)⁺.

Synthesis of 1-(3-((5-chloro-2-((1-methyl-1H-pyrazol-4-yl)amino)pyrimidin-4-yl)oxy)pyrrolidin-1-yl)prop-2-en-1-one (II-10 & II-11)

Title compound was prepared in a manner similar to general method-J.

5-chloro-N-(1-methyl-1H-pyrazol-4-yl)-4-(pyrrolidin-3-yloxy)pyrimidin-2-amine 123 and acryloyl chloride gave 1-(3-((5-chloro-2-((1-methyl-1H-pyrazol-4-yl)amino)pyrimidin-4-yl)oxy)pyrrolidin-1-yl)prop-2-en-1-one 124 as a mixture of enantiomers. The enantiomers were further separated by chiral HPLC using CHIRALPAK IA column and Mobile phase: n-Hexane:EtOH (80:20) with 0.01% DEA to obtain enantiomer-1 (II-10) as white solid with 6% yields and enantiomer-2 (II-11) as white solid with 7% yield.

II-10: $^1$HNMR (400 MHz, DMSO-d$_6$): δ 9.55 (s, 1H), 8.22 (s, 1H), 7.77 (s, 1H), 7.46 (s, 1H), 6.64-6.49 (m, 1H), 6.17-6.11 (m, 1H), 5.69-5.62 (m, 2H), 3.96-3.72 (m, 5H), 3.66-3.40 (m, 2H), 2.35-2.16 (m, 2H); MS: 349.3 (M+H)$^+$

II-11: $^1$HNMR (400 MHz, DMSO-d$_6$): δ 9.55 (s, 1H), 8.22 (s, 1H), 7.77 (s, 1H), 7.46 (s, 1H), 6.64-6.49 (m, 1H), 6.16-6.12 (m, 1H), 5.69-5.63 (m, 2H), 3.98-3.78 (m, 5H), 3.66-3.27 (m, 2H), 2.31-2.16 (m, 2H); MS: 349.3 (M+H)$^+$

The following compounds were prepared similarly:

Example 14: Synthesis of N-(3-((5-chloro-2-((1-methyl-1H-pyrazol-4-yl)amino)pyrimidin-4-yl)oxy)cyclohexyl)acrylamide Isomer 1 (I-88) and N-(3-((5-chloro-2-((1-methyl-1H-pyrazol-4-yl)amino)pyrimidin-4-yl)oxy)cyclohexyl)acrylamide Isomer 2 (I-89)

Scheme 50:

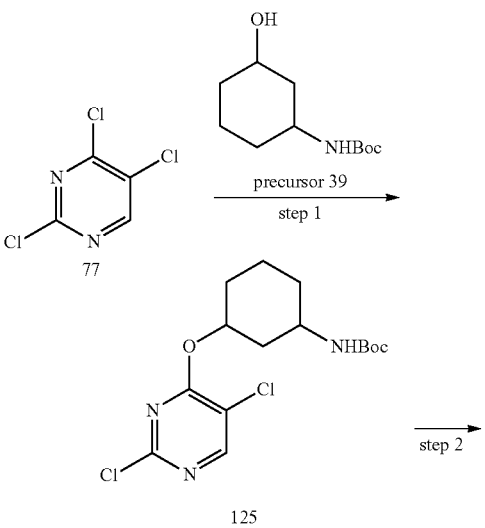

| Cmpd No. | Structure | Synthesis Method | LCMS (M + 1) | $^1$H-NMR (400 MHz, DMSO-d$_6$) |
|---|---|---|---|---|
| II-12 (Enantiomer 1) | 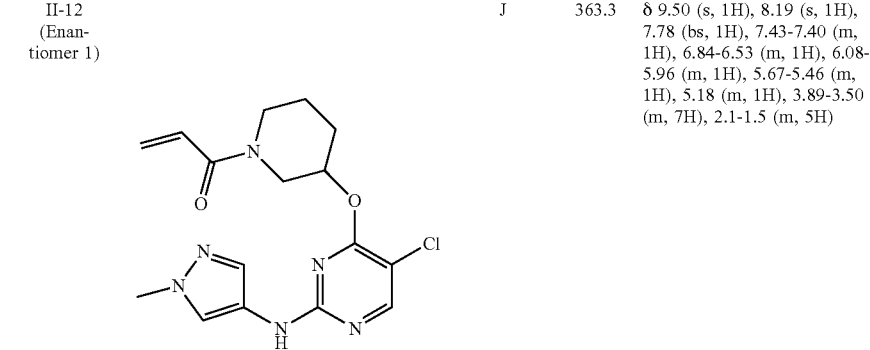 | J | 363.3 | δ 9.50 (s, 1H), 8.19 (s, 1H), 7.78 (bs, 1H), 7.43-7.40 (m, 1H), 6.84-6.53 (m, 1H), 6.08-5.96 (m, 1H), 5.67-5.46 (m, 1H), 5.18 (m, 1H), 3.89-3.50 (m, 7H), 2.1-1.5 (m, 5H) |
| II-13 (Enantiomer 2) | 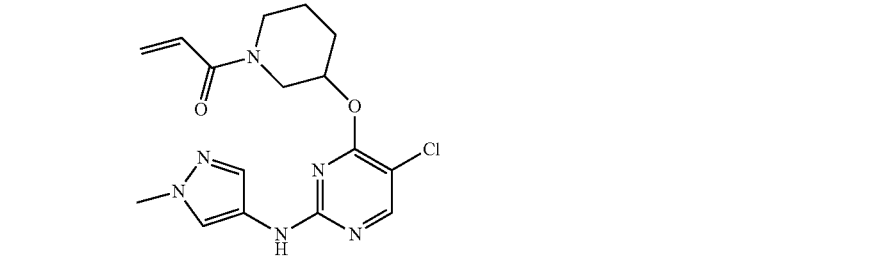 [SMILES: C=CC(=O)N1CCCC(Oc2nc(Nc3cnn(C)c3)ncc2Cl)C1] | J | 363.3 | δ 9.50 (s, 1H), 8.19 (s, 1H), 7.78 (bs, 1H), 7.43-7.40 (m, 1H), 6.84-6.53 (m, 1H), 6.08-5.96 (m, 1H), 5.67-5.46 (m, 1H), 5.18 (m, 1H), 3.89-3.50 (m, 7H), 2.1-1.5 (m, 5H) |

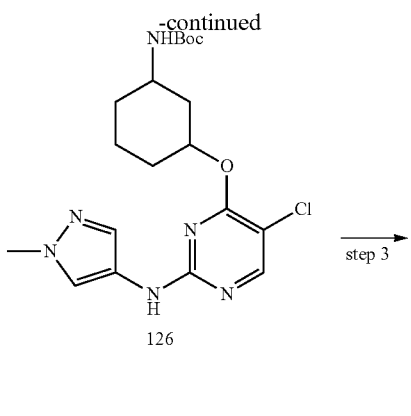

126

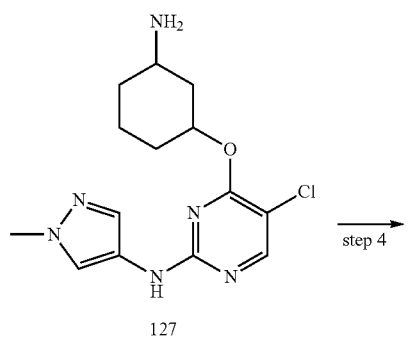

127

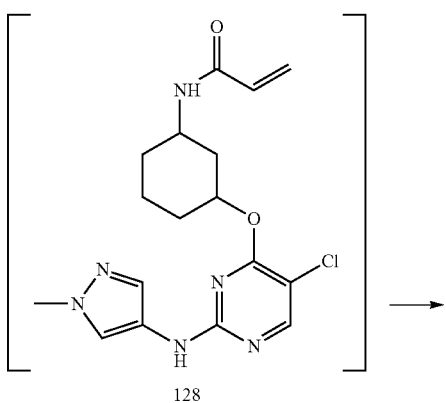

128

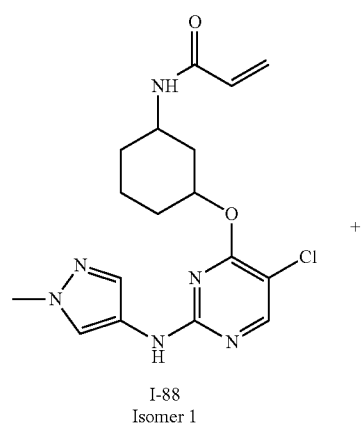

I-88
Isomer 1

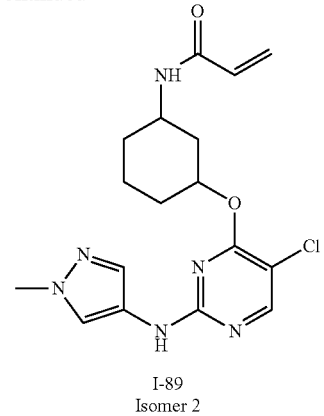

I-89
Isomer 2

Synthesis of tert-butyl (3-((2,5-dichloropyrimidin-4-yl)oxy)cyclohexyl) carbamate (125)

To a mixture of tert-butyl (3-hydroxycyclohexyl) carbamate (precursor-39) (3.0 g, 16.5 mmol) in dry THF (20 mL) in properly dried and inert condition, 2,4,5-trichloropyrimidine 77 (4.2 g, 19.8 mmol) was added drop wise under nitrogen atmosphere. The reaction mixture was stirred for 15-20 min at RT followed by addition of potassium tert-butoxide drop wise at 0° C. The reaction mixture was monitored properly by TLC. After 1 h starting was consumed, reaction was quenched with cold water at 0° C. and aqueous was extracted with EtOAc and washed with brine. The organic phase was dried and concentrated to get crude material. The crude material was purified by flash column chromatography (SiO2), eluting with 15-20% EtOAc-hexane to obtain tert-butyl (3-((2,5-dichloropyrimidin-4-yl)oxy)cyclohexyl) carbamate 125 (2.6 g, 44% yield) as white gummy solid. MS: 362.05 (M+H)$^+$.

Synthesis of tert-butyl (3-((5-chloro-2-((1-methyl-1H-pyrazol-4-yl)amino)pyrimidin-4-yl)oxy)cyclohexyl)carbamate (126)

Title compound was prepared in a manner similar to general method-D.
tert-butyl (3-((2,5-dichloropyrimidin-4-yl)oxy)cyclohexyl) carbamate 125 (1.2 g 3.4 mmol) & 1-methyl-1H-pyrazol-4-amine precursor-5 (0.39 g 4.0 mmol) gave tert-butyl (3-((5-chloro-2-((1-methyl-1H-pyrazol-4-yl)amino)pyrimidin-4-yl)oxy)cyclohexyl)carbamate 126 as brown solid that was proceeded as such for next step. MS: 423.20 (M+H)$^+$.

Synthesis of 4-((3-aminocyclohexyl)oxy)-5-chloro-N-(1-methyl-1H-pyrazol-4-yl)pyrimidin-2-amine (127)

To a stirred suspension of compound tert-butyl (3-((5-chloro-2-((1-methyl-1H-pyrazol-4-yl)amino)pyrimidin-4-yl)oxy)cyclohexyl) carbamate 126 (1.2 g, 2.9 mmol) in DCM (10 mL), at 0° C. was added TFA (2 mL) drop wise. The progress of the reaction was monitored by TLC and after completion of reaction, reaction mixture was concentrated fully under vacuum & was quenched with saturated NaHCO$_3$ solution and aqueous layer was extracted with 10% MeOH in DCM. The organic extracts were dried over Na$_2$SO$_4$ and concentrated to get crude. The crude material was purified by flash column chromatography (SiO2), eluting with 10% MeOH-DCM to obtain 4-((3-aminocyclohexyl)oxy)-5-chloro-N-(1-methyl-1H-pyrazol-4-yl)pyrimidin-2-amine 127 as white solid (0.30 g) with 32% yield. MS: 323.10 (M+H)$^+$.

Synthesis N-(3-((5-chloro-2-((1-methyl-1H-pyrazol-4-yl)amino)pyrimidin-4-yl)oxy)cyclohexyl)acrylamide (128)

Title compound was prepared in a manner similar to general method-J.
4-((3-aminocyclohexyl)oxy)-5-chloro-N-(1-methyl-1H-pyrazol-4-yl)pyrimidin-2-amine 127 (0.15 g, 0.47 mmol) and acryloyl chloride (0.043 g, 0.47 mmol gave two is N-(3-((5-chloro-2-((1-methyl-1H-pyrazol-4-yl)amino)pyrimidin-4-yl)oxy)cyclohexyl)acrylamide 128 as racemic compound, which was further purified by chiral HPLC using SUNFIRE (19×250) mm, 5, low rate 18 mL/min eluting with water-ACN gradient containing 0.1% TFA and obtained Isomers 1 & 2.
Isomer 1 (0.05 g) (I-88); $^1$HNMR (400 MHz, DMSO-d6): δ 9.56 (br s, 1H), 8.23 (s, 1H), 8.03 (d, J=6.8 Hz, 1H), 7.74 (m, 1H), 7.46 (s, 1H), 6.16-6.23 (m, 1H), 6.02-6.06 (m, 1H), 5.53-5.57 (m, 1H), 5.48 (m, 1H), 3.97-4.04 (m, 1H), 3.79 (s, 3H), 2.11-2.14 (m, 1H), 1.83-1.91 (m, 2H), 1.64 (m, 4H) and 1.25-1.36 (m, 1H); MS: 377.21 (M+H); Isomer 2 (15 mg) (I-89); δ 9.58 (br s, 1H), 8.21 (s, 1H), 8.11 (d, J=7.2 Hz, 1H), 7.83 (s, 1H), 7.41 (s, 1H), 6.15-6.22 (m, 1H), 6.05-6.10 (m, 1H), 5.57 (dd, J=10.0 & 1.6 Hz, 1H), 5.12-5.13 (m, 1H), 3.81 (s, 3H), 2.15 (m, 1H), 1.82 (m, 2H), 1.36-1.39 (m, 4H) and 1.21 (m, 2H); MS: 377.18 (M+H).
I-90 and I-91 were purified using XBridge Shield (19× 250) mm, 5µ, flow rate 18 mL/min eluting with water-ACN gradient containing 5 mmol ammonium bicarbonate (per liter).
Following compounds were prepared similarly Example 15: Synthesis of N-(3-((5-chloro-2-((1-methyl-1H-pyrazol-4-yl)amino)pyrimidin-4-yl)amino)cyclohexyl)acrylamide (I-92)

Scheme-51:

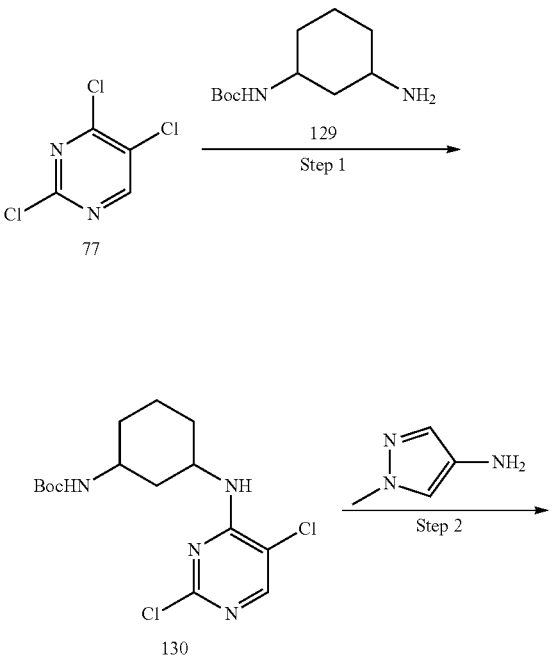

| Cmpd No. | Structure | Synthesis Method | LCMS (M + 1) | $^1$H-NMR (400 MHZ, DMSO-d$_6$) |
|---|---|---|---|---|
| I-90 (Isomer 1) | 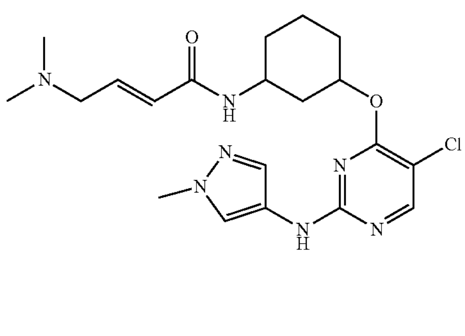 [SMILES: CN(C)C/C=C/C(=O)NC1CCCC(Oc2nc(Nc3cnn(C)c3)ncc2Cl)C1] | K | 434.20 | δ 9.61-9.56 (m, 1H), 8.23 (s, 1H), 7.96-7.94 (m, 1H), 7.80-7.76 (m, 1H), 7.46 (s, 1H), 6.54-6.47 (m, 1H), 6.04-5.99 (m, 1H), 5.48 (bs, 1H), 4.00-3.98 (m, 1H), 3.79 (s, 3H), 2.99-2.98 (m, 2H), 2.14 (s, 6H), 2.14-2.10 (m, 1H), 1.85-1.81 (m, 2H), 1.64 (bs, 4H), 1.29 (m, 1H) |
| I-91 (Isomer 2) | 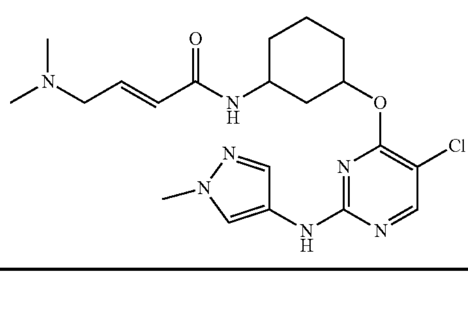 | K | 434.20 | δ 9.59-9.55 (m, 1H), 8.21 (s, 1H), 8.04-8.02 (m, 1H), 7.82 (s, 1H), 7.41 (s, 1H), 6.58-6.51 (m, 1H), 6.03-5.99 (m, 1H), 5.1 (m, 1H), 3.81 (s, 4H), 3.03 (s, 2H), 2.17 (s, 7H), 1.84-1.81 (m, 2H), 1.41-1.32 (m, 3H), 1.32-1.18 (m, 1H). |

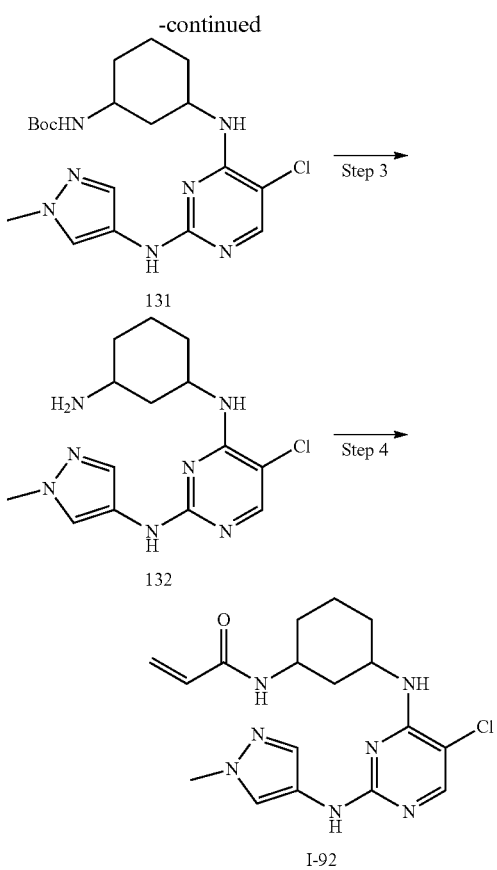

Synthesis of tert-butyl (3-((2,5-dichloropyrimidin-4-yl)amino)cyclohexyl)carbamate (130)

Title compound was prepared in a manner similar to general method-C.

2,4,5-trichloropyrimidine 77 (10.0 g, 54.59 mmol) and tert-butyl (3-aminocyclohexyl)carbamate 129 (14.0 g, 65.42 mmol) gave tert-butyl (3-((2,5-dichloropyrimidin-4-yl)amino)cyclohexyl)carbamate 130 as off white solid (12.0 g, 61% yield). MS: 361.2 (M+H)$^+$.

Synthesis of tert-butyl (3-((5-chloro-2-((1-methyl-1H-pyrazol-4-yl)amino)pyrimidin-4-yl)amino)cyclohexyl)carbamate (131)

Title compound was prepared in a manner similar to general method-E.

tert-butyl (3-((2,5-dichloropyrimidin-4-yl)amino)cyclohexyl)carbamate 130 (12.0 g, 33.32 mmol) and 1-methyl-1H-pyrazol-4-amine precursor-5 gave tert-butyl (3-((5-chloro-2-((1-methyl-1H-pyrazol-4-yl)amino)pyrimidin-4-yl)amino)cyclohexyl)carbamate 131 as crude (10.0 g), which was carried forward as such without further purification. MS: 422.1 (M+H)$^+$.

Synthesis of N4-(3-aminocyclohexyl)-5-chloro-N2-(1-methyl-1H-pyrazol-4-yl)pyrimidine-2,4-diamine (132)

To an ice-cold solution of tert-butyl (3-((5-chloro-2-((1-methyl-1H-pyrazol-4-yl)amino)pyrimidin-4-yl)amino)cyclohexyl) carbamate 131 (10.0 g, crude obtained as above) in MeOH (50 mL) & DCM (100 mL) was added HCl-1,4-dioxane solution (4N, 20 mL). The reaction mixture was stirred for 16 h at RT. Reaction was monitored by TLC, after the completion of reaction, the reaction mixture was concentrated, added water (50 mL) and saturated sodium bicarbonate (50 mL) to the residue followed by extraction with DCM (3×100 mL). The combined organic layer was washed with brine solution, dried over sodium sulphate and evaporated under reduced pressure to obtain crude product. The crude product was purified by using combiflash with 5-8% DCM in MeOH as a solvent to get pure product as N4-(3-aminocyclohexyl)-5-chloro-N2-(1-methyl-1H-pyrazol-4-yl)pyrimidine-2,4-diamine 132 (7.0 g 55% yield over 2 steps). MS: 322.22 (M+H)$^+$.

Synthesis of N-(3-((5-chloro-2-((1-methyl-1H-pyrazol-4-yl)amino)pyrimidin-4-yl)amino)cyclohexyl) acrylamide (I-92)

Title compound was prepared in a manner similar to general method-J.

N4-(3-aminocyclohexyl)-5-chloro-N2-(1-methyl-1H-pyrazol-4-yl)pyrimidine-2,4-diamine (1.0 g, 3.11 mmol) and acryloyl chloride (0.28 g, 3.11 mmol) gave N-(3-((5-chloro-2-((1-methyl-1H-pyrazol-4-yl)amino)pyrimidin-4-yl)amino)cyclohexyl)acrylamide (I-92) as white solid (0.58 g) with 50% yield, $^1$HNMR (400 MHz, DMSO-d$_6$): δ 9.05 (s, 1H), 8.08 (d, 1H), 7.86 (s, 1H), 7.78 (s, 1H), 7.37 (s, 1H), 6.75 (m, 1H), 6.23-6.16 (m, 1H), 6.08-6.04 (m, 1H), 5.57-5.54 (m, 1H), 4.05 (m, 1H), 3.79 (m, 4H), 2.07 (m, 1H), 1.88-1.81 (m, 3H), 1.39-1.29 (m, 3H), 1.14-1.09 (m, 1H); MS: 376.5 (M+H)$^+$.

For compounds I-102 & I-103, the racemate was separated by chiral HPLC purification using Column: CHIRALPAK IA (250 mm×4.6 mm×5 im); Mobile phase: nHexane: Ethanol (75:25) with 0.1% DEA The following compounds were prepared similarly using general method-J and K.

| Cmpd No. | Structure | Synthesis method | LCMS (M + 1) | $^1$H-NMR (400 MHz, DMSO-d$_6$) |
|---|---|---|---|---|
| I-93 | 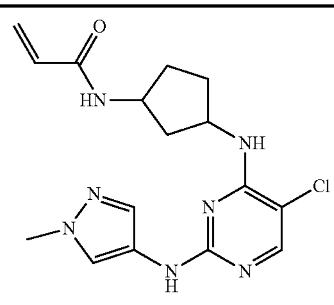 | J | 362.11 | δ 9.03 (br s, 1H), 8.17 (br s, 1H), 7.86 (s, 1H), 7.75 (s, 1H), 7.44 (s, 1H), 6.87 (d, 1H), 6.18-6.25 (m, 1H), 6.07 (d, 1H), 5.56 (d, 1H), 4.56-4.57 (m, 1H), 4.25-4.30 (m, 1H), 3.77 (s, 3H), 1.94-2.13 (m, 3H), 1.84-1.87 (m, 1H), 1.62-1.67 (m, 1H), 1.43-1.46 (m, 1H) |

| Cmpd No. | Structure | Synthesis method | LCMS (M + 1) | ¹H-NMR (400 MHz, DMSO-d₆) |
|---|---|---|---|---|
| I-94 | 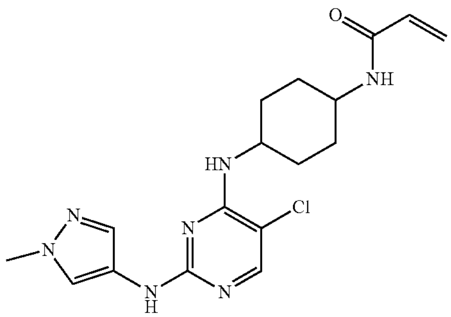 [SMILES: C=CC(=O)NC1CCC(Nc2nc(Nc3cnn(C)c3)ncc2Cl)CC1] | J | 376.48 | δ 9.07 (s, 1H), 7.88-7.93 (m, 2H), 7.73 (s, 1H), 7.43 (s, 1H), 6.28-6.35 (m, 2H), 6.06-6.10 (m, 1H), 5.55-5.58 (m, 1H), 4.0 (m, 1H), 3.87 (m, 1H), 3.77 (s, 3H), 1.64-1.75 (m, 8H) |
| I-95 | 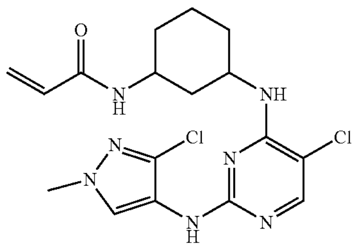 [SMILES: C=CC(=O)NC1CCCC(Nc2nc(Nc3cn(C)nc3Cl)ncc2Cl)C1] | J | 410.08 | δ 8.34 (s, 1H), 8.08-8.06 (m, 1H), 7.88 (s, 1H), 7.84 (s, 1H), 6.80-6.78 (m, 1H), 6.23-6.16 (m, 1H), 6.09-6.05 (d, 1H), 5.57-5.50 (m, 1H), 4.04 (bs, 1H), 3.79 (s, 3H), 3.72-3.61 (m, 1H), 2.01-1.95 (m, 1H), 1.85-1.79 (m, 3H), 1.37-1.28 (m, 3H), 1.23-1.11 (m, 1H) |
| I-96 | 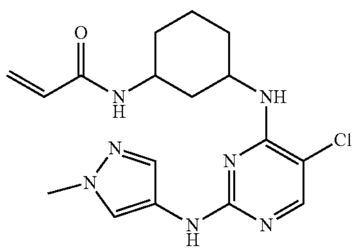 [SMILES: C=CC(=O)NC1CCCC(Nc2nc(Nc3cnn(C)c3)ncc2Cl)C1] | J | 376.23 | δ 9.29 (s, 1H), 8.07-8.06 (m, 1H), 7.86 (s, 1H), 7.49 (s, 1H), 6.82-6.80 (m, 1H), 6.47 (s, 1H), 6.23-6.16 (m, 1H), 6.08-6.05 (d, 1H), 5.57-5.47 (m, 1H), 4.03 (bs, 1H), 3.71 (s, 4H), 2.02-2.00 (m, 1H), 1.82-1.79 (m, 3H), 1.39-1.34 (m, 3H), 1.15-1.09 (m, 1H) |
| I-97 | 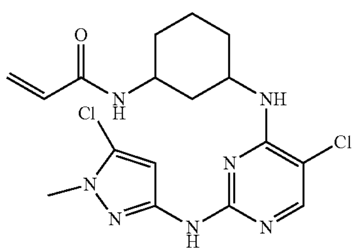 [SMILES: C=CC(=O)NC1CCCC(Nc2nc(Nc3cc(Cl)n(C)n3)ncc2Cl)C1] | J | 410.12 | δ 9.52 ( s, 1H), 8.07-8.05 (m, 1H), 7.88 (s, 1H), 6.89-6.87 (d, 1H), 6.61 (s, 1H), 6.23-6.16 (m, 1H), 6.08-6.04 (m, 1H), 5.57-5.54 (m, 1H), 4.01 (bs, 1H), 3.73-3.59 (m, 1H), 3.67 (s, 3H), 2.01-1.98 (m, 1H), 1.86-1.79 (m, 3H), 1.47-1.30 (m, 3H), 1.15-1.08 (m, 1H) |
| I-98 | 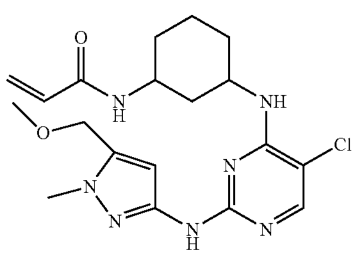 [SMILES: C=CC(=O)NC1CCCC(Nc2nc(Nc3cc(COC)n(C)n3)ncc2Cl)C1] | J | 420.30 | δ 9.29 (s, 1H), 8.09-8.07 (m, 1H), 7.86 (s, 1H), 6.84-6.82 (m, 1H), 6.53 (s, 1H), 6.23-6.17 (m, 1H), 6.09-6.04 (m, 1H), 5.58-5.55 (m, 1H), 4.44 (s, 2H), 4.05-4.04 (m, 1H), 3.74-3.72 (m, 1H), 3.65 (s, 3H), 3.27 (s, 3H), 2.07-2.02 (m, 1H), 1.83-1.71 (m, 3H), 1.43-1.33 (m, 3H), 1.14-1.06 (m, 1H). |
| I-99 | 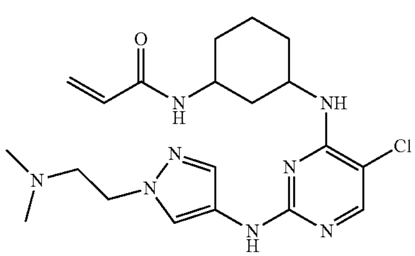 [SMILES: C=CC(=O)NC1CCCC(Nc2nc(Nc3cnn(CCN(C)C)c3)ncc2Cl)C1] | J | 433.41 | δ 9.07 (bs, 1H), 8.13-8.11 (m, 1H), 7.84 (d, 1H), 7.41 (s, 1H), 6.78-6.77 (m, 1H), 6.54 (s, 1H), 6.24-6.17 (m, 1H), 6.09-6.04 (m, 1H), 5.58-5.54 (m, 1H) 4.22-4.02 (m, 3H), 3.76 (bs, 1H), 2.72-2.67 (m, 2H), 2.23 (s, 6H), 2.10-2.05 (m, 1H), 1.91-1.75 (m, 3H),1.40-1.30 (m, 3H), 1.15-1.13 (m, 1H) |

| Cmpd No. | Structure | Synthesis method | LCMS (M + 1) | ¹H-NMR (400 MHz, DMSO-d$_6$) |
|---|---|---|---|---|
| I-100 | 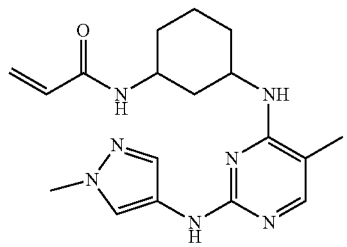 [SMILES: C=CC(=O)NC1CCCC(Nc2nc(Nc3cnn(C)c3)ncc2C)C1] | J | 356.17 | δ 8.60 (br s, 1H), 8.06 (d, 1H), 7.79 (s, 1H), 7.58 (s, 1H), 7.34 (s, 1H), 6.16-6.23 (m, 2H), 6.06 (dd, 1H), 5.56 (dd, 1H), 4.04-4.06 (m, 1H), 3.78 (s, 3H), 2.11-2.13 (m, 1H), 1.87 (s, 3H), 1.79-1.83 (m, 4H), 1.23-1.42 (m, 3H), 1.14-1.17 (m, 1H) |
| I-101 | 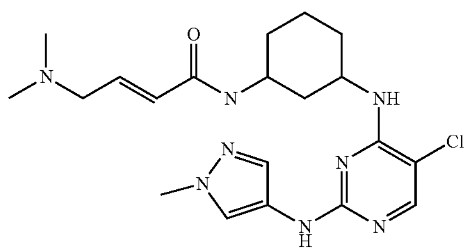 [SMILES: CN(C)C/C=C/C(=O)NC1CCCC(Nc2nc(Nc3cnn(C)c3)ncc2Cl)C1] | J | 433.16 | δ 9.05 (br s, 1H), 7.98 (d, 1H), 7.79-7.86 (m, 2H), 7.37 (s, 1H), 6.74 (d, 1H), 6.50-6.56 (m, 1H), 6.01 (d, 1H), 4.21 (m, 1H), 3.79 (m, 4H), 2.96-2.98 (m, 2H), 2.13 (m, 7H), 1.80 (s, 3H), 1.37 (m, 3H), 1.13 (m, 1H) |
| I-102 (diastereo-mer 1) | 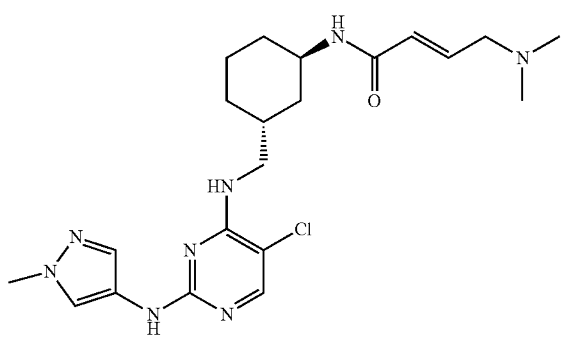 | K | 447.6 | δ 8.9 (brs, 1H), 7.82-7.78 (m, 2H), 7.73 (s, 1H), 7.38 (s, 1H), 7.04 (brs, 1H), 6.53-6.46 (m, 1H), 6.07 (d, 1H), 4.05 (brs, 1H), 3.73 (s, 3H), 2.93 (d, 2H), 2.10 (s, 6H), 2.0 (brs, 1H), 1.6-1.50 (m, 5H), 1.41-1.32 (m, 2H), 1.28-1.1 (m, 3H) |
| I-103 (diastereo-mer 2) | 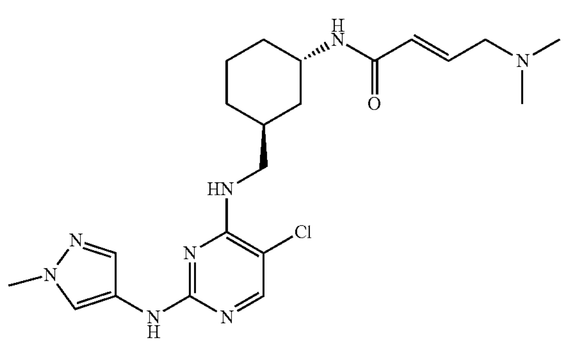 | K | 447.5 | 8.94 (brs, 1H), 7.85-7.82 (m, 2H), 7.73 (s, 1H), 7.40 (s, 1H), 7.06 (brs, 1H), 6.53-6.47 (m, 1H), 5.98 (d, 1H), 3.75 (s, 3H), 3.55 (brs, 1H), 2.95 (d, 2H), 2.12 (s, 6H), 1.88-1.67 (m, 6H), 1.28-1.06 (m, 3H), 0.83-0.78 (m, 2H) |

Example 16: N-((1S,3R)-3-(5-chloro-2-(1-methyl-1H-pyrazol-4-ylamino)pyrimidin-4-ylamino)cyclohexyl)acrylamide (I-104) (Enantiomer 3)
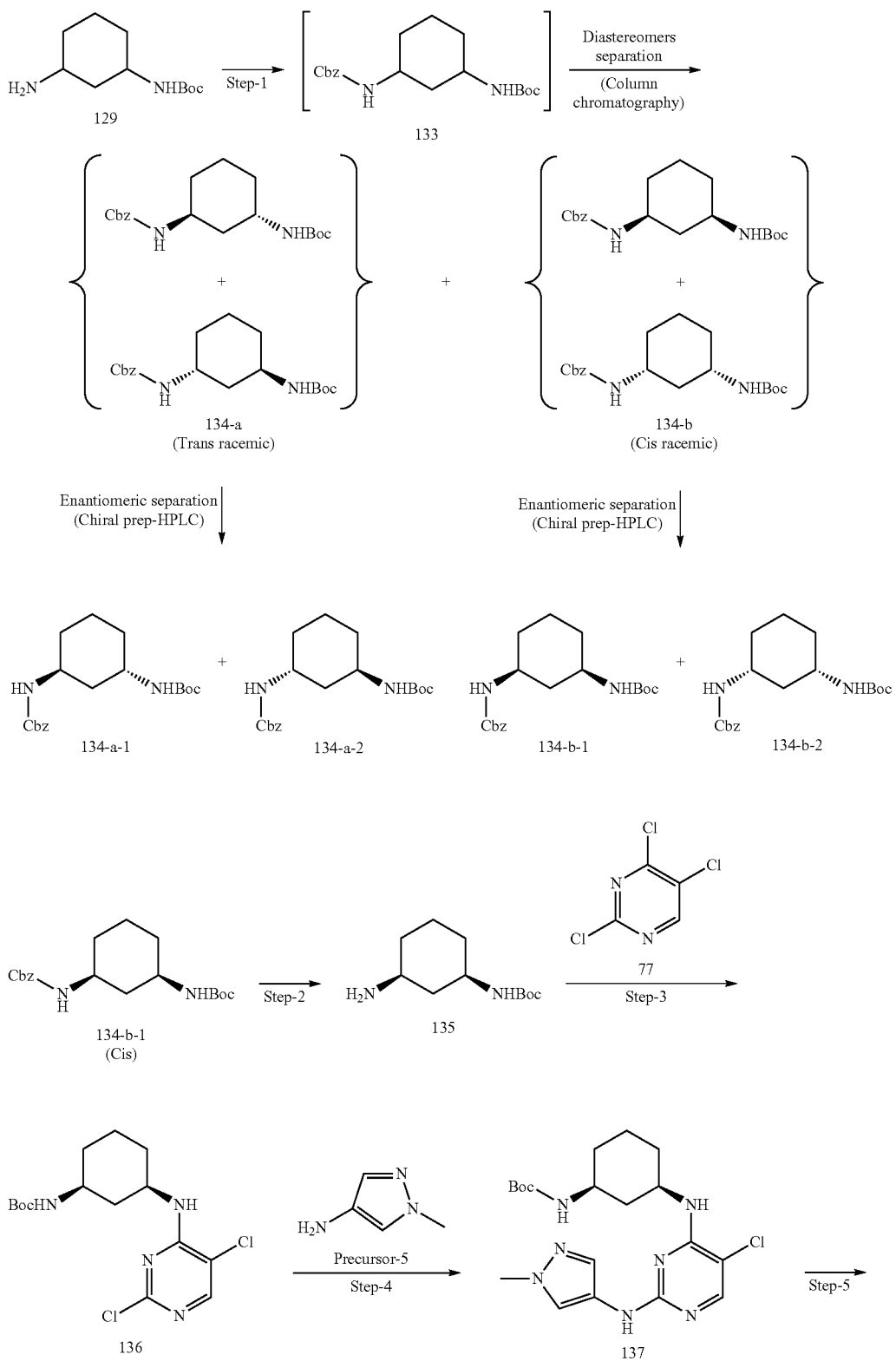
Scheme 52:

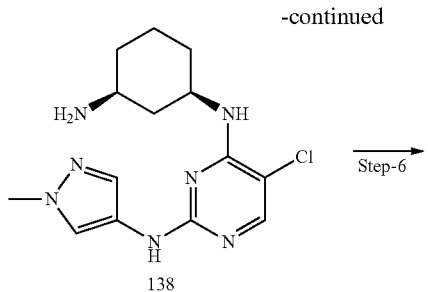

Synthesis of benzyl tert-butyl cyclohexane-1,3-diyldicarbamate (133)

To a mixture of tert-butyl (3-aminocyclohexyl)carbamate 129 (15 g, 70 mmol) and benzyloxycarbonyl chloride (11.9 g, 106 mmol) in DCM (100 ml) at −20° C. was added diisopropylethyl amine (11.8 ml, 210 mmol) dropwise under nitrogen atmosphere. The reaction mixture was stirred for 15 min at the same temperature, and it was allowed to warm to RT and stirred for an additional 2 h. The reaction mixture was diluted with DCM and washed with brine. The organic phase was dried and concentrated to get crude material 133. The crude material was purified by flash column chromatography eluting with 9% EtOAc in hexane to get the first fraction as 1,3-trans racemic mixture 134-a (3.10 g, 12.7% yield) and the second fraction as 1,3-cis racemic mixture 134-b (6.80 g, 27.9% yield). Compound 134-a: $^1$HNMR (400 MHz, CDCl$_3$); δ 7.36-7.37 (m, 5H), 5.08 (s, 2H), 4.76 (br s, 1H), 4.55 (br s, 1H), 3.76-3.84 (m, 2H), 1.70-1.81 (m, 4H), 1.33-1.49 (m, 2H), 1.45 (s, 9H), 1.25-1.29 (m, 2H). MS: 349.30 (M+H)$^+$.

Compound 134-b: $^1$HNMR (400 MHz, CDCl$_3$); δ 7.33-7.35 (m, 5H), 5.07 (s, 2H), 4.58 (br s, 1H), 4.37 (br s, 1H), 3.53 (br s, 2H), 2.27-2.30 (m, 1H), 1.98 (br s, 2H), 1.75-1.78 (m, 1H), 1.44 (s, 9H), 1.33-1.43 (m, 1H), 0.89-1.0 (m, 3H). MS: 349.30 (M+H)$^+$.

Separation of [3-(S)-Benzyloxycarbonylamino-cyclohexyl]-1-(S)-carbamic acid tert-butyl ester 134-a-1 & [3-(R)-Benzyloxycarbonylamino-cyclohexyl]-1-(R)-carbamic acid tert-butyl ester from 134-a-2

Compound 134-a was separated into two enantiomeric pure compounds by using Chiralpak IB (4.6×250) mm, 5μ column (mobile phase: 10% IPA in Hexane).

Compound 134-a-1 (1.30 g, first fraction) and compound 134-a-2 (1.4 g, second fraction). Compound 134-a-1: $^1$HNMR (400 MHz, CDCl$_3$); δ 7.33-7.36 (m, 5H), 5.08 (s, 2H), 4.79 (br s, 1H), 4.56 (br s, 1H), 3.76-3.84 (m, 2H), 1.70-1.81 (m, 4H), 1.33-1.49 (m, 2H), 1.45 (s, 9H), 1.25-1.29 (m, 2H). MS: 349.30 (M+H)$^+$, [α]$_D$=−5.50° (c=0.99 in CHCl$_3$).

Compound 134-a-2: $^1$HNMR (400 MHz, CDCl$_3$); δ 7.33-7.36 (m, 5H), 5.08 (s, 2H), 4.79 (br s, 1H), 4.56 (br s, 1H), 3.76-3.84 (m, 2H), 1.70-1.81 (m, 4H), 1.33-1.49 (m, 2H), 1.45 (s, 9H), 1.25-1.29 (m, 2H). MS: 349.30 (M+H)$^+$, [α]$_D$=+5.60° (c=0.99 in CHCl$_3$).

Separation of [3-(R)-Benzyloxycarbonylamino-cyclohexyl]-1-(S)-carbamic acid tert-butyl ester 134-b-1 & [3-(S)-Benzyloxycarbonylamino-cyclohexyl]-1-(R)-carbamic acid tert-butyl ester 134-b-2

Compound 134-b was separated into two enantiomeric pure compounds by using Chiralpak IB (4.6×250) mm, 5μ column (mobile phase: 10% IPA in Hexane).

Compound 134-b-1: $^1$HNMR (400 MHz, CDCl$_3$); δ 7.33-7.35 (m, 5H), 5.08 (s, 2H), 4.59 (br s, 1H), 4.37 (br s, 1H), 3.54 (br s, 2H), 2.28-2.31 (m, 1H), 1.98 (br s, 2H), 1.75-1.98 (m, 1H), 1.44 (s, 9H), 1.33-1.36 (m, 1H), 1.01-1.04 (m, 3H). MS: 349.30 (M+H)$^+$, [α]$_D$=−7.80° (c=1.20 in CHCl$_3$).

Compound 134-b-2: $^1$HNMR (400 MHz, CDCl$_3$); δ 7.33-7.35 (m, 5H), 5.08 (s, 2H), 4.59 (br s, 1H), 4.37 (br s, 1H), 3.54 (br s, 2H), 2.28-2.31 (m, 1H), 1.98 (br s, 2H), 1.75-1.98 (m, 1H), 1.44 (s, 9H), 1.33-1.36 (m, 1H), 0.89-1.04 (m, 3H). MS: 349.30 (M+H)$^+$, [α]$_D$=+8.30° (c=1.20 in CHCl$_3$).

Synthesis of tert-butyl ((1R,3S)-3-aminocyclohexyl)carbamate (135)

To a solution of compound 134-b-1 (2.60 g) in MeOH (100 mL) was added 10% Pd/C (0.80 g). The reaction mixture was stirred under a 40-psi H$_2$ atmosphere at RT for 2 h. The reaction mixture was filtered through celite bed and filtrate was evaporated in vacuo to afford the title compound 135 (1.30 g, 88% yield) as a white solid. The compound was used as such for next reaction without further purification. $^1$HNMR (400 MHz, CDCl$_3$): δ 4.45-4.55 (m, 1H), 3.47-3.48 (m, 1H), 2.75-2.80 (m, 1H), 2.09-2.11 (m, 1H), 1.90-1.93 (m, 1H), 1.74-1.82 (m, 2H), 1.44 (s, 9H), 1.25-1.44 (m, 1H), 0.94-1.04 (m, 3H); MS: m/z 215.0 (M+H)$^+$.

Synthesis of tert-butyl ((1S,3R)-3-((2,5-dichloropyrimidin-4-yl)amino)cyclohexyl)carbamate (136)

Title compound was prepared in a manner similar to general method-C.

2,4,5-trichloropyrimidine 77 (1.33 g) and tert-butyl ((1R,3S)-3-aminocyclohexyl)carbamate 135 (1.30 g) gave tert-butyl ((1S,3R)-(3-((2,5-dichloropyrimidin-4-yl)amino)cyclohexyl)carbamate 136 as off white solid (0.80 g, 36% yield). $^1$HNMR (400 MHz, CDCl$_3$): δ 8.14 (s, 1H), 7.62-7.64 (m, 1H), 6.86-6.87 (m, 1H), 3.90-3.95 (m, 1H), 3.16-3.28 (m, 1H), 1.89-1.98 (m, 1H), 1.71-1.73 (m, 3H), 1.45 (s, 9H), 1.29-1.38 (m, 3H), 1.03-1.11 (m, 1H). MS: 361.12 (M+H)$^+$.

Synthesis of tert-butyl ((1S,3R)-3-((5-chloro-2-((1-methyl-1H-pyrazol-4-yl)amino)pyrimidin-4-yl)amino)cyclohexyl)carbamate (137)

Title compound was prepared in a manner similar to general method-D.

tert-butyl ((1S,3R)-3-((2,5-dichloropyrimidin-4-yl) amino)cyclohexyl)carbamate 136 (0.85 g, 2.4 mmol) & 1-methyl-1H-pyrazol-4-amine precursor-5 gave tert-butyl ((1S,3R)-3-((5-chloro-2-((1-methyl-1H-pyrazol-4-yl) amino)pyrimidin-4-yl) amino)cyclohexyl)carbamate 137 as brown solid (0.80 g), which was carried forward to the next step without further purification. MS: 422.10 (M+H)+.

Synthesis of N4-((1R,3S)-3-aminocyclohexyl)-5-chloro-N2-(1-methyl-1H-pyrazol-4-yl)pyrimidin-2,4-diamine (138)

To an ice-cold solution of tert-butyl ((1S,3R)-3-((5-chloro-2-((1-methyl-1H-pyrazol-4-yl)amino)pyrimidin-4-yl)amino)cyclohexyl)carbamate 137 (0.80 g, 1.9 mmol) in MeOH (3 mL) & DCM (15 mL) was added HCl-1,4-dioxane solution (3 mL). The reaction mixture was stirred for 16 h at RT. Reaction was monitored by TLC, after the completion of reaction, reaction mixture was concentrated, added water (10 mL) and saturated sodium bicarbonate (10 mL) to the residue followed by extraction with DCM (3×50 mL). The combined organic layer was washed with brine solution (10 mL), dried over sodium sulphate and evaporated under reduced pressure to obtain crude product. The crude product was purified by using combiflash with 5-8% DCM in MeOH as a solvent to get pure product as N4-((1R,3S)-3-aminocyclohexyl)-5-chloro-N2-(1-methyl-1H-pyrazol-4-yl)pyrimidine-2,4-diamine 138 (0.40 g 52% yield over 2 steps).

1H-NMR (400 MHz, DMSO-$d_6$): δ 9.06 (br s, 1H), 7.92 (s, 1H), 7.84-7.81 (m, 1H), 7.39 (s, 1H), 6.39 (s, 1H), 4.46 (br s, 1H), 3.77 (s, 3H), 3.34 (s, 1H), 1.79 (br s, 2H), 1.66 (m, 2H), 1.47-1.42 (m, 6H). MS: 322.0 (M+H)+.

Synthesis of N-((1S,3R)-3-((5-chloro-2-((1-methyl-1H-pyrazol-4-yl)amino)pyrimidin-4-yl)amino)cyclohexyl)acrylamide (I-104) (Enantiomer 3)

Title compound was prepared in a manner similar to general method-J.

N4-((1R,3S)-3-aminocyclohexyl)-5-chloro-N2-(1-methyl-1H-pyrazol-4-yl)pyrimidine-2,4-diamine 138 (0.35 g) and acryloyl chloride gave N-((1S,3R)-3-((5-chloro-2-((1-methyl-1H-pyrazol-4-yl)amino)pyrimidin-4-yl)amino)cyclohexyl)acrylamide (I-104) as white solid (0.07 g) with 17.5% yield. 1HNMR (400 MHz, DMSO-d6): δ 9.06 (br s, 1H), 8.09 (d, 1H), 7.86 (s, 1H), 7.78 (s, 1H), 7.37 (s, 1H), 6.75-6.77 (m, 1H), 6.16-6.23 (m, 1H), 6.04-6.08 (m, 1H), 5.57-5.54 (m, 1H), 4.05 (br s, 1H), 3.79 (s, 4H), 2.08-2.09 (m, 1H), 1.88-1.81 (m, 3H), 1.39-1.29 (m, 3H), 1.12-1.14 (m, 1H); MS: 376.2 (M+H)+.

The following compounds were prepared similarly using 134-a-1, 134-a-2, 134-b-2:

| Cmpd No. | Structure | LCMS (M + 1) | 1H-NMR (400 MHz, DMSO-$d_6$) |
|---|---|---|---|
| I-105 (Enantiomer 4) | 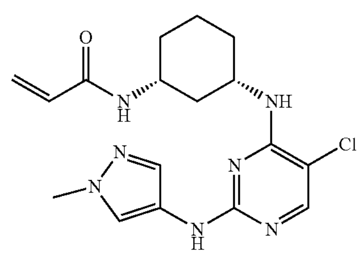 [SMILES: C=CC(=O)N[C@@H]1CCC[C@H](Nc2nc(Nc3cnn(C)c3)ncc2Cl)C1] | 376.2 | δ 9.06 (br s, 1H), 8.09 (d, 1H), 7.86 (s, 1H), 7.78 (s, 1H), 7.37 (s, 1H), 6.75-6.77 (m, 1H), 6.16-6.23 (m, 1H), 6.04-6.08 (m, 1H), 5.57-5.54 (m, 1H), 4.05 (br s, 1H), 3.79 (s, 4H), 2.08-2.09 (m, 1H), 1.88-1.81 (m, 3H), 1.39-1.29 (m, 3H), 1.12-1.14 (m, 1H) |
| I-106 (Enantiomer 1) | 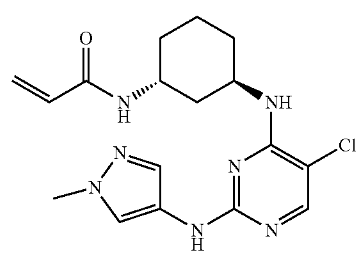 [SMILES: C=CC(=O)N[C@@H]1CCC[C@@H](Nc2nc(Nc3cnn(C)c3)ncc2Cl)C1] | 376.2 | δ 9.06 (br s, 1H), 8.09 (d, 1H), 7.86 (s, 1H), 7.78 (s, 1H), 7.37 (s, 1H), 6.75-6.77 (m, 1H), 6.16-6.23 (m, 1H), 6.04-6.08 (m, 1H), 5.57-5.54 (m, 1H), 4.05 (br s, 1H), 3.79 (s, 4H), 2.08-2.09 (m, 1H), 1.88-1.81 (m, 3H), 1.39-1.29 (m, 3H), 1.12-1.14 (m, 1H) |
| I-107 (Enantiomer 2) | 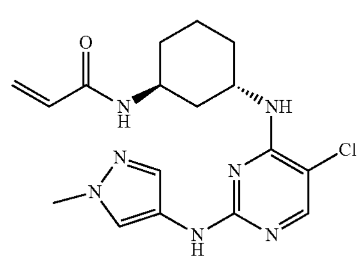 [SMILES: C=CC(=O)N[C@H]1CCC[C@H](Nc2nc(Nc3cnn(C)c3)ncc2Cl)C1] | 376.2 | δ 9.06 (br s, 1H), 8.09 (d, 1H), 7.86 (s, 1H), 7.78 (s, 1H), 7.37 (s, 1H), 6.75-6.77 (m, 1H), 6.16-6.23 (m, 1H), 6.04-6.08 (m, 1H), 5.57-5.54 (m, 1H), 4.05 (br s, 1H), 3.79 (s, 4H), 2.08-2.09 (m, 1H), 1.88-1.81 (m, 3H), 1.39-1.29 (m, 3H), 1.12-1.14 (m, 1H) |

Example 17: Synthesis of N-((3-((5-chloro-2-((1-methyl-1H-pyrazol-4-yl)amino)pyrimidin-4-yl)amino)cyclohexyl)methyl)acrylamide (I-108)

Scheme-53:

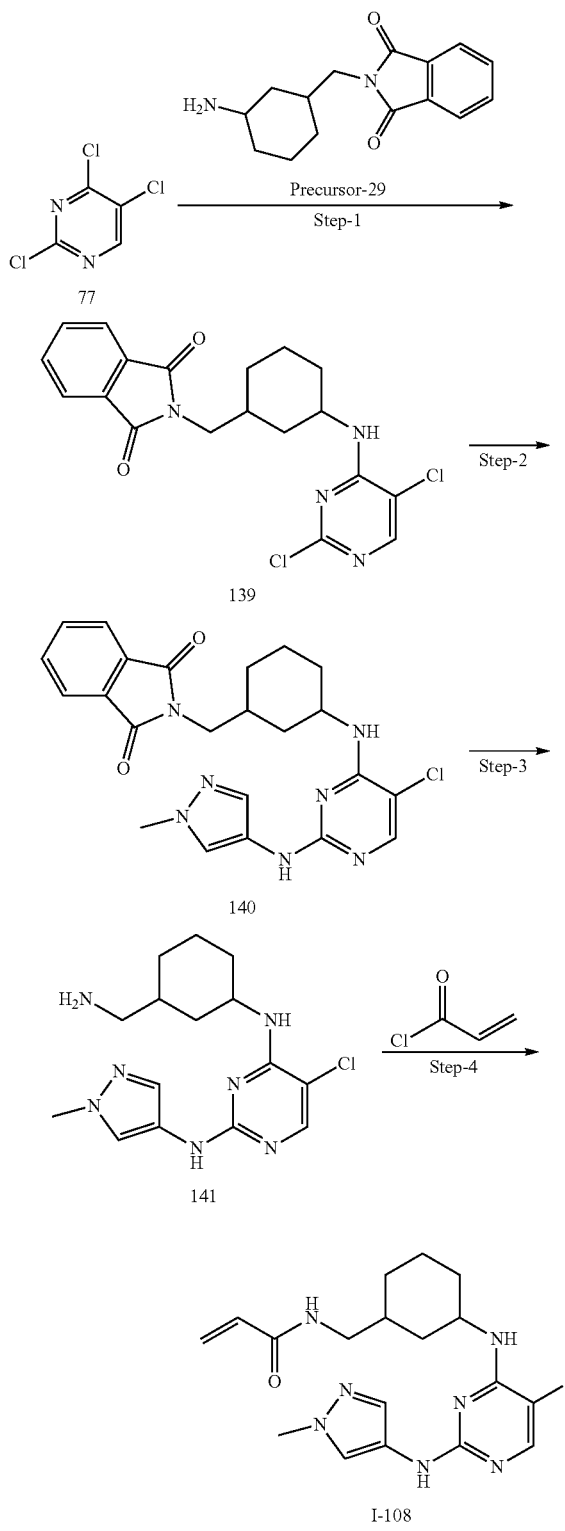

Synthesis of 2-((3-((2,5-dichloropyrimidin-4-yl)amino)cyclohexyl)methyl)isoindoline-1,3-dione (139)

Title compound was prepared in a manner similar to general method-C.

2,4,5-trichloropyrimidine 77 (0.99 g, 5.4 mmol) and 2-((3-aminocyclohexyl)methyl)isoindoline-1,3-dione precursor-29 (1.40 g, 5.4 mmol), gave 2-((3-((2,5-dichloropyrimidin-4-yl)amino)cyclohexyl)methyl) isoindoline-1,3-dione 139 as off white solid (0.92 g, quantitative yield). MS: 404.99 (M+H)$^+$.

Synthesis of 2-((3-((5-chloro-2-((1-methyl-1H-pyrazol-4-yl)amino)pyrimidin-4-yl)amino)cyclohexyl)methyl)isoindoline-1,3-dione (140)

Title compound was prepared in a manner similar to general method-D.

2-((3-((2,5-dichloropyrimidin-4-yl)amino)cyclohexyl) methyl) isoindoline-1,3-dione 139 (0.9 g 2.2 mmol) & 1-methyl-1H-pyrazol-4-amine precursor-5 gave 2-((3-((5-chloro-2-((1-methyl-1H-pyrazol-4-yl)amino)pyrimidin-4-yl)amino)cyclohexyl)methyl)isoindoline-1,3-dione 140 as off white solid (0.72 g, 72% yield). MS: 466.31 (M+H)$^+$.

Synthesis of N4-(3-(aminomethyl)cyclohexyl)-5-chloro-N2-(1-methyl-1H-pyrazol-4-yl)pyrimidine-2,4-diamine (141)

To a stirred suspension of compound 140 (0.70 g, 1.50 mmol) in EtOH was added hydrazine monohydrate (0.15 g, 3.0 mmol) and reaction mixture was heated at 80° C. for 3 h. Reaction was monitored by TLC, reaction mixture was filtered through celite & solid was given EtOH washing. Filtrate was concentrated under vacuum; residue obtained was partitioned between 10% MEOH in DCM & 10% NaOH solution. The organic layer was washed with water, brine solution, dried over Na$_2$SO$_4$ & was concentrated under reduced pressure. The crude thus obtained was crystallized using ether to get desired compound N4-(3-(aminomethyl)cyclohexyl)-5-chloro-N2-(1-methyl-1H-pyrazol-4-yl)pyrimidine-2,4-diamine 141 as a grey solid (0.27 g, 54% yield). $^1$HNMR (400 MHz, DMSO-d$_6$): δ 9.04 (br s, 1H), 7.87-7.85 (m, 1H), 7.73 (s, 1H), 7.42 (s, 1H), 6.63 (br s, 1H), 3.95 (br s, 1H), 3.77 (s, 3H), 2.45-2.40 (m, 2H), 1.81-1.63 (m, 3H), 1.51-1.32 (m, 3H), 1.23-1.17 (m, 2H), 0.98-1.09 (m, 1H). MS: 336.08 (M+H)$^+$.

Synthesis of N-((3-((5-chloro-2-((1-methyl-1H-pyrazol-4-yl)amino)pyrimidin-4-yl)amino)cyclohexyl)methyl)acrylamide (I-108)

Title compound was prepared in a manner similar to general method-J.

N4-(3-(aminomethyl)cyclohexyl)-5-chloro-N2-(1-methyl-1H-pyrazol-4-yl)pyrimidine-2,4-diamine 141 (0.10 g, 0.29 mmol) and acryloyl chloride (0.027 g, 0.29 mmol) gave N-((3-((5-chloro-2-((1-methyl-1H-pyrazol-4-yl)amino)pyrimidin-4-yl)amino)cyclohexyl)methyl)acrylamide (I-108) as white solid (0.05 g) with 42% yield. $^1$HNMR (400 MHz, DMSO-d$_6$): 9.02 (s, 1H), 8.09 (m, 1H), 7.87 (m, 1H), 7.71 (m, 1H), 7.40 (s, 1H), 6.68 (br s, 1H), 6.17-6.24 (m, 1H), 6.04 (d, 1H), 5.54 (d, 1H), 3.97 (m, 1H), 3.76 (s, 3H), 3.09 (m, 1H), 2.95-2.99 (m, 1H), 1.71-1.87 (m, 3H), 1.68 (m, 1H), 1.56 (m, 1H), 1.33-1.35 (m, 2H), 1.23 (m, 1H) and 1.05-1.13 (m, 1H); MS: 390.17 (M+H)$^+$.

The following compound was prepared similarly:

| Cmpd No. | Structure | Synthesis method | LCMS (M + 1) | ¹H-NMR (400 MHz, DMSO-d₆) |
|---|---|---|---|---|
| I-109 | 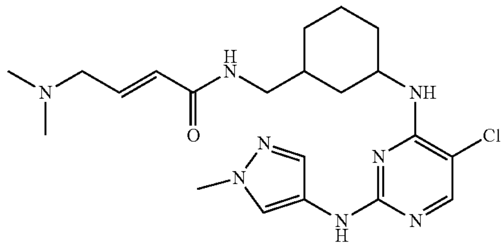 [SMILES: CN(C)C/C=C/C(=O)NCC1CCCC(Nc2nc(Nc3cnn(C)c3)ncc2Cl)C1] | K | 447.25 | δ 9.03 (br s, 1H), 8.02 (br s, 1H), 7.85 (m, 1H), 7.71 (m, 1H), 7.38-7.41 (m, 1H), 6.68 (m, 1H), 6.49-6.54 (m, 1H), 6.03 (d, 1H), 3.96 (m, 1H), 3.76 (s, 3H), 3.00 (m, 1H), 2.96 (m, 3H), 2.15 (s, 6H), 1.82-1.91 (m, 3H), 1.68-1.71 (m, 1H), 1.54-1.56 (m, 2H), 1.35 (m, 2H), 1.06-1.09 (m, 1H) |

Example 18: Synthesis of N-(3-((5-chloro-2-((1-methyl-1H-pyrazol-4-yl)amino)pyrimidin-4-yl)amino)-4-fluorophenyl)-N-methylacrylamide (I-110)

Scheme-54:

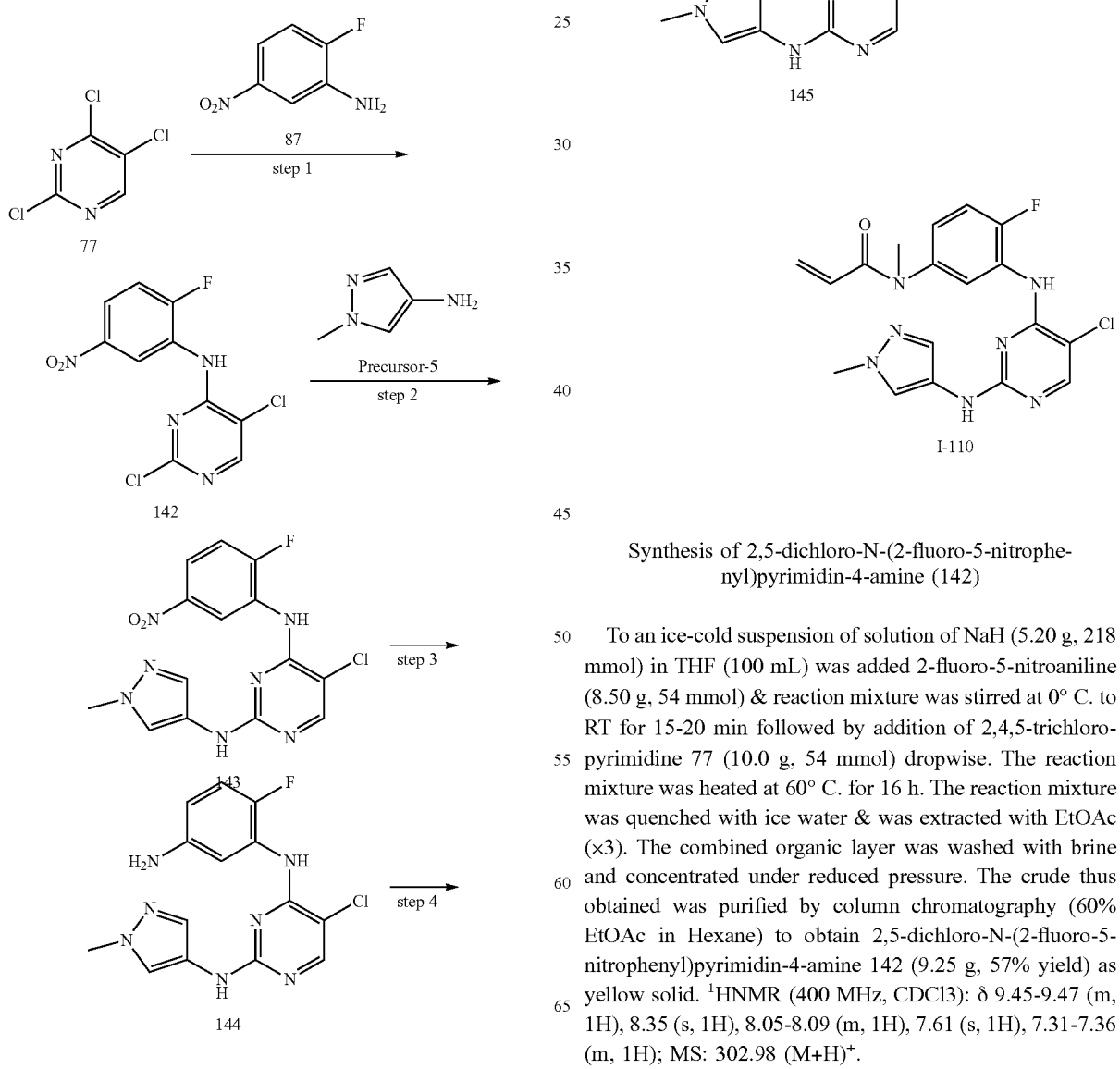

Synthesis of 2,5-dichloro-N-(2-fluoro-5-nitrophenyl)pyrimidin-4-amine (142)

To an ice-cold suspension of solution of NaH (5.20 g, 218 mmol) in THF (100 mL) was added 2-fluoro-5-nitroaniline (8.50 g, 54 mmol) & reaction mixture was stirred at 0° C. to RT for 15-20 min followed by addition of 2,4,5-trichloropyrimidine 77 (10.0 g, 54 mmol) dropwise. The reaction mixture was heated at 60° C. for 16 h. The reaction mixture was quenched with ice water & was extracted with EtOAc (×3). The combined organic layer was washed with brine and concentrated under reduced pressure. The crude thus obtained was purified by column chromatography (60% EtOAc in Hexane) to obtain 2,5-dichloro-N-(2-fluoro-5-nitrophenyl)pyrimidin-4-amine 142 (9.25 g, 57% yield) as yellow solid. ¹HNMR (400 MHz, CDCl3): δ 9.45-9.47 (m, 1H), 8.35 (s, 1H), 8.05-8.09 (m, 1H), 7.61 (s, 1H), 7.31-7.36 (m, 1H); MS: 302.98 (M+H)⁺.

Synthesis of 5-chloro-N4-(2-fluoro-5-nitrophenyl)-N2-(1-methyl-1H-pyrazol-4-yl)pyrimidine-2,4-diamine (143)

Title compound was prepared in a manner similar to general method-D.
2,5-dichloro-N-(2-fluoro-5-nitrophenyl)pyrimidin-4-amine 142 (1.3 g 4.3 mmol) & 1-methyl-1H-pyrazol-4-amine precursor-5 gave of 5-chloro-N4-(2-fluoro-5-nitrophenyl)-N2-(1-methyl-1H-pyrazol-4-yl)pyrimidine-2,4-diamine 138 as off white solid (0.85 g, 54% yield). $^1$HNMR (400 MHz, DMSO-$d_6$): δ 9.17 (br s, 1H), 8.63 (br s, 1H), 8.00 (s, 1H), 7.15-6.99 (m, 3H), 6.60-6.53 (m, 2H), 3.61 (s, 3H).

Synthesis of N4-(5-amino-2-fluorophenyl)-5-chloro-N2-(1-methyl-1H-pyrazol-4-yl)pyrimidine-2,4-diamine (144)

Title compound was prepared in a manner similar to general method-H.
5-chloro-N4-(2-fluoro-5-nitrophenyl)-N2-(1-methyl-1H-pyrazol-4-yl)pyrimidine-2,4-diamine 143 (0.8 g 2.2 mmol) gave N4-(5-amino-2-fluorophenyl)-5-chloro-N2-(1-methyl-1H-pyrazol-4-yl)pyrimidine-2,4-diamine 139 as off white solid (0.7 g, 95% yield). MS: 334.10 (M+H)$^+$.

Synthesis of 5-chloro-N4-(2-fluoro-5-(methylamino)phenyl)-N2-(1-methyl-1H-pyrazol-4-yl)pyrimidine-2,4-diamine (145)

To a stirred solution of N4-(5-amino-2-fluorophenyl)-5-chloro-N2-(1-methyl-1H-pyrazol-4-yl)pyrimidine-2,4-diamine 144 (0.4 g, 1.2 mmol) in THF (20 ml) at RT was added formaldehyde (0.15 g, 4.8 mmol) under nitrogen atmosphere. Charged catalytic amount of acetic acid & reaction was stirred at RT up to completion of starting material. After imine formation, sodium borohydride was charged at 0° C. portion wise. The reaction mixture was stirred at RT and was monitored by TLC. After completion of reaction, reaction mixture was diluted with EtOAc and washed with brine the organic phase was dried and concentrated to get crude material. The crude material was purified by flash column chromatography, eluting with 55% EtOAc in hexane to get the title compound 145 as off white solid (0.11 g, 26% yield). $^1$HNMR (400 MHz, DMSO-d6): δ 9.20 (br s, 1H), 8.70 (br s, 1H), 8.01 (s, 1H), 7.14-7.09 (m, 2H), 6.57-6.50 (m, 2H), 5.68 (br s, 1H), 3.58 (s, 3H), 2.66-2.65 (m, 3H). MS: 348.08 (M+H)$^+$.

Synthesis of N-(3-((5-chloro-2-((1-methyl-1H-pyrazol-4-yl)amino)pyrimidin-4-yl)amino)-4-fluorophenyl)-N-methylacrylamide (I-110)

Title compound was prepared in a manner similar to general method-J.
5-chloro-N4-(2-fluoro-5-(methylamino)phenyl)-N2-(1-methyl-1H-pyrazol-4-yl)pyrimidine-2,4-diamine 145 (0.10 g, 0.29 mmol) and acryloyl chloride (0.026 g, 0.29 mmol gave N-(3-((5-chloro-2-((1-methyl-1H-pyrazol-4-yl)amino)pyrimidin-4-yl)amino)-4-fluorophenyl)-N-methylacrylamide (I-110) as off white solid (8 mg) with 7% yield. $^1$HNMR (400 MHz, DMSO-d6) δ 9.26 (br s, 1H), 8.96 (br s, 1H), 8.07 (s, 1H), 7.02-7.44 (m, 5H), 6.14 (m, 2H), 5.54 (m, 1H), 3.59 (s, 3H) and 3.25 (s, 3H); MS: 402.09 (M+H)$^+$.

Example 19: Synthesis of N-(3-((5-chloro-2-((1-methyl-1H-pyrazol-4-yl)amino)pyrimidin-4-yl)(methyl)amino)-4-fluorophenyl)acrylamide (I-111)

Scheme-55:

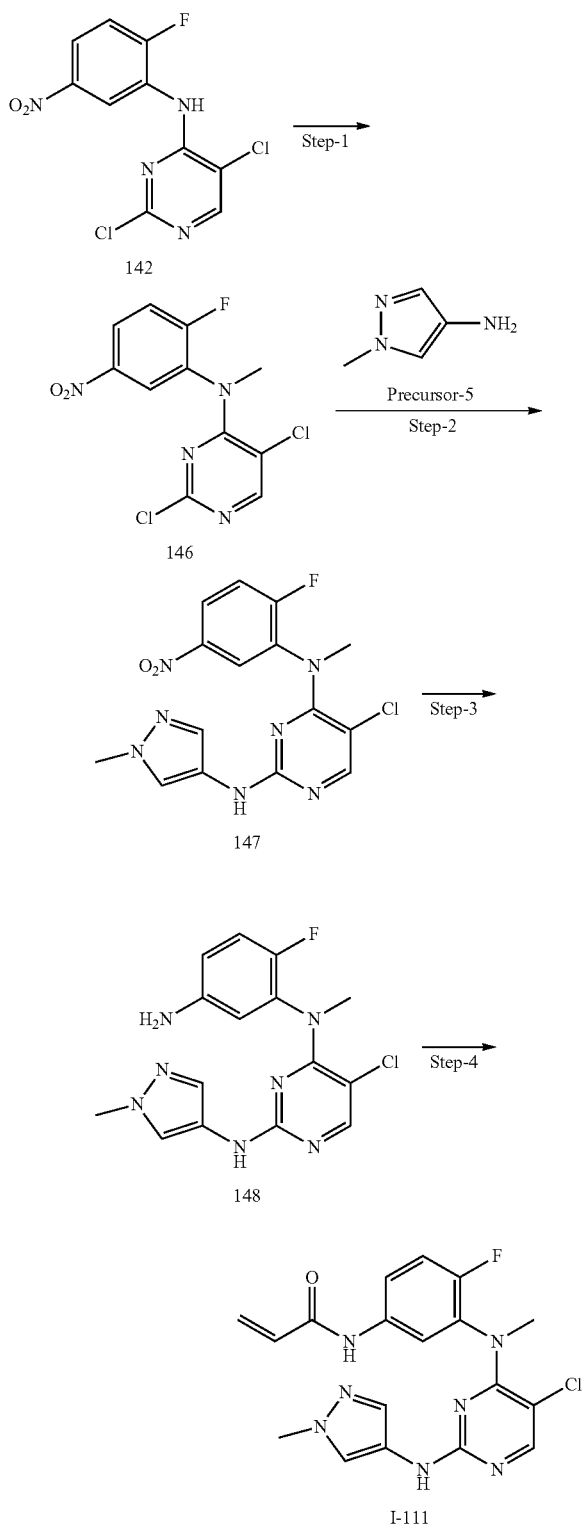

Synthesis of 2,5-dichloro-N-(2-fluoro-5-nitrophenyl)-N-methylpyrimidin-4-amine (141)

To a stirred solution of compound 2,5-dichloro-N-(2-fluoro-5-nitrophenyl)pyrimidin-4-amine 142 (2.0 g, 6.7 mmol) in DMF (20 mL) was added potassium carbonate (1.38 g, 10.05 mmol) and the resulting solution was stirred for 10 min at room temperature followed by addition of methyl iodide (1.38 g, 10.05 mmol) drop wise. The reaction mixture was stirred at room temperature for 3 h. The reaction mixture was quenched with ice & was extracted using EtOAc (×2). The combined organic layer was dried (Na$_2$SO$_4$) and evaporated under reduced pressure. The crude was purified by column chromatography (2% EtOAc in Hexane) to obtain 2,5-dichloro-N-(2-fluoro-5-nitrophenyl)-N-methylpyrimidin-4-amine 146 as off white solid (1.0 g, 50% yield). $^1$HNMR (400 MHz, DMSO-d$_6$): δ 8.52-8.54 (m, 1H), 8.41 (s, 1H), 8.30-8.33 (m, 1H), 7.66-7.70 (m, 1H), 3.46 (s, 3H); MS: 316.90 (M+H)$^+$.

Synthesis of 5-chloro-N4-(2-fluoro-5-nitrophenyl)-N4-methyl-N2-(1-methyl-1H-pyrazol-4-yl)pyrimidine-2,4-diamine (147)

Title compound was prepared in a manner similar to general method-D.

2,5-dichloro-N-(2-fluoro-5-nitrophenyl)-N-methylpyrimidin-4-amine 146 (1.0 g 3.17 mmol) & 1-methyl-1H-pyrazol-4-amine precursor-5 (0.37 g, 3.8 mmol) gave 5-chloro-N4-(2-fluoro-5-nitrophenyl)-N4-methyl-N2-(1-methyl-1H-pyrazol-4-yl)pyrimidine-2,4-diamine 147 as yellow solid (0.90 g, 75% yield). $^1$HNMR (400 MHz, DMSO-d$_6$): δ 9.48 (br s, 1H), 8.31-8.37 (m, 1H), 8.22-8.25 (m, 1H), 8.09 (s, 1H), 7.60-7.65 (m, 2H), 7.43 (s, 1H), 3.76 (s, 3H), 3.50 (s, 3H); MS: 378.04 (M+H)$^+$.

Synthesis of N4-(5-amino-2-fluorophenyl)-5-chloro-N4-methyl-N2-(1-methyl-1H-pyrazol-4-yl)pyrimidine-2,4-diamine (148)

Title compound was prepared in a manner similar to general method-H.

5-chloro-N4-(2-fluoro-5-nitrophenyl)-N4-methyl-N2-(1-methyl-1H-pyrazol-4-yl)pyrimidine-2,4-diamine 147 (0.85 g, 2.20 mmol) gave N4-(5-amino-2-fluorophenyl)-5-chloro-N4-methyl-N2-(1-methyl-1H-pyrazol-4-yl)pyrimidine-2,4-diamine 148 as off white solid (0.23 g, 23% yield). $^1$HNMR (400 MHz, DMSO-d$_6$): δ 9.32 (br s, 1H), 7.96 (s, 1H), 7.68 (br s, 1H), 7.44 (s, 1H), 6.90-6.94 (m, 1H), 6.41-6.47 (m, 2H), 5.03 (s, 2H), 3.77 (s, 3H), 3.32 (s, 3H); MS: 348.28 (M+H)$^+$.

Synthesis of N-(3-((5-chloro-2-((1-methyl-1H-pyrazol-4-yl)amino)pyrimidin-4-yl) (methyl)amino)-4-fluorophenyl) acrylamide (I-111)

Title compound was prepared in a manner similar to general method-J.

N4-(5-amino-2-fluorophenyl)-5-chloro-N4-methyl-N2-(1-methyl-1H-pyrazol-4-yl)pyrimidine-2,4-diamine 148 (0.15 g, 0.44 mmol) and acryloyl chloride (0.048 g, 0.53 mmol) afforded N-(3-((5-chloro-2-((1-methyl-1H-pyrazol-4-yl)amino)pyrimidin-4-yl) (methyl)amino)-4-fluorophenyl) acrylamide (I-111) as off white solid (0.07 g) with 41% yield, $^1$HNMR (400 MHz, DMSO-d$_6$): δ 10.25 (br s, 1H), 9.42 (br s, 1H), 8.02 (s, 1H), 7.56-7.66 (m, 3H), 7.45 (s, 1H), 7.25-7.30 (m, 1H), 6.34-6.41 (m, 1H), 6.22-6.26 (m, 1H), 5.76 (d, J=12.0 Hz, 1H), 3.77 (s, 3H) and 3.41 (s, 3H); MS: 402.10 (M+H)$^+$.

Example 19: Synthesis of N-((1S,3R)-3-((5-chloro-2-((1-methyl-1H-pyrazol-4-yl)amino)pyrimidin-4-yl)amino)cycloheptyl)acrylamide (I-112) (Isomer 1, Stereochemistry not Confirmed)

Scheme-56:

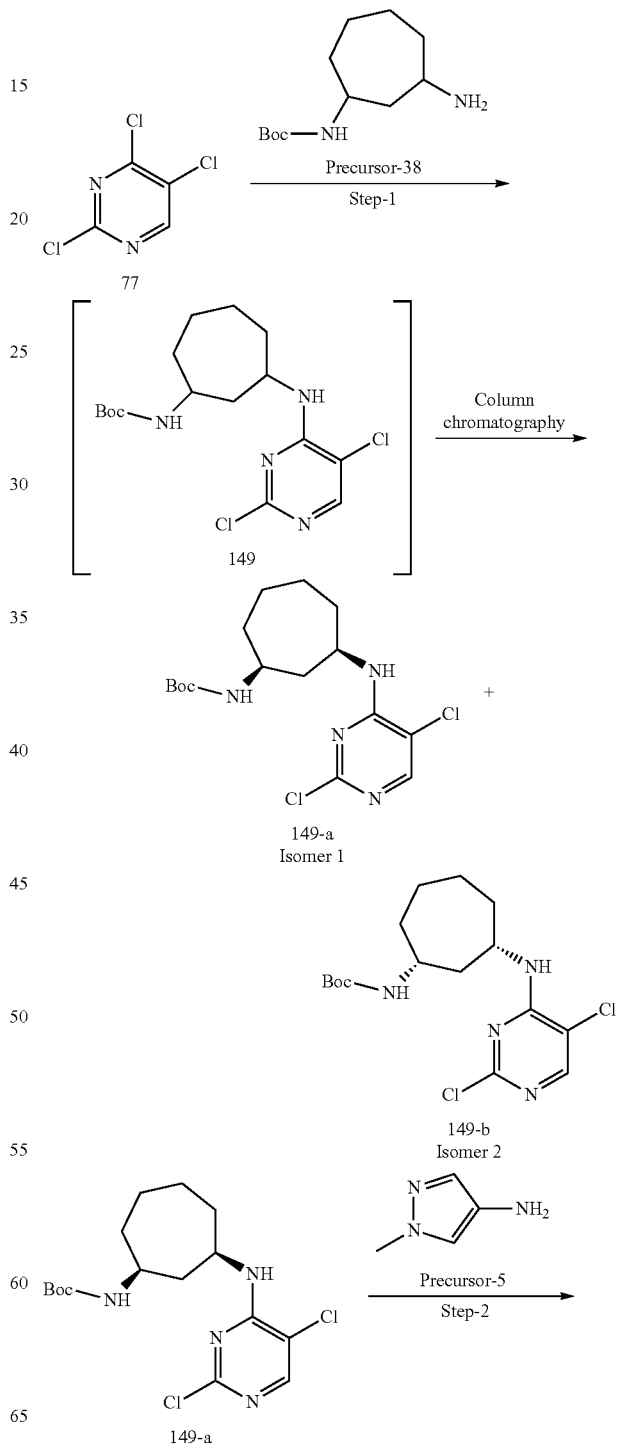

-continued

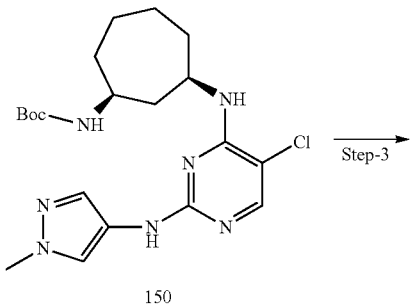

150

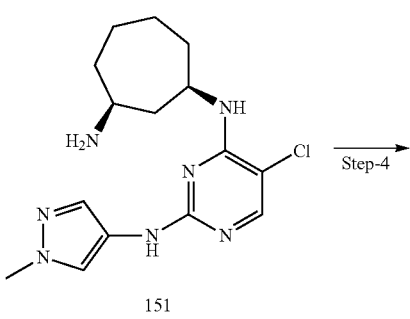

151

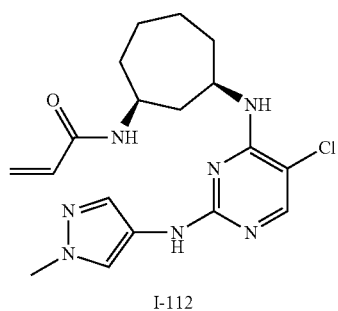

I-112

Synthesis of tert-butyl ((1S,3R)-3-((2,5-dichloropyrimidin-4-yl)amino)cycloheptyl)carbamate (149-a) (Isomer 1, Stereochemistry not Confirmed) and tert-butyl ((1R,3S)-3-((2,5-dichloropyrimidin-4-yl)amino)cycloheptyl)carbamate (149-b) (Isomer 2, Stereochemistry not Confirmed)

Title compound was prepared in a manner similar to general method-C.

2,4,5-trichloropyrimidine 77 (1.50 g, 8.20 mmol) and tert-butyl (3-aminocycloheptyl)carbamate precursor-38 (1.50 g, 6.60 mmol) afforded tert-butyl (3-((2,5-dichloropyrimidin-4-yl)amino)cycloheptyl)carbamate 149, which was purified over silica gel (100-200 M). The first eluting fraction (17% EtOAc-hexane) was arbitrarily assigned as tert-butyl ((1S,3R)-3-((2,5-dichloropyrimidin-4-yl)amino)cycloheptyl)carbamate 149-a (0.30 g) and the second eluting fraction (30% EtOAc-hexane) was assigned as tert-butyl ((1R,3S)-3-((2,5-dichloropyrimidin-4-yl)amino)cycloheptyl)carbamate 149-b (0.15 g).

1H-NMR (400 MHz, DMOS-d$_6$); 149-a: δ 8.15 (s, 1H), 7.66 (d, 1H), 6.86 (d, (1H), 4.14 (br s, 1H), 3.62 (br s, 1H), 1.86-1.99 (m, 4H), 1.64-1.70 (m, 2H), 1.59-1.62 (m, 1H), 1.36 (s, 9H), 1.23-1.26 (m, 2H), 0.82-0.85 (m, 1H). MS: 375.20 (M+H)$^+$.

1H-NMR (400 MHz, DMOS-d$_6$); 149-b: δ 8.14 (s, 1H), 7.71 (d, 1H), 6.89 (d, (1H), 4.07 (br s, 1H), 3.45 (br s, 1H), 1.78-1.88 (m, 4H), 1.59-1.60 (m, 3H), 1.47-1.52 (m, 3H), 1.37 (s, 9H). MS: 375.20 (M+H)$^+$.

Synthesis of tert-butyl ((1S,3R)-3-((5-chloro-2-((1-methyl-1H-pyrazol-4-yl)amino)pyrimidin-4-yl) amino)cycloheptyl)carbamate (150)

Title compound was prepared in a manner similar to general method-D.

tert-butyl ((1S,3R)-3-((2,5-dichloropyrimidin-4-yl) amino)cycloheptyl)carbamate 149-a (0.27 g 0.72 mmol) & 1-methyl-1H-pyrazol-4-amine precursor-5 (0.12 g, 0.87 mmol) gave tert-butyl ((1S,3R)-3-((5-chloro-2-((1-methyl-1H-pyrazol-4-yl)amino)pyrimidin-4-yl)amino)cycloheptyl) carbamate 150 (0.27 g, crude). Crude was carried forward as such without any further purification. MS: 436.20 (M+H)$^+$.

Synthesis of N4-((1R,3S)-3-aminocycloheptyl)-5-chloro-N2-(1-methyl-1H-pyrazol-4-yl)pyrimidine-2,4-diamine (151)

To a solution of tert-butyl ((1S,3R)-3-((5-chloro-2-((1-methyl-1H-pyrazol-4-yl)amino)pyrimidin-4-yl)amino)cycloheptyl)carbamate 150 (0.27 g) in MeOH-DCM (1:2, 30 mL) was added 4M HCl-1,4-dioxane solution (5 mL). The resulting solution was stirred at RT for 16 h. The solvent was evaporated, added 10% MeOH-DCM solution and washed sequentially with saturated NaHCO$_3$ solution and water. The organic layer was concentrated under reduced pressure and the residue was purified over silica gel (100-200 M, 4% MeOH-DCM) to get ether to get N4-((1R,3S)-3-aminocycloheptyl)-5-chloro-N2-(1-methyl-1H-pyrazol-4-yl)pyrimidine-2,4-diamine 151 (0.15 g, 63% yield over 2 steps) as beige solid. MS: 336.0 (M+H)$^+$.

Synthesis of N-((1S,3R)-3-((5-chloro-2-((1-methyl-1H-pyrazol-4-yl)amino)pyrimidin-4-yl)amino)cycloheptyl)acrylamide (I-112)

Title compound was prepared in a manner similar to general method-J.

N-((1S,3R)-3-((5-chloro-2-((1-methyl-1H-pyrazol-4-yl) amino)pyrimidin-4-yl)amino)cycloheptyl)acrylamide 151 (0.15 g, 0.45 mmol) and acryloyl chloride (0.04 g, 0.45 mmol) afforded N-((1S,3R)-3-((5-chloro-2-((1-methyl-1H-pyrazol-4-yl)amino)pyrimidin-4-yl)amino)cycloheptyl) acrylamide (I-112) as off white solid (0.025 g) with 15% yield, $^1$HNMR (400 MHz, DMSO-d$_6$): δ 8.92-9.04 (br s, 1H), 8.05-8.12 (m, 1H), 7.86 (s, 1H), 7.77 (s, 1H), 7.45 (s, 1H), 6.80-6.82 (d, 1H), 6.17-6.24 (m, 1H), 6.07-6.03 (m, 1H), 5.52-5.55 (m, 1H), 4.25 (br s, 1H), 3.98 (br s, 1H), 3.77 (s, 3H), 1.92-2.12 (m, 4H), 1.7-1.8 (m, 2H), 1.56-1.62 (m, 1H), 1.29-1.49 (m, 3H). MS: 390.17 (M+H)$^+$.

The following compound was prepared similarly using 149-b:

| Cmpd No. | Structure | Synthesis method | LCMS (M + 1) | $^1$H-NMR (400 MHz, DMSO-$d_6$) |
|---|---|---|---|---|
| I-113 (Isomer 2) | 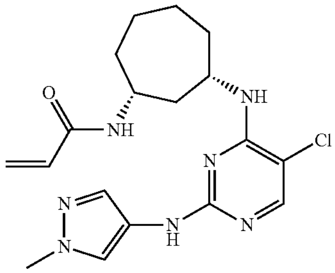 [SMILES: C=CC(=O)N[C@@H]1CCCC[C@H](Nc2nc(Nc3cnn(C)c3)ncc2Cl)C1] | J | 390.17 | δ 8.93-9.08 (br s, 1H), 8.11 (d, J = 8.0 Hz, 1H), 7.76-7.84 (m, 2H), 7.39 (s, 1H), 6.77-6.78 (m, 1H), 6.15-6.22 (m, 1H), 6.02-6.06 (m, 1H), 5.52-5.55 (m, 1H), 4.20 (br s, 1H), 3.91 (br s, 1H), 3.78 (s, 3H), 1.76-1.91 (m, 4H), 1.54-1.76 (m, 6H) |

Example 20: Synthesis of N-(3-((5-chloro-2-((3-methylisothiazol-5-yl)amino)pyrimidin-4-yl)amino)cyclohexyl)acrylamide (I-114)

Scheme-57:

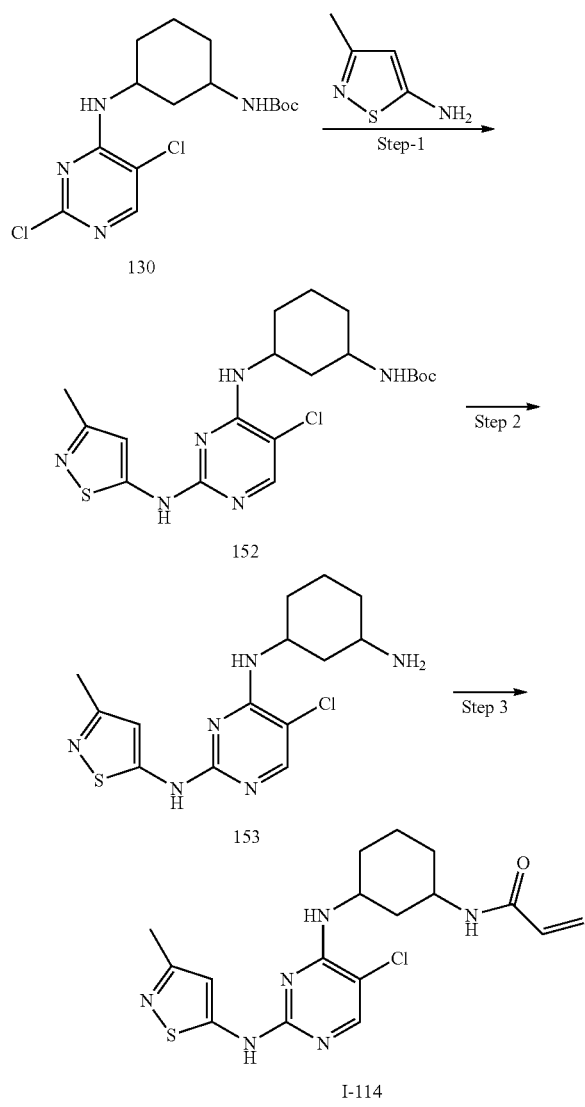

Synthesis of tert-butyl (3-((5-chloro-2-((3-methylisothiazol-5-yl)amino)pyrimidin-4-yl)amino)cyclohexyl)carbamate (152)

To a stirred suspension of 3-methylisothiazol-5-amine (0.27 g, 2.3 mmol) in 1,4-dioxane (15 mL), was added Cs$_2$CO$_3$ (1.80 g, 5.7 mmol) & tert-butyl (3-((2,5-dichloropyrimidin-4-yl)amino)cyclohexyl) carbamate 130 (0.70 g, 1.9 mmol). Reaction mixture was purged with argon for 10-15 min, charged X-phos (0.046 g, 0.09 mmol) followed by Pd2(dba)3 (0.18 g, 0.19 mmol). The resulting reaction mixture was stirred for 16 h at 90° C. Reaction progress was monitored by TLC & direct mass. After the completion of reaction, the reaction mixture was diluted with 5% MeOH: DCM & organic layer was given water wash followed by brine wash. The combined organic extracts were dried over Na$_2$SO$_4$ and concentrated under reduced pressure. The crude material was purified by flash column chromatography (SiO2), eluting with 0-8% MeOH in DCM to obtain tert-butyl (3-((5-chloro-2-((3-methylisothiazol-5-yl)amino)pyrimidin-4-yl)amino)cyclohexyl) carbamate 152 (0.33 g, 38% yield) as brown solid. MS: 438.97 (M+H)$^+$.

Synthesis of N4-(3-aminocyclohexyl)-5-chloro-N2-(3-methylisothiazol-5-yl)pyrimidine-2,4-diamine (153)

To a solution of tert-butyl (3-((5-chloro-2-((3-methylisothiazol-5-yl)amino)pyrimidin-4-yl)amino)cyclohexyl) carbamate 152 (0.32 g, 0.74 mmol) in MeOH-DCM (1:2, 30 mL) was added 4M HCl-1,4-dioxane solution (5 mL). The resulting solution was stirred at RT for 16 h. The solvent was evaporated, added 10% MeOH-DCM solution and washed sequentially with saturated NaHCO$_3$ solution and water. The organic layer was concentrated under reduced pressure and the residue was triturated with ether to get the N4-(3-aminocyclohexyl)-5-chloro-N2-(3-methylisothiazol-5-yl) pyrimidine-2,4-diamine 153 (0.11 g, 44% yield) as off-white solid. MS: 339.10 (M+H)$^+$.

Synthesis of N-(3-((5-chloro-2-((3-methylisothiazol-5-yl)amino)pyrimidin-4-yl)amino)cyclohexyl)acrylamide (I-114)

Title compound was prepared in a manner similar to general method-J.
N4-(3-aminocyclohexyl)-5-chloro-N2-(3-methylisothiazol-5-yl)pyrimidine-2,4-diamine 153 (0.11 g, 0.32 mmol) and acryloyl chloride (0.029 g, 0.32 mmol) afforded N-(3-((5-chloro-2-((3-methylisothiazol-5-yl)amino)pyrimidin-4-yl)amino)cyclohexyl)acrylamide (I-114) as beige solid (0.02 g) with 16% yield. $^1$HNMR (400 MHz, DMSO-$d_6$): δ 11.03 (br s, 1H), 8.05-8.10 (m, 2H), 7.19 (br s, 1H), 6.59 (s, 1H), 6.17-6.23 (m, 1H), 6.06 (d, 1H), 5.56 (d, 1H), 4.28 (m, 1H), 3.76-3.80 (m, 1H), 2.26 (s, 3H), 1.83-2.11 (m, 4H), 1.41 (m, 3H), 1.11-1.13 (m, 1H). MS: 393.09 (M+H)$^+$.

The following compound was prepared similarly:

| Cmpd No. | Structure | Synthesis method | LCMS (M + 1) | $^1$H-NMR (400 MHz, DMSO-$d_6$) |
|---|---|---|---|---|
| I-115 | 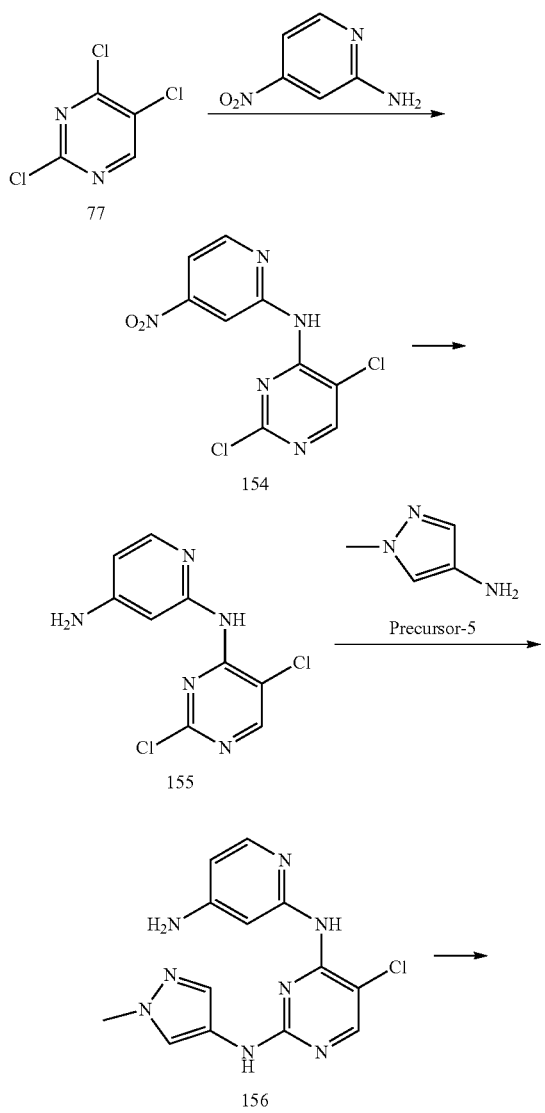 | K | 450.15 | δ 11.05 (br s, 1H), 7.98-8.04 (m, 2H), 7.17-7.21 (m, 1H), 6.59 (s, 1H), 6.49-6.56 (m, 1H), 6.01 (d, 1H), 4.28-4.31 (m, 1H), 3.73-3.74 (m, 1H), 2.95-2.96 (m, 2H), 2.39 (s, 3H), 2.12 (s, 6H), 1.83-1.98 (m, 5H), 1.39-1.41 (m, 3H) |

Example 21: Synthesis of N-(3-((5-chloro-2-((3-methylisothiazol-5-yl)amino)pyrimidin-4-yl)amino)cyclohexyl)acrylamide I-116

Scheme-57:

Synthesis of 2,5-dichloro-N-(4-nitropyridin-2-yl)pyrimidin-4-amine (154)

To a stirred solution of NaH (0.58 g, 24.2 mmol), in DMF (20 mL) at 0° C. was added 4-nitropyridin-2-amine (1.36 g, 9.8 mmol) & reaction mixture was stirred at 0-° C.-RT for 15-20 min followed by addition of 2,4,5-trichloropyrimidine (1.50 g, 8.1 mmol) drop wise. The reaction mixture was stirred at RT for 1 h and then quenched with ice cold water & was extracted using 5% MeOH in DCM twice. The combined organic layer was dried (Na$_2$SO$_4$) and evaporated to obtain the crude. The crude was purified by column chromatography (Silica gel, 15% EtOAc-hexane) to obtain 2,5-dichloro-N-(4-nitropyridin-2-yl)pyrimidin-4-amine 154 as brown solid (0.30 g, 13% yield). MS: 284.02 (M–H)$^+$.

Synthesis of N2-(2,5-dichloropyrimidin-4-yl)pyridine-2,4-diamine (155)

To a stirred solution of 2,5-dichloro-N-(4-nitropyridin-2-yl)pyrimidin-4-amine 154 (0.30 g, 1.05 mmol), in EtOH (16 mL) & water (4 mL) was added iron powder (0.22 g, 4.2 mmol) & calcium chloride (0.44 g, 4.2 mmol) and the reaction mixture was stirred at 90° C. for 3 h. The reaction mixture was quenched with ice water and extracted with 10% MeOH in DCM twice. The combined organic layer was dried (Na$_2$SO$_4$) and evaporated to obtain the crude. The crude was triturated with ether:MeOH mixture to obtain N2-(2,5-dichloropyrimidin-4-yl)pyridine-2,4-diamine 155 as off white solid (0.12 g, 44% yield). $^1$HNMR (400 MHz, DMSO-$d_6$): δ 8.17 (s, 1H), 7.66 (d, 1H), 6.85 (s, 1H), 6.70 (br s, 2H), 6.23-6.26 (m, 1H), MS: 256.04 (M+H)$^+$.

Synthesis of N4-(4-aminopyridin-2-yl)-5-chloro-N2-(1-methyl-1H-pyrazol-4-yl)pyrimidine-2,4-diamine (156)

Title compound was prepared in a manner similar to general method-D.

N2-(2,5-dichloropyrimidin-4-yl)pyridine-2,4-diamine 155 (0.12 g 0.48 mmol) & 1-methyl-1H-pyrazol-4-amine precursor-5 gave N4-(4-aminopyridin-2-yl)-5-chloro-N2-(1-methyl-1H-pyrazol-4-yl)pyrimidine-2,4-diamine 156 as off white solid (0.09 g, 61% yield). $^1$HNMR (400 MHz, DMSO-$d_6$): δ 9.21 (br s, 1H), 8.11 (s, 1H), 7.83-7.73 (m, 2H), 7.35 (br s, 3H), 6.34 (s, 1H), 6.06-6.00 (m, 2H), 3.75 (s, 3H); MS: 317.15 (M+H)$^+$.

Synthesis of N-(2-((5-chloro-2-((1-methyl-1H-pyrazol-4-yl)amino)pyrimidin-4-yl)amino)pyridin-4-yl)acrylamide (I-116)

Title compound was prepared in a manner similar to general method-J.

N4-(4-aminopyridin-2-yl)-5-chloro-N2-(1-methyl-1H-pyrazol-4-yl)pyrimidine-2,4-diamine 156 (0.11 g, 0.35 mmol) and acryloyl chloride (0.026 g, 0.35 mmol) gave N-(2-((5-chloro-2-((1-methyl-1H-pyrazol-4-yl)amino)pyrimidin-4-yl)amino)pyridin-4-yl) acrylamide (I-116) as white solid (0.018 g, 14% yield), $^1$HNMR (400 MHz, DMSO-$d_6$) δ 10.55 (s, 1H), 9.32 (br s, 1H), 8.93 (br s, 1H), 8.30 (br s, 1H), 8.16 (s, 1H), 7.91 (br s, 1H), 7.58 (m, 2H), 7.32 (br s, 1H), 6.43-6.50 (m, 1H), 6.29-6.33 (m, 1H), 5.86 (d, J=10 Hz, 1H), 3.62 (br s, 3H); MS: 371.41 (M+H)$^+$.

Example 22: N-(3-((5-chloro-2-((3-methylisothiazol-5-yl)amino)pyrimidin-4-yl)amino)-4-fluorophenyl)acrylamide (I-117)

Scheme-58:

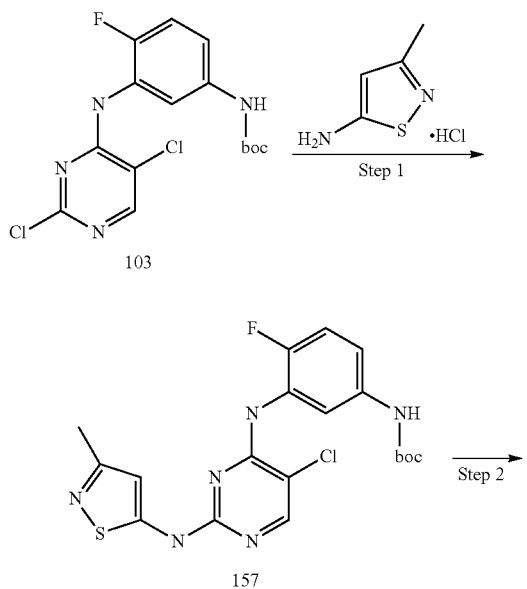

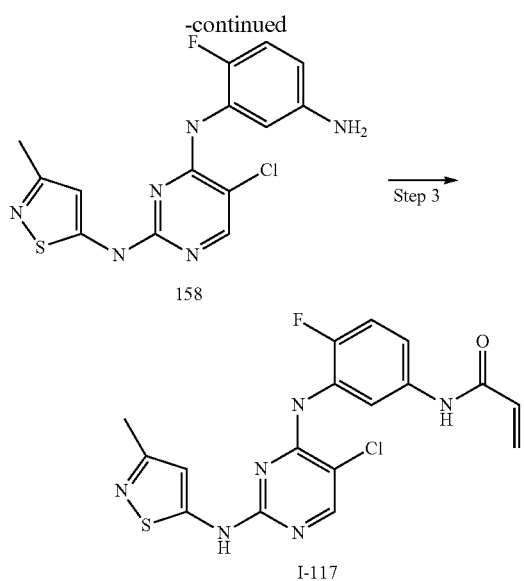

Synthesis of tert-butyl (3-((5-chloro-2-((3-methylisothiazol-5-yl)amino)pyrimidin-4-yl)amino)-4-fluorophenyl)carbamate (157)

To a solution of tert-butyl (3-((2,5-dichloropyrimidin-4-yl)amino)-4-fluorophenyl)carbamate (103) (0.6 g, 1.60 mmol) in 1,4 dioxane (10 ml) were added 3-methylisothiazol-5-amine.HCl (0.29 g, 1.93 mmoles), cesiumcabonate (1.04, 3.21 mmoles) and X-phos (0.186 g, 0.16 mmoles). The reaction mixture was degassed under N2 atm for 30 min, Pd2dba3 was added and again degassed for 10 min. The reaction mixture was stirred for 16 h at 90° C. Reaction was monitored by TLC, after the completion of reaction, reaction mixture was concentrated, filter through ceilite washed with DCM, the filtrate was concentrated. The crude product was purified by using biotage with 100% DCM as a solvent to get pure product as tert-butyl (3-((5-chloro-2-((3-methylisothiazol-5-yl)amino)pyrimidin-4-yl)amino)-4-fluorophenyl) carbamate (157). (0.66 g, 91.6% yield). LCMS Calcd [M+H]$^+$ 451.1. found 451.1.

Synthesis of N4-(5-amino-2-fluorophenyl)-5-chloro-N2-(3-methylisothiazol-5-yl)pyrimidine-2,4-diamine (158)

To a solution of tert-butyl (3-((5-chloro-2-((3-methylisothiazol-5-yl)amino)pyrimidin-4-yl)amino)-4-fluorophenyl) carbamate (157) (0.5 g, 1.1 mmoles) in DCM (15 ml) was cooled 0° C., TFA (1.26 g, 11.09 mmoles) was added slowly. The reaction mixture was stirred for 16 h at RT. Reaction was monitored by TLC, after the completion of reaction, reaction mixture was concentrated, water (10 ml) and sat. sodium bicarbonate (10 mL) were added to the residue and extracted with DCM (3×50 ml), organic layer was washed with brine solution (10 ml), organic layer was dried over sodium sulphate and evaporated under reduced pressure to obtain crude product. The crude product was purified by using combiflash with 100% DCM as a solvent to get pure product as N4-(5-amino-2-fluorophenyl)-5-chloro-N2-(3-methylisothiazol-5-yl)pyrimidine-2,4-diamine (158) (0.25 g, 64.26% yield). LCMS Calcd [M+H]$^+$ 351.05. found 351.1.

Synthesis of N-(3-((5-chloro-2-((3-methylisothiazol-5-yl)amino)pyrimidin-4-yl)amino)-4-fluorophenyl)acrylamide (I-117)

Title compound was prepared in a manner substantially similar to general procedure J.
N4-(5-amino-2-fluorophenyl)-5-chloro-N2-(3-methylisothiazol-5-yl)pyrimidine-2,4-diamine (158) and acryloyl chloride gave N-(3-((5-chloro-2-((3-methylisothiazol-5-yl)amino)pyrimidin-4-yl)amino)-4-fluorophenyl)acrylamide (I-117) as a white solid in 20% yield. 1HNMR (400 MHz, DMSO-d6): δ 10.97 (s, 1H), 10.24 (s, 1H), 9.17 (s, 1H), 8.23 (s, 1H), 7.78 (s, 1H), 7.59 (s, 1H), 7.30-7.25 (t, 1H), 6.49 (s, 1H), 6.44-6.39 (m, 1H), 6.26-6.22 (d, 1H), 5.76-5.73 (d, 1H), 2.16 (s, 3H); LCMS Calcd [M+H]$^+$ 405.06. found 405.1. HPLC purity 98.46%.

The following compounds were prepared similarly

| Comp No | Structure | Synthesis Method | LCMS (M + 1) | $^1$H-NMR (400 MHz, DMSO-d$_6$) |
|---|---|---|---|---|
| I-118 | 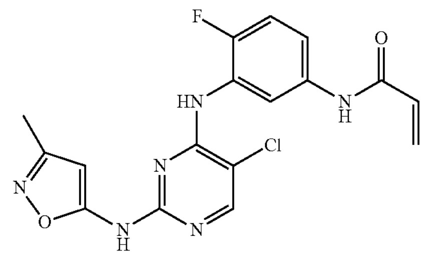 [SMILES: C=CC(=O)Nc1ccc(F)c(Nc2nc(Nc3cc(C)no3)ncc2Cl)c1] | J | 389.1 | δ 10.87 (s, 1H), 10.25 (s, 1H), 9.17 (s, 1H), 8.20 (s, 1H), 7.79-7.78 (m, 1H), 7.63 (bs, 1H), 7.33-7.29 (t, 1H), 6.44-6.39 (m, 1H), 6.37-6.22 (d, 1H), 5.76-5.74 (d, 1H), 5.31 (s, 1H), 1.93 (s, 3H) |
| I-119 | 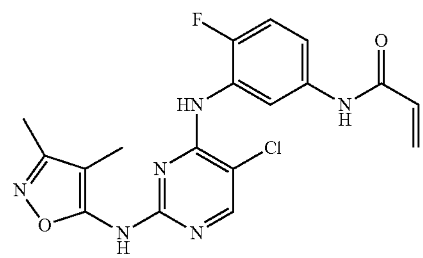 [SMILES: C=CC(=O)Nc1ccc(F)c(Nc2nc(Nc3onc(C)c3C)ncc2Cl)c1] | J | 403.1 | δ 10.14 (s, 1H), 9.49 (s, 1H), 8.86 (s, 1H), 8.08 (s, 1H), 7.75-7.74 (d, 1H), 7.57-7.55 (m, 1H), 7.18-7.13 (t, 1H), 6.45-6.41 (m, 1H), 6.27-6.22 (d, 1H), 5.76-5.73 (d, 1H), 2.02 (s, 3H), 1.50 (s, 3H); |
| I-120 | 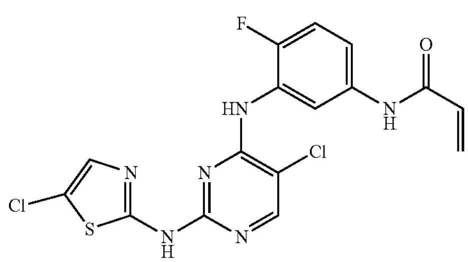 [SMILES: C=CC(=O)Nc1ccc(F)c(Nc2nc(Nc3ncc(Cl)s3)ncc2Cl)c1] | J | 427 | δ 11.52 (s, 1H), 10.24 (s, 1H), 9.27 (s, 1H), 8.25 (s, 1H), 7.82 (m, 1H), 7.66 (s, 1H), 7.31-7.24 (m, 2H), 6.44-6.37 (m, 1H), 6.26-6.21 (d, 1H), 5.75-5.73 (d, 1H) |
| I-121 | 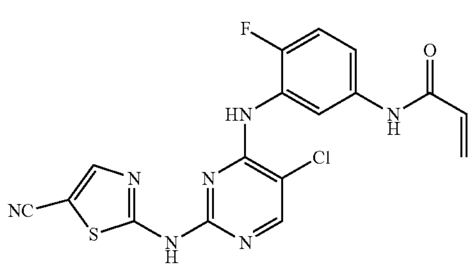 [SMILES: C=CC(=O)Nc1ccc(F)c(Nc2nc(Nc3ncc(C#N)s3)ncc2Cl)c1] | J | 416.1 | δ 12.26 (s, 1H), 10.27 (s, 1H), 9.39 (s, 1H), 8.33 (s, 1H), 8.10 (s, 1H), 7.91 (s, 1H), 7.58 (s, 1H), 7.33-7.29 (t, 1H), 6.44-6.40 (m, 1H), 6.25-6.21 (d, 1H), 5.75-5.73 (d, 1H) |

Example 23: N-(3-((5-chloro-2-((3-methylisothiazol-5-yl)amino)pyrimidin-4-yl)amino)phenyl)acrylamide (I-122)

Scheme 59:

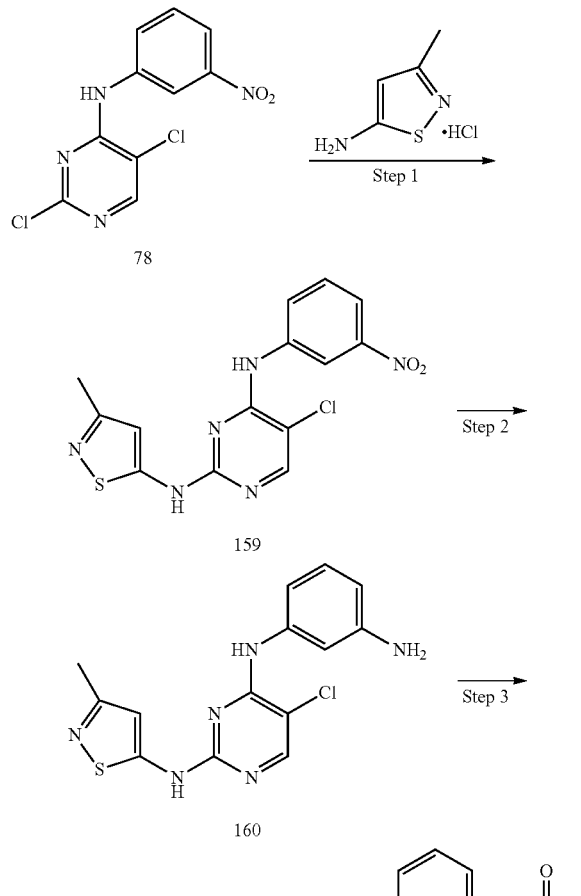

Synthesis of 5-chloro-N2-(3-methylisothiazol-5-yl)-N4-(3-nitrophenyl)pyrimidine-2,4-diamine (159)

To a solution of 2,5-dichloro-N-(3-nitrophenyl)pyrimidin-4-amine (78) (0.75 g, 2.60 mmol) in 1,4 dioxane (12 ml) were added 3-methylisothiazol-5-amine.HCl (0.475 g, 3.1 mmoles), cesiumcabonate (1.71 g, 5.26 mmol) and Xanthophos (0.304 g, 0.526 mmol). The reaction mixture was degassed under N2 atm for 30 min, Pd2dba3 was added and again degassed for 10 min. The reaction mixture was stirred for 16 h at 90° C. Reaction was monitored by TLC, after the completion of reaction, reaction mixture was concentrated, filtered through celite washed with DCM, the filtrate was concentrated. The crude product was purified by using biotage with 100% DCM as a solvent to get pure product as 5-chloro-N2-(3-methylisothiazol-5-yl)-N4-(3-nitrophenyl)pyrimidine-2,4-diamine (159) (0.45 g, 47.1% yield). LCMS Calcd [M+H]+ 363.7. found 363.1.

Synthesis of N4-(3-aminophenyl)-5-chloro-N2-(3-methylisothiazol-5-yl)pyrimidine-2,4-diamine (160)

To a solution of 5-chloro-N2-(3-methylisothiazol-5-yl)-N4-(3-nitrophenyl)pyrimidine-2,4-diamine (159) (0.3 g, 0.826 mmol) in ethanol (10 ml) was added anhydrous stannous chloride (0.313 g, 1.6 mmol). The reaction mixture was stirred for 2 h at 78° C. Reaction was monitored by TLC, after the completion of reaction, reaction mixture was concentrated, water (10 ml) and sat. Sodium bicarbonate (10 mL) were added to the residue and extracted with EtOAc (3×50 ml), organic layer was washed with brine solution (10 ml), organic layer was dried over sodium sulphate and evaporated under reduced pressure to obtain crude product. The crude product was purified by using combiflash with 100% DCM as a solvent to get pure product as N4-(3-aminophenyl)-5-chloro-N2-(3-methylisothiazol-5-yl)pyrimidine-2,4-diamine (160) (0.16 g, 58.39% yield).

Synthesis of N-(3-((5-chloro-2-((3-methylisothiazol-5-yl)amino)pyrimidin-4-yl)amino)phenyl)acrylamide (I-122)

Title compound was prepared in a manner substantially similar to general procedure J.

N4-(3-aminophenyl)-5-chloro-N2-(3-methylisothiazol-5-yl)pyrimidine-2,4-diamine (160) and acryloyl chloride gave N-(3-((5-chloro-2-((3-methylisothiazol-5-yl)amino)pyrimidin-4-yl)amino)phenyl)acrylamide (I-122) as a white solid with 24.13% yield. 1HNMR (400 MHz, DMSO-d6): δ 10.95 (s, 1H), 10.14 (s, 1H), 9.12 (s, 1H), 8.25 (s, 1H), 7.77 (s, 1H), 7.50 (s, 1H), 7.33 (bs, 2H), 6.55 (s, 1H), 6.46-6.40 (m, 1H), 6.25-6.21 (d, 1H), 5.75-5.72 (d, 1H), 2.19 (s, 3H); LCMS Calcd [M+H]+ 387.87. found 387.4. HPLC purity 97.91%. The following compounds were prepared similarly

| Comp No | Structure | Synthesis Method | LCMS (M + 1) | 1H-NMR (400 MHz, DMSO-d6) |
|---|---|---|---|---|
| I-123 | 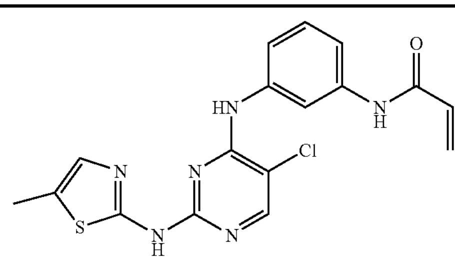 | J | 387.1 | δ 10.99 (s, 1H), 10.08 (s, 1H), 9.07 (s, 1H), 8.20 (s, 1H), 7.85 (s, 1H), 7.57 (s, 1H), 7.31 (s, 2H), 6.95 (s, 1H), 6.46-6.39 (m, 1H), 6.25-6.21 (d, 1H), 5.74-5.72 (d, 1H), 2.16 (s, 3H). |

| Comp No | Structure | Synthesis Method | LCMS (M + 1) | $^1$H-NMR (400 MHz, DMSO-$d_6$) |
|---|---|---|---|---|
| I-124 | 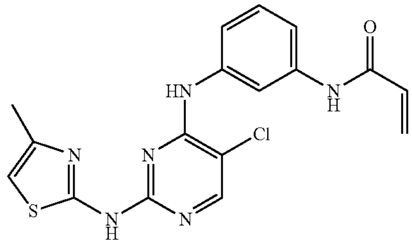 [SMILES: C=CC(=O)Nc1cccc(Nc2nc(Nc3nc(C)cs3)ncc2Cl)c1] | J | 387.1 | δ 11.11 (s, 1H), 10.03 (s, 1H), 9.05 (s, 1H), 8.24 (s, 1H), 7.88 (s, 1H), 7.51-7.49 (d, 1H), 7.39 (s, 1H), 7.30-7.26 (t, 1H), 6.46-6.40 (m, 2H), 6.26-6.21 (m, 1H), 5.75-5.72 (dd, 1H), 2.18 (s, 3H). |
| I-125 | 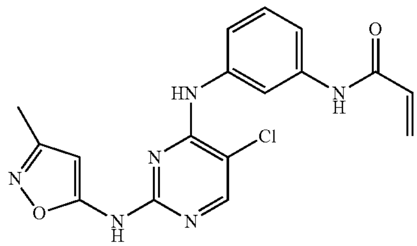 [SMILES: C=CC(=O)Nc1cccc(Nc2nc(Nc3cc(C)no3)ncc2Cl)c1] | J | 371.2 | δ 10.85 (s, 1H), 10.15 (s, 1H), 9.15 (s, 1H), 8.20 (s, 1H), 7.84 (s, 1H), 7.56-7.54 (d, 1H), 7.36-7.31 (t, 1H), 7.21-7.19 (d, 1H), 6.46-6.40 (m, 1H), 6.25-6.21 (d, 1H), 5.75-5.70 (m, 2H), 1.96 (s, 3H). |

Example 24: N-(3-((5-chloro-2-((1-methyl-1H-pyrazol-4-yl)amino)pyrimidin-4-yl)amino)cyclohexyl) acrylamide 4-methylbenzenesulfonate (I-126)

Scheme-60:

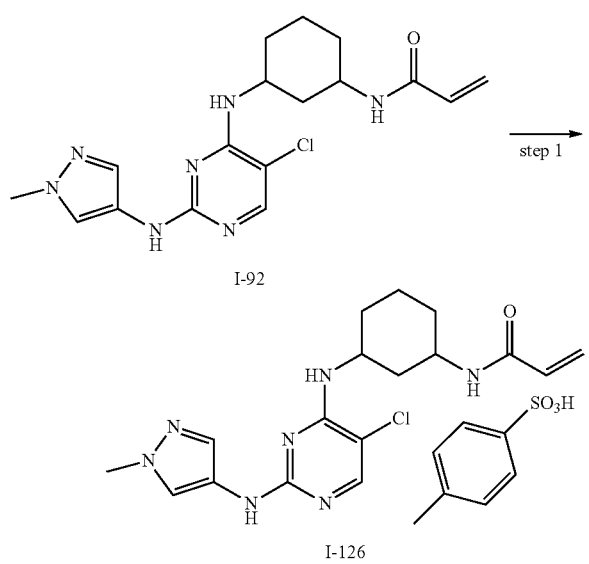

Synthesis of N-(3-((5-chloro-2-((1-methyl-1H-pyrazol-4-yl)amino)pyrimidin-4-yl)amino)cyclohexyl) acrylamide 4-methylbenzenesulfonate (I-126)

To a solution of (E)-N-(3-(3-benzyl-7-((3-chloro-1-methyl-1H-pyrazol-4-yl)amino)-2-oxo-3,4-dihydropyrimido[4,5-d]pyrimidin-1(2H)-yl)phenyl)-4-(dimethylamino)but-2-enamide (I-92) (0.087 mmol) in MeOH (15 ml) was added corresponding 4-methylbenzenesulfonic acid (0.087 mmol) at 10° C. Allowed reaction mixture to stir at room temperature for 4 h. Organic solvent was concentrated and the solid obtained was washed with n-pentane and dried over vacuum to get title compound I-126 as white solid with 55% yield. 1HNMR (400 MHz, DMSO-d6): δ 9.81 (bs, 1H), 8.07-8.06 (d, 2H), 8.00 (bs, 1H), 7.83 (s, 1H), 7.46-7.44 (m, 3H), 7.09-7.07 (d, 2H), 6.21-6.14 (m, 1H), 6.06-6.02 (m, 1H), 5.56-5.53 (d, 1H), 4.08 (bs, 1H), 3.82 (s, 3H), 3.71 (bs, 2H), 2.26 (s, 3H), 2.06 (bs, 1H), 1.81-1.79 (m, 3H), 1.50-1.33 (m, 3H). LCMS Calcd [M-PhMeSO3H]$^+$ 376.1. found 376.1. HPLC purity 99.28%

Example 25: Biological Activity: EGFR T790M Assay Protocol

Aim:
The objective of the experiment is to find the IC50 for the compounds using HTRF method.
Reagents for Enzyme Assay:
1. Enzyme Assay Buffer: 60 mM HEPES (pH 7.4), 50 mM NaCl, 20 mM MgCl$_2$, 5 mM MnCl$_2$, filter using 0.2 m pore size, store at 4° C.
Supplements (add fresh to the enzyme buffer): Make 1M DTT stock, 5% BSA stock and 0.1M Na$_3$OV$_4$ stored at 4° C. Enzyme assay buffer 50 ml, 1 M DTT 100 µl, 5% BSA 500 µl, 0.1M Na$_3$OV$_4$ 50 µl.
2. GST-hEGFR (L858R), active: EGFR (T790M/L858R), active (Proqinase), 3.6 µM stock; 2.5 nM in final assay.
3. Gastrin Precursor-Biotinylated: Gastrin precursor (Tyr87) biotinylated peptide (EEAY*GWM), Cell Signaling Tech 1310, Lot-7, Want final 0.5 µM in assay
4. ATP: 10 mM stock in 100 µl Enzyme assay buffer pH 7.4 prepared freshly, want 5 µM in final assay.
5. Test compounds: Dissolve powders in 100% DMSO to a final stock concentration of 10 mM (volume in µL to add for 10 mM=mg powder×10$^5$/MW). Final comp concentration in the assay plate is starting at 10 µM.
Reagents for HTRF Assay:
1. HTRF buffer: 50 mM Tris-HCl, pH-7.5, 100 mM NaCl, 0.1% BSA, 0.05% Tween20, 0.5 mM EDTA, filter using 0.2 m pore size, store at 4° C.

Phycolink® Streptavidin-Allophycocyanin (SA-APC) Prozyme, Cat. #PJ25S, Lot #896 085, 2.06 mg/mL, APC concentration is 11.6 µM, streptavidin concentration is 15.5 µM. Want 12 nM final in assay (based on streptavidin concentration).

2. Europium-W1024-PT-66 Anti Phospho Tyrosine Antibody: Perkin Elmer (AD0068), monoclonal IgG1 that recognizes phospho tyrosine peptide 100 µg/ml stock. Want 0.1 nM final in assay.

Assay Procedure
1. Make the compound dilution by TECAN as per the above scheme.
2. Add 16 µl of diluted compound to the assay plate by using TECAN
3. Add 10 µl of enzyme mix to each well except mins.
4. Add 20 µl of substrate and ATP mix into each well of the assay plate manually.
5. Incubate the plate at room temperature for 60 min with shaking.
6. Meanwhile prepare the HTRF mix and add 75 µl to the HTRF plate.
7. When the incubation is over, transfer 10 µl of the reaction mixture to the HTRF assay plate and incubate for 30 min at room temperature with shaking.
8. Take the reading in Pherastar (ext 337 nm, em 665 & 620 nm).
9. Analyze the results using Graphpad prism after calculation the z factor, signal window and % inhibition to get the IC50.

Example 26

Table 1 shows the activity of compounds of this invention in the EGFR (L858R & T790M) inhibition assay. Compounds having IC50<10 nM are designated as "A"; 10-100 nM are designated as "B"; and >100 nM as "C".

TABLE 1

Biochemical EGFR (L858R & T790M) inhibition data

| Cmpd No. | EGFR (L858R + T790M) |
|---|---|
| I-1 | A |
| I-2 | C |
| I-3 | B |
| I-4 | B |
| I-5 | B |
| I-6 | C |
| I-7 | B |
| I-8 | C |
| I-9 | C |
| I-10 | B |
| I-11 | C |
| I-12 | B |
| I-13 | B |
| I-14 | C |
| I-15 | B |
| I-16 | A |
| I-17 | C |
| I-18 | B |
| I-19 | A |
| I-20 | B |
| I-21 | A |
| I-22 | B |
| I-23 | C |
| I-24 | B |
| I-25 | C |
| I-26 | C |
| I-27 | C |
| I-28 | C |
| I-29 | C |
| I-30 | C |
| I-31 | B |
| I-32 | B |
| I-33 | C |
| I-34 | A |
| I-35 | A |
| I-36 | B |
| I-37 | C |
| I-38 | C |
| I-39 | A |
| I-40 | B |
| I-41 | B |
| I-42 | C |
| I-43 | B |
| I-44 | C |
| I-45 | B |
| I-46 | C |
| I-47 | A |
| I-48 | B |
| I-49 | B |
| I-50 | C |
| I-51 | C |
| I-52 | C |
| I-53 | C |
| I-54 | C |
| I-55 | C |
| I-56 | C |
| I-57 | C |
| I-58 | A |
| I-59 | C |
| I-60 | B |
| I-61 | B |
| I-62 | A |
| I-63 | C |
| I-64 | B |
| I-65 | B |
| I-66 | B |
| I-67 | B |
| I-68 | B |
| I-69 | A |
| I-70 | A |
| I-71 | B |
| I-72 | B |
| I-73 | B |
| I-74 | C |
| I-75 | B |
| I-76 | B |
| I-77 | B |
| I-78 | B |
| I-79 | B |
| I-80 | B |
| I-81 | C |
| I-82 | B |
| I-83 | C |
| I-84 | C |
| I-85 | A |
| I-86 | A |
| I-87 | B |
| I-88 (Isomer 1) | C |
| I-89 (Isomer 2) | C |
| I-90 (Isomer 1) | C |
| I-91 (Isomer 2) | C |
| I-92 | B |
| I-93 | C |
| I-94 | C |
| I-95 | B |
| I-96 | C |
| I-97 | C |
| I-98 | C |
| I-99 | C |
| I-100 | C |
| I-101 | C |
| I-102 (diastereomer 1) | C |
| I-103 (diastereomer 2) | C |
| I-104 (Enantiomer 3) | B |
| I-105 (Enantiomer 4) | C |
| I-106 (Enantiomer 1) | C |

TABLE 1-continued

Biochemical EGFR (L858R & T790M) inhibition data

| Cmpd No. | EGFR (L858R + T790M) |
|---|---|
| I-107 (Enantiomer 2) | C |
| I-108 | C |
| I-109 | C |
| I-110 | C |
| I-111 | A |
| I-112 (Isomer 1) | C |
| I-113 (Isomer 2) | B |
| I-114 | B |
| I-115 | C |
| I-116 | B |
| I-117 | A |
| I-118 | B |
| I-119 | C |
| I-120 | C |
| I-121 | C |
| I-122 | A |
| I-123 | B |
| I-124 | B |
| I-125 | B |
| I-126 | C |
| II-1 (Enantiomer 1) | C |
| II-2 (Enantiomer 2) | C |
| II-3 (Enantiomer 1) | C |
| II-4 (Enantiomer 2) | C |
| II-5 (Enantiomer 1) | C |
| II-6 (Enantiomer 2) | C |
| II-7 (Racemic) | C |
| II-8 | C |
| II-9 | C |
| II-10 (Enantiomer 1) | C |
| II-11 (Enantiomer 2) | C |
| II-12 (Enantiomer 1) | C |
| II-13 (Enantiomer 2) | C |

Although the subject matter has been described in considerable detail with reference to certain preferred embodiments thereof, other embodiments are possible. As such, the spirit and scope of the appended claims should not be limited to the description of the preferred embodiment contained therein.

We claim:

1. A compound represented by Formula I

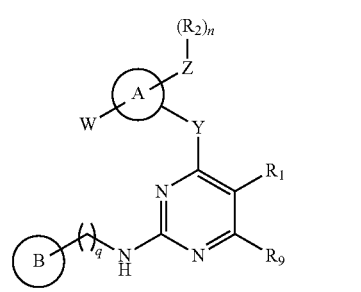

Formula I or its stereoisomers, tautomers, pharmaceutically acceptable salts, and hydrates thereof wherein, ring A is selected from the group consisting of

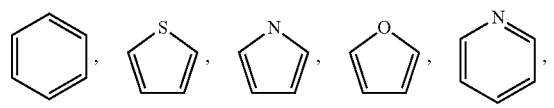

ring B is selected from the group consisting of

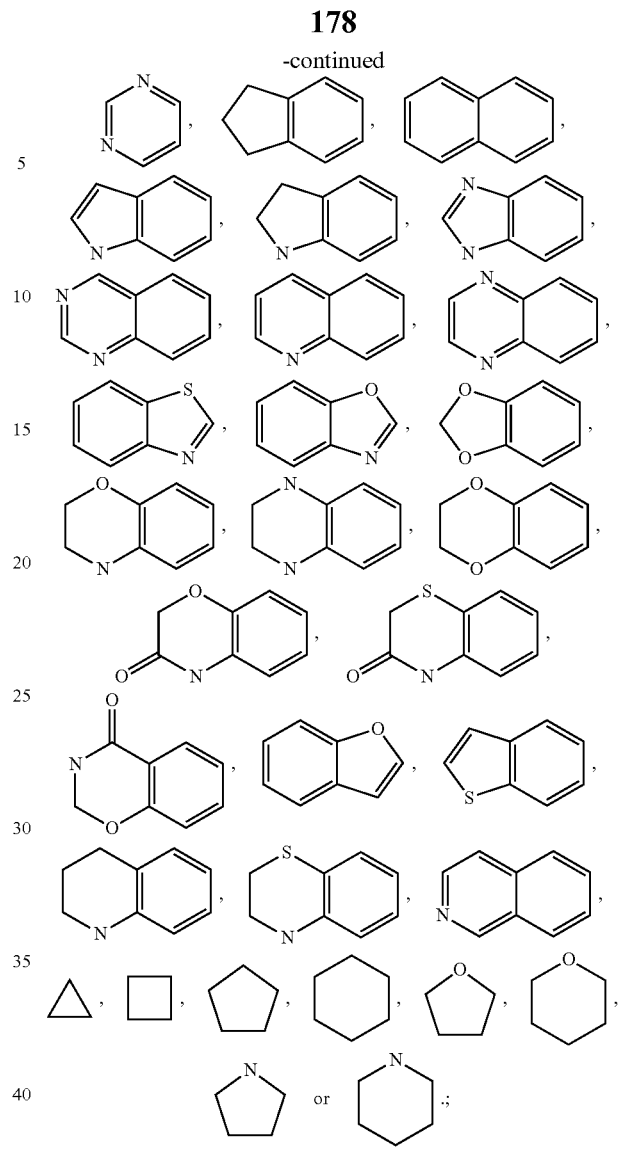

-continued

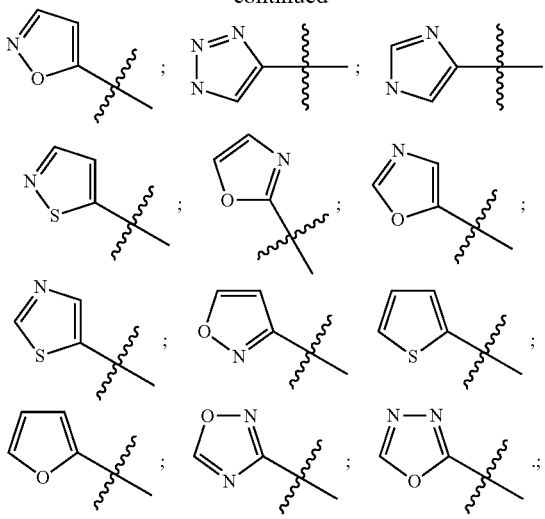

wherein ring B is optionally substituted with 1 to 4 substituents independently selected from the group consisting of hydrogen, halogen, cyano, $CF_3$, $C_{1-6}$ alkyl, $-C(R_aR_aR_a')$, $-C(R_aR_a)[C(R_aR_a)]_n OC(R_{a'})_p$, $-S(O)_p C(R_{a'})_p$, $-C(R_aR_a)C(R_aR_a)N(R_{a'})_p$, $-C(R_aR_a)C(R_aR_a)OR_{a'}$, $C_{3-6}$ cycloalkyl, $C_{5-6}$ aryl, $C_{5-6}$ heteroaryl, $C_{3-6}$ alkylcycloalkyl, alkyl $C_{3-6}$ heterocycloalkyl, and monocyclic or bicyclic $C_{3-8}$ heterocycloalkyl with heteroatoms selected from the group consisting of N, O, and S; wherein cycloalkyl, aryl, alkyl, heteroaryl, monocyclic or bicyclic heterocycloalkyl are further optionally substituted with one or more of the groups selected from the group consisting of hydrogen, $C_{1-6}$ alkyl, halogen, haloalkyl, OH, and $-C(O)$;

W is selected from the group consisting of

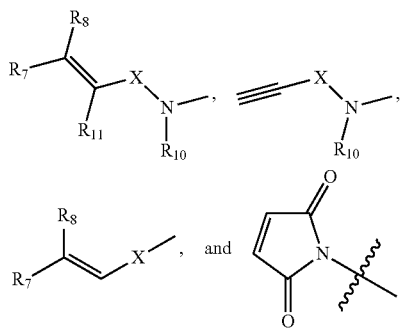

X is $-C(O)-$, $-S(O)_2-$ or $-S(O)-$;
$R_{11}$ is selected from the group consisting of hydrogen, alkyl, and halogen;
$R_{10}$ is H or alkyl;
Y is selected from the group of $-O-$, $-NR-$ and $-S-$; where R is selected from H, alkyl;
Z is absent or $-O-$;
$R_2$ is selected from the group consisting of hydrogen, halogen, alkyl, $C_{3-6}$ cycloalkyl, and $C_{3-6}$ heterocycloalkyl;
$R_7$ is selected from the group consisting of hydrogen, halogen, methyl, and $-CH_2NR_aR_a$;
$R_8$ is selected from the group consisting of hydrogen, halogen, optionally substituted $C_{1-6}$ alkyl, $C_{4-6}$ cycloalkyl, and $C_{4-7}$ heterocycloalkyl; or $R_7$ and $R_8$ taken together from a 4-7 membered cycloalkyl, 4-7 membered heterocycloalkyl, wherein said groups can be optionally substituted with 1 to 3 substituents independently selected from the group consisting of hydrogen, halogen, unsubstituted alkyl, haloalkyl;
$R_1$ is selected from the group consisting of hydrogen, halogen, $C_{1-6}$ alkyl, alkoxy, haloalkyl, $C_{3-6}$ cycloalkyl, $C_{5-6}$ aryl, $C_{5-6}$ heteroaryl, alkoxyalkyl, cyano, $-C(R_aR_aR_a')$, $-C(R_aR_a)[C(R_aR_a)]_n OC(R_{a'})_p$, $-S(O)_p C(R_{a'})_p$, $-C(R_aR_a)C(R_aR_a)N(R_{a'})_p$, $-C(R_aR_a)C(R_aR_a)OR_{a'}$, and monocyclic or bicyclic $C_{4-8}$ heterocycloalkyl with heteroatoms selected from N, O, S;
  wherein $C_{1-6}$ alkyl, $C_{3-6}$ cycloalkyl, $C_{5-6}$ aryl, $C_{5-6}$ heteroaryl, monocyclic or bicyclic $C_{4-8}$ heterocycloalkyl with heteroatoms selected from N, O, S is optionally substituted with one or more of the groups selected from hydrogen, $C_{1-6}$ alkyl, halogen, OH, $-C(O)$;
$R_9$ is selected from the group consisting of hydrogen, halogen, alkyl, haloalkyl, alkoxy, alkoxyalkyl, and cyano;
$R_a$ is independently selected from the group consisting of hydrogen, $-CH_3$, $-CH_2-$, halogen, and OH;
$R_{a'}$ is selected from the group consisting of hydrogen, $-CH_3$, $-CH_2-$, and $C_{3-6}$ cycloalkyl;
or $R_a R_{a'}$ taken together form a $C_{3-6}$ cycloalkyl ring or a $C_{4-6}$ heterocycloalkyl ring;
q is 0 or 1;
n is 0, 1 or 2; and
p is 1, 2, 3 or 4; and
wherein the following compound is excluded

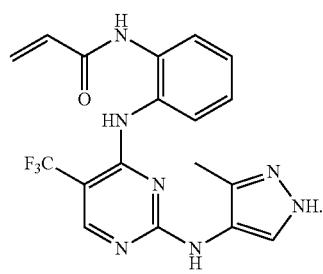 [SMILES: C=CC(=O)Nc1ccccc1Nc1nc(Nc2c[nH]nc2C)ncc1C(F)(F)F]

2. The compound as claimed in claim 1, or its stereoisomers, tautomers, pharmaceutically acceptable salts, and hydrates thereof wherein ring-A is selected from the group consisting of

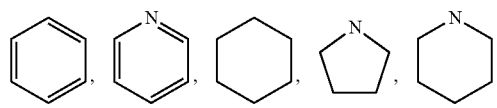

ring B is selected from the group consisting of

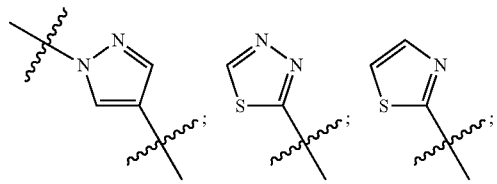

-continued

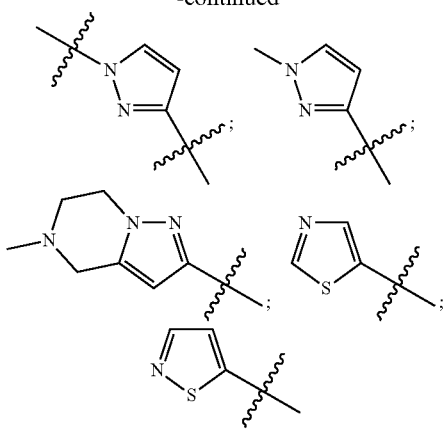

wherein ring B is optionally substituted with 1 to 4 substituents independently selected from the group consisting of hydrogen, halogen, cyano, $CF_3$, $C_{1-6}$ alkyl, $-C(R_aR_aR_{a'})$, $-C(R_aR_a)[C(R_aR_a)]_nOC(R_a)_p$, $-S(O)_pC(R_a)_p$, $-C(R_aR_a)C(R_aR_a)N(R_{a'})_p$, $-C(R_aR_a)C(R_aR_a)OR_{a'}$, $C_{3-6}$ cycloalkyl, $C_{5-6}$ aryl, $C_{5-6}$ heteroaryl, $C_{3-6}$ alkylcycloalkyl, alkyl $C_{3-6}$ heterocycloalkyl, monocyclic or bicyclic $C_{3-8}$ heterocycloalkyl with heteroatoms selected from N, O, S;

wherein cycloalkyl, alkyl, aryl, heteroaryl, monocyclic or bicyclic heterocycloalkyl are further optionally substituted with one or more of the groups selected from hydrogen, $C_{1-6}$ alkyl, halogen, haloalkyl, OH, $-C(O)$;

W is selected from the group consisting of

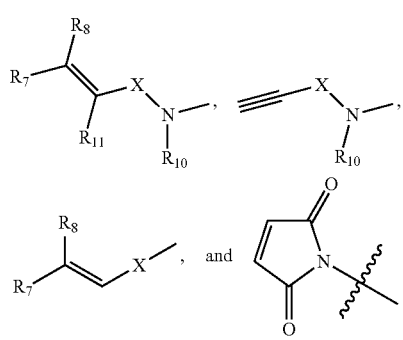

Z is absent or $-O-$;
$R_2$ is selected from the group consisting of hydrogen, halogen, alkyl, $C_{3-6}$ cycloalkyl, and $C_{3-6}$ heterocycloalkyl;
X is $-C(O)-$ or $-S(O)_2-$ or $-S(O)-$;
$R_7$ is selected from the group consisting of hydrogen, halogen, methyl, and $-CH_2NR_aR_a$;
$R_8$ is selected from the group consisting of hydrogen, halogen, optionally substituted $C_{1-6}$ alkyl, $C_{4-6}$ cycloalkyl, and $C_{4-7}$ heterocycloalkyl; or
$R_7$ and $R_8$ taken together form a 4-7 membered cycloalkyl, 4-7 membered heterocycloalkyl, wherein said groups can be optionally substituted with 1 to 3 substituents independently selected from the group consisting of hydrogen, halogen, unsubstituted alkyl, haloalkyl;
$R_{11}$ is selected from the group consisting of hydrogen, alkyl, and halogen;

$R_{10}$ is H or alkyl;
Y is selected from the group the group consisting of $-O-$, $-NR-$ and $-S$, wherein R is selected from hydrogen and alkyl;
$R_1$ is selected from the group consisting of hydrogen, halogen, $C_{1-6}$ alkyl, alkoxy, haloalkyl, $C_{3-6}$ cycloalkyl, $C_{5-6}$ aryl, $C_{5-6}$ heteroaryl, alkoxyalkyl, cyano, $-C(R_aR_aR_{a'})$, $-C(R_aR_a)[C(R_aR_a)]_nOC(R_a)_p$, $-S(O)_pC(R_a)_p$, $-C(R_aR_a)C(R_aR_a)N(R_{a'})_p$, $-C(R_aR_a)C(R_aR_a)OR_{a'}$, and monocyclic or bicyclic $C_{4-8}$ heterocycloalkyl with heteroatoms selected from N, O, S;
wherein $C_{1-6}$ alkyl, $C_{3-6}$ cycloalkyl, $C_{5-6}$ aryl, $C_{5-6}$ heteroaryl, and monocyclic or bicyclic $C_{4-8}$ heterocycloalkyl with heteroatoms selected from N, O, S is optionally substituted with one or more of the groups selected from hydrogen, $C_{1-6}$ alkyl, halogen, OH, $-C(O)$;
$R_9$ is selected from the group consisting of hydrogen, halogen, alkyl, haloalkyl, alkoxy, alkoxyalkyl, and cyano;
$R_a$ is independently selected from the group consisting of hydrogen, $-CH_3$, $-CH_2-$, halogen, and OH;
$R_{a'}$ is selected from the group consisting of hydrogen, $-CH_3$, $-CH_2-$, and $C_{3-6}$ cycloalkyl; or $R_a$ and $R_{a'}$ taken together form a $C_{3-6}$ cycloalkyl ring or a $C_{4-6}$ heterocycloalkyl ring;
q is 0 to 1;
n is 0, 1 or 2; and
p is 1 to 4.

3. The compound as claimed in claim 1, or its stereoisomers, tautomers, pharmaceutically acceptable salts, and hydrates thereof wherein ring-A is selected from the group consisting of

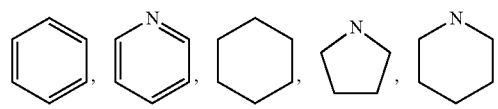

ring B is selected from the group consisting of

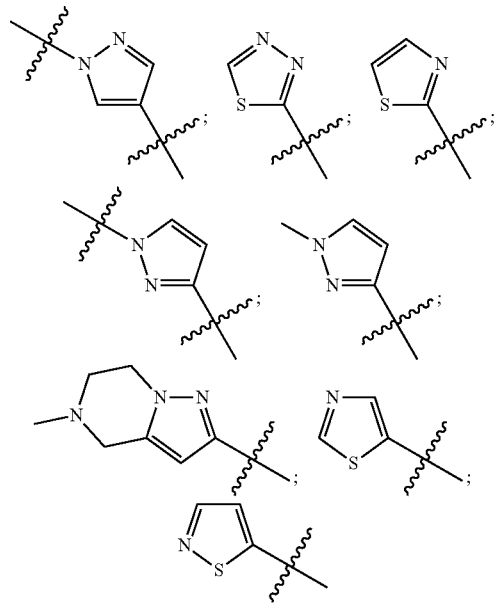

ring B is optionally substituted with 1 to 4 substituents independently selected from the group consisting of hydrogen, CF$_3$, C$_{1-6}$ alkyl, —C(R$_a$R$_a$R$_{a'}$), —C(R$_a$R$_a$)[C(R$_a$R$_a$)]$_n$OC(R$_{a'}$)p, —S(O)$_p$C(R$_{a'}$)$_p$, —C(R$_a$R$_a$)C(R$_a$R$_a$)N(R$_{a'}$)$_p$, —C(R$_a$R$_a$)C(R$_a$R$_a$)OR$_{a'}$, C$_{3-6}$ cycloalkyl, C$_{5-6}$ aryl, C$_{5-6}$ heteroaryl, C$_{3-6}$ alkylcycloalkyl, alkyl C$_{3-8}$ heterocycloalkyl, monocyclic or bicyclic C$_{3-8}$ heterocycloalkyl with heteroatoms selected from N, O; wherein cycloalkyl, alkyl, aryl, heteroaryl, monocyclic or bicyclic heterocycloalkyl are further optionally substituted with one or more of the groups selected from hydrogen, C$_{1-6}$ alkyl, halogen, haloalkyl, OH, —C(O);

W is selected from the group consisting of

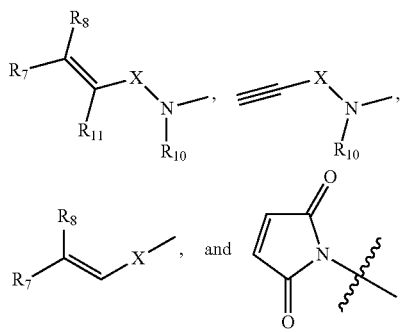

Z is absent;
R$_2$ is selected from the group consisting of hydrogen and halogen;
X is —C(O)— or —S(O)$_2$—;
R$_7$ is selected from the group consisting of hydrogen, methyl, and —CH$_2$NR$_a$R$_a$;
R$_8$ is selected from the group consisting of hydrogen, optionally substituted C$_{1-6}$ alkyl, C$_{4-6}$ cycloalkyl, and C$_{4-7}$ heterocycloalkyl; or
R$_7$ and R$_8$ taken together form a 4-7 membered cycloalkyl, 4-7 membered heterocycloalkyl, wherein said groups can be optionally substituted with 1 to 3 substituents independently selected from the group consisting of hydrogen, halogen;
R$_1$ is selected from the group consisting of hydrogen, halogen, C$_{1-6}$ alkyl, alkoxy, haloalkyl, and C$_{3-6}$ cycloalkyl;
R$_9$ is selected from the group consisting of hydrogen, halogen, alkyl, haloalkyl, alkoxy, alkoxyalkyl, and cyano;
R$_{11}$ is hydrogen;
Y is selected from the group the group consisting of —O—, and —NR—, wherein R is selected from hydrogen and alkyl;
R$_{10}$ is H or alkyl;
R$_a$ is selected from the group consisting of hydrogen, —CH$_3$, —CH$_2$—, halogen and OH;
R$_{a'}$ is selected from the group consisting of hydrogen, —CH$_3$, —CH$_2$— and C$_{3-6}$ cycloalkyl;
q is 0;
n is 0, 1 or 2;
p is 1 to 4.

4. A compound as claimed in claim 1 or its stereoisomers, tautomers, pharmaceutically acceptable salts, and hydrates thereof, which is selected from the group consisting of:

N-(3-((5-chloro-2-((1-(1-methylpiperidin-4-yl)-1H-pyrazol-4-yl)amino)pyrimidin-4-yl)amino)phenyl)acrylamide;
N-(3-((5-chloro-2-((1-(2-methoxyethyl)-3-methyl-1H-pyrazol-4-yl)amino)pyrimidin-4-yl)amino)phenyl)acrylamide;
N-(3-((5-chloro-2-((1-(2-methoxyethyl)-5-methyl-1H-pyrazol-4-yl)amino)pyrimidin-4-yl)amino)phenyl)acrylamide;
N-(3-((5-chloro-2-((1-isopropyl-1H-pyrazol-4-yl)amino)pyrimidin-4-yl)amino)phenyl)acrylamide;
N-(3-((5-chloro-2-((1-(2-(dimethylamino)ethyl)-1H-pyrazol-4-yl)amino)pyrimidin-4-yl)amino)phenyl)acrylamide;
N-(3-((5-chloro-2-((1-(2-methoxyethyl)-1H-pyrazol-4-yl)amino)pyrimidin-4-yl)amino)phenyl)-2-cyclohexylideneacetamide;
N-(3-((5-chloro-2-((1-(cyclopropylmethyl)-1H-pyrazol-4-yl)amino)pyrimidin-4-yl)amino)phenyl)acrylamide;
N-(3-((5-chloro-2-((3,5-dimethyl-1-(1-methylpiperidin-4-yl)-1H-pyrazol-4-yl)amino)pyrimidin-4-yl)amino)phenyl)acrylamide;
N-(3-((5-chloro-2-((1-(1-methylpiperidin-4-yl)-1H-pyrazol-4-yl)amino)pyrimidin-4-yl)amino)phenyl)methacrylamide;
N-(3-((5-chloro-2-((1-(methylsulfonyl)-1H-pyrazol-4-yl)amino)pyrimidin-4-yl)amino)phenyl)acrylamide;
N-(3-((5-chloro-2-((1,3,5-trimethyl-1H-pyrazol-4-yl)amino)pyrimidin-4-yl)-amino)phenyl)acrylamide;
N-(3-((5-methoxy-2-((1-(1-methylpiperidin-4-yl)-1H-pyrazol-4-yl)amino)pyrimidin-4-yl)amino)phenyl)acrylamide;
N-(3-((5-methyl-2-((1-(1-methylpiperidin-4-yl)-1H-pyrazol-4-yl)amino)pyrimidin-4-yl)amino)phenyl)acrylamide;
N-(3-((2-((1-(1-methylpiperidin-4-yl)-1H-pyrazol-4-yl)amino)-5-(trifluoro-methyl)pyrimidin-4-yl)amino)phenyl)acrylamide;
N-(3-((5-methyl-2-((1-methyl-1H-pyrazol-4-yl)amino)pyrimidin-4-yl)amino)phenyl)acrylamide;
N-(3-((5-chloro-2-((1-(1-(2-fluoroethyl)piperidin-4-yl)-1H-pyrazol-4-yl)amino)pyrimidin-4-yl)amino)phenyl)acrylamide;
N-(3-((5-chloro-2-((1-(2-hydroxy-2-methylpropyl)-1H-pyrazol-4-yl)amino)pyrimidin-4-yl)amino)phenyl)acrylamide;
N-(3-((5-fluoro-2-((1-(1-methylpiperidin-4-yl)-1H-pyrazol-4-yl)amino)pyrimidin-4-yl)amino)phenyl)acrylamide;
N-(3-((5-chloro-2-((1-methyl-1H-pyrazol-4-yl)amino)pyrimidin-4-yl)amino)phenyl)acrylamide;
N-(3-((5-chloro-2-((1-(2-methoxyethyl)-1H-pyrazol-4-yl)amino)pyrimidin-4-yl)amino)phenyl)acrylamide;
N-(3-((5-chloro-2-((1-(2-hydroxyethyl)-1H-pyrazol-4-yl)amino)pyrimidin-4-yl)amino)phenyl)acrylamide;
N-(3-((5-chloro-2-((1-(cyclopropylsulfonyl)-1H-pyrazol-4-yl)amino)pyrimidin-4-yl)amino)phenyl)acrylamide;
N-(3-((5-chloro-2-((1,5-dimethyl-1H-pyrazol-4-yl)amino)pyrimidin-4-yl)amino)phenyl)acrylamide;
N-(3-((5-chloro-2-((5-(methoxymethyl)-1-methyl-1H-pyrazol-3-yl)amino)pyrimidin-4-yl)amino)phenyl)acrylamide;
N-(3-((5-chloro-2-((1-(1-methylpiperidin-4-yl)-1H-pyrazol-4-yl)amino)pyrimidin-4-yl)amino)phenyl)-2-(4,4-difluorocyclohexylidene)acetamide;

N-(3-((5-chloro-2-((1-(1-methylpiperidin-4-yl)-1H-pyrazol-4-yl)amino)pyrimidin-4-yl)amino)phenyl)-2-(dihydro-2H-pyran-4(3H)-ylidene)acetamide;
N-(5-((5-chloro-2-((1-(1-methylpiperidin-4-yl)-1H-pyrazol-4-yl)amino)pyri-midin-4-yl)amino)-2-fluorophenyl)-2-cyclohexylideneacetamide;
N-(3-((5-chloro-2-((1-(1-methylpiperidin-4-yl)-1H-pyrazol-4-yl)amino)pyrimidin-4-yl)amino)phenyl)-2-cyclohexylideneacetamide;
N-(3-((5-chloro-2-((1-(1-methylpiperidin-4-yl)-1H-pyrazol-4-yl)amino)pyrimidin-4-yl)amino)phenyl)-2-cyclobutylideneacetamide;
N-(3-((5-chloro-2-((1-(1-methylpiperidin-4-yl)-1H-pyrazol-4-yl)amino)pyrimidin-4-yl)amino)phenyl)-2-cyclopentylideneacetamide;
N-(3-((5-chloro-2-((1-(oxetan-3-yl)-1H-pyrazol-4-yl)amino)pyrimidin-4-yl)-amino)phenyl)acrylamide;
N-(3-((5-chloro-2-((1-methyl-1H-pyrazol-4-yl)amino)pyrimidin-4-yl)amino)phenyl)propiolamide;
N-(3-((5-chloro-2-((1-methyl-1H-pyrazol-4-yl)amino)pyrimidin-4-yl)amino)phenyl)-2-fluoroacrylamide;
N-(3-((5-chloro-2-((1,3-dimethyl-1H-pyrazol-4-yl)amino)pyrimidin-4-yl)amino)phenyl)acrylamide;
N-(3-chloro-5-((5-chloro-2-((1-methyl-1H-pyrazol-4-yl)amino)pyrimidin-4-yl)amino)phenyl)acrylamide;
N-(3-((5-chloro-2-((1-(3-hydroxycyclopentyl)-1H-pyrazol-4-yl)amino)pyrimidin-4-yl)amino)phenyl)acrylamide;
N-(3-((5-fluoro-2-((1-(3-hydroxycyclopentyl)-1H-pyrazol-4-yl)amino)pyrimidin-4-yl)amino)phenyl)acrylamide;
N-(3-((5-chloro-2-((1-(3-hydroxycyclohexyl)-1H-pyrazol-4-yl)amino)pyrimidin-4-yl)amino)phenyl)acrylamide;
N-(3-((5-chloro-2-((1-methyl-1H-pyrazol-4-yl)amino)pyrimidin-4-yl)amino)-4-fluorophenyl)acrylamide;
N-(3-((5-chloro-2-((5-(4-methylpiperazin-1-yl)thiazol-2-yl)amino)pyrimidin-4-yl)amino)phenyl)acrylamide;
N-(3-((5-chloro-2-((5-(4-methylpiperazin-1-yl)-1,3,4-thiadiazol-2-yl)amino)pyrimidin-4-yl)amino)phenyl)acrylamide;
N-(3-((2-((5-(azetidin-1-ylmethyl)-1-methyl-1H-pyrazol-3-yl)amino)-5-chloropyrimidin-4-yl)amino)phenyl)acrylamide, acetate salt;
N-(3-((5-chloro-2-((1-(2-oxopiperidin-4-yl)-1H-pyrazol-4-yl)amino)pyrimidin-4-yl)amino)phenyl)acrylamide;
N-(3-((5-chloro-2-((5-(trifluoromethyl)-1,3,4-thiadiazol-2-yl)amino)pyrimidin-4-yl)amino)phenyl)acrylamide;
N-(3-((5-chloro-2-((1-(tetrahydro-2H-pyran-4-yl)-1H-pyrazol-4-yl)amino)pyrimidin-4-yl)amino)phenyl)acrylamide;
N-(3-((5-chloro-2-((1-methyl-5-(morpholinomethyl)-1H-pyrazol-3-yl)amino)pyrimidin-4-yl)amino)phenyl)acrylamide;
N-(3-((5-chloro-2-((1-(2-hydroxyethyl)-1H-pyrazol-4-yl)amino)pyrimidin-4-yl)oxy)phenyl)acrylamide;
N-(3-((5-chloro-2-((1-(8-methyl-8-azabicyclo[3.2.1]octan-3-yl)-1H-pyrazol-4-yl)amino)pyrimidin-4-yl)amino)phenyl)acrylamide;
N-(3-((5-chloro-2-((1-(tetrahydrofuran-3-yl)-1H-pyrazol-4-yl)amino)pyrimidin-4-yl)amino)phenyl)acrylamide;
2-cyclohexylidene-N-(3-((5-fluoro-2-((1-(1-methylpiperidin-4-yl)-1H-pyrazol-4-yl)amino)pyrimidin-4-yl)amino)phenyl)acetamide;
(E)-N-(3-((5-chloro-2-((1-(1-methylpiperidin-4-yl)-1H-pyrazol-4-yl)amino)-pyrimidin-4-yl)amino)phenyl)but-2-enamide;
N-(3-((5-chloro-2-((1-((6-methylpyridin-2-yl)methyl)-1H-pyrazol-4-yl)amino)pyrimidin-4-yl)amino)phenyl)acrylamide;
(E)-N-(3-((5-chloro-2-((1-(1-methylpiperidin-4-yl)-1H-pyrazol-4-yl)amino)-pyrimidin-4-yl)amino)phenyl)-4-(dimethylamino)but-2-enamide;
N-(3-((5-chloro-2-((1-(piperidin-4-yl)-1H-pyrazol-4-yl)amino)pyrimidin-4-yl)amino)phenyl)acrylamide, 2,2,2-trifluoroacetate salt;
1-(3-((5-chloro-2-((1-methyl-i H-pyrazol-4-yl)amino)pyrimidin-4-yl)amino)phenyl)-1H-pyrrole-2,5-dione;
N-(5-((5-chloro-2-((1-(1-methylpiperidin-4-yl)-1H-pyrazol-4-yl)amino)pyri-midin-4-yl)amino)-2-fluorophenyl)ethenesulfonamide;
N-(3-((5-chloro-2-((1-methyl-1H-pyrazol-4-yl)amino)pyrimidin-4-yl)amino)phenyl)ethenesulfonamide;
N-(5-((5-chloro-2-((1-methyl-1H-pyrazol-4-yl)amino)pyrimidin-4-yl)amino)-2-fluorophenyl)acrylamide;
N-(5-((5-chloro-2-((1-(1-methylpiperidin-4-yl)-1H-pyrazol-4-yl)amino)pyrimidin-4-yl)amino)-2-fluorophenyl)acrylamide;
N-(5-((5-chloro-2-((1-methyl-1H-pyrazol-4-yl)amino)pyrimidin-4-yl)amino)-2,4-difluorophenyl)acrylamide;
N-(5-((5-chloro-2-((1-(1-methylpiperidin-4-yl)-1H-pyrazol-4-yl)amino)pyrimidin-4-yl)amino)-2,4-difluorophenyl)acrylamide;
N-(3-((5-chloro-2-((1,3-dimethyl-1H-pyrazol-4-yl)amino)pyrimidin-4-yl)amino)-4-fluorophenyl)acrylamide;
N-(3-((5-chloro-2-((1,5-dimethyl-1H-pyrazol-4-yl)amino)pyrimidin-4-yl)amino)-4-fluorophenyl)acrylamide;
N-(3-((5-chloro-2-((1-(1-methylpiperidin-4-yl)-1H-pyrazol-4-yl)amino)pyrimidin-4-yl)(methyl)amino)phenyl)acrylamide;
N-(6-((5-chloro-2-((1,3-dimethyl-1H-pyrazol-4-yl)amino)pyrimidin-4-yl)amino)pyridin-2-yl)acrylamide;
N-(6-((5-chloro-2-((1,5-dimethyl-1H-pyrazol-4-yl)amino)pyrimidin-4-yl)amino)pyridin-2-yl)acrylamide;
N-(6-((5-chloro-2-((1-methyl-1H-pyrazol-4-yl)amino)pyrimidin-4-yl)amino)pyridin-2-yl)acrylamide;
N-(3-((5-cyclopropyl-2-((1-methyl-1H-pyrazol-4-yl)amino)pyrimidin-4-yl)amino)phenyl)acrylamide;
N-(3-((5-chloro-2-((1-(1-methylpiperidin-4-yl)-1H-pyrazol-4-yl)amino)pyrimidin-4-yl)oxy)phenyl)acrylamide;
N-(3-((5-chloro-2-((5-methyl-4,5,6,7-tetrahydropyrazolo[1,5-a]pyrazin-2-y-1)amino)pyrimidin-4-yl)oxy)phenyl)acrylamide;
N-(3-((5-chloro-2-((1-isopropyl-1H-pyrazol-4-yl)amino)pyrimidin-4-yl)oxy)-phenyl)acrylamide;
N-(3-((5-chloro-2-((1-(2-(dimethylamino)ethyl)-1H-pyrazol-4-yl)amino)pyrimidin-4-yl)oxy)phenyl)acrylamide;
N-(3-((5-chloro-2-((1-(2-hydroxy-2-methylpropyl)-1H-pyrazol-4-yl)amino)pyrimidin-4-yl)oxy)phenyl)acrylamide;
N-(3-((5-chloro-2-((1-(cyclopropylmethyl)-1H-pyrazol-4-yl)amino)pyrimidin-4-yl)oxy)phenyl)acrylamide;
N-(3-((5-chloro-2-((3,5-dimethyl-1-(1-methylpiperidin-4-yl)-1H-pyrazol-4-yl)amino)pyrimidin-4-yl)oxy)phenyl)acrylamide;
N-(3-((5-chloro-2-((1,3,5-trimethyl-1H-pyrazol-4-yl)amino)pyrimidin-4-yl)-oxy)phenyl)acrylamide;
N-(3-((5-chloro-2-((1-methyl-1H-pyrazol-4-yl)amino)pyrimidin-4-yl)oxy)phe-nyl)acrylamide;

N-(3-((5-chloro-2-((1-(2-hydroxyethyl)-1H-pyrazol-4-yl)amino)pyrimidin-4-yl)oxy)phenyl)acrylamide;
N-(3-((5-chloro-2-((1-(2-methoxyethyl)-1H-pyrazol-4-yl)amino)pyrimidin-4-yl)oxy)phenyl)acrylamide;
N-(3-((5-chloro-2-((2-methylpyrazolo[1,5-a]pyrimidin-7-yl)amino)pyrimidin-4-yl)oxy)phenyl)acrylamide;
N-(3-((5-chloro-2-((1-methyl-1H-pyrazol-4-yl)amino)pyrimidin-4-yl)amino)cyclohexyl)acrylamide;
1-(3-((5-chloro-2-((1-methyl-1H-pyrazol-4-yl)amino)pyrimidin-4-yl)amino)piperidin-1-yl)prop-2-en-1-one;
1-(3-((5-chloro-2-((1-methyl-1H-pyrazol-4-yl)amino)pyrimidin-4-yl)amino)piperidin-1-yl)prop-2-en-1-one;
(E)-1-(3-((5-chloro-2-((1-methyl-1H-pyrazol-4-yl)amino)pyrimidin-4-yl)ami-no)piperidin-1-yl)-4-(dimethylamino)but-2-en-1-one;
(E)-1-(3-((5-chloro-2-((1-methyl-1H-pyrazol-4-yl)amino)pyrimidin-4-yl)ami-no)piperidin-1-yl)-4-(dimethylamino)but-2-en-1-one;
1-(3-((5-chloro-2-((1-cyclobutyl-1H-pyrazol-4-yl)amino)pyrimidin-4-yl)amino)piperidin-1-yl)prop-2-en-1-one (Enantiomer 1);
1-(3-((5-chloro-2-((1-cyclobutyl-1H-pyrazol-4-yl)amino)pyrimidin-4-yl)amino)piperidin-1-yl)prop-2-en-1-one (Enantiomer 2);
1-(3-((5-chloro-2-((1-methyl-1H-pyrazol-4-yl)amino)pyrimidin-4-yl)amino)pyrrolidin-1-yl)prop-2-en-1-one;
1-(3-((5-chloro-2-((1-methyl-1H-pyrazol-4-yl)amino)pyrimidin-4-yl)oxy)pyrrolidin-1-yl)prop-2-en-1-one (Enantiomer 1);
1-(3-((5-chloro-2-((1-methyl-1H-pyrazol-4-yl)amino)pyrimidin-4-yl)oxy)pyrrolidin-1-yl)prop-2-en-1-one (Enantiomer 2);
1-(3-((5-chloro-2-((1-methyl-1H-pyrazol-4-yl)amino)pyrimidin-4-yl)oxy)piperidin-1-yl)prop-2-en-1-one (Enantiomer 1);
1-(3-((5-chloro-2-((1-methyl-1H-pyrazol-4-yl)amino)pyrimidin-4-yl)oxy)piperidin-1-yl)prop-2-en-1-one (Enantiomer 2);
N-(3-((5-chloro-2-((1-methyl-1H-pyrazol-4-yl)amino)pyrimidin-4-yl)amino)-4-((tetrahydrofuran-3-yl)oxy)phenyl)acrylamide;
N-(5-((5-chloro-2-((1-methyl-1H-pyrazol-4-yl)amino)pyrimidin-4-yl)amino)-2-((tetrahydrofuran-3-yl)oxy)phenyl)acrylamide;
N-(3-(1-((5-chloro-2-((1-methyl-1H-pyrazol-4-yl)amino)pyrimidin-4-yl)amino)ethyl)phenyl)acrylamide;
(E)-N-(3-(1-((5-chloro-2-((1-methyl-1H-pyrazol-4-yl)amino)pyrimidin-4-yl)-amino)ethyl)phenyl)-4-(dimethylamino)but-2-enamide;
N-(3-((5-chloro-2-((3-chloro-1-methyl-1H-pyrazol-4-yl)amino)pyrimidin-4-yl)amino)-4-fluorophenyl)acrylamide;
N-(3 ((5-chloro-6-methyl-2-((1-methyl-1H-pyrazol-4-yl)amino)pyrimidin-4-yl)amino)phenyl)acrylamide;
N-(3-((5-chloro-2-((1-methyl-1H-imidazol-4-yl)amino)pyrimidin-4-yl)amino)-phenyl)acrylamide;
N-(3-((5-chloro-2-(((1-methyl-1H-pyrazol-4-yl)methyl)amino)pyrimidin-4-yl-)amino)phenyl)acrylamide;
N-(3-((5-chloro-2-((1-methyl-1H-pyrazol-4-yl)amino)pyrimidin-4-yl)oxy)cyclohexyl)acrylamide (Isomer 1);
N-(3-((5-chloro-2-((1-methyl-1H-pyrazol-4-yl)amino)pyrimidin-4-yl)oxy)cyclohexyl)acrylamide (Isomer 2);
(E)-N-(3-((5-chloro-2-((1-methyl-1H-pyrazol-4-yl)amino)pyrimidin-4-yl)oxy-)cyclohexyl)-4-(dimethylamino)but-2-enamide (Isomer 1);
(E)-N-(3-((5-chloro-2-((1-methyl-1H-pyrazol-4-yl)amino)pyrimidin-4-yl)oxy-)cyclohexyl)-4-(dimethylamino)but-2-enamide (Isomer 2);
N-(3-((5-chloro-2-((1-methyl-1H-pyrazol-4-yl)amino)pyrimidin-4-yl)amino)cyclopentyl)acrylamide;
N-(4-((5-chloro-2-((1-methyl-1H-pyrazol-4-yl)amino)pyrimidin-4-yl)amino)cyclohexyl)acrylamide;
N-(3-((5-chloro-2-((3-chloro-1-methyl-1H-pyrazol-4-yl)amino)pyrimidin-4-y-1)amino)cyclohexyl)acrylamide;
N-(3-((5-chloro-2-((1-methyl-1H-pyrazol-3-yl)amino)pyrimidin-4-yl)amino)cyclohexyl)acrylamide;
N-(3-((5-chloro-2-((5-chloro-1-methyl-1H-pyrazol-3-yl)amino)pyrimidin-4-y-1)amino)cyclohexyl)acrylamide;
N-(3-((5-chloro-2-((5-(methoxymethyl)-1-methyl-1H-pyrazol-3-yl)amino)pyrimidin-4-yl)amino)cyclohexyl)acrylamide;
N-(3-((5-chloro-2-((1-(2-(dimethylamino)ethyl)-1H-pyrazol-4-yl)amino)pyrimidin-4-yl)amino)cyclohexyl)acrylamide;
N-(3-((5-methyl-2-((1-methyl-1H-pyrazol-4-yl)amino)pyrimidin-4-yl)amino)cyclohexyl)acrylamide;
(E)-N-(3-((5-chloro-2-((1-methyl-1H-pyrazol-4-yl)amino)pyrimidin-4-yl)ami-no)cyclohexyl)-4-(dimethylamino)but-2-enamide;
(E)-N-((1R,3R)-3-(((5-chloro-2-((1-methyl-1H-pyrazol-4-yl)amino)pyrimidin-4-yl)amino)methyl)cyclohexyl)-4-(dimethylamino)but-2-enamide (dieastereomer 1);
(E)-N-((1R,3R)-3-(((5-chloro-2-((1-methyl-1H-pyrazol-4-yl)amino)pyrimidin-4-yl)amino)methyl)cyclohexyl)-4-(dimethylamino)but-2-enamide (dieastereomer 2);
N-((1 S,3R)-3-((5-chloro-2-((1-methyl-1H-pyrazol-4-yl)amino)pyrimidin-4-yl-)amino)cyclohexyl)acrylamide (Enantiomer 3);
N-((1R,3S)-3-((5-chloro-2-((1-methyl-1H-pyrazol-4-yl)amino)pyrimidin-4-yl-)amino)cyclohexyl)acrylamide (Enantiomer 4);
N-((1R,3R)-3-((5-chloro-2-((1-methyl-1H-pyrazol-4-yl)amino)pyrimidin-4-yl-)amino)cyclohexyl)acrylamide (Enantiomer 1);
N-((1 S,3S)-3-((5-chloro-2-((1-methyl-1H-pyrazol-4-yl)amino)pyrimidin-4-yl-)amino)cyclohexyl)acrylamide (Enantiomer 2);
N-((3-((5-chloro-2-((1-methyl-1H-pyrazol-4-yl)amino)pyrimidin-4-yl)amino)-cyclohexyl)methyl)acrylamide;
(E)-N-((3-((5-chloro-2-((1-methyl-1H-pyrazol-4-yl)amino)pyrimidin-4-yl)amino)cyclohexyl)methyl)-4-(dimethylamino)but-2-enamide;
N-(3-((5-chloro-2-((1-methyl-1H-pyrazol-4-yl)amino)pyrimidin-4-yl)amino)-4-fluorophenyl)-N-methylacrylamide;
N-(3-((5-chloro-2-((1-methyl-1H-pyrazol-4-yl)amino)pyrimidin-4-yl)(methyl)amino)-4-fluorophenyl)acrylamide;
N-((1 S,3R)-3-((5-chloro-2-((1-methyl-1H-pyrazol-4-yl)amino)pyrimidin-4-yl-)amino)cycloheptyl)acrylamide (Isomer 1);
N-((1R,3S)-3-((5-chloro-2-((1-methyl-1H-pyrazol-4-yl)amino)pyrimidin-4-yl-)amino)cycloheptyl)acrylamide (Isomer 2);
N-(3-((5-chloro-2-((3-methylisothiazol-5-yl)amino)pyrimidin-4-yl)amino)cyclohexyl)acrylamide;
(E)-N-(3-((5-chloro-2-((3-methylisothiazol-5-yl)amino)pyrimidin-4-yl)amino)cyclohexyl)-4-(dimethylamino)but-2-enamide;
N-(2-((5-chloro-2-((1-methyl-1H-pyrazol-4-yl)amino)pyrimidin-4-yl)amino)pyridin-4-yl)acrylamide;

N-(3-((5-chloro-2-((3-methylisothiazol-5-yl)amino)pyrimidin-4-yl)amino)-4-fluorophenyl)acrylamide;
N-(3-((5-chloro-2-((3-methylisoxazol-5-yl)amino)pyrimidin-4-yl)amino)-4-fluorophenyl)acrylamide;
N-(3-((5-chloro-2-((3,4-dimethylisoxazol-5-yl)amino)pyrimidin-4-yl)amino)-4-fluorophenyl)acrylamide;
N-(3-((5-chloro-2-((5-chlorothiazol-2-yl)amino)pyrimidin-4-yl)amino)-4-fluorophenyl)acrylamide;
N-(3-((5-chloro-2-((5-cyanothiazol-2-yl)amino)pyrimidin-4-yl)amino)-4-fluorophenyl)acrylamide;
N-(3-((5-chloro-2-((3-methylisothiazol-5-yl)amino)pyrimidin-4-yl)amino)phenyl)acrylamide;
N-(3-((5-chloro-2-((5-methylthiazol-2-yl)amino)pyrimidin-4-yl)amino)pheny-1)acrylamide;
N-(3-((5-chloro-2-((4-methylthiazol-2-yl)amino)pyrimidin-4-yl)amino)pheny-1)acrylamide;
N-(3-((5-chloro-2-((3-methylisoxazol-5-yl)amino)pyrimidin-4-yl)amino)phen-yl)acrylamide;
1-(4-((5-chloro-2-((1-methyl-1H-pyrazol-4-yl)amino)pyrimidin-4-yl)amino)piperidin-1-yl)prop-2-en-1-one;
1-(3-(((5-chloro-2-((1-methyl-1H-pyrazol-4-yl)amino)pyrimidin-4-yl)amino)-methyl)piperidin-1-yl)prop-2-en-1-one; and
N-(3-((5-chloro-2-((1-methyl-1H-pyrazol-4-yl)amino)pyrimidin-4-yl)amino)cyclohexyl)acrylamide4-methylbenzenesulfonate.

5. A compound of formula (I), as claimed in any one of the claim 1, 2, 3, or 4, or its stereoisomers, tautomers, pharmaceutically acceptable salts, and hydrates thereof, for treating disease associated with epidermal growth factor receptor (EGFR) family kinases.

6. A compound of formula (I), as claimed in any one of the claim 1, 2, 3, or 4, or its stereoisomers, tautomers, pharmaceutically acceptable salts, and hydrates thereof, for treating disease or condition associated with non-small cell or small cell lung cancer or prostate cancer or head and neck cancer or breast cancer or conditions related to cancer.

7. A pharmaceutical composition comprising a compound of formula (I) or a pharmaceutically acceptable salt thereof of as claimed in any of claim 1, 2, 3, or 4, together with a pharmaceutically acceptable carrier, optionally in combination with one or more other pharmaceutical compositions.

* * * * *

UNITED STATES PATENT AND TRADEMARK OFFICE
CERTIFICATE OF CORRECTION

PATENT NO. : 10,273,224 B2  
APPLICATION NO. : 14/913508  
DATED : April 30, 2019  
INVENTOR(S) : Chandregowda Venkateshappa et al.

Page 1 of 2

It is certified that error appears in the above-identified patent and that said Letters Patent is hereby corrected as shown below:

In the Claims

Claim 1: Column 179, Lines 26-28: "–C($R_aR_aR_a$'), –C($R_aR_a$)[C($R_aR_a$)]$_n$OC($R_a$')$_p$, –S(O)$_p$C($R_a$')$_p$, –C($R_aR_a$)C($R_aR_a$)N($R_{.a}$')$_p$, C($R_aR_a$)C($R_aR_a$)O$R_a$'," should read -- –C($R_aR_aR_a$'), –C($R_aR_a$)[C($R_aR_a$)]$_n$OC($R_a$')$_p$, –S(O)$_p$C($R_a$')$_p$, –C($R_aR_a$)C($R_aR_a$)N($R_a$')$_p$, –C($R_aR_a$)C($R_aR_a$)O$R_a$', --.

Claim 2: Column 181, Lines 22-24: "–C($R_aR_a$)[C($R_aR_a$)]$_n$OC($R_a$)$_p$" should read -- –C($R_aR_a$)[C($R_aR_a$)]$_n$OC($R_a$')$_p$ --.

Claim 2: Column 182, Line 2: "Y is selected from the group the group consisting of" should read -- Y is selected from the group consisting of --.

Claim 2: Column 182, Line 8: "–C($R_aR_aR_a$), –C($R_aR_a$)[C($R_aR_a$)]$_n$OC($R_a$)$_p$" should read -- –C($R_aR_aR_a$'), –C($R_aR_a$)[C($R_aR_a$)]$_n$OC($R_a$')$_p$ --.

Claim 3: Column 183, Lines 3-4: "–C($R_aR_a$)[C($R_aR_a$)]$_n$OC($R_a$')p" should read -- –C($R_aR_a$)[C($R_aR_a$)]$_n$OC($R_a$')$_p$ --.

Claim 4: Column 184, Lines 3-5: "N-(3-((5-chloro-2-((1-(2-methoxyethyl)-3-methyl-iH-pyrazol-4-yl)amino)pyrimidin-4-yl)amino)phenyl)acrylamide" should read -- N-(3-((5-chloro-2-((1-(2-methoxyethyl)-3-methyl-1H-pyrazol-4-yl)amino)pyrimidin-4-yl)amino)phenyl)acrylamide --.

Claim 4: Column 184, Lines 6-8: "N-(3-((5-chloro-2-((1-(2-methoxyethyl)-5-methyl-iH-pyrazol-4-yl)amino)pyrimidin-4-yl)amino)phenyl)acrylamide" should read -- N-(3-((5-chloro-2-((1-(2-methoxyethyl)-5-methyl-1H-pyrazol-4-yl)amino)pyrimidin-4-yl)amino)phenyl)acrylamide --.

Claim 4: Column 186, Lines 10-11: "1-(3-((5-chloro-2-((1-methyl-iH-pyrazol-4-yl)amino)pyrimidin-4-yl)amino)phenyl)-1H-pyrrole-2,5-dione" should read -- 1-(3-((5-chloro-2-((1-methyl-1H-pyrazol-4-yl)amino)pyrimidin-4-yl)amino)phenyl)-1H-pyrrole-2,5-dione --.

Signed and Sealed this  
Tenth Day of November, 2020

Andrei Iancu  
*Director of the United States Patent and Trademark Office*

CERTIFICATE OF CORRECTION (continued)
U.S. Pat. No. 10,273,224 B2

Claim 4: Column 186, Lines 12-14: "N-(5-((5-chloro-2-((1-(1-methylpiperidin-4-yl)-1H-pyrazol-4-yl)amino)pyri-midin-4-yl)amino)-2-fluorophenyl)ethenesulfonamide" should read -- N-(5-((5-chloro-2-((1-(1-methylpiperidin-4-yl)-1H-pyrazol-4-yl)amino)pyrimidin-4-yl)amino)-2-fluorophenyl)ethenesulfonamide --.

Claim 4: Column 186, Lines 66-67: "N-(3-((5-chloro-2-((1-methyl-1H-pyrazol-4-yl)amino)pyrimidin-4-yl)oxy)phe-nyl)acrylamide" should read -- N-(3-((5-chloro-2-((1-methyl-1H-pyrazol-4-yl)amino)pyrimidin-4-yl)oxy)phenyl)acrylamide --.

Claim 5: Column 190, Lines 4-5: "A compound of formula (I), as claimed in any one of the claim 1, 2, 3, or 4" should read -- A compound of formula (I), as claimed in any one of the claims 1, 2, 3, or 4 --.

Claim 6: Column 190, Lines 9-10: "A compound of formula (I), as claimed in any one of the claim 1, 2, 3, or 4" should read -- A compound of formula (I), as claimed in any one of the claims 1, 2, 3, or 4 --.

Claim 7: Column 190, Line 17: "of as claimed in any of claim 1, 2, 3, or 4" should read -- as claimed in any of claims 1, 2, 3, or 4 --.